US010273310B2

(12) United States Patent
Grasso et al.

(10) Patent No.: US 10,273,310 B2
(45) Date of Patent: Apr. 30, 2019

(54) CYS80 CONJUGATED IMMUNOGLOBULINS

(71) Applicant: Eisai R&D Management Co., Ltd., Tokyo (JP)

(72) Inventors: Luigi Grasso, Bryn Mawr, PA (US); Jared Spidel, Downingtown, PA (US); James Bradford Kline, Morgantown, PA (US); Earl Albone, Blue Bell, PA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 140 days.

(21) Appl. No.: 15/185,879

(22) Filed: Jun. 17, 2016

(65) Prior Publication Data

US 2016/0369011 A1 Dec. 22, 2016

Related U.S. Application Data

(60) Provisional application No. 62/182,020, filed on Jun. 19, 2015.

(51) Int. Cl.
| | |
|---|---|
| *C07K 16/40* | (2006.01) |
| *A61K 47/68* | (2017.01) |
| *A61K 39/00* | (2006.01) |
| *C07K 16/28* | (2006.01) |
| *C07K 16/30* | (2006.01) |
| *G01N 33/533* | (2006.01) |

(52) U.S. Cl.
CPC .......... *C07K 16/40* (2013.01); *A61K 47/6849* (2017.08); *A61K 47/6851* (2017.08); *A61K 47/6898* (2017.08); *C07K 16/28* (2013.01); *C07K 16/2851* (2013.01); *C07K 16/30* (2013.01); *G01N 33/533* (2013.01); *A61K 2039/507* (2013.01); *C07K 2317/20* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/567* (2013.01); *C07K 2317/73* (2013.01); *C07K 2317/92* (2013.01)

(58) Field of Classification Search
CPC ........ C07K 16/00; C07K 16/40; C07K 16/28; C07K 16/2851; C07K 16/30; C07K 2317/20; C07K 2317/24; C07K 2317/31; C07K 2317/55; C07K 2317/56; C07K 2317/565; C07K 2317/567; C07K 2317/73; C07K 2317/92; A61K 47/6851; A61K 47/6898; A61K 47/6849; G01N 33/533

See application file for complete search history.

(56) References Cited

U.S. PATENT DOCUMENTS

| | | | |
|---|---|---|---|
| 7,402,409 B2 | 7/2008 | Yu | |
| 2009/0175865 A1 | 7/2009 | Eigenbrot et al. | |
| 2011/0033378 A1* | 2/2011 | Dimasi | ............ A61K 47/48215 424/1.49 |
| 2014/0050746 A1 | 2/2014 | Senter et al. | |

FOREIGN PATENT DOCUMENTS

| | | |
|---|---|---|
| WO | WO 2005-016950 A1 | 2/2005 |
| WO | WO 2006-017759 A2 | 2/2006 |
| WO | WO 2008-136694 A1 | 11/2008 |
| WO | WO 2008-144757 A1 | 11/2008 |
| WO | WO 2011-156328 A1 | 12/2011 |
| WO | WO 2014-031476 A1 | 2/2014 |
| WO | WO 2014-033074 A1 | 3/2014 |

OTHER PUBLICATIONS

Lyon et al., Methods in Enzymology 502: 123-137, 2012.*
Strosberg et al., J Immunology 115: 1422-1424, 1975.*
Rudikoff et al., Proc Natl Acad Sci USA 79: 1979-1983, 1982.*
MacCallum et al., J. Mol. Biol. 262: 732-745, 1996.*
Pascalis et al., The Journal of Immunology 169: 3076-3084, 2004.*
Corpet et al., "Multiple Sequence Alignment with Hierarchical Clustering," Nucleic Acids Research (1988) 16:22 (10881-10890).
Deonarain et al., "Emerging formats for next-generation antibody drug conjugates", Expert Opin. Drug Discov. (2015) 10(5): 463-481.
Eisenberg et al., "Analysis of membrane and surface protein sequences with the hydrophobic moment plot", J. Mol. Biol. (1984) 179:1 (125-142).
Higgins et al., "CLUSTAL: A package for performing multiple sequence alignment on a microcomputer", Gene, (1988) 73:1 (237-244).

(Continued)

*Primary Examiner* — Phuong Huynh
(74) *Attorney, Agent, or Firm* — Baker & Hostetler LLP

(57) ABSTRACT

Provided herein are methods for generating conjugated immunoglobulins, the method comprising: decapping a cysteine at amino acid position 80 ("Cys80") in a light chain variable region of an immunoglobulin, wherein the immunoglobulin comprises a heavy chain variable region and the light chain variable region; and conjugating a thiol-reactive compound to the Cys80, wherein the thiol-reactive compound comprises a thiol-reactive group. Antigen-binding molecules and methods for generating the same, immunoglobulins as well as nucleic acid molecules encoding the immunoglobulins and host cells comprising the nucleic acid molecules, conjugated immunoglobulins, and light chain variable regions for use in a conjugated immunoglobulin are also provided.

15 Claims, 25 Drawing Sheets

Specification includes a Sequence Listing.

(56) References Cited

OTHER PUBLICATIONS

Junutula et al., "Rapid identification of reactive cysteine residues for site-specific labeling of antibody-Fabs", Journal of Immunological Methods (2008) 332:41-52.
Lyons et al., "Chapter 6: Conjugation of Anticancer Drugs Through Endogenous Monoclonal Antibody Systeine Residues", Methods in Enzymology, Academic Press, US, 502, Jan. 2012, pp. 123-138.
McCartney-Francis et al., "k-chain allotypes and isotypes in the rabbit: cDNA sequences of clones encoding b9 suggest an evolutionary pathway and possible role of the interdomain disulfide bond in quantitative allotype expression", Proc. Natl. Acad. Sci. USA (1984) 81:1794-1798.
Needleman et al., "A general method applicable to search for similarities in the amino acid sequence of two proteins", J. Mol. Biol. (1970) 48(3):443-453.
Neuberger et al., "A hapten-specific chimaeric IgE antibody with human physiological effector function", Nature (1985) 314(6008):268-270.
Pearson et al., "Improved tools for biological sequence comparison", Proc. Nat. Acad. Sci. USA (1988) 85:2444-2448.
Pearson et al., "Using the FASTA program to search protein and DNA sequence databases", Methods Mol. Biol. (1994) 24:307-331.
Popkov et al., "Rabbit Immune Repertoires as Sources for Therapeutic Monoclonal Antibodies: The Impact of Kappa Alloype-correlated Variation in Cysteine Content on Antibody Libraries Selected by Phage Display", J. Mol. Biol. (2003) 325:325-335.
Riechmann et al., "Reshaping human antibodies for therapy", Nature (1988) 332(6162):323-327.
Smith et al., "Comparison of Biosequences," Advances in Applied Mathematics (1981) 2:482-489.
Voynov et al., "Design and Application of Antibody Cysteine Variants", Bioconjugate Chem. (2010) 21:385-392.

* cited by examiner

A

```
rb-IGKV1S2*01    AQVLTQTESPVSAPVGGTVTINCQASQSVYDNNWLSWYQQKPGQPPKLLIYDASKLASGVPSRFSGSGSGTQFTLTISGVQCDDAATYYCQGSYYSSGWY  (SEQ ID NO:403)
hu-IGKV1-5*01    DIQMTQSPSTLSASVGDRVTITCRASQSISS--WLAWYQQKPGKAPKLLIYDASSLESGVPSRFSGSGSGTEFTLTISSLQPDDFATYYCQQYNSYS---  (SEQ ID NO:404)
     Consensus        LTQS S LSA VG  VTI C ASQSI     WLAWYQQKPG  PKLLIYDAS L  SGVPSRFSGSGSGT F LTIS  LQ DD ATYYCQ      S
```

B

```
rb-IGKC1*01      -DPVAPTVLIFPPAADQVATGTVTIVCVANKYFP-DVTVTWEVDGTTQTTGIENSKTPQNSADCTYNLSSTLTLTSTQYNSHKEYTCKVTQG-TTSVQSFNRGDC  (SEQ ID NO:405)
hu-IGKC*01       RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC  (SEQ ID NO:406)
     Consensus         APSV IFPPA DQL SGT SIVCL N FFP D  V W VD   QS       STQ S D TY LSSTLTLS   Y HK Y C VT   SS V SFNRGDC
```

```
15505-VH      <----------FWR1---------->  <CR1>   <----FWR2---->   <-------CDR2------->   <----------FWR3---------->
              -QSVKESGGGLVTPSTELTLTCTVSGFSLN  SYAMI  WVRQAPGKGLEYIG  FITT---GGTTYYASWAKG  RFTISR--TSTTVQLKLTSTTEDTATYFCAR        (SEQ ID NO:476)
IGHV3-64*04  QVQLV...G..Q..GS.R.S.SA...TFS  ....H  .......K....VS  A.SSN--..S....DSV..  .....DMSKN.LX.QMNSLRA.....V.Y...      (SEQ ID NO:477)
IGHV3-49*04  ------...G..Q..RS.R.S..A...TFG  D....S  .......K....WV  ..RSKAY...E..ASV..  .....EDSKSIAY.QMNSLK.....V.Y.T..      (SEQ ID NO:478)
IGHV3-64*01  ------...G..Q..GS.R.S.AA...TFS  ....H  .......K....VS  A.SSN--..S....NSV..  .....DMSKN.LX.QMGSLRA..M.V.Y...       (SEQ ID NO:479)

15505-VL      <----------FWR1---------->  <---CDR1--->  <---FWR2--->   <-CDR2->   <--------FWR3-------->
              ELVMTQTPSSVSAAVGGTVTINC  QASQSISSYLA  WYQQKPGQPPKLLIY  YASTLAS  GVPSRFKGSGSGTEFTLTITGVQCDDAATYYC  LGVYGYS        (SEQ ID NO:480)
IGKV1-5*03  DIQ...S..TL..S..DR...T.  R........W..  .......KA......  K..S.E.  ...............S..............  QQYNS..        (SEQ ID NO:481)
IGKV1-5*01  DIQ...S..TL..S..DR...T.  R........W..  .......KA......  D..S.E.  ...............S..............  QQYNS..        (SEQ ID NO:482)
IGKV1-8*01  ----...S..P..ST.DR...T.  R........G..  .......KA......  A....Q.  ...............D..............SCL.SE.F....  QQYS.-  (SEQ ID NO:483)
```

FIG. 8

FIG. 14
A
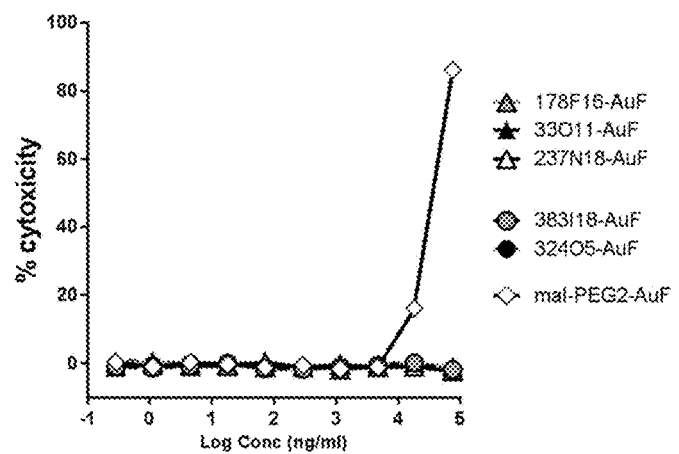
B
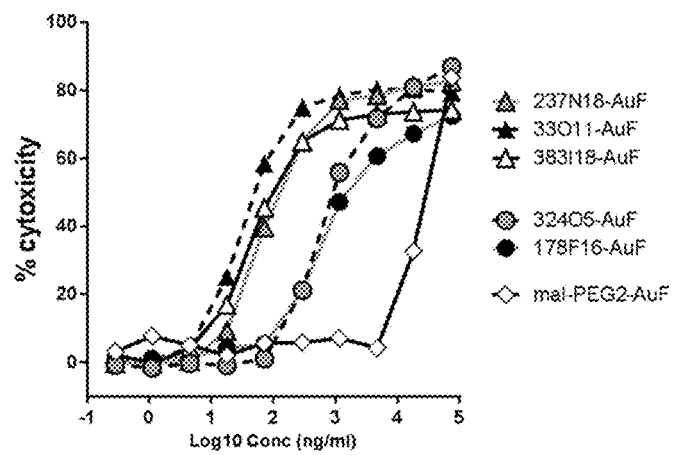

FIG. 16
A
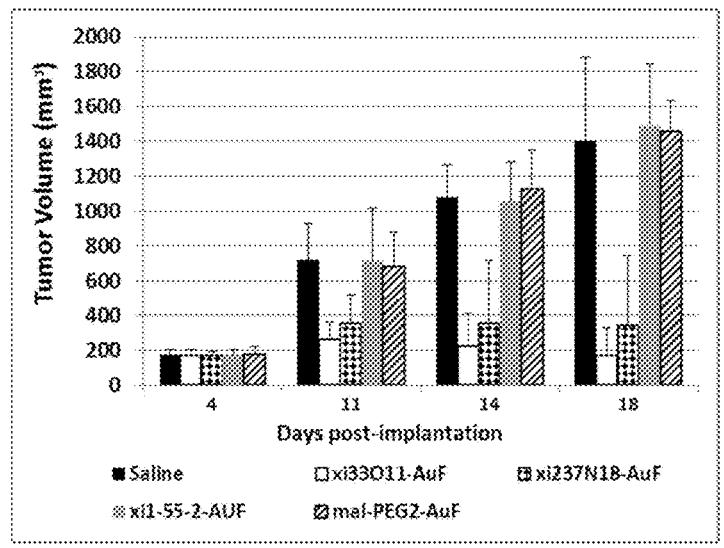
B
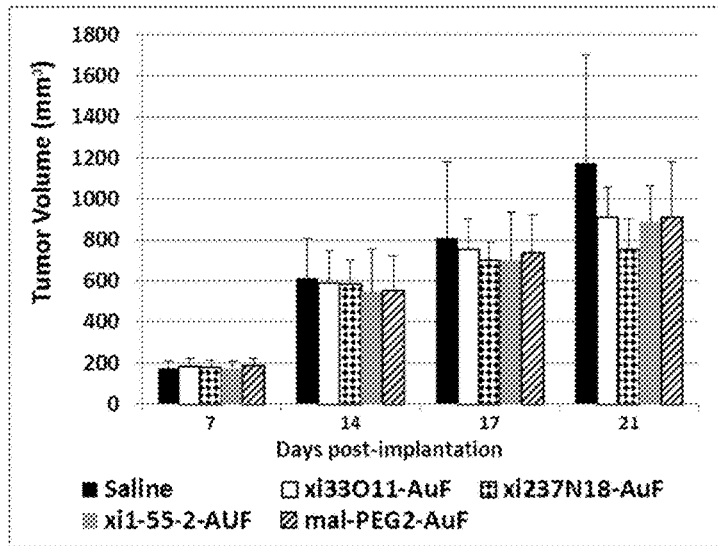

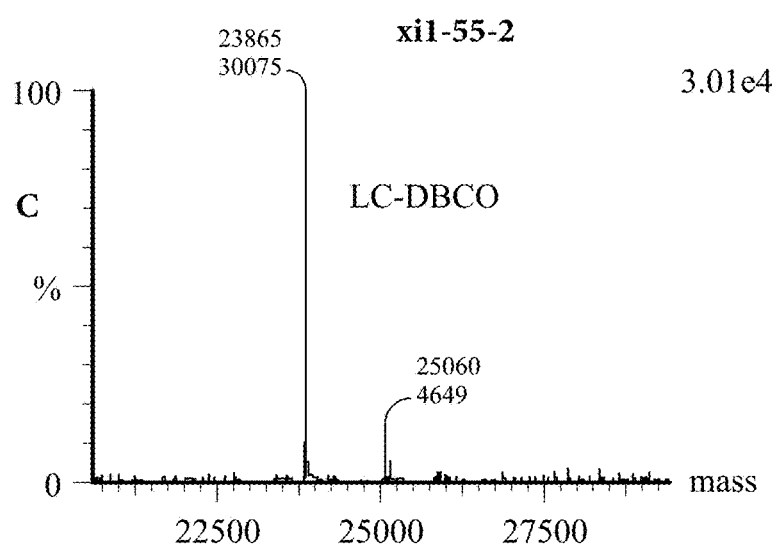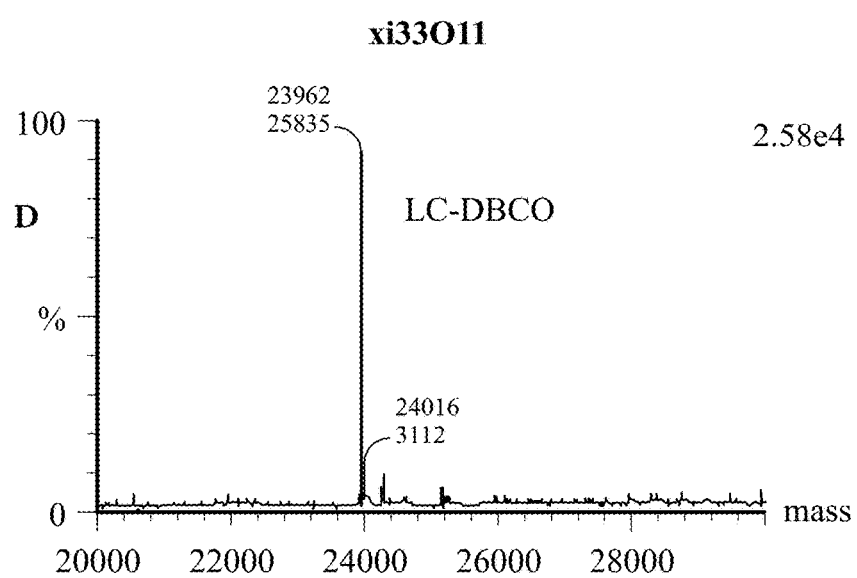
FIG. 22 (Continued)

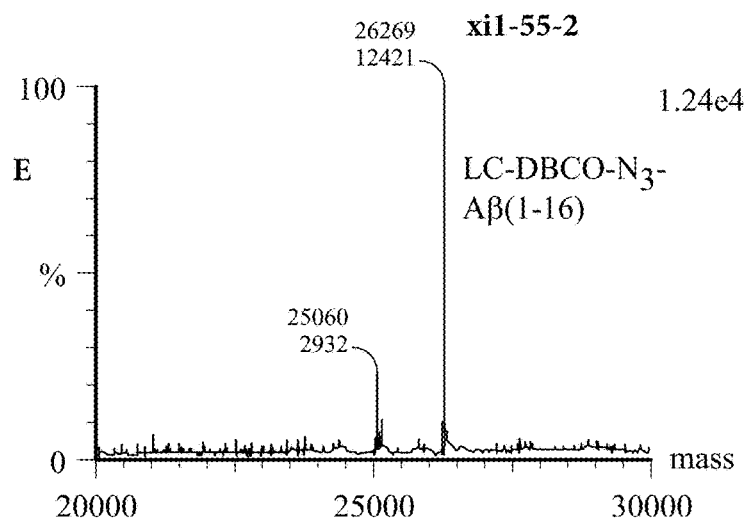
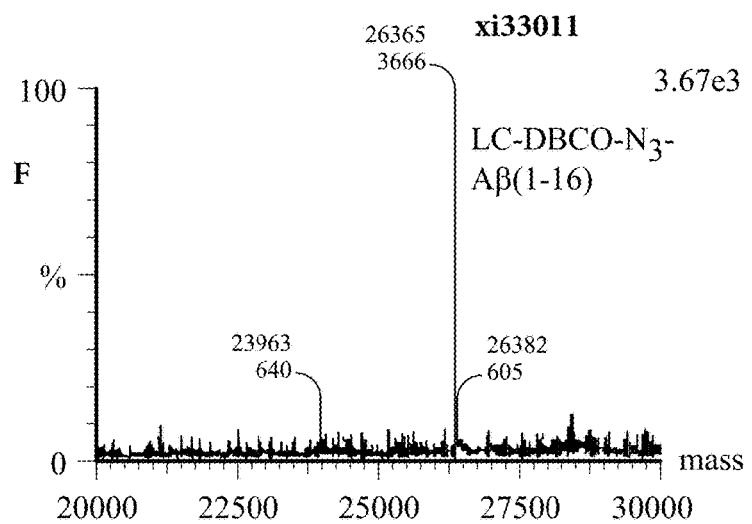
FIG. 22 (Continued)

CYS80 CONJUGATED IMMUNOGLOBULINS

CROSS REFERENCE TO RELATED APPLICATIONS

This application claims priority to U.S. Provisional Application No. 62/182,020, filed Jun. 19, 2015, the disclosure of which is hereby incorporated by reference in its entirety.

SEQUENCE LISTING

The instant application contains a Sequence Listing which has been submitted electronically in ASCII format and is hereby incorporated by reference in its entirety. The ASCII copy, created on Jun. 16, 2016, is named 104018.000952_SL.txt and is 368,769 bytes in size.

TECHNICAL FIELD

Provided herein are Cys80 conjugated immunoglobulins and methods of creating the same.

BACKGROUND

The utility of monoclonal antibodies extends from basic research to therapeutic and diagnostic applications. The ability to conjugate antibodies to functional agents extends their functionality even further. The manufacture of conjugated antibodies usually involves conjugation of a linker, drug, or other functional agent to reactive lysine or cysteine residues on the heavy (HC) and light (LC) chains of a monoclonal antibody (mAb). Lysine conjugation is typically mediated by succinimide (NHS)-based or isothiocyanate-based chemistry. Given the number of exposed lysines on the surface of an antibody, amine-based conjugation approaches result in multiple lysines being modified, though not all lysine residues are modified to the same extent. Therefore, the final product is a heterogeneous mixture of mAbs with a distribution of drug-to-antibody (DAR) ratios.

Most cysteines within an antibody are involved in either inter- or intra-chain disulfide bonds. Conjugation to cysteines thus requires at least partial reduction of the antibody. Like lysine-based conjugation, cysteine-based conjugation results in a heterogeneous mixture of conjugated antibodies differing in drug load and conjugation site. Each species of conjugated antibody may have distinct properties, which in turn could lead to wide variation of in vivo pharmacokinetic properties. Additionally, such heterogeneity can present challenges in manufacturing of the conjugated antibody.

SUMMARY

Disclosed herein are methods for generating a conjugated immunoglobulin, the methods comprising: decapping a cysteine at amino acid position 80 ("Cys80") in a light chain variable region of an immunoglobulin derived from rabbit, wherein the immunoglobulin comprises a heavy chain variable region and the light chain variable region; and conjugating a thiol-reactive compound to the Cys80, wherein the thiol-reactive compound comprises a thiol-reactive group.

Also provided are methods for generating an antigen-binding molecule, the methods comprising incubating a first conjugated immunoglobulin with a second conjugated immunoglobulin to generate the antigen-binding molecule, wherein: the first conjugated immunoglobulin comprises a first heavy chain variable region and a first light chain variable region, the first light chain variable region having a cysteine at position 80 ("Cys80$^1$") wherein Cys80$^1$ is conjugated to a first thiol-reactive compound comprising a first thiol-reactive group; and the second conjugated immunoglobulin comprises a second heavy chain variable region and a second light chain variable region, the second light chain variable region having a cysteine at position 80 ("Cys80$^2$") wherein Cys80$^2$ is conjugated to a second thiol-reactive compound comprising a second thiol-reactive group.

Immunoglobulins comprising a heavy chain variable region and a light chain variable region, the light chain variable region having a cysteine at position 80 ("Cys80") and an amino acid other than Phe, Lys, or Cys at position 83 are also provided herein, as are nucleic acid molecules encoding the immunoglobulins and host cells comprising the nucleic acid molecules.

Further provided are conjugated immunoglobulins comprising the disclosed immunoglobulins, wherein the cysteine at position 80 is conjugated to a thiol-reactive compound, the thiol-reactive compound comprising a thiol-reactive group.

Also disclosed herein are methods of treating cancer in a subject comprising administering to the subject a pharmaceutically effective amount of a conjugated mesothelin immunoglobulin, wherein the conjugated mesothelin immunoglobulin comprises: any of the disclosed mesothelin immunoglobulins, and a thiol-reactive compound comprising a thiol-reactive group, a linker, and a functional agent.

Provided are antigen-binding molecules comprising: a first conjugated immunoglobulin comprising a first heavy chain variable region and a first light chain variable region, the first light chain variable region having a cysteine at position 80 ("Cys80$^1$"), wherein Cys80$^1$ is conjugated to a first thiol-reactive compound comprising a first thiol-reactive group, and a second conjugated immunoglobulin comprising a second heavy chain variable region and a second light chain variable region, the second light chain variable region having a cysteine at position 80 ("Cys80$^2$") wherein Cys80$^2$ is conjugated to a second thiol-reactive compound comprising a second thiol-reactive group.

Light chain variable regions for use in a conjugated immunoglobulin, the light chain variable region having a cysteine at amino acid position 80 ("Cys80") and an amino acid residue other than Phe, Lys, or Cys at amino acid position 83, wherein the Cys80 is unpaired are also disclosed herein.

BRIEF DESCRIPTION OF THE DRAWINGS

The summary, as well as the following detailed description, is further understood when read in conjunction with the appended drawings. For the purpose of illustrating the disclosed methods, conjugated immunoglobulins, antigen-binding molecules, immunoglobulins, and light chain variable regions, there are shown in the drawings exemplary embodiments; however, the methods, conjugated immunoglobulins, antigen-binding molecules, immunoglobulins, and light chain variable regions are not limited to the specific embodiments disclosed. In the drawings:

FIG. 1 represents an alignment of rabbit and human light chain sequences. (A) Alignment of the germline VK sequences from rabbit (IGKV1S2, X02336) and human (IGKV1-5, Z00001). The bold residue indicates Cys80 (according to either Kabat or Chothia numbering) in the rabbit sequence. (B) Alignment of the germline CK sequences from rabbit (IGKC1, K01360) and human (IGKC, 100241). The bold residue indicates Cys171 (EU numbering) in the rabbit sequence.

FIG. 3 illustrates an alignment of rabbit germline Vκ families. The residue at position 80 is indicated by the arrow.

FIG. 8 represents rabbit 155D5 Vκ and VH sequences aligned with the most homologous human germline variable domains. Framework region (FWR) and complementary determining region (CDR) based on Kabat numbering are identified above the sequences. CDRs based on Chothia numbering are underlined. The C-terminal half of Kabat CDR2 is not considered a CDR by Chothia numbering and is italicized.

FIG. 14 illustrates (A) MSLN-AuF Cys80 conjugated mAbs cytotoxicity against MSLN-negative A431 cells and (B) MSLN-AuF Cys80 conjugated mAbs cytotoxicity against MSLN-positive A431-MSLN cells.

FIG. 16 represents (A) the average A431-MSLN (left flank) tumor volumes among different treatment groups and (B) the average tumor volumes among different treatment groups for A431 (right flank).

DETAILED DESCRIPTION OF ILLUSTRATIVE EMBODIMENTS

Figure 2:
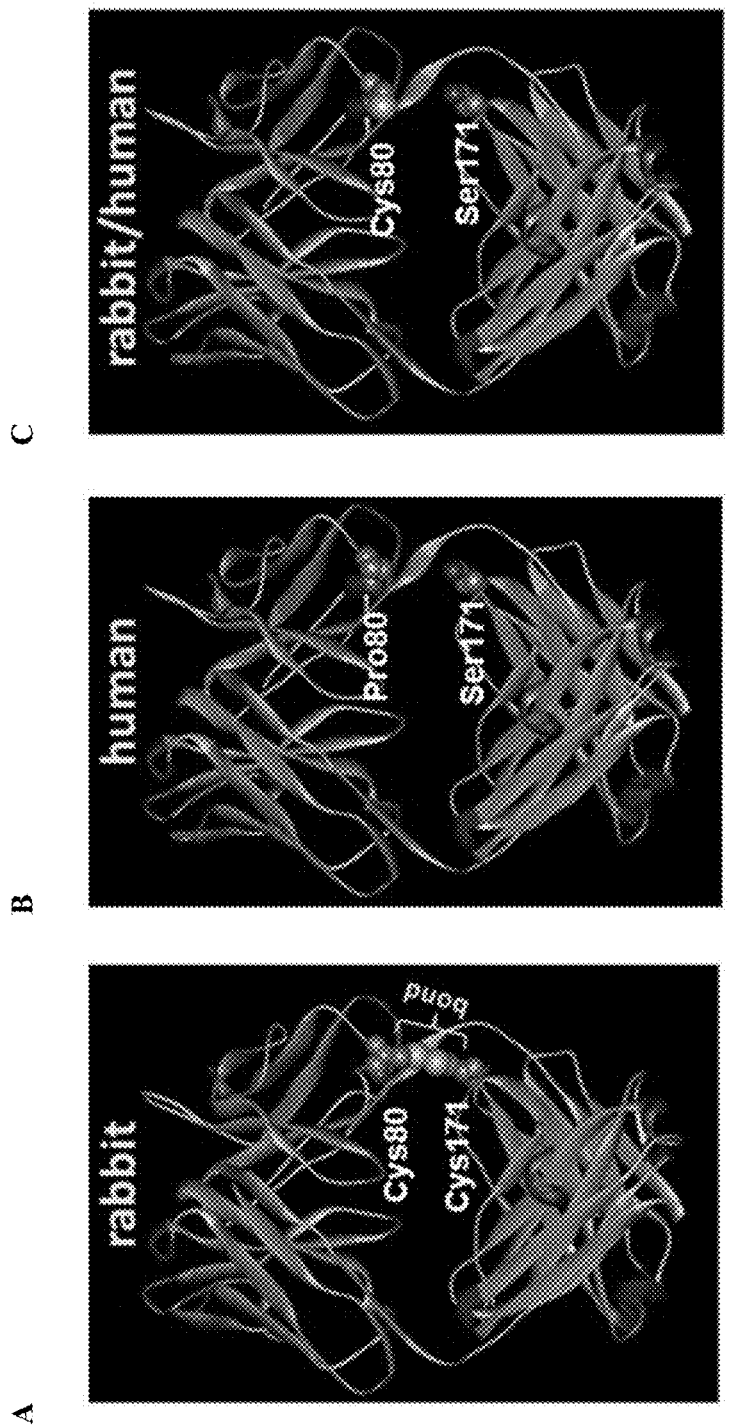
FIG. 2 represents structural models of (A) rabbit mAb, showing the Cys80-Cys171 disulfide bond, (B) human mAb, and (C) rabbit-human chimeric mAb showing the unpaired Cys80.

The disclosed methods, conjugated immunoglobulins, antigen-binding molecules, immunoglobulins, and light chain variable regions may be understood more readily by reference to the following detailed description taken in connection with the accompanying figures, which form a part of this disclosure. It is to be understood that the disclosed methods, conjugated immunoglobulins, antigen-binding molecules, immunoglobulins, and light chain variable regions are not limited to the specific embodiments described and/or shown herein, and that the terminology used herein is for the purpose of describing particular embodiments by way of example only and is not intended to be limiting of the claimed methods, conjugated immunoglobulins, antigen-binding molecules, immunoglobulins, and light chain variable regions.

Unless specifically stated otherwise, any description as to a possible mechanism or mode of action or reason for improvement is meant to be illustrative only, and the disclosed methods, conjugated immunoglobulins, antigen-binding molecules, immunoglobulins, and light chain variable regions are not to be constrained by the correctness or incorrectness of any such suggested mechanism or mode of action or reason for improvement.

Throughout this text, the descriptions refer to conjugated immunoglobulins, antigen-binding molecules, immunoglobulins, and light chain variable regions and methods of generating the same. Where the disclosure describes or claims a feature or embodiment associated with a conjugated immunoglobulin, antigen-binding molecule, immunoglobulin, or light chain variable region, such a feature or embodiment is equally applicable to the methods of generating the same. Likewise, where the disclosure describes or claims a feature or embodiment associated with a method of generating a conjugated immunoglobulin, antigen-binding molecule, immunoglobulin, or light chain variable region, such a feature or embodiment is equally applicable to the conjugated immunoglobulin, antigen-binding molecule, immunoglobulin, or light chain variable region.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed methods, conjugated immunoglobulins, antigen-binding molecules, immunoglobulins, and light chain variable regions which are, for clarity, described herein in the context of separate embodiments, may also be provided in combination in a single embodiment. Conversely, various features of the disclosed methods, conjugated immunoglobulins, antigen-binding molecules, immunoglobulins, and light chain variable regions that are, for brevity, described in the context of a single embodiment, may also be provided separately or in any subcombination.

As used herein, the singular forms "a," "an," and "the" include the plural.

The term "comprising" is intended to include examples encompassed by the terms "consisting essentially of" and "consisting of"; similarly, the term "consisting essentially of" is intended to include examples encompassed by the term "consisting of."

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

As used herein, the term "biological sample" refers to a sample obtained from a subject, including sample of biological tissue or fluid origin obtained in vivo or in vitro. Such samples can be, but are not limited to, body fluid (e.g., blood, blood plasma, serum, milk, spinal fluid, ascites, or urine), organs, tissues, fractions, and cells isolated from mammals including, humans. Biological samples also may include sections of the sample obtained from a subject including tissues (e.g., sectional portions of an organ or tissue). Biological samples may also include extracts from a sample obtained from a subject, for example, an antigen from a biological fluid (e.g., blood or urine).

The term "capping cysteine" refers to a free cysteine from solution that forms a disulfide bond with Cys80 of the light chain variable region.

The term "chimerized," "chimeric," "chimeric antibody" and like terms refer to an immunoglobulin comprising a heavy chain variable region and light chain variable region, i.e., antigen-binding region, from one source or species and at least a portion of a heavy chain constant region and light chain constant region derived from a different source or species. These portions may be joined together chemically by conventional techniques (e.g., synthetic) or prepared as a contiguous polypeptide using genetic engineering techniques (e.g., DNA encoding the protein portions of the chimeric antibody may be expressed to produce a contiguous polypeptide chain). Exemplary chimeric immunoglobulins include those comprising a rabbit variable region and a human constant region. Such rabbit/human chimeric immunoglobulins are the product of expressed immunoglobulin genes comprising DNA segments encoding rabbit immunoglobulin variable regions and DNA segments encoding human immunoglobulin constant regions. Other forms of "chimeric immunoglobulins" encompassed by the present disclosure are those in which the class or subclass has been modified or changed from that of the original immunoglobulin (also referred to as "class-switched immunoglobulins"). Throughout the disclosure, chimeric immunoglobulins are designated "xi." Herein, "chimeric immunoglobulin" and like terms refer to the sequence of the immunglobulin rather than the process used to generate the antibody.

As used herein, "Cys80" refers to a cysteine residue at amino acid position 80 of the light chain variable region relative to a light chain variable region absent a leader sequence. For example, the light chain variable regions disclosed in Table 25 comprise a 19 amino acid (encoded by a 57 nucleotide) leader sequence. "Cys80" occurs at amino acid position 99 when the leader sequence is present and amino acid position 80 when the leader sequence is absent. The Cys80 numbering is based upon Kabat/Chothia numbering system.

The term "decapping" refers to removal of the capping cysteine using the methods provided herein under conditions that minimize disruption of the native intra- and inter-chain disulfides of the immunoglobulin.

The term "immunoglobulin derived from" refers to immunoglobulins, or portions thereof, having at least the CDR regions of a rabbit immunoglobulin. "Immunoglobulin derived from" includes rabbit/human chimeras or humanized rabbit immunoglobulins. The level of variability tolerated when deriving an immunoglobulin from a rabbit can be determined, for example, by the United States Adopted Names Counsel (USAN) of the American Medical Association (AMA).

As used herein, "functional agent" refers to an agent having therapeutic, diagnostic, or other functional property(ies). Various functional agents that fall within the scope of the disclosure are described elsewhere herein.

The term "humanized," "humanized immunoglobulin" and like terms refer to immunoglobulins of rabbit origin in which the sequence of amino acids throughout the variable regions are changed to sequences having homology to a human variable region. Exemplary humanized immunoglobulins can comprise a rabbit variable domain whereby residues throughout the framework region (FWR) and/or the CDRs are replaced by sequences homologous to a human immunoglobulin. In some instances, FWR residues of the rabbit immunoglobulin are not replaced by corresponding human residues. Alternatively, "humanized," "humanized immunoglobulin" and like terms can refer to immunoglobulins of human origin in which residues throughout the FWR and/or CDRs were replaced by sequences homologous to a rabbit immunoglobulin. For example, humanized immunoglobulins can be human immunoglobulins in which residues from a hypervariable region of the human immunoglobulin are replaced by residues from a hypervariable region of a rabbit immunoglobulin having the desired specificity, affinity, and capacity. Furthermore, humanized immunoglobulins may comprise residues that are not found in the recipient immunoglobulin or in the donor immunoglobulin. These modifications are made to further refine immunoglobulin performance. In general, the humanized immunoglobulin will comprise substantially all of at least one, and typically two, variable domains, in which all or substantially all of the hypervariable loops correspond to those of a non-human immunoglobulin and all or substantially all of the FWRs are those of a human immunoglobulin sequence. The humanized immunoglobulin can optionally also comprise at least a portion of an immunoglobulin constant region (Fc), typically that of a human immunoglobulin. See, e.g., Riechmann, L., et al., Nature 332 (1988) 323-327; and Neuberger, M. S., et al., Nature 314 (1985) 268-270. Throughout the disclosure, "humanized immunoglobulins" are designated "zu." Herein, "humanized immunoglobulin" and like terms refer to the sequence of the immunoglobulin rather than the process used to generate the immunoglobulin.

The term "donor immunoglobulin" refers to a non-human immunoglobulin that contributes the amino acid sequences of its variable regions, CDRs, or other functional fragments or analogs thereof to the humanized immunoglobulin, and thereby provides the humanized immunoglobulin with the antigenic specificity and neutralizing activity characteristic of the donor immunoglobulin.

The term "recipient immunoglobulin" refers to an immunoglobulin heterologous to the donor immunoglobulin, which provides the amino acid sequences of its heavy and/or light chain framework regions and/or its heavy and/or light chain constant regions to the humanized immunoglobulin. The recipient immunoglobulin may be derived from any mammal. In preferred embodiments, the recipient immunoglobulin is non-immunogenic in humans. Preferably the recipient immunoglobulin is a human immunoglobulin.

"Humanizing" refers to a process of generating a humanized immunoglobulin and includes any process for generating humanized immunoglobulins having the above characteristics, including, but not limited to, in silico humanization, engineering species/host CDRs into human immunoglobulins, substituting framework region residues of a chimeric immunoglobulin to match a corresponding human framework region, etc.

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Genetically encoded hydrophobic amino acids include Pro (P), Ile (I), Phe (F), Val (V), Leu (L), Trp (W), Met (M), Ala (A), Gly (G) and Tyr (Y).

"Immunoglobulin," as used herein, refers to a protein consisting of one or more polypeptides substantially encoded by immunoglobulin genes including the kappa and lambda light chains and the alpha, gamma, delta, epsilon and mu heavy chains. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). "Immunoglobulins" include: (a) immunoglobulin polypeptides, i.e., polypeptides of the immunoglobulin family that contain an antigen binding site that specifically binds to a specific antigen (e.g., MSLN, CA9, TEM1, etc.), including all immunoglobulin isotypes (IgG, IgA, IgE, IgM, IgD, and IgY), classes (e.g. IgG1, IgG2, IgG3, IgG4, IgA1, IgA2), subclasses, and various monomeric and polymeric forms of each isotype, unless otherwise specified; and (b) conservatively substituted variants of such immunoglobulin polypeptides that immunospecifically bind to the antigen (e.g., MSLN, CA9, TEM1, etc.). Immunoglobulins are generally described in, for example, Harlow & Lane, Antibodies: A Laboratory Manual (Cold Spring Harbor Laboratory Press, 1988).

One form of immunoglobulin disclosed herein constitutes the basic structural unit of an antibody. For example, an antibody can include a tetramer and consist of two identical pairs of immunoglobulin chains, each pair having one light chain and one heavy chain. Generally, in each pair, the light chain and heavy chain variable regions are together responsible for binding to an antigen, and the constant regions are responsible for the antibody effector functions.

In addition to antibodies, immunoglobulins may exist in a variety of other forms including, for example: antigen-binding fragments or portions of an immunoglobulin, such as Fv, Fab, (Fab')$_2$ and Fv fragments; and alternative antibody formats such as single chain immunoglobulins (scFV and scFab), diabodies, triabodies, tetrabodies, linear antibodies, and multispecific antibodies, to name a few. See, for example, James D. Marks, Antibody Engineering, Chapter 2, Oxford University Press (1995) (Carl K. Borrebaeck, Ed.)

As used herein, the term "immunospecifically" refers to the ability of an immunoglobulin to specifically bind to an antigen against which the immunoglobulin was generated and not specifically bind to other peptides or proteins. An immunoglobulin that immunospecifically binds to an antigen against which the immunoglobulin was generated may not bind to other polypeptides or proteins, or may bind to other polypeptides or proteins with a lower binding affinity than the antigen against which the immunoglobulin was generated as determined by, for example, immunoassays, BIAcore, or other assays known in the art. An immunoglobulin binds immunospecifically to an antigen against which the immunoglobulin was generated when it binds to the antigen with a higher binding affinity than to any cross-reactive antigen as determined using experimental techniques, such as, but not limited to, radioimmunoassays (RIA) and enzyme-linked immunosorbent assays (ELISAs) (See, for example, Paul, ed., Fundamental Immunology, 2nd ed., Raven Press, New York, pages 332-336 (1989) for a discussion regarding antibody specificity.).

"Linker," as used herein, refers to a spacer, which may be a straight or branched chain, for connecting an immunoglobulin (through a thiol-reactive group on the unpaired Cys80) to a functional agent. Such linkers may be cleavable (e.g., acid labile or protease cleavable) or non-cleavable.

The term "monoclonal antibody" refers to an antibody that is derived from a single cell clone, including any eukaryotic or prokaryotic cell clone, or a phage clone, and not the method by which it is produced. A monoclonal antibody displays a single binding specificity and affinity for a particular epitope. The term "monoclonal antibody" is not limited to antibodies produced through hybridoma technology.

"Native" refers to the wild type immunoglobulin sequence from the species in which the immunoglobulin is derived. For example, in embodiments wherein a Cys80 is present in the light chain variable region from the species from which it is derived, the Cys80 is said be present in the native light chain variable region.

As used herein, "percent identity" and like terms is used to describe the sequence relationships between two or more nucleic acids, polynucleotides, proteins, or polypeptides, and is understood in the context of and in conjunction with the terms including: (a) reference sequence, (b) comparison window, (c) sequence identity and (d) percentage of sequence identity.

(a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, exemplary lengths of the reference polypeptide sequence include at least about 16 amino acids, at least about 20 amino acids, at least about 25 amino acids, at least about 35 amino acids, at least about 50 amino acids, or at least about 100 amino acids. For nucleic acids, exemplary length of the reference nucleic acid sequence include at least about 50 nucleotides, at least about 60 nucleotides, at least about 75 nucleotides, at least about 100 nucleotides, or at least about 300 nucleotides, or any integer thereabout or therebetween.

(b) A "comparison window" includes reference to a contiguous and specified segment of a polynucleotide or polypeptide sequence, wherein the polynucleotide or polypeptide sequence may be compared to a reference sequence and wherein the portion of the polynucleotide or polypeptide sequence in the comparison window may comprise additions, substitutions, or deletions (i.e., gaps) compared to the reference sequence (which does not comprise additions, substitutions, or deletions) for optimal alignment of the two sequences. Exemplary comparison windows can be at least 20 contiguous nucleotides or amino acids in length, and optionally may be 30, 40, 50, 100, or longer. Those of skill in the art understand that to avoid a misleadingly high similarity to a reference sequence due to inclusion of gaps in the polynucleotide or polypeptide sequence a gap penalty is typically introduced and is subtracted from the number of matches.

(c) Methods of alignment of sequences for comparison are well known in the art. Optimal alignment of sequences for comparison may be conducted by the local homology algorithm of Smith and Waterman, Adv. Appl. Math., 2: 482, 1981; by the homology alignment algorithm of Needleman and Wunsch, J. Mol. Biol., 48: 443, 1970; by the search for similarity method of Pearson and Lipman, Proc. Natl. Acad. Sci. USA, 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, Gene, 73: 237-244, 1988; Corpet, et al., Nucleic Acids Research, 16:881-90, 1988; Huang, et al., Computer Applications in the Biosciences, 8:1-6, 1992; and Pearson, et al., Methods in Molecular Biology, 24:7-331, 1994. The BLAST family of programs which may be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and may be used with the present disclosure.

(d) "Percent identity" means the value determined by comparing two optimally aligned sequences over a comparison window, wherein the portion of the polynucleotide or polypeptide sequence in the comparison window may comprise additions, substitutions, or deletions (i.e., gaps) as compared to the reference sequence (which does not comprise additions, substitutions, or deletions) for optimal alignment of the two sequences.

The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Pharmaceutically effective amount" refers to an amount of an immunoglobulin that treats the subject.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

The term "subject" as used herein refers to a human or non-human organism. Thus, the methods, immunoglobulins, and conjugated immunoglobulins described herein are applicable to both human and veterinary diseases and conditions. Subjects can be "patients," i.e., living humans or non-human organisms that are receiving medical care for a disease or condition, or humans or non-human organisms with no defined illness who are being investigated for signs of pathology or presence/absence of a particular condition.

"Substituting" refers to the replacement of one amino acid residue for another. "Substituting" includes, for example, missense mutations in one or more DNA base pairs encoding the amino acid residue or engineering the protein to exchange one amino acid with another.

As used herein, "treating" and like terms refer to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Exemplary diseases include, but are not limited to, cancer.

"Thiol-reactive group" refers to a reagent or group that can form a covalent bond with the thiol group in a cysteine.

"Unpaired Cys80" refers to a Cys80 present in an immunoglobulin that has a thiol functional group that is not involved in an intramolecular or intermolecular disulfide bond. For example, a thiol functional group of an "unpaired Cys80" is not involved in a disulfide bond with Cys171.

As used herein "90% identical to" encompasses at least 90% identical, 91% identical, 92% identical, 93% identical, 94% identical, 95% identical, 96% identical, 97% identical, 98% identical, 99% identical, or 100% identical to the reference item (e.g., a biological sequence).

The following abbreviations are used throughout the disclosure: antibody drug conjugates (ADCs); drug-to-antibody (DAR); frame work region (FWR); complementary determining region (CDR); carbonic anhydrase IX (CA9); mesothelin (MSLN); auristatin F (AuF); variable heavy region (VH); variable light region (VL); variable kappa (Vκ); rabbit (Rb; rabb); gamma constant region (Cγ); kappa constant region (Cκ); monoclonal antibody (mAb); cysteine at amino acid position 80 (Cys80).

Generation of Conjugated Immunoglobulins

Disclosed herein are methods for generating a conjugated immunoglobulin, the methods comprising:
decapping a cysteine at amino acid position 80 ("Cys80") in a light chain variable region of an immunoglobulin derived from rabbit, wherein the immunoglobulin comprises a heavy chain variable region and the light chain variable region; and
conjugating a thiol-reactive compound to the Cys80, wherein the thiol-reactive compound comprises a thiol-reactive group.

Suitable light chain variable regions include, for example, a kappa light chain variable region. The light chain variable region of the disclosed immunglobulins are derived from rabbit. In some embodiments, the Cys80 can be present in the native light chain variable region of the rabbit immunoglobulin. Exemplary rabbits from which a light chain variable region having a Cys80 can be derived include, but are not limited to, *Oryctolagus cuniculus*. In some aspects, for example, the light chain variable region can be derived from a New Zealand White (NZW) rabbit. In other aspects, the light chain variable region can be derived from a b9 rabbit.

Exemplary methods of decapping a Cys80 in a light chain variable region of an immunoglobulin include incubating the immunoglobulin with a reducing buffer followed by incubating the immunoglobulin with an oxidizing buffer. Reducing buffers comprise one or more reducing agents. Suitable reducing agents include, for example, cysteine (including L-cysteine and D-cysteine), 2-mercaptoethylamine, Tris (2-carboxyethyl) phosphine, 2-mercaptoethanesulfonic acid, 2-mercaptopropionic acid, or combinations thereof. In preferred embodiments, the reducing buffer can comprise a mild reductant such as cysteine. The concentration of reducing agent can range from about 0.2 mM to about 100 mM, from about 1 mM to about 100 mM, from about 2 mM to about 100 mM, from about 5 mM to about 100 mM, from about 10 mM to about 100 mM, from about 20 mM to about 100 mM, from about 40 mM to about 100 mM, from about 50 mM to about 100 mM, from about 0.2 mM to about 90 mM, from about 0.2 mM to about 80 mM, from about 0.2 mM to about 70 mM, from about 0.2 mM to about 50 mM, from about 0.2 mM to about 30 mM, from about 0.2 mM to about 25 mM, from about 0.2 mM to about 10 mM, or from about 0.2 mM to about 5 mM. The concentration of reducing agent can be about 0.2 mM. The concentration of reducing agent can be about 1 mM. The concentration of reducing agent can be about 2 mM. The concentration of reducing agent can be about 5 mM. The concentration of reducing agent can be about 10 mM. The concentration of reducing agent can be about 15 mM. The concentration of reducing agent can be about 20 mM. The concentration of reducing agent can be about 25 mM. The concentration of reducing agent can be about 30 mM. The concentration of reducing agent can be about 40 mM. The concentration of reducing agent can be about 50 mM. The concentration of reducing agent can be about 60 mM. The concentration of reducing agent can be about 70 mM. The concentration of reducing agent can be about 80 mM. The concentration of reducing agent can be about 90 mM. The concentration of reducing agent can be about 100 mM.

In some embodiments, for example, the reducing agent can comprise from about 2 mM to about 10 mM cysteine. In some embodiments, the reducing agent can comprise from about 2 mM to about 10 mM D-cysteine. In some embodiments, the reducing agent can comprise from about 2 mM to about 10 mM L-cysteine. In some embodiments, the reducing agent can comprise from about 10 mM to about 100 mM 2-mercaptoethylamine. In some embodiments, the reducing agent can comprise from about 0.2 mM to about 5 mM Tris (2-carboxyethyl) phosphine. In some embodiments, the reducing agent can comprise from about 2 mM to about 20 mM 2-mercaptoethanesulfonic acid. In some embodiments, the reducing agent can comprise from about 2 mM to about 20 mM 2-mercaptopropionic acid.

The reducing buffer can further comprise buffering agents such as sodium phosphate, potassium phosphate, MOPS, HEPES, sodium borate, potassium borate, or any combination thereof. Suitable buffering agent concentrations include, but are not limited to, from about 10 mM to about 100 mM, from about 15 mM to about 100 mM, from about 20 mM to about 100 mM, from about 30 mM to about 100 mM, from about 35 mM to about 100 mM, from about 40 mM to about 100 mM, from about 60 mM to about 100 mM, from about 80 mM to about 100 mM, from about 10 mM to about 90 mM, from about 10 mM to about 80 mM, from about 10 mM to about 60 mM, from about 10 mM to about 40 mM, from about 10 mM to about 30 mM, or from about 10 mM to about 20 mM.

In some embodiments, for example, the reducing buffer can contain from about 10 mM to about 100 mM sodium phosphate. In some embodiments, the reducing buffer can contain from about 10 mM to about 100 mM potassium phosphate. In some embodiments, the reducing buffer can contain from about 10 mM to about 100 mM MOPS. In some embodiments, the reducing buffer can contain from about 10 mM to about 100 mM HEPES. In some embodiments, the reducing buffer can contain from about 10 mM to about 100 mM sodium borate. In some embodiments, the reducing buffer can contain from about 10 mM to about 100 mM potassium borate.

The reducing buffer can also contain a chelating agent including, but not limited to, EDTA (ethylenediaminetetraacetic acid), DTPA (diethylene triamine pentaacetic acid), or a combination thereof. Suitable concentrations of chelating agents include from about 10 mM to about 100 mM, from about 10 mM to about 80 mM, from about 10 mM to about 60 mM, from about 10 mM to about 40 mM, from about 10 mM to about 30 mM, from about 10 mM to about 20 mM, from about 20 mM to about 100 mM, from about 30 mM to about 100 mM, from about 40 mM to about 100 mM, from about 50 mM to about 100 mM, from about 60 mM to about 100 mM, or from about 80 mM to about 100 mM.

Suitable pH ranges of the reducing buffer include from about 6.8 to about 8.0. In some embodiments, the pH of the reducing buffer can be about 6.8. In some embodiments, the pH of the reducing buffer can be about 6.9. In some embodiments, the pH of the reducing buffer can be about 7.0. In some embodiments, the pH of the reducing buffer can be about 7.1. In some embodiments, the pH of the reducing buffer can be about 7.2. In some embodiments, the pH of the reducing buffer can be about 7.3. In some embodiments, the pH of the reducing buffer can be about 7.4. In some embodiments, the pH of the reducing buffer can be about 7.5. In some embodiments, the pH of the reducing buffer can be about 7.6. In some embodiments, the pH of the reducing buffer can be about 7.7. In some embodiments, the pH of the reducing buffer can be about 7.8. In some embodiments, the pH of the reducing buffer can be about 7.9. In some embodiments, the pH of the reducing buffer can be about 8.0.

The immunoglobulin can be incubated with the reducing buffer for about 12 hours to about 96 hours, from about 18 hours to about 96 hours, from about 24 hours to about 96 hours, from about 30 hours to about 96 hours, from about 36 hours to about 96 hours, from about 42 hours to about 96 hours, from about 48 hours to about 96 hours, from about 54 hours to about 96 hours, from about 60 hours to about 96 hours, from about 12 hours to about 90 hours, from about 12 hours to about 84 hours, from about 12 hours to about 78 hours, from about 12 hours to about 72 hours, from about 12 hours to about 66 hours, from about 12 hours to about 60 hours, from about 12 hours to about 54 hours, from about 12 hours to about 48 hours, from about 12 hours to about 42 hours, from about 12 hours to about 36 hours, or from about 12 hours to about 30 hours. In some embodiments, the immunoglobulin can be incubated with the reducing buffer for about 12 hours. In some embodiments, the immunoglobulin can be incubated with the reducing buffer for about 18 hours. In some embodiments, the immunoglobulin can be incubated with the reducing buffer for about 24 hours. In some embodiments, the immunoglobulin can be incubated with the reducing buffer for about 30 hours. In some embodiments, the immunoglobulin can be incubated with the reducing buffer for about 36 hours. In some embodiments, the immunoglobulin can be incubated with the reducing buffer for about 42 hours. In some embodiments, the immunoglobulin can be incubated with the reducing buffer for about 48 hours. In some embodiments, the immunoglobulin can be incubated with the reducing buffer for about 54 hours. In some embodiments, the immunoglobulin can be incubated with the reducing buffer for about 60 hours. In some embodiments, the immunoglobulin can be incubated with the reducing buffer for about 66 hours. In some embodiments, the immunoglobulin can be incubated with the reducing buffer for about 72 hours. In some embodiments, the immunoglobulin can be incubated with the reducing buffer for about 78 hours. In some embodiments, the immunoglobulin can be incubated with the reducing buffer for about 84 hours. In some embodiments, the immunoglobulin can be incubated with the reducing buffer for about 90 hours. In some embodiments, the immunoglobulin can be incubated with the reducing buffer for about 96 hours. In some embodiments, the immunoglobulin can be incubated with the reducing buffer for greater than 96 hours.

Suitable oxidizing buffers include, but are not limited to, Tris-based, glutamine-based, arginine-based or other amino acid-based, or primary amine-based buffers. The concentration of oxidizing buffer can range from about 20 mM to about 100 mM, from about 40 mM to about 100 mM, from about 60 mM to about 100 mM, from about 80 mM to about 100 mM, from about 20 mM to about 80 mM, from about 20 mM to about 60 mM, or from about 20 mM to about 40 mM. The concentration of oxidizing buffer can be about 20 mM. The concentration of oxidizing buffer can be about 25 mM. The concentration of oxidizing buffer can be about 30 mM. The concentration of oxidizing buffer can be about 40 mM. The concentration of oxidizing buffer can be about 50 mM. The concentration of oxidizing buffer can be about 60 mM. The concentration of oxidizing buffer can be about 70 mM. The concentration of oxidizing buffer can be about 80 mM. The concentration of oxidizing buffer can be about 90 mM. The concentration of reducing agent can be about 100 mM.

The immunoglobulin can be incubated with the oxidizing buffer for about 24 hours to about 96 hours, from about 30 hours to about 96 hours, from about 36 hours to about 96 hours, from about 42 hours to about 96 hours, from about 48 hours to about 96 hours, from about 54 hours to about 96 hours, from about 60 hours to about 96 hours, from about 24 hours to about 90 hours, from about 24 hours to about 84 hours, from about 24 hours to about 78 hours, from about 24 hours to about 72 hours, from about 24 hours to about 66 hours, from about 24 hours to about 60 hours, from about 24 hours to about 54 hours, from about 24 hours to about 48 hours, from about 24 hours to about 42 hours, or from about 24 hours to about 36 hours. In some embodiments, the immunoglobulin can be incubated with the oxidizing buffer for about 24 hours. In some embodiments, the immunoglobulin can be incubated with the oxidizing buffer for about 30 hours. In some embodiments, the immunoglobulin can be incubated with the oxidizing buffer for about 36 hours. In some embodiments, the immunoglobulin can be incubated with the oxidizing buffer for about 42 hours. In some embodiments, the immunoglobulin can be incubated with the oxidizing buffer for about 48 hours. In some embodiments, the immunoglobulin can be incubated with the oxidizing buffer for about 54 hours. In some embodiments, the immunoglobulin can be incubated with the oxidizing buffer for about 60 hours. In some embodiments, the immunoglobulin can be incubated with the oxidizing buffer for about 66 hours. In some embodiments, the immunoglobulin can be incubated with the oxidizing buffer for about 72 hours. In some embodiments, the immunoglobulin can be incubated with the oxidizing buffer for about 78 hours. In some embodiments, the immunoglobulin can be incubated with the oxidizing buffer for about 84 hours. In some embodiments, the immunoglobulin can be incubated with the oxidizing buffer for about 90 hours. In some embodiments, the immunoglobulin can be incubated with the oxidizing buffer for about 96 hours. In some embodiments, the immunoglobulin can be incubated with the oxidizing buffer for greater than 96 hours.

Suitable pH ranges of the oxidizing buffer include from about 7.5 to about 9.0. In some embodiments, the pH of the oxidizing buffer can be about 7.5. In some embodiments, the pH of the oxidizing buffer can be about 7.6. In some embodiments, the pH of the oxidizing buffer can be about 7.7. In some embodiments, the pH of the oxidizing buffer can be about 7.8. In some embodiments, the pH of the oxidizing buffer can be about 7.9. In some embodiments, the pH of the oxidizing buffer can be about 8.0. In some embodiments, the pH of the oxidizing buffer can be about 8.1. In some embodiments, the pH of the oxidizing buffer can be about 8.2. In some embodiments, the pH of the oxidizing buffer can be about 8.3. In some embodiments, the pH of the oxidizing buffer can be about 8.4. In some embodiments, the pH of the oxidizing buffer can be about 8.5. In some embodiments, the pH of the oxidizing buffer can be about 8.6. In some embodiments, the pH of the oxidizing buffer can be about 8.7. In some embodiments, the pH of the oxidizing buffer can be about 8.8. In some embodiments, the pH of the oxidizing buffer can be about 8.9. In some embodiments, the pH of the oxidizing buffer can be about 9.0.

The method can further comprise immobilizing the immunoglobulin on a matrix prior to the incubating with the reducing agent and eluting the immunoglobulin from the matrix following the incubating with the oxidizing buffer. Suitable matrices include any surface to which an immunoglobulin can be bound and eluted from including, but not limited to, protein A, protein G, protein L, anti-Fab antibody, anti-Fc antibody, anti-Mab-based affinity supports, and strong cation exchange resins. In some embodiments, the matrix can be protein A. In some embodiments, the matrix can be protein G. In some embodiments, the matrix can be protein L. In some embodiments, the matrix can comprise an anti-Fab antibody. In some embodiments, the matrix can comprise an anti-Fc antibody. In some embodiments, the matrix can comprise an anti-MAb. In some embodiments, the matrix can comprise a strong cation exchange resin.

The disclosed methods for decapping an immunoglobulin can comprise: equilibrating a matrix; immobilizing the immunoglobulin onto the matrix; incubating the immobilized immunoglobulin on the matrix with a reducing buffer to remove capping group; incubating the immobilized immunoglobulin on the matrix with an oxidizing buffer; eluting the immunoglobulin from the matrix, and neutralizing the immunoglobulin.

Those skilled in the art would recognize that the buffer, concentration, pH, and time for eluting the immunoglobulin from the matrix will depend, at least in part, on the matrix. For example, in embodiments wherein the matrix is protein A, the immunoglobulin can be eluted from the protein A using glycine (for example, 0.1 M at pH 2.9). In some embodiments, the eluting can be performed in a low pH buffer.

Neutralizing the immunoglobulin can comprise incubating the immunoglobulin in a Tris-based, sodium phosphate-based, or potassium phosphate-based buffer (herein referred to as "neutralization buffer"). The neutralization buffer can have a concentration from about 0.5 M to about 2 M, and a pH from about 8.0 to about 9.5.

Conjugation can be performed by dissolving a thiol-reactive compound in a dissolution solution and incubating the dissolved thiol-reactive compound with the immunoglobulin in a conjugation buffer.

For aqueous-insoluble thiol-reactive compounds, which may include, but are not limited to, maleimide-based compounds, suitable dissolution solutions include organic, water-miscible solvents such as dimethylsulfoxide (DMSO). For aqueous-soluble thiol-reactive compounds, suitable dissolution solutions include, but are not limited to, water or buffered aqueous solutions, such as phosphate-buffered saline, pH 7.2 (1×PBS).

Suitable concentrations of thiol-reactive compounds include from about 5 mM to about 100 mM, from about 10 mM to about 100 mM, from about 25 mM to about 100 mM, from about 40 mM to about 100 mM, from about 55 mM to about 100 mM, from about 70 mM to about 100 mM, from about 10 mM to about 90 mM, from about 10 mM to about 75 mM, from about 10 mM to about 60 mM, from about 10 mM to about 50 mM, from about 10 mM to about 40 mM, or from about 10 mM to about 30 mM. In some embodiments, the concentration of the thiol-reactive compound can be about 10 mM. In some embodiments, the concentration of the thiol-reactive compound can be about 20 mM. In some embodiments, the concentration of the thiol-reactive compound can be about 30 mM. In some embodiments, the concentration of the thiol-reactive compound can be about 40 mM. In some embodiments, the concentration of the thiol-reactive compound can be about 50 mM. In some embodiments, the concentration of the thiol-reactive compound can be about 60 mM. In some embodiments, the concentration of the thiol-reactive compound can be about 70 mM. In some embodiments, the concentration of the thiol-reactive compound can be about 80 mM. In some embodiments, the concentration of the thiol-reactive compound can be about 90 mM. In some embodiments, the concentration of the thiol-reactive compound can be about 100 mM.

Suitable concentrations of immunoglobulin include from about 0.1 mg/ml to about 20 mg/ml, from about 0.5 mg/ml to about 20 mg/ml, from about 1 mg/ml to about 20 mg/ml, from about 5 mg/ml to about 20 mg/ml, from about 10 mg/ml to about 20 mg/ml, from about 0.1 mg/ml to about 15 mg/ml, from about 0.1 mg/ml to about 12 mg/ml, from about 0.1 mg/ml to about 10 mg/ml, from about 0.1 mg/ml to about 5 mg/ml, or from about 0.1 mg/ml to about 2 mg/ml. In some embodiments, the concentration of immunoglobulin can be about 0.1 mg/ml. In some embodiments, the concentration of immunoglobulin can be about 0.5 mg/ml. In some embodiments, the concentration of immunoglobulin can be about 1 mg/ml. In some embodiments, the concentration of immunoglobulin can be about 2 mg/ml. In some embodiments, the concentration of immunoglobulin can be about 5 mg/ml. In some embodiments, the concentration of immunoglobulin can be about 10 mg/ml. In some embodiments, the concentration of immunoglobulin can be about 15 mg/ml. In some embodiments, the concentration of immunoglobulin can be about 20 mg/ml.

Suitable ratios of thiol-reactive compound:immunoglobulin include from about 3:1 to 20:1. In some embodiments, the ratio of thiol-reactive compound:immunoglobulin can be 3:1. In some embodiments, the ratio of thiol-reactive compound: immunoglobulin can be 4:1. In some embodiments, the ratio of thiol-reactive compound:immunoglobulin can be 5:1. In some embodiments, the ratio of thiol-reactive compound:immunoglobulin can be 6:1. In some embodiments, the ratio of thiol-reactive compound:immunoglobulin can be 7:1. In some embodiments, the ratio of thiol-reactive compound:immunoglobulin can be 8:1. In some embodiments, the ratio of thiol-reactive compound:immunoglobulin can be 9:1. In some embodiments, the ratio of thiol-reactive compound:immunoglobulin can be 10:1. In some embodiments, the ratio of thiol-reactive compound:immunoglobulin can be 11:1. In some embodiments, the ratio of thiol-reactive compound:immunoglobulin can be 12:1. In some embodiments, the ratio of thiol-reactive compound:immunoglobulin can be 13:1. In some embodiments, the ratio of thiol-reactive compound:immunoglobulin can be 14:1. In some embodiments, the ratio of thiol-reactive compound:immunoglobulin can be 15:1. In some embodiments, the ratio of thiol-reactive compound:immunoglobulin can be 16:1. In some embodiments, the ratio of thiol-reactive compound:immunoglobulin can be 17:1. In some embodiments, the ratio of thiol-reactive compound:immunoglobulin can be 18:1. In some embodiments, the ratio of thiol-reactive compound: immunoglobulin can be 19:1. In some embodiments, the ratio of thiol-reactive compound:immunoglobulin can be 20:1.

The incubating can be performed in a number of suitable conjugation buffers including, for example, 1×PBS, pH 7.2, sodium phosphate, potassium phosphate, sodium borate, and HEPES, to name a few. The concentration of conjugation buffer include from about 5 mM to about 100 mM, from about 10 mM to about 100 mM, from about 20 mM to about 100 mM, from about 30 mM to about 100 mM, from about 45 mM to about 100 mM, from about 60 mM to about 100 mM, from about 75 mM to about 100 mM, from about 10 mM to about 90 mM, from about 10 mM to about 75 mM, from about 10 mM to about 60 mM, from about 10 mM to about 45 mM, or from about 10 mM to about 30 mM. In some embodiments, the concentration of the conjugation buffer can be about 10 mM. In some embodiments, the concentration of the conjugation buffer can be about 20 mM. In some embodiments, the concentration of the conjugation buffer can be about 30 mM. In some embodiments, the concentration of the conjugation buffer can be about 40 mM. In some embodiments, the concentration of the conjugation buffer can be about 50 mM. In some embodiments, the concentration of the conjugation buffer can be about 60 mM. In some embodiments, the concentration of the conjugation buffer can be about 70 mM. In some embodiments, the concentration of the conjugation buffer can be about 80 mM. In some embodiments, the concentration of the conjugation buffer can be about 90 mM. In some embodiments, the concentration of the conjugation buffer can be about 100 mM.

The conjugation buffer can further include sodium chloride. Suitable concentrations of sodium chloride include from about 0 mM to about 500 mM, from about 25 mM to about 500 mM, from about 50 mM to about 500 mM, from about 75 mM to about 500 mM, from about 100 mM to about 500 mM, from about 150 mM to about 500 mM, from about 200 mM to about 500 mM, from about 250 mM to about 500 mM, from about 300 mM to about 500 mM, from about 350 mM to about 500 mM, from about 400 mM to about 500 mM, from about 0 mM to about 400 mM, from about 0 mM to about 350 mM, from about 0 mM to about 300 mM, from about 0 mM to about 250 mM, from about 0 mM to about 200 mM, from about 0 mM to about 150 mM, from about 0 mM to about 100 mM, from about 0 mM to about 50 mM, or from about 0 mM to about 25 mM. In some embodiments, the concentration of sodium chloride can be about 25 mM. In some embodiments, the concentration of sodium chloride can be about 50 mM. In some embodiments, the concentration of sodium chloride can be about 75 mM. In some embodiments, the concentration of sodium chloride can be about 100 mM. In some embodiments, the concentration of sodium chloride can be about 150 mM. In some embodiments, the concentration of sodium chloride can be about 200 mM. In some embodiments, the concentration of sodium chloride can be about 250 mM. In some embodiments, the concentration of sodium chloride can be about 300 mM. In some embodiments, the concentration of sodium chloride can be about 350 mM. In some embodiments, the concentration of sodium chloride can be about 400 mM. In some embodiments, the concentration of sodium chloride can be about 500 mM.

The pH of the conjugation buffer can be from about 6.5 to about 8.5. In some embodiments, the pH of the conjugation buffer can be about 6.5. In some embodiments, the pH of the conjugation buffer can be about 6.6. In some embodiments, the pH of the conjugation buffer can be about 6.7. In some embodiments, the pH of the conjugation buffer can be about 6.8. In some embodiments, the pH of the conjugation buffer can be about 6.9. In some embodiments, the pH of the conjugation buffer can be about 7.0. In some embodiments, the pH of the conjugation buffer can be about 7.1. In some embodiments, the pH of the conjugation buffer can be about 7.2. In some embodiments, the pH of the conjugation buffer can be about 7.3. In some embodiments, the pH of the conjugation buffer can be about 7.4. In some embodiments, the pH of the conjugation buffer can be about 7.5. In some embodiments, the pH of the conjugation buffer can be about 7.6. In some embodiments, the pH of the conjugation buffer can be about 7.7. In some embodiments, the pH of the conjugation buffer can be about 7.8. In some embodiments, the pH of the conjugation buffer can be about 7.9. In some embodiments, the pH of the conjugation buffer can be about 8.0. In some embodiments, the pH of the conjugation buffer can be about 8.1. In some embodiments, the pH of the conjugation buffer can be about 8.2. In some embodiments, the pH of the conjugation buffer can be about 8.3. In some embodiments, the pH of the conjugation buffer can be about 8.4. In some embodiments, the pH of the conjugation buffer can be about 8.5.

To facilitate solubility of the thiol-reactive compound in the conjugation buffer, a final concentration of organic, water-miscible solvent in the conjugation buffer may be from about 0% to about 20%, from about 2% to about 20%, from about 5% to about 20%, from about 8% to about 20%, from about 11% to about 20%, from about 16% to about 20%, from about 0% to about 18%, from about 0% to about 15%, from about 0% to about 12%, from about 0% to about 10%, from about 0% to about 8%, from about 0% to about 6%, or from about 0% to about 2%.

The conjugation buffer can further comprise propylene glycol to facilitate solubility of the thiol-reactive compound in the conjugation buffer. Suitable concentrations of propylene glycol include from about 10% to about 50%, from about 20% to about 50%, from about 30% to about 50%, from about 40% to about 50%, from about 10% to about 40%, from about 10% to about 30%, or from about 10% to about 20%. In some embodiments, the concentration of propylene glycol can be about 10%. In some embodiments, the concentration of propylene glycol can be about 20%. In some embodiments, the concentration of propylene glycol can be about 30%. In some embodiments, the concentration of propylene glycol can be about 40%. In some embodiments, the concentration of propylene glycol can be about 50%.

The conjugation buffer can further comprise a non-ionic detergent to facilitate solubility of the conjugated immunoglobulin in the conjugation buffer. Exemplary non-ionic detergents include, but are not limited to, polysorbate-20 or polysorbate-80. Suitable concentrations of non-ionic detergent include from about 0% to about 1%, from about 0.1% to about 1%, from about 0.3% to about 1%, from about 0.5% to about 1%, from about 0.7% to about 1%, from about 0% to about 0.8%, from about 0% to about 0.6%, from about 0% to about 0.4%, or from about 0% to about 0.2%. In some embodiments, the concentration of non-ionic detergent can be about 0.1%. In some embodiments, the concentration of non-ionic detergent can be about 0.2%. In some embodiments, the concentration of non-ionic detergent can be about 0.3%. In some embodiments, the concentration of non-ionic detergent can be about 0.4%. In some embodiments, the concentration of non-ionic detergent can be about 0.5%. In some embodiments, the concentration of non-ionic detergent can be about 0.6%. In some embodiments, the concentration of non-ionic detergent can be about 0.7%. In some embodiments, the concentration of non-ionic detergent can be about 0.8%. In some embodiments, the concentration of non-ionic detergent can be about 0.9%. In some embodiments, the concentration of non-ionic detergent can be about 1.0%.

The incubating can be performed for about 2 hours to about 48 hours, for about 6 hours to about 48 hours, for about 12 hours to about 48 hours, for about 24 hours to about 48 hours, for about 30 hours to about 48 hours, for about 36 hours to about 48 hours, for about 42 hours to about 48 hours, for about 2 hours to about 42 hours, for about 2 hours to about 36 hours, for about 2 hours to about 30 hours, for about 2 hours to about 24 hours, for about 2 hours to about 18 hours, for about 2 hours to about 12 hours, or for about 2 hours to about 6 hours. In some embodiments, the incubating can be performed for 2 hours. In some embodiments, the incubating can be performed for 6 hours. In some embodiments, the incubating can be performed for 12 hours. In some embodiments, the incubating can be performed for 18 hours. In some embodiments, the incubating can be performed for 24 hours. In some embodiments, the incubating can be performed for 30 hours. In some embodiments, the incubating can be performed for 36 hours. In some embodiments, the incubating can be performed for 42 hours. In some embodiments, the incubating can be performed for 48 hours.

The temperature of the incubating can be from about 18° C. to about 37° C., from about 20° C. to about 37° C., from about 22° C. to about 37° C., from about 24° C. to about 37° C., from about 26° C. to about 37° C., from about 28° C. to about 37° C., from about 30° C. to about 37° C., from about 32° C. to about 37° C., from about 34° C. to about 37° C., from about 18° C. to about 34° C., from about 18° C. to about 32° C., from about 18° C. to about 30° C., from about 18° C. to about 28° C., from about 18° C. to about 26° C., or from about 18° C. to about 24° C. In some embodiments, the incubating can be performed at 18° C. In some embodiments, the incubating can be performed at 20° C. In some embodiments, the incubating can be performed at 22° C. In some embodiments, the incubating can be performed at 24° C. In some embodiments, the incubating can be performed at 26° C. In some embodiments, the incubating can be performed at 28° C. In some embodiments, the incubating can be performed at 30° C. In some embodiments, the incubating can be performed at 32° C. In some embodiments, the incubating can be performed at 34° C. In some embodiments, the incubating can be performed at 37° C.

Unincorporated thiol-reactive compounds can be separated from the conjugated immunoglobulin by desalting chromatography using a number of suitable resins including, but not limited to, G-25 resin, G-50 resin, Biogel P10, or other resins with exclusion limits of ranges 5,000-10,000 Da. Chromatography can be performed in column format or spin-column format, depending on scale. Suitable buffers for desalting include, for example, 1×PBS, sodium phosphate, potassium phosphate, sodium borate, or HEPES-based buffers may substitute for 1×PBS.

In an exemplary embodiment, the conjugating can be performed by dissolving a maleimido-based thiol reactive compound in 100% dimethylsulfoxide (DMSO) at a final concentration of thiol-reactive compound of 10 mM. The dissolved thiol-reactive compound can then be incubated with an immunoglobulin at an immunoglobulin concentration of 5 mg/ml in 1×PBS, pH 7.2 at a molar ratio of 5:1 thiol-reactive compound:immunoglobulin and mixed thoroughly. The incubating can be performed for 24 hours at 22° C. Unincorporated thiol-reactive compound can be removed from the conjugated immunoglobulin by desalting chromatography using G-25 resin with 1×PBS as running buffer.

Preferably, the thiol-reactive compound is conjugated to the Cys80 via the thiol-reactive group. Thiol-reactive groups include haloacetyls, maleimides, aziridines, acryloyls, arylating agents, vinylsulfones, pyridyl disulfides, TNB-thiols and disulfide reducing agents. In some embodiments, the thiol-reactive group can comprise a maleimide. In some embodiments, the thiol-reactive group can comprise a haloacetyl. In some embodiments, the thiol-reactive group can comprise an aziridine. In some embodiments, the thiol-reactive group can comprise an acryloyl. In some embodiments, the thiol-reactive group can comprise an arylating agent. In some embodiments, the thiol-reactive group can comprise a vinylsulfone. In some embodiments, the thiol-reactive group can comprise a pyridyl disulfide. In some embodiments, the thiol-reactive group can comprise a TNB-thiol. In some embodiments, the thiol-reactive group can comprise a disulfide reducing agent.

Thiol reactive groups can be derived from a number of suitable reagents including iodoacetamides, maleimides, benzylic halides and bromomethylketones, which can react by S-alkylation of thiols to generate stable thioether products.

The thiol-reactive group can be appended to a linker. Linkers can be non-cleavable linkers or cleavable linkers. Exemplary linkers include, for example, disulfide containing linkers, acetal-based linkers, and ketal-based linkers. In some aspects, the linker can be a non-cleavable linker. Suitable non-cleavable linkers include, but are not limited to, polyethylene glycol (PEG) or an alkyl. In some embodiments, the linker can comprise PEG. In some aspects, the linker can be a cleavable linker. Suitable cleavable linkers include, for example, valine-citrulline-para aminobenzyl. In some aspects, the linker can be a disulfide containing linker. In some aspects, the linker can be an acetal-based linker. In some aspects, the linker can be a ketal-based linker. Examples of linkers covalently appended to a thiol-reactive group are provided, for example, in U.S. Publ. No. 20140050746.

The thiol-reactive compound can further comprise a functional agent. Suitable functional agents include, for example, fluorophores, fluorescent dyes, polypeptides, immunoglobulins, antibiotics, nucleic acids, radionuclides, chemical linkers, small molecules, chelators, lipids, and drugs. In some aspects, the functional agent can comprise a fluorophore. In some aspects, the functional agent can comprise a fluorescent dye. In some aspects, the functional agent can comprise a polypeptide. In some aspects, the functional agent can comprise an immunoglobulin. In some aspects, the functional agent can comprise an antibiotic. In some aspects, the functional agent can comprise a nucleic acid (such as DNA or RNA). In some aspects, the functional agent can comprise a radionuclide. In some aspects, the functional agent can comprise a chemical linker (for example dibenzylcyclooctyne (DBCO) or azide). In some aspects, the functional agent can comprise a small molecule. In some aspects, the functional agent can comprise a chelator (for example, DOTA, CHX-A"-DTPA, NOTA, among others). In some aspects, the functional agent can comprise a lipid. In some aspects, the functional agent can comprise a drug. In some aspects, the functional agent can comprise a combination of any of the above listed functional agents.

The thiol-reactive compound (i.e. a first thiol-reactive compound) can be bound to a second thiol-reactive compound, the second thiol-reactive compound being bound to a second immunoglobulin having a second heavy chain variable region and a second light chain variable region, the second light chain variable region having a cysteine at amino acid position 80 ("Cys80$^2$"), wherein the second thiol-reactive compound comprises a second thiol-reactive group bound to the Cys80$^2$. For example, the first thiol-reactive compound and the second thiol-reactive compounds can have a first and second chemical linker as the first and second functional agents, respectively. The first and second chemical linkers can be bound to each other by a number of suitable means including, for example, by click chemistry.

In preferred embodiments, the Cys80 can be unpaired. Suitable means for unpairing Cys80 include, for example, chimerizing a light chain variable region having Cys80 with a constant domain having an amino acid residue other than cysteine at position 171.

The disclosed methods can be performed on a chimerized immunoglobulin. Thus, in some embodiments, the immunoglobulin can be a chimerized immunoglobulin. In embodiments wherein the immunoglobulin is chimerized, the methods for generating a conjugated immunoglobulin can comprise: decapping a Cys80 in a light chain variable region of a chimerized immunoglobulin, wherein the chimerized immunoglobulin comprises a heavy chain variable region and the light chain variable region; and conjugating a thiol-reactive compound to the Cys80, wherein the thiol-reactive compound comprises a thiol-reactive group.

Alternatively, the disclosed methods can further comprise chimerizing an immunoglobulin prior to the decapping. For example, the methods for generating a conjugated immunoglobulin can comprise: chimerizing an immunoglobulin comprising a heavy chain variable region and a light chain variable region, the light chain variable region having a Cys80; decapping the Cys80; and conjugating a thiol-reactive compound to the Cys80, wherein the thiol-reactive compound comprises a thiol-reactive group.

The disclosed methods can be performed on a humanized immunoglobulin. Thus, in some embodiments, the immunoglobulin can be a humanized immunoglobulin. In embodiments wherein the immunoglobulin is humanized, the methods for generating a conjugated immunoglobulin can comprise: decapping a Cys80 in a light chain variable region of a humanized immunoglobulin, wherein the humanized immunoglobulin comprises a heavy chain variable region and the light chain variable region; and conjugating a thiol-reactive compound to the Cys80, wherein the thiol-reactive compound comprises a thiol-reactive group.

Alternatively, the disclosed methods can further comprise humanizing an immunoglobulin prior to the decapping. For example, the methods for generating a conjugated immunoglobulin can comprise: humanizing an immunoglobulin comprising a heavy chain variable region and a light chain variable region, the light chain variable region having a Cys80; decapping the Cys80; and conjugating a thiol-reactive compound to the Cys80, wherein the thiol-reactive compound comprises a thiol-reactive group.

The methods can further comprise substituting an amino acid at position 83 with an amino acid residue other than Phe, Lys, or Cys. In some aspects, the methods can comprise substituting the phenylalanine at position 83 of the light chain variable region with alanine ("Ala83"). In some aspects, the methods can comprise substituting the phenylalanine at position 83 of the light chain variable region with valine ("Val83"). In some aspects, the methods can comprise substituting the phenylalanine at position 83 of the light chain variable region with isoleucine ("Ile83"). In some aspects, the methods can comprise substituting the phenylalanine at position 83 of the light chain variable region with threonine ("Thr83"). In some aspects, the methods can comprise substituting the phenylalanine at position 83 of the light chain variable region with arginine ("Arg83"). In some aspects, the methods can comprise substituting the phenylalanine at position 83 of the light chain variable region with asparagine ("Asn83"). In some aspects, the methods can comprise substituting the phenylalanine at position 83 of the light chain variable region with aspartic acid ("Asp83"). In some aspects, the methods can comprise substituting the phenylalanine at position 83 of the light chain variable region with glutamic acid ("Glu83"). In some aspects, the methods can comprise substituting the phenylalanine at position 83 of the light chain variable region with glutamine ("Gln83"). In some aspects, the methods can comprise substituting the phenylalanine at position 83 of the light chain variable region with glycine ("Gly83"). In some aspects, the methods can comprise substituting the phenylalanine at position 83 of the light chain variable region with histidine ("His83"). In some aspects, the methods can comprise substituting the phenylalanine at position 83 of the light chain variable region with leucine ("Leu83"). In some aspects, the methods can comprise substituting the phenylalanine at position 83 of the light chain variable region with methionine ("Met83"). In some aspects, the methods can comprise substituting the phenylalanine at position 83 of the light chain variable region with proline ("Pro83"). In some aspects, the methods can comprise substituting the phenylalanine at position 83 of the light chain variable region with serine ("Ser83"). In some aspects, the methods can comprise substituting the phenylalanine at position 83 of the light chain variable region with tryptophan ("Trp83"). In some aspects, the methods can comprise substituting the phenylalanine at position 83 of the light chain variable region with tyrosine ("Tyr83"). In some embodiments, the methods can comprise substituting an amino acid at position 83 with a polar or hydrophobic amino acid including, but not limited to, alanine, valine, isoleucine, or threonine.

The amino acid residue other than Phe, Lys, or Cys at amino acid position 83 in combination with the disclosed decapping methods can decrease the aggregation, and increase the Cys80 conjugation efficiency, of the immunoglobulin. Suitable immunoglobulin aggregation achieved by the disclosed methods include, for example, less than about 5%, less than about 7%, less than about 10%, less than about 12%, less than about 15%, less than about 17%, less than about 20%, less than about 22%, or less than about 25%. Suitable conjugation efficiencies achieved by the disclosed methods include, for example, greater than about 70%, greater than about 73%, greater than about 76%, greater than about 79%, greater than about 82%, greater than about 85%, greater than about 88%, greater than about 91%, greater than about 94%, greater than about 97%, or greater than about 99%.

Methods of Generating Antigen-Binding Molecules

Also provided herein are methods for generating an antigen-binding molecule, the method comprising incubating a first conjugated immunoglobulin with a second conjugated immunoglobulin to generate the antigen-binding molecule, wherein:

the first conjugated immunoglobulin comprises a first heavy chain variable region and a first light chain variable region, the first light chain variable region having a cysteine at position 80 ("Cys80$^1$") wherein Cys80$^1$ is conjugated to a first thiol-reactive compound comprising a first thiol-reactive group; and the second conjugated immunoglobulin comprises a second heavy chain variable region and a second light chain variable region, the second light chain variable region having a cysteine at position 80 ("Cys80$^2$") wherein Cys80$^2$ is conjugated to a second thiol-reactive compound comprising a second thiol-reactive group.

Antigen-binding molecules include multivalent and/or multispecific antigen-binding molecules. For example, antigen-binding molecules include bivalent, trivalent, and tetravalent antigen-binding molecules that are monospecific or bispecific. In some aspects, the antigen-binding molecule can be bivalent and monospecific. In some aspects, the antigen-binding molecule can be bivalent and bispecific. In some aspects, the antigen-binding molecule can be trivalent and monospecific. In some aspects, the antigen-binding molecule can be trivalent and bispecific. In some aspects, the antigen-binding molecule can be tetravalent and monospecific. In some aspects, the antigen-binding molecule can be tetravalent and bispecific. In some aspects, the valency can be greater than tetravalent. In some aspects, the specificity can be greater than bispecific.

The Cys80$^1$, the Cys80$^2$, or both, can be unpaired. Suitable means for unpairing Cys80 include, for example, chimerizing a light chain variable region having Cys80 with a constant domain having an amino acid residue other than cysteine at position 171.

In some aspects, the methods can further comprise decapping the Cys80$^1$. In some aspects, the methods can further comprise decapping the Cys80$^2$. In other aspects, the methods can further comprise decapping the Cys80$^1$ and Cys80$^2$.

The decapping can comprise incubating the first immunoglobulin, the second immunoglobulin, or both, with a reducing buffer followed by incubating the first immunoglobulin, the second immunoglobulin, or both, with an oxidizing buffer. In some aspects of the methods for generating antigen-binding molecules, the decapping can further comprise immobilizing the first immunoglobulin, the second immunoglobulin, or both on a matrix prior to the incubating with the reducing buffer and eluting the first immunoglobulin, the second immunoglobulin, or both from the matrix following the incubating with the oxidizing buffer.

Suitable decapping and conjugating conditions, including reducing buffers, oxidizing buffers, concentrations, pHs, times and matrices, are disclosed in the section entitled "generation of conjugated immunoglobulins" and are equally applicable herein.

In some aspects, the methods can further comprise conjugating a first thiol-reactive compound to the Cys80$^1$, wherein the first thiol-reactive compound comprises a first thiol-reactive group. In some aspects, the methods can further comprise conjugating a second thiol-reactive compound to the Cys80$^2$, wherein the second thiol-reactive compound comprises a second thiol-reactive group. In yet other aspects, the methods can further comprise conjugating a first thiol-reactive compound to the Cys80$^1$ and a second thiol-reactive compound to the Cys80$^2$, wherein the first thiol-reactive compound comprises a first thiol-reactive group and the second thiol-reactive compound comprises a second thiol-reactive group.

The methods can further comprise both decapping and conjugating. For example, the methods can further comprise, prior to the incubating step, decapping the Cys80$^1$, Cys80$^2$, or both; and conjugating a first thiol-reactive compound to the Cys80$^1$, a second thiol-reactive compound to the Cys80$^2$, or both, wherein the first thiol-reactive compound comprises a first thiol-reactive group and the second thiol-reactive compound comprises a second thiol-reactive group.

The first immunoglobulin, the second immunoglobulin, or both, can be chimerized. Conversely, the methods can further comprise chimerizing the first immunoglobulin, chimerizing the second immunoglobulin, or chimerizing both the first immunoglobulin and the second immunoglobulin. For example, and without intending to be limiting, the methods can further comprise, prior to the incubating step:

chimerizing a first immunoglobulin comprising a Cys80$^1$ to generate a first chimeric immunoglobulin;

chimerizing the second immunoglobulin comprising a Cys80$^2$ to generate a second chimeric immunoglobulin;

decapping the Cys80$^1$, Cys80$^2$, or both; and conjugating a first thiol-reactive compound to the Cys80$^1$, a second thiol-reactive compound to the Cys80$^2$, or both, wherein the first thiol-reactive compound comprises a first thiol-reactive group and the second thiol-reactive compound comprises a second thiol-reactive group.

The first immunoglobulin, the second immunoglobulin, or both, can be humanized. Conversely, the methods can further comprise humanizing the first immunoglobulin, humanizing the second immunoglobulin, or humanizing both the first immunoglobulin and the second immunoglobulin. For example, and without intending to be limiting, the methods can further comprise, prior to the incubating step:

humanizing a first immunoglobulin comprising a Cys80$^1$ to generate a first humanized immunoglobulin;

humanizing the second immunoglobulin comprising a Cys80$^2$ to generate a second humanized immunoglobulin;

decapping the Cys80$^1$, Cys80$^2$, or both; and conjugating a first thiol-reactive compound to the Cys80$^1$, a second thiol-reactive compound to the Cys80$^2$, or both, wherein the first thiol-reactive compound comprises a first thiol-reactive group and the second thiol-reactive compound comprises a second thiol-reactive group.

Preferably, the first and second thiol-reactive compounds are conjugated to the Cys80$^1$ and Cys80$^2$, respectively, via the first thiol-reactive group and the second thiol-reactive group. Suitable, thiol-reactive groups include haloacetyls, maleimides, aziridines, acryloyls, arylating agents, vinylsulfones, pyridyl disulfides, TNB-thiols and disulfide reducing agents. In some embodiments, the first thiol-reactive group, the second-thiol reactive group, or both, can comprise a maleimide. In some embodiments, the first thiol-reactive group, the second-thiol reactive group, or both, can comprise a haloacetyl. In some embodiments, the first thiol-reactive group, the second-thiol reactive group, or both, can comprise an aziridine. In some embodiments, the first thiol-reactive group, the second-thiol reactive group, or both, can comprise an acryloyl. In some embodiments, the first thiol-reactive group, the second-thiol reactive group, or both, can comprise an arylating agent. In some embodiments, the first thiol-reactive group, the second-thiol reactive group, or both, can comprise a vinylsulfone. In some embodiments, the first thiol-reactive group, the second-thiol reactive group, or both, can comprise a pyridyl disulfide. In some embodiments, the first thiol-reactive group, the second-thiol reactive group, or both, can comprise a TNB-thiol. In some embodiments, the first thiol-reactive group, the second-thiol reactive group, or both, can comprise a disulfide reducing agent.

The first thiol-reactive group, the second-thiol reactive group, or both can be appended to a linker. In some aspects, the first thiol-reactive group can be appended to a linker ("first linker"). In some aspects, the second thiol-reactive group can be appended to a linker ("second linker"). In yet other aspects the first thiol-reactive group can be appended to a first linker and the second thiol-reactive group can be appended to a second linker. Suitable first and second linkers can be non-cleavable linkers or cleavable linkers. Exemplary first and second linkers include, for example, disulfide containing linkers, acetal-based linkers, and ketal-based linkers. In some aspects, the first linker, second linker, or both, can be a non-cleavable linker. Suitable non-cleavable linkers include, but are not limited to, polyethylene glycol (PEG) or an alkyl. In some embodiments, the first linker, second linker, or both, can comprise PEG. In some aspects, the first linker, second linker, or both, can be a cleavable linker. Suitable cleavable linkers include, for example, valine-citrulline-para aminobenzyl. In some aspects, the first linker, second linker, or both, can be a disulfide containing linker. In some aspects, the first linker, second linker, or both can be an acetal-based linker. In some aspects, the first linker, second linker, or both, can be a ketal-based linker. Examples of linkers covalently appended to a thiol-reactive group are provided, for example, in U.S. Publ. No. 20140050746.

The first thiol-reactive compound, the second thiol-reactive compound, or both, can further comprise a functional agent. In some aspects, the first thiol-reactive compound can further comprise a functional agent ("first functional agent"). In some aspects, the second thiol-reactive compound can further comprise a functional agent ("second functional agent"). In yet other aspects, the first thiol-reactive compound can further comprise a first functional agent and the second thiol-reactive compound can further comprise a second functional agent.

Suitable functional agents include, for example, chemical linkers. Preferably, the chemical linker of the first thiol-reactive compound ("first chemical linker") and the chemical linker of the second thiol-reactive compound ("second chemical linker") can be coupled. For example, and without intent to be limiting, one of the first or second chemical linkers can be dibenzylcyclooctyne (DBCO) and the other of the first or second chemical linkers can be azide. In some embodiments, for example, the first chemical linker can be DBCO and the second chemical linker can be azide. Conversely, the first chemical linker can be azide and the second chemical linker can be DBCO. The DBCO and azide can be coupled, this resulting in the conjugation of the first immunoglobulin and the second immunoglobulin. For example, the first immunoglobulin and the second immunoglobulin can be conjugated to each other by click chemistry.

In an exemplary embodiment, thiol-reactive compounds can include maleimido-PEG4-azide and maleimido-PEG4-dibenzocyclooctyne. In some aspects, for example, the first thiol-reactive compound can be maleimido-PEG4-azide and the second thiol-reactive compound can be maleimido-PEG4-dibenzocyclooctyne. In some aspects, the first thiol-reactive compound can be maleimido-PEG4-dibenzocyclooctyne and the second thiol-reactive compound can be maleimido-PEG4-azide.

The first immunoglobulin, second immunoglobulin, or both, can be Fabs. In some embodiments, the first immunoglobulin can be a Fab ("first Fab"). In some embodiments, the second immunoglobulin can be a Fab ("second Fab"). In yet other embodiments, the first immunoglobulin can be a first Fab and the second immunoglobulin can be a second Fab.

In some embodiments, the methods comprise generating a first Fab, a second Fab, or both, prior to the incubating. Suitable techniques for generating Fabs are known in the art and include, for example, digesting a full or partial immunoglobulin to produce a Fab or recombinantly expressing the immunoglobulin as a Fab. For example, the methods of generating antigen-binding molecules can further comprise, prior to the incubating, digesting a first immunoglobulin, a second immunoglobulin, or both, with papain to generate a first Fab, second Fab, or first and second Fab, wherein the first immunoglobulin comprises a first heavy chain and a first light chain, the first light chain having a cysteine at position 80 ("Cys80$^1$"), and wherein the second immunoglobulin comprises a second heavy chain and a second light chain, the second light chain having a cysteine at position 80 ("Cys80$^2$"); or recombinantly expressing a first Fab comprising a first heavy chain and a first light chain having a cysteine at position 80 (Cys80$^1$), recombinantly expressing a second Fab comprising a second heavy chain and a second light chain having a cysteine at position 80 (Cys80$^2$), or both;

and conjugating the first Fab at Cys80$^1$ to a first thiol-reactive compound to generate a first conjugated Fab, conjugating the second Fab at Cys80$^2$ to a second thiol-reactive compound to generate a second conjugated Fab, or both.

The methods of generating antigen-binding molecules can further comprise substituting an amino acid at position 83 of the first light chain variable region with an amino acid residue other than Phe, Lys, or Cys. The methods of generating antigen-binding molecules can further comprise substituting an amino acid at position 83 of the second light chain variable region with an amino acid residue other than Phe, Lys, or Cys. The methods of generating antigen-binding molecules can further comprise substituting an amino acid at position 83 of the first light chain variable region with an amino acid residue other than Phe, Lys, or Cys and substituting an amino acid at position 83 of the second light chain variable region with an amino acid residue other than Phe, Lys, or Cys.

In some aspects, the methods can comprise substituting an amino acid at position 83 of the first light chain variable region, substituting an amino acid at position 83 of the second light chain variable region, or substituting an amino acid at position 83 of the first light chain variable region and the second light chain variable region with alanine ("Ala83"), valine ("Val83"), isoleucine ("Ile83"), threonine ("Thr83"), arginine ("Arg83"), asparagine ("Asn83"), aspartic acid ("Asp83"), glutamic acid ("Glu83"), glutamine ("Gln83"), glycine ("Gly83"), histidine ("His83"), leucine ("Leu83"), methionine ("Met83"), proline ("Pro83"), serine ("Ser83"), tryptophan ("Trp83"), or tyrosine ("Tyr83").

The amino acid at position 83 in the first light chain variable region can be the same as the amino acid at position 83 in the second light chain variable region. Conversely, theamino acid at position 83 in the first light chain variable region region can be different from the polar or hydrophobic amino acid at position 83 in the second light chain variable region. The amino acid at position 83 other than Phe, Lys, or Cys in the first light chain variable region and/or the amino acid at position 83 other than Phe, Lys, or Cys in the second light chain variable region can be a polar or hydrophobic amino acid including, but not limited to, alanine, valine, isoleucine, or threonine. In some aspects, the methods can comprise substituting an amino acid at position 83 of the first light chain variable region, substituting an amino acid at position 83 of the second light chain variable region, or substituting an amino acid at position 83 of the first light chain variable region and the second light chain variable region with valine ("Val83"). In some aspects, the methods can comprise substituting an amino acid at position 83 of the first light chain variable region, substituting an amino acid at position 83 of the second light chain variable region, or substituting an amino acid at position 83 of the first light chain variable region and the second light chain variable region with isoleucine ("Ile83"). In some aspects, the methods can comprise substituting an amino acid at position 83 of the first light chain variable region, substituting an amino acid at position 83 of the second light chain variable region, or substituting an amino acid at position 83 of the first light chain variable region and the second light chain variable region with threonine ("Thr83"). The polar or hydrophobic amino acid at position 83 in the first light chain variable region region can be the same as or different from the polar or hydrophobic amino acid at position 83 in the second light chain variable region.

Suitable light chain variable regions include, for example, a kappa light chain variable region. In some embodiments, the Cys80$^1$, Cys80$^2$, or both, can be present in the native light chain variable region. The first light chain variable region and second light chain variable region are derived from rabbit. Exemplary rabbits from which a first light chain variable region, second light chain variable region, or both, can be derived from include, but are not limited to, *Oryctolagus cuniculus*. In some aspects, for example, the light chain variable region(s) can be derived from a New Zealand White (NZW) rabbit. In other aspects, the light chain variable region(s) can be derived from a b9 rabbit.

Immunoglobulin Components of Conjugated Immunoglobulins

Disclosed herein are immunoglobulins comprising a heavy chain variable region and a light chain variable region, the light chain variable region having a cysteine at position 80 ("Cys80") and an amino acid other than Phe, Lys, or Cys at position 83.

Suitable light chain variable regions include, for example, a kappa light chain variable region. The light chain variable region is derived from rabbit. In some embodiments, the Cys80 can be present in the native light chain variable region of the rabbit immunoglobulin. Exemplary rabbits from which a light chain variable region having a Cys80 can be derived include, but are not limited to, *Oryctolagus cuniculus*. In some aspects, for example, the light chain variable region can be derived from a New Zealand White (NZW) rabbit. In other aspects, the light chain variable region can be derived from a b9 rabbit.

The amino acid other than Phe, Lys, or Cys at position 83 includes alanine ("Ala83"), valine ("Val83"), isoleucine ("Ile83"), threonine ("Thr83"), arginine ("Arg83"), asparagine ("Asn83"), aspartic acid ("Asp83"), glutamic acid ("Glu83"), glutamine ("Gln83"), glycine ("Gly83"), histidine ("His83"), leucine ("Leu83"), methionine ("Met83"), proline ("Pro83"), serine ("Ser83"), tryptophan ("Trp83"), or tyrosine ("Tyr83").

In some embodiments, the amino acid other than Phe, Lys, or Cys at position 83 can be a polar or hydrophobic amino acid including, but not limited to, alanine, valine, isoleucine, or threonine. In some aspects, the polar or hydrophobic amino acid other than Phe at position 83 is alanine ("Ala83"). In some aspects, the polar or hydrophobic amino acid other than Phe at position 83 is valine ("Val83"). In some aspects, the polar or hydrophobic amino acid other than Phe at position 83 is isoleucine ("Ile83"). In some aspects, the polar or hydrophobic amino acid other than Phe at position 83 is threonine ("Thr83").

The Cys80 can be unpaired. For example, a light chain variable region having Cys80 can be chimerized with a constant domain having an amino acid residue other than cysteine at position 171.

Preferably, the Cys80 is decapped.

In some embodiments, the immunoglobulins can be chimerized. In other embodiments, the immunoglobulins can be humanized.

In some embodiment, the disclosed immunoglobulin immunospecifically binds to human CA9. In some embodiments, the immunoglobulin that immunospecifically binds to human CA9 comprises:

a. a heavy chain variable region having an amino acid sequence at least 90% identical to amino acids 20-141 of xi155D5HC (SEQ ID NO:52) and a light chain variable region having an amino acid sequence at least 90% identical to amino acids 20-130 of xi155D5LC (SEQ ID NO:78);

b. a heavy chain variable region having an amino acid sequence at least 90% identical to amino acids 20-144 of zu155D5HC (SEQ ID NO:54) and a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or
zu155D5LC-huVK7-3-Glu81 (SEQ ID NO:106);
c. a heavy chain variable region having an amino acid sequence at least 90% identical to amino acids 20-138 of xi1E4HC (SEQ ID NO:58) and a light chain variable region having an amino acid sequence at least 90% identical to amino acids 20-130 of xi1E4LC (SEQ ID NO:110);
d. a heavy chain variable region having an amino acid sequence at least 90% identical to amino acids 20-140 of zu1E4HC (SEQ ID NO:60) and a light chain variable region having an amino acid sequence at least 90% identical to amino acids 20-130 of zu1E4LC-CXXA (SEQ ID NO:114);
e. a heavy chain variable region having an amino acid sequence at least 90% identical to amino acids 20-142 of xi166B3HC (SEQ ID NO:74) and a light chain variable region having an amino acid sequence at least 90% identical to amino acids 20-130 of xi166B3LC (SEQ ID NO:132); or
f. a heavy chain variable region having an amino acid sequence at least 90% identical to amino acids 20-145 of zu166B3HC (SEQ ID NO:76) and a light chain variable region having an amino acid sequence at least 90% identical to amino acids 20-130 of zu166B3LC-CXXA (SEQ ID NO:136).

In some embodiments, the immunoglobulin that immunospecifically binds to human CA9 comprises:
a. a heavy chain variable region as set forth as amino acids 20-141 of xi155D5HC (SEQ ID NO:52) and a light chain variable region as set forth as amino acids 20-130 of xi155D5LC (SEQ ID NO:78);
b. a heavy chain variable region as set forth as amino acids 20-144 of zu155D5HC (SEQ ID NO:54) and a light chain variable region as set forth as amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
c. a heavy chain variable region as set forth as amino acids 20-138 of xi1E4HC (SEQ ID NO:58) and a light chain variable as set forth as amino acids 20-130 of xi1E4LC (SEQ ID NO:110);
d. a heavy chain variable region as set forth as amino acids 20-140 of zu1E4HC (SEQ ID NO:60) and a light chain variable region as set forth as amino acids 20-130 of zu1E4LC-CXXA (SEQ ID NO:114);
e. a heavy chain variable region as set forth as amino acids 20-142 of xi166B3HC (SEQ ID NO:74) and a light chain variable region as set forth as amino acids 20-130 of xi166B3LC (SEQ ID NO:132); or
f. a heavy chain variable region as set forth as amino acids 20-145 of zu166B3HC (SEQ ID NO:76) and a light chain variable region as set forth as amino acids 20-130 of zu166B3LC-CXXA (SEQ ID NO:136).

In some embodiments, the immunoglobulin that immunospecifically binds to human CA9 comprises:
a. a heavy chain CDR1, CDR2, and CDR3 of xi155D5HC as set forth as SEQ ID NO:146, 148, and 150, respectively, and a light chain CDR1, CDR2, and CDR3 of xi155D5LC as set forth as SEQ ID NO:224, 226, and 228, respectively;
b. a heavy chain CDR1, CDR2, and CDR3 of zu155D5HC as set forth as SEQ ID NO:152, 154, and 156, respectively, and a light chain CDR1, CDR2, and CDR3 of zu155D5LC-3 as set forth as SEQ ID NO:242, 244, and 246, respectively, zu155D5LC-4 as set forth as SEQ ID NO:248, 250, and 252, respectively, zu155D5LC-5 as set forth as SEQ ID NO:254, 256, and 258, respectively, zu155D5LC-6 as set forth as SEQ ID NO:260, 262, and 264, respectively, zu155D5LC-7 as set forth as SEQ ID NO:266, 268, and 270, respectively, zu155D5LC-huVK2-40 as set forth as SEQ ID NO 278, 280, and 282, respectively, zu155D5LC-huVK4-1 as set forth as SEQ ID NO 290, 292, and 294, respectively, zu155D5LC-huVK6-21 as set forth as SEQ ID NO 296, 298, and 300, respectively, zu155D5LC-huVK6D-41 as set forth as SEQ ID NO 302, 304, and 306, respectively; or zu155D5LC-huVK7-3-Glu81 as set forth as SEQ ID NO 308, 310, and 312, respectively;
c. a heavy chain CDR1, CDR2, and CDR3 of xi1E4HC as set forth as SEQ ID NO 164, 166, and 168, respectively and a light chain CDR1, CDR2, and CDR3 of xi1E4LC as set forth as SEQ ID NO 320, 322, and 324, respectively;
d. a heavy chain CDR1, CDR2, and CDR3 of zu1E4HC as set forth as SEQ ID NO:170, 172, and 174, respectively, and a light chain CDR1, CDR2, and CDR3 of zu1E4LC-CXXA as set forth as SEQ ID NO:332, 334, and 336, respectively;
e. a heavy chain CDR1, CDR2, and CDR3 of xi166B3HC as set forth as SEQ ID NO:212, 214, and 216, respectively and a light chain CDR1, CDR2, and CDR3 of xi166B3LC as set forth as SEQ ID NO:386, 388, and 390, respectively; or
f. a heavy chain CDR1, CDR2, and CDR3 of zu166B3HC as set forth as SEQ ID NO:218, 220, and 222, respectively, and a light chain CDR1, CDR2, and CDR3 of zu166B3LC-CXXA as set forth as SEQ ID NO:398, 400, and 402, respectively.

In some embodiments, the disclosed immunoglobulins immunospecifically bind to human TEM1. In some embodiments, the immunoglobulin that immunospecifically binds to human TEM1 comprises a heavy chain variable region having an amino acid sequence at least 90% identical to amino acids 20-139 of xi1-55-2HC (SEQ ID NO:56) and a light chain variable region having an amino acid sequence at least 90% identical to amino acids 20-129 of xi1-55-2LC (SEQ ID NO:108).

In some embodiments, the immunoglobulin that immunospecifically binds to human TEM1 comprises a heavy chain variable region as set forth as amino acids 20-139 of xi1-55-2HC (SEQ ID NO:56) and a light chain variable region as set forth as amino acids 20-129 of xi1-55-2LC (SEQ ID NO:108).

In some embodiments, the immunoglobulin that immunospecifically binds to human TEM1 comprises a heavy chain CDR1, CDR2, and CDR3 of xi1-55-2HC as set forth as SEQ ID NO:158, 160, and 162, respectively, and a light chain CDR1, CDR2, and CDR3 of xi1-55-2LC as set forth as SEQ ID NO:314, 316, and 318, respectively.

In some embodiments, the disclosed immunoglobulins immunospecifically bind to human mesothelin. In some embodiments, the immunoglobulin that immunospecifically binds to human mesothelin comprises:
a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);
b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);
c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);
d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);
e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128); or
f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130).

In some embodiments, the immunoglobulin that immunospecifically binds to human mesothelin comprises:
a. a heavy chain variable region as set forth as amino acids 20-142 of xi33O11HC (SEQ ID NO:62) and a light chain variable region as set forth as amino acids 20-131 of xi33O11LC (SEQ ID NO:116);
b. a heavy chain variable region as set forth as amino acids 20-145 of zu33O11HC (SEQ ID NO:64) and a light chain variable region as set forth as amino acids 20-131 of zu33O11LC-CXXA (SEQ ID NO:120) or zu33O11LC-CXXI (SEQ ID NO:122);
c. a heavy chain variable region as set forth as amino acids 20-137 of xi324O5HC (SEQ ID NO:66) and a light chain variable region as set forth as amino acids 20-127 of xi324O5LC (SEQ ID NO:124);
d. a heavy chain variable region as set forth as amino acids 20-137 of xi178F16HC (SEQ ID NO:68) and a light chain variable region as set forth as amino acids 20-127 of xi178F16LC (SEQ ID NO:126);
e. a heavy chain variable region as set forth as amino acids 20-132 of xi237N18HC (SEQ ID NO:70) and a light chain variable region as set forth as amino acids 20-127 of xi237N18LC (SEQ ID NO:128); or
f. a heavy chain variable region as set forth as amino acids 20-137 of xi383I18HC (SEQ ID NO:72) and a light chain variable region as set forth as amino acids 20-127 of xi383I18LC (SEQ ID NO:130).

In some embodiments, the immunoglobulin that immunospecifically binds to human mesothelin comprises:
a. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth as SEQ ID NO:338, 340, and 342, respectively;
b. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively or zu33O11LC-CXXI as set forth as SEQ ID NO:356, 358, and 360, respectively;
c. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
d. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
e. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
f. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

Conjugated Immunoglobulins

Also disclosed herein are conjugated immunoglobulins comprising any of the immunoglobulins disclosed herein, wherein the cysteine at position 80 ("Cys80") is conjugated to a thiol-reactive compound, the thiol-reactive compound comprising a thiol-reactive group.

In some embodiments, the conjugated immunoglobulins comprise an immunoglobulin comprising a heavy chain variable region and a light chain variable region, the light chain variable region having a Cys80 and an amino acid other than Phe, Lys, or Cys at position 83, wherein Cys80 is conjugated to a thiol-reactive compound, the thiol-reactive compound comprising a thiol-reactive group. In some embodiments, the light chain variable region can have a Cys80 and a polar or hydrophobic amino acid other than Phe, Lys, or Cys at position 83.

The immunoglobulin comprises a heavy chain variable region and a light chain variable region. Suitable light chain variable regions include, for example, a kappa light chain variable region. The light chain variable region is derived from rabbit. In some embodiments, the Cys80 can be present in the native light chain variable region of the rabbit immunoglobulin. Exemplary rabbits from which a light chain variable region having a Cys80 can be derived include, but is not limited to, *Oryctolagus cuniculus*. In some aspects, for example, the light chain variable region can be derived from a New Zealand White (NZW) rabbit. In other aspects, the light chain variable region can be derived from a b9 rabbit.

The light chain variable region can have a Cys80 and an amino acid other than Phe, Lys, or Cys at position 83. The amino acid other than Phe, Lys, or Cys at position 83 includes alanine ("Ala83"), valine ("Val83"), isoleucine ("Ile83"), threonine ("Thr83"), arginine ("Arg83"), asparagine ("Asn83"), aspartic acid ("Asp83"), glutamic acid ("Glu83"), glutamine ("Gln83"), glycine ("Gly83"), histidine ("His83"), leucine ("Leu83"), methionine ("Met83"), proline ("Pro83"), serine ("Ser83"), tryptophan ("Trp83"), or tyrosine ("Tyr83"). In some embodiments, the light chain variable region can have a Cys80 and a polar or hydrophobic amino acid other than Phe, Lys, or Cys at position 83. Suitable polar or hydrophobic amino acids include, but are not limited to, alanine, valine, isoleucine, or threonine. In some aspects, the polar or hydrophobic amino acid other than Phe at position 83 is alanine ("Ala83"). In some aspects, the polar or hydrophobic amino acid other than Phe at position 83 is valine ("Val83"). In some aspects, the polar or hydrophobic amino acid other than Phe at position 83 is isoleucine ("Ile83"). In some aspects, the polar or hydrophobic amino acid other than Phe at position 83 is threonine ("Thr83").

The Cys80 can be unpaired. For example, the light chain variable region having Cys80 can be chimerized with a constant domain having an amino acid residue other than cysteine at position 171.

Preferably, the Cys80 is decapped.

In some embodiments, the immunoglobulin can be chimerized. In other embodiments, the immunoglobulin can be humanized.

Preferably, the thiol-reactive compound is conjugated to the Cys80 via the thiol-reactive group. Thiol-reactive groups include haloacetyls, maleimides, aziridines, acryloyls, arylating agents, vinylsulfones, pyridyl disulfides, TNB-thiols and disulfide reducing agents. In some embodiments, the thiol-reactive group can comprise a maleimide. In some embodiments, the thiol-reactive group can comprise a haloacetyl. In some embodiments, the thiol-reactive group can comprise an aziridine. In some embodiments, the thiol-reactive group can comprise an acryloyl. In some embodiments, the thiol-reactive group can comprise an arylating agent. In some embodiments, the thiol-reactive group can comprise a vinylsulfone. In some embodiments, the thiol-reactive group can comprise a pyridyl disulfide. In some embodiments, the thiol-reactive group can comprise a TNB-thiol. In some embodiments, the thiol-reactive group can comprise a disulfide reducing agent.

The thiol-reactive group can be appended to a linker. Linkers can be non-cleavable linkers or cleavable linkers. Exemplary linkers include, for example, disulfide containing linkers, acetal-based linkers, and ketal-based linkers. In some aspects, the linker can be a non-cleavable linker. Suitable non-cleavable linkers include, but are not limited to, polyethylene glycol (PEG) or an alkyl. In some embodiments, the linker can comprise PEG. In some aspects, the linker can be a cleavable linker. Suitable cleavable linkers include, for example, valine-citrulline-para aminobenzyl. In some aspects, the linker can be a disulfide containing linker. In some aspects, the linker can be an acetal-based linker. In some aspects, the linker can be a ketal-based linker. Examples of linkers covalently appended to a thiol-reactive group are provided, for example, in U.S. Publ. No. 20140050746.

The thiol-reactive compound can further comprise a functional agent. Suitable functional agents include, for example, fluorophores, fluorescent dyes, polypeptides, immunoglobulins, antibiotics, nucleic acids, radionuclides, chemical linkers, small molecules, chelators, lipids, and drugs. In some aspects, the functional agent can comprise a fluorophore. In some aspects, the functional agent can comprise a fluorescent dye. In some aspects, the functional agent can comprise a polypeptide. In some aspects, the functional agent can comprise an immunoglobulin. In some aspects, the functional agent can comprise an antibiotic. In some aspects, the functional agent can comprise a nucleic acid (such as DNA or RNA). In some aspects, the functional agent can comprise a radionuclide. In some aspects, the functional agent can comprise a chemical linker (for example dibenzylcyclooctyne (DBCO) or azide). In some aspects, the functional agent can comprise a small molecule. In some aspects, the functional agent can comprise a chelator (for example, DOTA, CHX-A"-DTPA, NOTA, among others). In some aspects, the functional agent can comprise a lipid. In some aspects, the functional agent can comprise a drug. In some aspects, the functional agent can comprise a combination of any of the above listed functional agents.

Accordingly, the disclosed conjugated immunoglobulins include: immunoglobulin-fluorophore Cys80 conjugates, immunoglobulin-fluorescent dye Cys80 conjugates, immunoglobulin-polypeptide Cys80 conjugates, immunoglobulin-immunoglobulin Cys80 conjugates, immunoglobulin-antibiotic Cys80 conjugates, immunoglobulin-nucleic acid Cys80 conjugates, immunoglobulin-radionuclide Cys80 conjugates, immunoglobulin-chemical linker Cys80 conjugates, immunoglobulin-small molecule Cys80 conjugates, immunoglobulin-chelator Cys80 conjugates, immunoglobulin-lipid Cys80 conjugates, and immunoglobulin-drug Cys80 conjugates.

Any of the immunoglobulins disclosed herein can be conjugated to any of the functional agents disclosed herein. For example, the conjugated immunoglobulin can comprise an immunoglobulin that immunospecifically binds to human CA9 and a fluorophore, fluorescent dye, polypeptide, immunoglobulin, antibiotic, nucleic acid, radionuclide, chemical linker, small molecule, chelator, lipid, or drug. In some embodiments, the conjugated immunoglobulin is a CA9-fluorophore Cys80 conjugate. In some embodiments, the conjugated immunoglobulin is a CA9-fluorescent dye Cys80 conjugate. In some embodiments, the conjugated immunoglobulin is a CA9-polypeptide Cys80 conjugate. In some embodiments, the conjugated immunoglobulin is a CA9-immunoglobulin Cys80 conjugate. In some embodiments, the conjugated immunoglobulin is a CA9-antibiotic Cys80 conjugate. In some embodiments, the conjugated immunoglobulin is a CA9-nucleic acid Cys80 conjugate. In some embodiments, the conjugated immunoglobulin is a CA9-radionuclide Cys80 conjugate. In some embodiments, the conjugated immunoglobulin is a CA9-chemical linker Cys80 conjugate. In some embodiments, the conjugated immunoglobulin is a CA9-small molecule Cys80 conjugate. In some embodiments, the conjugated immunoglobulin is a CA9-chelator Cys80 conjugate. In some embodiments, the conjugated immunoglobulin is a CA9-lipid Cys80 conjugate. In some embodiments, the conjugated immunoglobulin is a CA9-drug Cys80 conjugate.

Suitable immunoglobulins that immunospecifically bind to human CA9 that can be conjugated at Cys80 to any of the above functional agents include:

a. a heavy chain variable region having an amino acid sequence at least 90% identical to amino acids 20-141 of xi155D5HC (SEQ ID NO:52) and a light chain variable region having an amino acid sequence at least 90% identical to amino acids 20-130 of xi155D5LC (SEQ ID NO:78);

b. a heavy chain variable region having an amino acid sequence at least 90% identical to amino acids 20-144 of zu155D5HC (SEQ ID NO:54) and a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
c. a heavy chain variable region having an amino acid sequence at least 90% identical to amino acids 20-138 of xi1E4HC (SEQ ID NO:58) and a light chain variable region having an amino acid sequence at least 90% identical to amino acids 20-130 of xi1E4LC (SEQ ID NO:110);
d. a heavy chain variable region having an amino acid sequence at least 90% identical to amino acids 20-140 of zu1E4HC (SEQ ID NO:60) and a light chain variable region having an amino acid sequence at least 90% identical to amino acids 20-130 of zu1E4LC-CXXA (SEQ ID NO:114);
e. a heavy chain variable region having an amino acid sequence at least 90% identical to amino acids 20-142 of xi166B3HC (SEQ ID NO:74) and a light chain variable region having an amino acid sequence at least 90% identical to amino acids 20-130 of xi166B3LC (SEQ ID NO:132);
f. a heavy chain variable region having an amino acid sequence at least 90% identical to amino acids 20-145 of zu166B3HC (SEQ ID NO:76) and a light chain variable region having an amino acid sequence at least 90% identical to amino acids 20-130 of zu166B3LC-CXXA (SEQ ID NO:136);
g. a heavy chain variable region as set forth as amino acids 20-141 of xi155D5HC (SEQ ID NO:52) and a light chain variable region as set forth as amino acids 20-130 of xi155D5LC (SEQ ID NO:78);
h. a heavy chain variable region as set forth as amino acids 20-144 of zu155D5HC (SEQ ID NO:54) and a light chain variable region as set forth as amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
i. a heavy chain variable region as set forth as amino acids 20-138 of xi1E4HC (SEQ ID NO:58) and a light chain variable as set forth as amino acids 20-130 of xi1E4LC (SEQ ID NO:110);
j. a heavy chain variable region as set forth as amino acids 20-140 of zu1E4HC (SEQ ID NO:60) and a light chain variable region as set forth as amino acids 20-130 of zu1E4LC-CXXA (SEQ ID NO:114);
k. a heavy chain variable region as set forth as amino acids 20-142 of xi166B3HC (SEQ ID NO:74) and a light chain variable region as set forth as amino acids 20-130 of xi166B3LC (SEQ ID NO:132);
l. a heavy chain variable region as set forth as amino acids 20-145 of zu166B3HC (SEQ ID NO:76) and a light chain variable region as set forth as amino acids 20-130 of zu166B3LC-CXXA (SEQ ID NO:136);
m. a heavy chain CDR1, CDR2, and CDR3 of xi155D5HC as set forth as SEQ ID NO:146, 148, and 150, respectively, and a light chain CDR1, CDR2, and CDR3 of xi155D5LC as set forth as SEQ ID NO:224, 226, and 228, respectively;
n. a heavy chain CDR1, CDR2, and CDR3 of zu155D5HC as set forth as SEQ ID NO:152, 154, and 156, respectively, and a light chain CDR1, CDR2, and CDR3 of zu155D5LC-3 as set forth as SEQ ID NO:242, 244, and 246, respectively, zu155D5LC-4 as set forth as SEQ ID NO:248, 250, and 252, respectively, zu155D5LC-5 as set forth as SEQ ID NO:254, 256, and 258, respectively, zu155D5LC-6 as set forth as SEQ ID NO:260, 262, and 264, respectively, zu155D5LC-7 as set forth as SEQ ID NO:266, 268, and 270, respectively, zu155D5LC-huVK2-40 as set forth as SEQ ID NO 278, 280, and 282, respectively, zu155D5LC-huVK4-1 as set forth as SEQ ID NO 290, 292, and 294, respectively, zu155D5LC-huVK6-21 as set forth as SEQ ID NO 296, 298, and 300, respectively, zu155D5LC-huVK6D-41 as set forth as SEQ ID NO 302, 304, and 306, respectively; or zu155D5LC-huVK7-3-Glu81 as set forth as SEQ ID NO 308, 310, and 312, respectively;
o. a heavy chain CDR1, CDR2, and CDR3 of xi1E4HC as set forth as SEQ ID NO:164, 166, and 168, respectively, and a light chain CDR1, CDR2, and CDR3 of xi1E4LC as set forth as SEQ ID NO:320, 322, and 324, respectively;
p. a heavy chain CDR1, CDR2, and CDR3 of zu1E4HC as set forth as SEQ ID NO:170, 172, and 174, respectively, and a light chain CDR1, CDR2, and CDR3 of zu1E4LC-CXXA as set forth as SEQ ID NO:332, 334, and 336, respectively;
q. a heavy chain CDR1, CDR2, and CDR3 of xi166B3HC as set forth as SEQ ID NO:212, 214, and 216, respectively, and a light chain CDR1, CDR2, and CDR3 of xi166B3LC as set forth as SEQ ID NO:386, 388, and 390, respectively; or
r. a heavy chain CDR1, CDR2, and CDR3 of zu166B3HC as set forth as SEQ ID NO:218, 220, and 222, respectively, and a light chain CDR1, CDR2, and CDR3 of zu166B3LC-CXXA as set forth as SEQ ID NO:398, 400, and 402, respectively.

The conjugated immunoglobulin can comprise an immunoglobulin that immunospecifically binds to human TEM1 and a fluorophore, fluorescent dye, polypeptide, immunoglobulin, antibiotic, nucleic acid, radionuclide, chemical linker, small molecule, chelator, lipid, or drug. In some embodiments, the conjugated immunoglobulin is a TEM1-fluorophore Cys80 conjugate. In some embodiments, the conjugated immunoglobulin is a TEM1-fluorescent dye Cys80 conjugate. In some embodiments, the conjugated immunoglobulin is a TEM1-polypeptide Cys80 conjugate. In some embodiments, the conjugated immunoglobulin is a TEM1-immunoglobulin Cys80 conjugate. In some embodiments, the conjugated immunoglobulin is a TEM1-antibiotic Cys80 conjugate. In some embodiments, the conjugated immunoglobulin is a TEM1-nucleic acid Cys80 conjugate. In some embodiments, the conjugated immunoglobulin is a TEM1-radionuclide Cys80 conjugate. In some embodiments, the conjugated immunoglobulin is a TEM1-chemical linker Cys80 conjugate. In some embodiments, the conjugated immunoglobulin is a TEM1-small molecule Cys80 conjugate. In some embodiments, the conjugated immunoglobulin is a TEM1-chelator Cys80 conjugate. In some embodiments, the conjugated immunoglobulin is a TEM1-lipid Cys80 conjugate. In some embodiments, the conjugated immunoglobulin is a TEM1-drug Cys80 conjugate.

Suitable immunoglobulins that immunospecifically bind to human TEM1 that can be conjugated at Cys80 to any of the above functional agents include:
a. a heavy chain variable region having an amino acid sequence at least 90% identical to amino acids 20-139 of xi1-55-2HC (SEQ ID NO:56) and a light chain variable region having an amino acid sequence at least 90% identical to amino acids 20-129 of xi1-55-2LC (SEQ ID NO:108);
b. a heavy chain variable region as set forth as amino acids 20-139 of xi1-55-2HC (SEQ ID NO:56) and a light chain variable region as set forth as amino acids 20-129 of xi1-55-2LC (SEQ ID NO:108); or
c. a heavy chain CDR1, CDR2, and CDR3 of xi1-55-2HC as set forth as SEQ ID NO:158, 160, and 162, respectively, and a light chain CDR1, CDR2, and CDR3 of xi1-55-2LC as set forth as SEQ ID NO:314, 316, and 318, respectively.

The conjugated immunoglobulin can comprise an immunoglobulin that immunospecifically binds to human MSLN and a fluorophore, fluorescent dye, polypeptide, immunoglobulin, antibiotic, nucleic acid, radionuclide, chemical linker, small molecule, chelator, lipid, or drug. In some embodiments, the conjugated immunoglobulin is a MSLN-fluorophore Cys80 conjugate. In some embodiments, the conjugated immunoglobulin is a MSLN-fluorescent dye Cys80 conjugate. In some embodiments, the conjugated immunoglobulin is a MSLN-polypeptide Cys80 conjugate. In some embodiments, the conjugated immunoglobulin is a MSLN-immunoglobulin Cys80 conjugate. In some embodiments, the conjugated immunoglobulin is a MSLN-antibiotic Cys80 conjugate. In some embodiments, the conjugated immunoglobulin is a MSLN-nucleic acid Cys80 conjugate. In some embodiments, the conjugated immunoglobulin is a MSLN-radionuclide Cys80 conjugate. In some embodiments, the conjugated immunoglobulin is a MSLN-chemical linker Cys80 conjugate. In some embodiments, the conjugated immunoglobulin is a MSLN-small molecule Cys80 conjugate. In some embodiments, the conjugated immunoglobulin is a MSLN-chelator Cys80 conjugate. In some embodiments, the conjugated immunoglobulin is a MSLN-lipid Cys80 conjugate. In some embodiments, the conjugated immunoglobulin is a MSLN-drug Cys80 conjugate.

Suitable immunoglobulins that immunospecifically bind to human MSLN that can be conjugated at Cys80 to any of the above functional agents include:
a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);
b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);
c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);
d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);
e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128);
f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130);
g. a heavy chain variable region as set forth as amino acids 20-142 of xi33O11HC (SEQ ID NO:62) and a light chain variable region as set forth as amino acids 20-131 of xi33O11LC (SEQ ID NO:116);
h. a heavy chain variable region as set forth as amino acids 20-145 of zu33O11HC (SEQ ID NO:64) and a light chain variable region as set forth as amino acids 20-131 of zu33O11LC-CXXA (SEQ ID NO:120) or zu33O11LC-CXXI (SEQ ID NO:122);
i. a heavy chain variable region as set forth as amino acids 20-137 of xi324O5HC (SEQ ID NO:66) and a light chain variable region as set forth as amino acids 20-127 of xi324O5LC (SEQ ID NO:124);
j. a heavy chain variable region as set forth as amino acids 20-137 of xi178F16HC (SEQ ID NO:68) and a light chain variable region as set forth as amino acids 20-127 of xi178F16LC (SEQ ID NO:126);
k. a heavy chain variable region as set forth as amino acids 20-132 of xi237N18HC (SEQ ID NO:70) and a light chain variable region as set forth as amino acids 20-127 of xi237N18LC (SEQ ID NO:128);
l. a heavy chain variable region as set forth as amino acids 20-137 of xi383I18HC (SEQ ID NO:72) and a light chain variable region as set forth as amino acids 20-127 of xi383I18LC (SEQ ID NO:130);
m. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth in SEQ ID NO:338, 340, and 342, respectively;
n. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively or zu33O11LC-CXXI as set forth as SEQ ID NO:356, 358, and 360, respectively;
o. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
p. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
q. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
r. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

In some embodiments, the immunoglobulin that immunospecifically binds to human MSLN can be conjugated to a small molecule antineoplastic agent such as an auristatin. In some aspects, the functional agent can be auristatin F (AuF). Thus, the disclosed conjugated immunoglobulins include any of the above disclosed immunoglobulins that immunospecifically bind to human MSLN, wherein the immunoglobulin is conjugated to auristatin F (MSLN-AuF Cys80 conjugate).

In embodiments wherein the immunoglobulin comprises two light chain variable regions, the conjugated immunoglobulin can have an immunoglobulin:functional agent ratio of 2:1, with each light chain having a functional agent conjugated at Cys80.

Antigen-Binding Molecules

Further provided herein are antigen-binding molecules comprising:
a first conjugated immunoglobulin comprising a first heavy chain variable region and a first light chain variable region, the first light chain variable region having a cysteine at position 80 ("Cys80$^1$"), wherein Cys80$^1$ is conjugated to a first thiol-reactive compound comprising a first thiol-reactive group, and
a second conjugated immunoglobulin comprising a second heavy chain variable region and a second light chain variable region, the second light chain variable region having a cysteine at position 80 ("Cys80$^2$") wherein Cys80$^2$ is conjugated to a second thiol-reactive compound comprising a second thiol-reactive group.

The first conjugated immunoglobulin and second conjugated immunoglobulin can be any one of the conjugated immunoglobulins disclosed herein.

Suitable light chain variable regions include, for example, a kappa light chain variable region. The first light chain variable region and the second light chain variable region are derived from rabbit. In some embodiments, the Cys80$^1$, Cys80$^2$, or both, can be present in the native light chain variable region of the rabbit immunoglobulin. Exemplary rabbits from which a first light chain variable region, second light chain variable region, or both, can be derived from include, but are not limited to, *Oryctolagus cuniculus*. In some aspects, for example, the light chain variable region(s) can be derived from a New Zealand White (NZW) rabbit. In other aspects, the light chain variable region(s) can be derived from a b9 rabbit.

The Cys80$^1$, the Cys80$^2$, or both, can be unpaired. Suitable means for unpairing Cys80$^1$ and/or Cys80$^2$ include, for example, chimerizing a light chain variable region (a first light chain variable region, a second light chain variable region, or both) having a Cys80 with a constant domain having an amino acid residue other than cysteine at position 171.

The first immunoglobulin, the second immunoglobulin, or both, can be chimerized. In some embodiments, the first immunoglobulin can be chimerized. In some embodiments, the second immunoglobulin can be chimerized. In some embodiments, the first immunoglobulin and the second immunoglobulin can be chimerized.

The first immunoglobulin, the second immunoglobulin, or both, can be humanized. In some embodiments, the first immunoglobulin can be humanized. In some embodiments, the second immunoglobulin can be humanized. In some embodiments, the first immunoglobulin and the second immunoglobulin can be humanized.

In some embodiments, the first immunoglobulin can be chimerized and the second immunoglobulin can be humanized. In some embodiments, the first immunoglobulin can be humanized and the second immunoglobulin can be chimerized.

The amino acid at position 83 of the first light chain variable region can be an amino acid other than Phe, Lys, or Cys if the amino acid at position 83 is Phe. The amino acid at position 83 of the second light chain variable region can be an amino acid other than Phe, Lys, or Cys if the amino acid at position 83 is Phe. The amino acid at position 83 of the first light chain variable region can be an amino acid other than Phe, Lys, or Cys if the amino acid at position 83 is Phe and the amino acid at position 83 of the second light chain variable region can be an amino acid other than Phe, Lys, or Cys if the amino acid at position 83 is Phe. The amino acid at position 83 of the first light chain variable region and/or second light chain variable region can be alanine ("Ala83"), valine ("Val83"), isoleucine ("Ile83"), threonine ("Thr83"), arginine ("Arg83"), asparagine ("Asn83"), aspartic acid ("Asp83"), glutamic acid ("Glu83"), glutamine ("Gln83"), glycine ("Gly83"), histidine ("His83"), leucine ("Leu83"), methionine ("Met83"), proline ("Pro83"), serine ("Ser83"), tryptophan ("Trp83"), or tyrosine ("Tyr83"). The amino acid at position 83 of the first light chain variable region can be the same as the amino acid at position 83 of the second light chain variable region. Conversely, the amino acid at position 83 of the first light chain variable region can be different from the amino acid at position 83 of the second light chain variable region.

In some embodiments, the amino acid at position 83 of the first light chain variable region can be a polar or hydrophobic residue other than Phe if the amino acid at position 83 is Phe. In some embodiments, the amino acid at position 83 of the second light chain variable region can be a polar or hydrophobic residue other than Phe if the amino acid at position 83 is Phe. In some embodiments, the amino acid at position 83 of the first light chain variable region can be a polar or hydrophobic residue other than Phe if the amino acid at position 83 is Phe and the amino acid at position 83 of the second light chain variable region can be a polar or hydrophobic residue other than Phe if the amino acid at position 83 is Phe. Suitable polar or hydrophobic amino acids include, but are not limited to alanine, valine, isoleucine, or threonine. In some aspects, the amino acid at position 83 of the first light chain variable region, the amino acid at position 83 of the second light chain variable region, or the amino acid at position 83 of the first light chain variable region and the amino acid at position 83 of the second light chain variable region can be alanine ("Ala83"). In some aspects, the amino acid at position 83 of the first light chain variable region, the amino acid at position 83 of the second light chain variable region, or the amino acid at position 83 of the first light chain variable region and the amino acid at position 83 of the second light chain variable region can be valine ("Val83"). In some aspects, the amino acid at position 83 of the first light chain variable region, the amino acid at position 83 of the second light chain variable region, or the amino acid at position 83 of the first light chain variable region and the amino acid at position 83 of the second light chain variable region can be isoleucine ("Ile83"). In some aspects, the amino acid at position 83 of the first light chain variable region, the amino acid at position 83 of the second light chain variable region, or the amino acid at position 83 of the first light chain variable region and the amino acid at position 83 of the second light chain variable region can be Threonine ("Thr83"). The polar or hydrophobic amino acid at position 83 in the first light chain variable region can be the same as, or different from, the polar or hydrophobic amino acid at position 83 in the second light chain variable region.

The first immunoglobulin and the second immunoglobulin can bind to the same antigens. In some aspects, the first immunoglobulin and the second immunoglobulin can bind to the same epitope of the same antigen. In other aspects, the first immunoglobulin and the second immunoglobulin can bind to different epitopes of the same antigen. In some embodiments, for example, the first immunoglobulin and the second immunoglobulin can be an immunoglobulin that immunospecifically binds to human CA9, wherein the first immunoglobulin, second immunoglobulin, or both are conjugated to any one of a fluorophore, fluorescent dye, polypeptide, immunoglobulin, antibiotic, nucleic acid, radionuclide, chemical linker, small molecule, chelator, lipid, or drug. In some embodiments, the first immunoglobulin and the second immunoglobulin can be an immunoglobulin that immunospecifically binds to human TEM1, wherein the first immunoglobulin, second immunoglobulin, or both are conjugated to any one of a fluorophore, fluorescent dye, polypeptide, immunoglobulin, antibiotic, nucleic acid, radionuclide, chemical linker, small molecule, chelator, lipid, or drug. In some embodiments, the first immunoglobulin and the second immunoglobulin can be an immunoglobulin that immunospecifically binds to human MSLN, wherein the first immunoglobulin, second immunoglobulin, or both are conjugated to any one of a fluorophore, fluorescent dye, polypeptide, immunoglobulin, antibiotic, nucleic acid, radionuclide, chemical linker, small molecule, chelator, lipid, or drug.

The first immunoglobulin and the second immunoglobulin can bind to different antigens. In some embodiments, for example, the first conjugated immunoglobulin can be an immunoglobulin that immunospecifically binds to human CA9, wherein the first immunoglobulin that binds to human CA9 is conjugated to any one of a fluorophore, fluorescent dye, polypeptide, immunoglobulin, antibiotic, nucleic acid, radionuclide, chemical linker, small molecule, chelator, lipid, or drug, whereas the second immunoglobulin can be an immunoglobulin that immunospecifically binds to human TEM1 or human MSLN. In such embodiments, the second immunoglobulin can be conjugated to any one of a fluorophore, fluorescent dye, polypeptide, immunoglobulin, antibiotic, nucleic acid, radionuclide, chemical linker, small molecule, chelator, lipid, or drug. In some embodiments, the first conjugated immunoglobulin can be an immunoglobulin that immunospecifically binds to human TEM1, wherein the immunoglobulin is conjugated to any one of a fluorophore, fluorescent dye, polypeptide, immunoglobulin, antibiotic, nucleic acid, radionuclide, chemical linker, small molecule, chelator, lipid, or drug, whereas the second immunoglobulin can be an immunoglobulin that immunospecifically binds to human CA9 or human MSLN. In such embodiments, the second immunoglobulin can be conjugated to any one of a fluorophore, fluorescent dye, polypeptide, immunoglobulin, antibiotic, nucleic acid, radionuclide, chemical linker, small molecule, chelator, lipid, or drug. In some embodiments, the first conjugated immunoglobulin can be an immunoglobulin that immunospecifically binds to human MSLN, wherein the immunoglobulin is conjugated to any one of a fluorophore, fluorescent dye, polypeptide, immunoglobulin, antibiotic, nucleic acid, radionuclide, chemical linker, small molecule, chelator, lipid, or drug, whereas the second immunoglobulin can be an immunoglobulin that immunospecifically binds to human CA9 or human TEM1. In such embodiments, the second immunoglobulin can be conjugated to any one of a fluorophore, fluorescent dye, polypeptide, immunoglobulin, antibiotic, nucleic acid, radionuclide, chemical linker, small molecule, chelator, lipid, or drug.

Suitable, thiol-reactive groups include haloacetyls, maleimides, aziridines, acryloyls, arylating agents, vinylsulfones, pyridyl disulfides, TNB-thiols and disulfide reducing agents. In some embodiments, the first thiol-reactive group, the second-thiol reactive group, or both, can comprise a maleimide. In some embodiments, the first thiol-reactive group, the second-thiol reactive group, or both, can comprise a haloacetyl. In some embodiments, the first thiol-reactive group, the second-thiol reactive group, or both, can comprise an aziridine. In some embodiments, the first thiol-reactive group, the second-thiol reactive group, or both, can comprise an acryloyl. In some embodiments, the first thiol-reactive group, the second-thiol reactive group, or both, can comprise an arylating agent. In some embodiments, the first thiol-reactive group, the second-thiol reactive group, or both, can comprise a vinylsulfone. In some embodiments, the first thiol-reactive group, the second-thiol reactive group, or both, can comprise a pyridyl disulfide. In some embodiments, the first thiol-reactive group, the second-thiol reactive group, or both, can comprise a TNB-thiol. In some embodiments, the first thiol-reactive group, the second-thiol reactive group, or both, can comprise a disulfide reducing agent.

The first thiol-reactive group, the second-thiol reactive group, or both can be appended to a linker. In some aspects, the first thiol-reactive group can be appended to a linker ("first linker"). In some aspects, the second thiol-reactive group can be appended to a linker ("second linker"). In yet other aspects the first thiol-reactive group can be appended to a first linker and the second thiol-reactive group can be appended to a second linker. Suitable first and second linkers can be non-cleavable linkers or cleavable linkers. Exemplary first and second linkers include, for example, disulfide containing linkers, acetal-based linkers, and ketal-based linkers. In some aspects, the first linker, second linker, or both, can be a non-cleavable linker. Suitable non-cleavable linkers include, but are not limited to, polyethylene glycol (PEG) or an alkyl. In some embodiments, the first linker, second linker, or both, can comprise PEG. In some aspects, the first linker, second linker, or both, can be a cleavable linker. Suitable cleavable linkers include, for example, valine-citrulline-para aminobenzyl. In some aspects, the first linker, second linker, or both, can be a disulfide containing linker. In some aspects, the first linker, second linker, or both can be an acetal-based linker. In some aspects, the first linker, second linker, or both, can be a ketal-based linker. Examples of linkers covalently appended to a thiol-reactive group are provided, for example, in U.S. Publ. No. 20140050746.

The first thiol-reactive compound, the second thiol-reactive compound, or both, can further comprise a functional agent. In some aspects, the first thiol-reactive compound can further comprise a functional agent ("first functional agent"). In some aspects, the second thiol-reactive compound can further comprise a functional agent ("second functional agent"). In yet other aspects, the first thiol-reactive compound can further comprise a first functional agent and the second thiol-reactive compound can further comprise a second functional agent.

Suitable functional agents include, for example, chemical linkers. Preferably, the chemical linker of the first thiol-reactive compound ("first chemical linker") and the chemical linker of the second thiol-reactive compound ("second chemical linker") can be coupled. For example, and without intent to be limiting, one of the first or second chemical linkers can be dibenzylcyclooctyne (DBCO) and the other of the first or second chemical linkers can be azide. In some embodiments, for example, the first chemical linker can be DBCO and the second chemical linker can be azide. Conversely, the first chemical linker can be azide and the second chemical linker can be DBCO. The DBCO and azide can be coupled, thus resulting in the conjugation of the first immunoglobulin and the second immunoglobulin. For example, the first immunoglobulin and the second immunoglobulin can be conjugated to each other by click chemistry.

In an exemplary embodiment, thiol-reactive compounds can include maleimido-PEG4-azide and maleimido-PEG4-dibenzocyclooctyne. In some aspects, for example, the first thiol-reactive compound can be maleimido-PEG4-azide and the second thiol-reactive compound can be maleimido-PEG4-dibenzocyclooctyne. In some aspects, the first thiol-reactive compound can be maleimido-PEG4-dibenzocyclooctyne and the second thiol-reactive compound can be maleimido-PEG4-azide. Thus, the first thiol-reactive compound can differ from the second thiol-reactive compound.

The first immunoglobulin, second immunoglobulin, or both, can be Fabs. In some embodiments, the first immunoglobulin can be a Fab ("first Fab"). In some embodiments, the second immunoglobulin can be a Fab ("second Fab"). In yet other embodiments, the first immunoglobulin can be a first Fab and the second immunoglobulin can be a second Fab.

Methods of Treating Cancer in a Subject

Also disclosed herein are methods of treating cancer in a subject comprising administering to the subject a pharmaceutically effective amount of a conjugated mesothelin immunoglobulin, wherein the conjugated mesothelin immunoglobulin comprises:
  any of the conjugated mesothelin immunoglobulins disclosed herein, and a thiol-reactive compound comprising a thiol-reactive group, a linker, and a functional agent.

It is to be understood that any of the characteristics, features, and embodiments relating to the disclosed conjugated immunoglobulins are equally applicable to those conjugated immunoglobulins used in the disclosed methods of treating cancer. Accordingly, the disclosed methods can comprise administering to the subject a pharmaceutically effective amount of a conjugated mesothelin immunoglobulin, wherein the conjugated mesothelin immunoglobulin comprises a heavy chain variable region and a light chain variable region, the light chain variable region having a cysteine at position 80 ("Cys80") and an amino acid other than Phe, Lys, or Cys at position 83, wherein the Cys80 is conjugated to a thiol-reactive compound, the thiol-reactive compound comprising a thiol-reactive group, a linker, and a functional agent. In some embodiments, the amino acid other than Phe, Lys, or Cys at position 83 is a polar or hydrophobic amino acid.

Preferably, the cancer is a mesothelin-expressing cancer. In some embodiments, the conjugated antibodies for use in the disclosed methods can comprise:
  a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);
  b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);
  c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);
  d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);
  e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128); or
  f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130).

Antibodies (a)-(f) can be conjugated to a number of suitable thiol-reactive compounds including, but not limited to, those having an antineoplastic agent, such as an auristatin, as the functional agent. Thus, in some embodiments, the methods can comprise administering to the subject a pharmaceutically effective amount of a conjugated immunoglobulin, wherein the conjugated immunoglobulin comprises one or more of immunogloublins (a)-(f), each being conjugated to a thiol-reactive compound comprising auristatin F, wherein the thiol-reactive compound is conjugated to the light chain variable region of the immunoglobulin at the Cys80.

In some embodiments, the conjugated antibodies for use in the disclosed methods can comprise:
  a. a heavy chain variable region as set forth as amino acids 20-142 of xi33O11HC (SEQ ID NO:62) and a light chain variable region as set forth as amino acids 20-131 of xi33O11LC (SEQ ID NO:116);
  b. a heavy chain variable region as set forth as amino acids 20-145 of zu33O11HC (SEQ ID NO:64) and a light chain variable region as set forth as amino acids 20-131 of zu33O11LC-CXXA (SEQ ID NO:120) or zu33O11LC-CXXI (SEQ ID NO:122);
  c. a heavy chain variable region as set forth as amino acids 20-137 of xi324O5HC (SEQ ID NO:66) and a light chain variable region as set forth as amino acids 20-127 of xi324O5LC (SEQ ID NO:124);
  d. a heavy chain variable region as set forth as amino acids 20-137 of xi178F16HC (SEQ ID NO:68) and a light chain variable region as set forth as amino acids 20-127 of xi178F16LC (SEQ ID NO:126);
  e. a heavy chain variable region as set forth as amino acids 20-132 of xi237N18HC (SEQ ID NO:70) and a light chain variable region as set forth as amino acids 20-127 of xi237N18LC (SEQ ID NO:128); or
  f. a heavy chain variable region as set forth as amino acids 20-137 of xi383I18HC (SEQ ID NO:72) and a light chain variable region as set forth as amino acids 20-127 of xi383I18LC (SEQ ID NO:130).

Antibodies (a)-(f) can be conjugated to a number of suitable thiol-reactive compounds including, but not limited to, those having an antineoplastic agent, such as an auristatin, as the functional agent. Thus, in some embodiments, the methods can comprise administering to the subject a pharmaceutically effective amount of a conjugated immunoglobulin, wherein the conjugated immunoglobulin comprises one or more of immunogloublins (a)-(f), each being conjugated to a thiol-reactive compound comprising auristatin F, wherein the thiol-reactive compound is conjugated to the light chain variable region of the immunoglobulin at the Cys80.

In some embodiments, the conjugated antibodies for use in the disclosed methods can comprise:
- a. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth in SEQ ID NO:338, 340, and 342, respectively;
- b. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively or zu33O11LC-CXXI as set forth as SEQ ID NO:356, 358, and 360, respectively;
- c. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
- d. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
- e. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
- f. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

Antibodies (a)-(f) can be conjugated to a number of suitable thiol-reactive compounds including, but not limited to, those having an antineoplastic agent, such as an auristatin, as the functional agent. Thus, in some embodiments, the methods can comprise administering to the subject a pharmaceutically effective amount of a conjugated immunoglobulin, wherein the conjugated immunoglobulin comprises one or more of immunogloublins (a)-(f), each being conjugated to a thiol-reactive compound comprising auristatin F, wherein the thiol-reactive compound is conjugated to the light chain variable region of the immunoglobulin at the Cys80.

Methods for Detecting Cancer

Also disclosed herein are methods of detecting cancer in a subject. In some embodiments, the methods can be performed on the subject. For example, the methods can comprise administering to the subject a pharmaceutically effective amount of a conjugated immunoglobulin, wherein the conjugated immunoglobulin comprises a heavy chain variable region and a light chain variable region, the light chain variable region having a cysteine at position 80 ("Cys80") and an amino acid other than Phe, Lys, or Cys at position 83, wherein the Cys80 is conjugated to a thiol-reactive compound, the thiol-reactive compound comprising a thiol-reactive group, a linker, and a functional agent. In some embodiments, the amino acid other than Phe, Lys, or Cys at position 83 is a polar or hydrophobic.

Alternatively, the methods can be performed on a biological sample obtained from the subject. For example, the methods can comprise contacting a biological sample with a conjugated immunoglobulin, wherein the conjugated immunoglobulin comprises a heavy chain variable region and a light chain variable region, the light chain variable region having a cysteine at position 80 ("Cys80") and an amino acid other than Phe, Lys, or Cys at position 83, wherein the Cys80 is conjugated to a thiol-reactive compound, the thiol-reactive compound comprising a thiol-reactive group, a linker, and a functional agent. The amino acid other than Phe, Lys, or Cys at position 83 is a polar or hydrophobic. In some embodiments, the methods can be performed ex vivo. In some embodiments, the methods can be performed in vivo.

The functional agent is a fluorophore or fluorescent dye.

Any of the immunoglobulins disclosed herein can be conjugated to a fluorophore or fluorescent dye and used in the disclosed methods of detecting cancer. In some embodiments, the cancer is a CA9-expressing cancer and the conjugated immunoglobulin is a CA9-fluorophore Cys80 conjugate or a CA9-fluorescent dye Cys80 conjugate comprising:
- a. a heavy chain variable region having an amino acid sequence at least 90% identical to amino acids 20-141 of xi155D5HC (SEQ ID NO:52) and a light chain variable region having an amino acid sequence at least 90% identical to amino acids 20-130 of xi155D5LC (SEQ ID NO:78);
- b. a heavy chain variable region having an amino acid sequence at least 90% identical to amino acids 20-144 of zu155D5HC (SEQ ID NO:54) and a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
- c. a heavy chain variable region having an amino acid sequence at least 90% identical to amino acids 20-138 of xi1E4HC (SEQ ID NO:58) and a light chain variable region having an amino acid sequence at least 90% identical to amino acids 20-130 of xi1E4LC (SEQ ID NO:110);
- d. a heavy chain variable region having an amino acid sequence at least 90% identical to amino acids 20-140 of zu1E4HC (SEQ ID NO:60) and a light chain variable region having an amino acid sequence at least 90% identical to amino acids 20-130 of zu1E4LC-CXXA (SEQ ID NO:114);
- e. a heavy chain variable region having an amino acid sequence at least 90% identical to amino acids 20-142 of xi166B3HC (SEQ ID NO:74) and a light chain variable region having an amino acid sequence at least 90% identical to amino acids 20-130 of xi166B3LC (SEQ ID NO:132);

f. a heavy chain variable region having an amino acid sequence at least 90% identical to amino acids 20-145 of zu166B3HC (SEQ ID NO:76) and a light chain variable region having an amino acid sequence at least 90% identical to amino acids 20-130 of zu166B3LC-CXXA (SEQ ID NO:136);
g. a heavy chain variable region as set forth as amino acids 20-141 of xi155D5HC (SEQ ID NO:52) and a light chain variable region as set forth as amino acids 20-130 of xi155D5LC (SEQ ID NO:78);
h. a heavy chain variable region as set forth as amino acids 20-144 of zu155D5HC (SEQ ID NO:54) and a light chain variable region as set forth as amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
i. a heavy chain variable region as set forth as amino acids 20-138 of xi1E4HC (SEQ ID NO:58) and a light chain variable as set forth as amino acids 20-130 of xi1E4LC (SEQ ID NO:110);
j. a heavy chain variable region as set forth as amino acids 20-140 of zu1E4HC (SEQ ID NO:60) and a light chain variable region as set forth as amino acids 20-130 of zu1E4LC-CXXA (SEQ ID NO:114);
k. a heavy chain variable region as set forth as amino acids 20-142 of xi166B3HC (SEQ ID NO:74) and a light chain variable region as set forth as amino acids 20-130 of xi166B3LC (SEQ ID NO:132);
l. a heavy chain variable region as set forth as amino acids 20-145 of zu166B3HC (SEQ ID NO:76) and a light chain variable region as set forth as amino acids 20-130 of zu166B3LC-CXXA (SEQ ID NO:136);
m. a heavy chain CDR1, CDR2, and CDR3 of xi155D5HC as set forth as SEQ ID NO:146, 148, and 150, respectively, and a light chain CDR1, CDR2, and CDR3 of xi155D5LC as set forth as SEQ ID NO:224, 226, and 228, respectively;
n. a heavy chain CDR1, CDR2, and CDR3 of zu155D5HC as set forth as SEQ ID NO:152, 154, and 156, respectively, and a light chain CDR1, CDR2, and CDR3 of zu155D5LC-3 as set forth as SEQ ID NO:242, 244, and 246, respectively, zu155D5LC-4 as set forth as SEQ ID NO:248, 250, and 252, respectively, zu155D5LC-5 as set forth as SEQ ID NO:254, 256, and 258, respectively, zu155D5LC-6 as set forth as SEQ ID NO:260, 262, and 264, respectively, zu155D5LC-7 as set forth as SEQ ID NO:266, 268, and 270, respectively, zu155D5LC-huVK2-40 as set forth as SEQ ID NO 278, 280, and 282, respectively, zu155D5LC-huVK4-1 as set forth as SEQ ID NO 290, 292, and 294, respectively, zu155D5LC-huVK6-21 as set forth as SEQ ID NO 296, 298, and 300, respectively, zu155D5LC-huVK6D-41 as set forth as SEQ ID NO 302, 304, and 306, respectively; or zu155D5LC-huVK7-3-Glu81 as set forth as SEQ ID NO 308, 310, and 312, respectively;
o. a heavy chain CDR1, CDR2, and CDR3 of xi1E4HC as set forth as SEQ ID NO:164, 166, and 168, respectively, and a light chain CDR1, CDR2, and CDR3 of xi1E4LC as set forth as SEQ ID NO:320, 322, and 324, respectively;
p. a heavy chain CDR1, CDR2, and CDR3 of zu1E4HC as set forth as SEQ ID NO:170, 172, and 174, respectively, and a light chain CDR1, CDR2, and CDR3 of zu1E4LC-CXXA as set forth as SEQ ID NO:332, 334, and 336, respectively;
q. a heavy chain CDR1, CDR2, and CDR3 of xi166B3HC as set forth as SEQ ID NO:212, 214, and 216, respectively, and a light chain CDR1, CDR2, and CDR3 of xi166B3LC as set forth as SEQ ID NO:386, 388, and 390, respectively; or
r. a heavy chain CDR1, CDR2, and CDR3 of zu166B3HC as set forth as SEQ ID NO:218, 220, and 222, respectively, and a light chain CDR1, CDR2, and CDR3 of zu166B3LC-CXXA as set forth as SEQ ID NO:398, 400, and 402, respectively.

In some embodiments, the cancer is a TEM1-expressing cancer and the conjugated immunoglobulin is a TEM1-fluorophore Cys80 conjugate or a TEM1-fluorescent dye Cys80 conjugate comprising:
a. a heavy chain variable region having an amino acid sequence at least 90% identical to amino acids 20-139 of xi1-55-2HC (SEQ ID NO:56) and a light chain variable region having an amino acid sequence at least 90% identical to amino acids 20-129 of xi1-55-2LC (SEQ ID NO:108);
b. a heavy chain variable region as set forth as amino acids 20-139 of xi1-55-2HC (SEQ ID NO:56) and a light chain variable region as set forth as amino acids 20-129 of xi1-55-2LC (SEQ ID NO:108); or
c. a heavy chain CDR1, CDR2, and CDR3 of xi1-55-2HC as set forth as SEQ ID NO:158, 160, and 162, respectively, and a light chain CDR1, CDR2, and CDR3 of xi1-55-2LC as set forth as SEQ ID NO:314, 316, and 318, respectively.

In some embodiments, the cancer is a MSLN-expressing cancer and the conjugated immunoglobulin is a MSLN-fluorophore Cys80 conjugate or a MSLN-fluorescent dye Cys80 conjugate comprising:
a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);
b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);
c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);
d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);
e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128);
f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130);
g. a heavy chain variable region as set forth as amino acids 20-142 of xi33O11HC (SEQ ID NO:62) and a light chain variable region as set forth as amino acids 20-131 of xi33O11LC (SEQ ID NO:116);
h. a heavy chain variable region as set forth as amino acids 20-145 of zu33O11HC (SEQ ID NO:64) and a light chain variable region as set forth as amino acids 20-131 of zu33O11LC-CXXA (SEQ ID NO:120) or zu33O11LC-CXXI (SEQ ID NO:122);
i. a heavy chain variable region as set forth as amino acids 20-137 of xi324O5HC (SEQ ID NO:66) and a light chain variable region as set forth as amino acids 20-127 of xi324O5LC (SEQ ID NO:124);
j. a heavy chain variable region as set forth as amino acids 20-137 of xi178F16HC (SEQ ID NO:68) and a light chain variable region as set forth as amino acids 20-127 of xi178F16LC (SEQ ID NO:126);
k. a heavy chain variable region as set forth as amino acids 20-132 of xi237N18HC (SEQ ID NO:70) and a light chain variable region as set forth as amino acids 20-127 of xi237N18LC (SEQ ID NO:128);
l. a heavy chain variable region as set forth as amino acids 20-137 of xi383I18HC (SEQ ID NO:72) and a light chain variable region as set forth as amino acids 20-127 of xi383I18LC (SEQ ID NO:130);
m. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth in SEQ ID NO:338, 340, and 342, respectively;
n. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively or zu33O11LC-CXXI as set forth as SEQ ID NO:356, 358, and 360, respectively;
o. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
p. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
q. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
r. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

Exemplary fluorophores for conjugation to the immunoglobulin include, for example, IRDye-800CW.

The methods can comprise administering the conjugated immunoglobulin to the subject or contacting the biological sample with the conjugated immunoglobulin and detecting binding of the conjugated immunoglobulin to an antigen (CA9, TEM1, or MSLN) present in the subject or in the biological sample, respectively. Suitable methods of detection include, for example, fluorescent imaging. Detection of binding of the conjugated immunoglobulin to the antigen (through the emission of a fluorescent signal, for example) is indicative of cancer.

Pharmaceutical Compositions

Also provided herein are pharmaceutical compositions. In some embodiments, the pharmaceutical compositions can comprise any of the immunoglobulins disclosed herein. In some embodiments, the pharmaceutical compositions can comprise any of the conjugated immunoglobulins disclosed herein.

Administration of a conjugated immunoglobulin in accordance with the methods of treatment or diagnosis described herein may be by any means known in the art.

Light Chains Variable Regions for Use in Conjugated Immunoglobulins

Provided herein are light chain variable regions for use in a conjugated immunoglobulin, the light chain variable region having a cysteine at amino acid position 80 ("Cys80") and an amino acid residue other than Phe, Lys, or Cys at amino acid position 83, wherein the Cys80 is unpaired. In some embodiments, the amino acid other than Phe, Lys, or Cys at position 83 is a polar or hydrophobic.

In preferred embodiments, the light chain has a Cys80-$Xaa_1$-$Xaa_2$-$Xaa_3$ motif, wherein $Xaa_3$ is an amino acid other than Phe, Lys, or Cys.

Suitable light chain variable regions include, for example, a kappa light chain variable region. The light chain variable region is derived from rabbit. In some embodiments, the Cys80 can be present in the native light chain variable region of the rabbit immunoglobulin. Exemplary rabbits from which a light chain variable region having a Cys80 can be derived include, but is not limited to, *Oryctolagus cuniculus*. In some aspects, for example, the light chain variable region can be derived from a New Zealand White (NZW) rabbit. In other aspects, the light chain variable region can be derived from a b9 rabbit.

The Cys80 can be uncapped, can be involved in an intramolecular or intermolecular disulfide bond, or can have a capping cysteine.

In some embodiments, the light chain variable region can be chimerized. In other embodiments, the light chain variable region can be humanized.

The light chain variable region can comprise, consist of, or consist essentially of:
a. a light chain variable region having an amino acid sequence at least 90% identical to amino acids 20-130 of xi155D5LC (SEQ ID NO:78);
b. a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);

c. a light chain variable region having an amino acid sequence at least 90% identical to amino acids 20-130 of xi1E4LC (SEQ ID NO:110);
d. a light chain variable region having an amino acid sequence at least 90% identical to amino acids 20-130 of zu1E4LC-CXXA (SEQ ID NO:114);
e. a light chain variable region having an amino acid sequence at least 90% identical to amino acids 20-130 of xi166B3LC (SEQ ID NO:132);
f. a light chain variable region having an amino acid sequence at least 90% identical to amino acids 20-130 of zu166B3LC-CXXA (SEQ ID NO:136);
g. a light chain variable region having an amino acid sequence at least 90% identical to amino acids 20-129 of xi1-55-2LC (SEQ ID NO:108);
h. a light chain variable region having an amino acid sequence at least 90% identical to amino acids 20-131 of xi33O11LC (SEQ ID NO:116);
i. a light chain variable region having an amino acid sequence at least 90% identical to amino acids 20-131 of zu33O11LC-CXXA (SEQ ID NO:120) or zu33O11LC-CXXI (SEQ ID NO:122);
j. a light chain variable region having an amino acid sequence at least 90% identical to amino acids 20-127 of xi324O5LC (SEQ ID NO:124);
k. a light chain variable region having an amino acid sequence at least 90% identical to amino acids 20-127 of xi178F16LC (SEQ ID NO:126);
l. a light chain variable region having an amino acid sequence at least 90% identical to amino acids 20-127 of xi237N18LC (SEQ ID NO:128); or
m. a light chain variable region having an amino acid sequence at least 90% identical to amino acids 20-127 of xi383I18LC (SEQ ID NO:130).

Nucleic Acid Molecules Encoding Immunoglobulins and Host Cells Comprising the Same Also provided herein are nucleic acid molecules encoding any of the above disclosed immunoglobulins. In some embodiments, the nucleic acid molecules encode an immunoglobulin comprising a heavy chain variable region and a light chain variable region, the light chain variable region having a cysteine at position 80 ("Cys80") and an amino acid other than Phe, Lys, or Cys at position 83. In some embodiments, the amino acid other than Phe, Lys, or Cys at position 83 is polar or hydrophobic.

The disclosed nucleic acid molecules can encode an immunoglobulin that can immunospecifically bind to human CA9. In some embodiments, the nucleic acid molecule encodes:
a. a heavy chain variable region having an amino acid sequence at least 90% identical to amino acids 20-141 of xi155D5HC (SEQ ID NO:52) and a light chain variable region having an amino acid sequence at least 90% identical to amino acids 20-130 of xi155D5LC (SEQ ID NO:78);
b. a heavy chain variable region having an amino acid sequence at least 90% identical to amino acids 20-144 of zu155D5HC (SEQ ID NO:54) and a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
c. a heavy chain variable region having an amino acid sequence at least 90% identical to amino acids 20-138 of xi1E4HC (SEQ ID NO:58) and a light chain variable region having an amino acid sequence at least 90% identical to amino acids 20-130 of xi1E4LC (SEQ ID NO:110);
d. a heavy chain variable region having an amino acid sequence at least 90% identical to amino acids 20-140 of zu1E4HC (SEQ ID NO:60) and a light chain variable region having an amino acid sequence at least 90% identical to amino acids 20-130 of zu1E4LC-CXXA (SEQ ID NO:114);
e. a heavy chain variable region having an amino acid sequence at least 90% identical to amino acids 20-142 of xi166B3HC (SEQ ID NO:74) and a light chain variable region having an amino acid sequence at least 90% identical to amino acids 20-130 of xi166B3LC (SEQ ID NO:132); or
f. a heavy chain variable region having an amino acid sequence at least 90% identical to amino acids 20-145 of zu166B3HC (SEQ ID NO:76) and a light chain variable region having an amino acid sequence at least 90% identical to amino acids 20-130 of zu166B3LC-CXXA (SEQ ID NO:136).

In some embodiments, the nucleic acid molecule encodes:
a. a heavy chain variable region as set forth as amino acids 20-141 of xi155D5HC (SEQ ID NO:52) and a light chain variable region as set forth as amino acids 20-130 of xi155D5LC (SEQ ID NO:78);
b. a heavy chain variable region as set forth as amino acids 20-144 of zu155D5HC (SEQ ID NO:54) and a light chain variable region as set forth as amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
c. a heavy chain variable region as set forth as amino acids 20-138 of xi1E4HC (SEQ ID NO:58) and a light chain variable as set forth as amino acids 20-130 of xi1E4LC (SEQ ID NO:110);
d. a heavy chain variable region as set forth as amino acids 20-140 of zu1E4HC (SEQ ID NO:60) and a light chain variable region as set forth as amino acids 20-130 of zu1E4LC-CXXA (SEQ ID NO:114);
e. a heavy chain variable region as set forth as amino acids 20-142 of xi166B3HC (SEQ ID NO:74) and a light chain variable region as set forth as amino acids 20-130 of xi166B3LC (SEQ ID NO:132); or
f. a heavy chain variable region as set forth as amino acids 20-145 of zu166B3HC (SEQ ID NO:76) and a light chain variable region as set forth as amino acids 20-130 of zu166B3LC-CXXA (SEQ ID NO:136).

In some embodiments, the nucleic acid molecule encodes:
a. a heavy chain CDR1, CDR2, and CDR3 of xi155D5HC as set forth as SEQ ID NO:146, 148, and 150, respectively, and a light chain CDR1, CDR2, and CDR3 of xi155D5LC as set forth as SEQ ID NO:224, 226, and 228, respectively;
b. a heavy chain CDR1, CDR2, and CDR3 of zu155D5HC as set forth as SEQ ID NO:152, 154, and 156, respectively, and a light chain CDR1, CDR2, and CDR3 of zu155D5LC-3 as set forth as SEQ ID NO:242, 244, and 246, respectively, zu155D5LC-4 as set forth as SEQ ID NO:248, 250, and 252, respectively, zu155D5LC-5 as set forth as SEQ ID NO:254, 256, and 258, respectively, zu155D5LC-6 as set forth as SEQ ID NO:260, 262, and 264, respectively, zu155D5LC-7 as set forth as SEQ ID NO:266, 268, and 270, respectively, zu155D5LC-huVK2-40 as set forth as SEQ ID NO 278, 280, and 282, respectively, zu155D5LC-huVK4-1 as set forth as SEQ ID NO 290, 292, and 294, respectively, zu155D5LC-huVK6-21 as set forth as SEQ ID NO 296, 298, and 300, respectively, zu155D5LC-huVK6D-41 as set forth as SEQ ID NO 302, 304, and 306, respectively; or zu155D5LC-huVK7-3-Glu81 as set forth as SEQ ID NO 308, 310, and 312, respectively;

c. a heavy chain CDR1, CDR2, and CDR3 of xi1E4HC as set forth as SEQ ID NO:164, 166, and 168, respectively, and a light chain CDR1, CDR2, and CDR3 of xi1E4LC as set forth as SEQ ID NO:320, 322, and 324, respectively;

d. a heavy chain CDR1, CDR2, and CDR3 of zu1E4HC as set forth as SEQ ID NO:170, 172, and 174, respectively, and a light chain CDR1, CDR2, and CDR3 of zu1E4LC-CXXA as set forth as SEQ ID NO:332, 334, and 336, respectively;

e. a heavy chain CDR1, CDR2, and CDR3 of xi166B3HC as set forth as SEQ ID NO:212, 214, and 216, respectively, and a light chain CDR1, CDR2, and CDR3 of xi166B3LC as set forth as SEQ ID NO:386, 388, and 390, respectively; or f. a heavy chain CDR1, CDR2, and CDR3 of zu166B3HC as set forth as SEQ ID NO:218, 220, and 222, respectively, and a light chain CDR1, CDR2, and CDR3 of zu166B3LC-CXXA as set forth as SEQ ID NO:398, 400, and 402, respectively.

The disclosed nucleic acid molecules can encode an immunoglobulin that can immunospecifically bind to human TEM1. In some embodiments, the nucleic acid molecule encodes a heavy chain variable region having an amino acid sequence at least 90% identical to amino acids 20-139 of xi1-55-2HC (SEQ ID NO:56) and a light chain variable region having an amino acid sequence at least 90% identical to amino acids 20-129 of xi1-55-2LC (SEQ ID NO:108). In some embodiments, the nucleic acid molecule encodes a heavy chain variable region as set forth as amino acids 20-139 of xi1-55-2HC (SEQ ID NO:56) and a light chain variable region as set forth as amino acids 20-129 of xi1-55-2LC (SEQ ID NO:108). In some embodiments, the nucleic acid molecule encodes a heavy chain CDR1, CDR2, and CDR3 of xi1-55-2HC as set forth as SEQ ID NO:158, 160, and 162, respectively, and a light chain CDR1, CDR2, and CDR3 of xi1-55-2LC as set forth as SEQ ID NO:314, 316, and 318, respectively.

The disclosed nucleic acid molecules can encode an immunoglobulin that can immunospecifically bind to human MSLN. In some embodiments, the nucleic acid molecule encodes:

a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);

b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);

c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);

d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);

e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128); or f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130).

In some embodiments, the nucleic acid molecule encodes:

a. a heavy chain variable region as set forth as amino acids 20-142 of xi33O11HC (SEQ ID NO:62) and a light chain variable region as set forth as amino acids 20-131 of xi33O11LC (SEQ ID NO:116);

b. a heavy chain variable region as set forth as amino acids 20-145 of zu33O11HC (SEQ ID NO:64) and a light chain variable region as set forth as amino acids 20-131 of zu33O11LC-CXXA (SEQ ID NO:120) or zu33O11LC-CXXI (SEQ ID NO:122);

c. a heavy chain variable region as set forth as amino acids 20-137 of xi324O5HC (SEQ ID NO:66) and a light chain variable region as set forth as amino acids 20-127 of xi324O5LC (SEQ ID NO:124);

d. a heavy chain variable region as set forth as amino acids 20-137 of xi178F16HC (SEQ ID NO:68) and a light chain variable region as set forth as amino acids 20-127 of xi178F16LC (SEQ ID NO:126);

e. a heavy chain variable region as set forth as amino acids 20-132 of xi237N18HC (SEQ ID NO:70) and a light chain variable region as set forth as amino acids 20-127 of xi237N18LC (SEQ ID NO:128); or f. a heavy chain variable region as set forth as amino acids 20-137 of xi383I18HC (SEQ ID NO:72) and a light chain variable region as set forth as amino acids 20-127 of xi383I18LC (SEQ ID NO:130).

In some embodiments, the nucleic acid molecule encodes:

a. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth in SEQ ID NO:338, 340, and 342, respectively;

b. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively or zu33O11LC-CXXI as set forth as SEQ ID NO:356, 358, and 360, respectively;

c. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
d. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
e. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
f. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

Also disclosed are host cells comprising any of the disclosed nucleic acid molecules. Suitable host cells include, but are not limited to, mammalian cells, bacterial cells, yeast cells, insect cells, to name a few.

The following examples are provided to further describe some of the embodiments disclosed herein. The examples are intended to illustrate, not to limit, the disclosed embodiments.

EXAMPLES

Example 1—Exemplary Methods

Generation of Rabbit mAbs Specific to Human TEM1 (Endosialin/CD248)

Rabbit Immunization:

To generate rabbit mAbs specific to human TEM1 (hTEM1), a soluble human endosialin extracellular domain-mouse Fc fusion protein was prepared ("human endosialin/TE M1 extracellular domain fused to mouse IgG2b Fc"). The extracellular domain of hTEM1 was cloned in-frame EcoRI/HpaI to pEF6-EK-IgG2b, which contained an enterokinase cleavage site followed by the murine IgG2b Fc gamma fragment. CHO-K1 cells were transfected with this construct and selected with 5 μg/mL blasticidin. Secreted TEM1-Fc was electrophoresed on a 4-12% PAGE gel and Coomassie stained, followed by excision of the bands. The gel slices were emulsified in complete/incomplete adjuvant, and injected into New Zealand White rabbits every 3 to 4 weeks, four injections. The spleen from a rabbit showing the best titers against hTEM1 as assessed by ELISA was harvested for the generation of hybridomas.

Generation of Hybridomas:

Fusions were performed as follows: spleen cells (1.5-3× $10^8$) of immunized rabbits and the fusion partner 240E 1-1-2 were fused at a ratio of 2:1 with 50% PEG 4000 (EM Science, Cherry Hill, N.J.) at 37° C. in serum-free medium. The cells were plated in 48-well microtiter plates, at approximately $2 \times 10^5$ spleen cells per well, in medium with 15% FCS. After 72 hr, hypoxanthine-aminopterin-thymidine (HAT) was added. Medium was changed every 5-6 days. Supernatants were screened by ELISA for the presence of antibody specific for TEM-1 using TEM1-Fc coated plates and counter-screened against mouse Fc. Supernatants from hybridomas were screened for hTEM1 reactivity by ELISA and clone 1-55-2 was chosen for recombinant cloning.

Amplification of Anti-hTEM1 1-55-2 Light and Heavy Chain Variable Regions:

RNA was isolated from rabbit hybridoma 1-55-2 using the RNeasy mini kit (Qiagen, Valencia, Calif.). Two μg RNA was used for RT-PCR using SuperScript III One-Step RT-PCR System with Platinum Taq High Fidelity (Invitrogen). The rabbit variable heavy chain and full length light chain gene fragments were amplified using primer pairs N02937/N02898 and N02937/N02347 respectively (Table 1). The cycling parameters for the RT-PCR amplification were as follows: 55° C. 30 min; 94° C. 2 min; 30 cycles of (94° C. 15 sec, 55° C. 30 sec, 68° C. 1 min); 68° C. 2 min.

These PCR products were subsequently used in a second round PCR to amplify fragments amenable to generating chimeric rabbit/human IgGs using primer pairs N02416/N02761 and N02417/N02764 (Table 1). The cycling parameters for the second round PCR were as follows: 94° C. for 2 min; 30 cycles of (94° C. 30 sec, 55° C. 30 sec, 68° C. 1 min); 68° C. 2 min,

TABLE 1

Primers used for RT-PCR and cloning of anti-hTEM1 1-55-2

| Primer ID | Primer sequence | Fragment |
|---|---|---|
| N02937 | GATCAAGCTTGCCGCCACCATGGGCTGGTCCTGCATCATCCTGTT TCTGGTGGCGGCCGCCACCGGCGTGCACTCC (SEQ ID NO: 1) | Rabbit VH |
| N02898 | GTGCCTTTGGCTGGCCTGARGAGAYGGTGACCAGGGTGCC (SEQ ID NO: 2) | Rabbit VH |
| N02937 | GATCAAGCTTGCCGCCACCATGGGCTGGTCCTGCATCATCCTGTT TCTGGTGGCGGCCGCCACCGGCGTGCACTCC (SEQ ID NO: 3) | Rabbit LC |
| N02347 | GATCGGCGCGCCTCACTTGCCGGGGCTCCGG (SEQ ID NO: 4) | Rabbit LC |
| N02416 | GCCACCGGCGTGCACTCCCAGTCGGTGRAGGAGTCCRGGGG (SEQ ID NO: 5) | xi rb-hu HC |
| N02761 | GGGCCCTTGGTGGATGCTGARGAGAYGGTGACCAGGGTGCC (SEQ ID NO: 6) | xi rb-hu HC |

TABLE 1-continued

Primers used for RT-PCR and cloning of anti-hTEM1 1-55-2

| Primer ID | Primer sequence | Fragment |
|---|---|---|
| N02417 | GCCACCGGCGTGCACTCCGAGCTCGTGATGACCCAGACTCCA (SEQ ID NO: 7) | xi rb-hu LC |
| N02764 | AGCCACAGTTCGTTTGACSACCACCTCGGTCCC (SEQ ID NO: 8) | xi rb-hu LC |

PCR products were then separated by electrophoresis in an agarose gel. PCR products having the correct molecular sizes for the VL and VH products were purified by QIAquick® Gel Extraction Kit (Qiagen, Valencia, Calif.) and cloned as described below.

Generation of Rabbit mAbs Specific to Human CA9

Rabbit Immunization:

To generate rabbit antibodies specific to human CA9, human CA9 extracellular domain ("human CA9 extracellular domain" or "CA9-ECD") was recombinantly generated. Two b9 rabbits were immunized using CA9-ECD. Briefly, the rabbits were subcutaneously injected with the antigens every 21 days. Each rabbit received 400 µg of CA9-ECD and Freund's complete adjuvant (FCA) in the first injection and 200 µg of CA9-ECD and Freund's Incomplete Adjuvant (FIA) in the subsequent boosts. The pre- and test-bleed were collected for the antibody titer testing.

The pre- and post-immunization blood was tested for CA9 binding using an Enzyme-Linked Immunosorbent Assay (ELISA) as described herein. The bleeds were serial diluted and added to CA9-ECD protein-coated microplates. When the titer reached 1:15,000 after four injections, the rabbits were finally boosted by intravenous injection of 400 µg of CA9-ECD without adjuvant. Rabbit spleens were collected one week after the final boosting. Up to 100 mL exsanguination bleeds were collected in the presence of anti-coagulant and the lymphocytes from spleens and lymph nodes were isolated from each rabbit.

Generation of Hybridomas:

Rabbit splenocytes were quickly thawed, spun down at 1200 rpm at room temperature for 5 min, and re-suspended in cIMDM plus 10% FBS containing 100 µg/mL DNase. Cells were stimulated with 2.5 µg/mL pokeweed mitogen at 37° C. for at least 1 hour. After stimulation, cells were spun down at 1200 rpm at room temperature for 5 min and re-suspended in fresh media. Cell counts and viability were determined.

Fusion partner cells CBF7 were thawed out and cultured at 37° C. with 5% $CO_2$ for one week before fusion. An appropriate amount of rabbit splenocytes and fusion partner cells CBF7 were mixed at the desired ratio (1:1.55~1:4) in 50 mL tubes. The mixture of cells was spun down at 1000 rpm at room temperature for 5 min and washed twice with ice-cold 20 mL CytoPulse Fusion Medium (CPFM Formula C: CytoPulse Sciences #LCM-C) at 4° C. The cells were re-suspended in CPFM to $10^6$ cells/mL.

CytoPulse cell fusion apparatus CEEF-50 (CytoPulse Sciences) was used for the fusion. An appropriate volume of cells was moved to the fusion chamber and fusion was performed by activating high voltage connection. After fusion, the cells were incubated in the chamber at RT for 5 min, gently re-suspended in Post-Fusion Medium (RPMI1640 with 10% FBS, containing glutamate, pyruvate, non-essential amino acids, β-mercaptoethanol, penicillin, streptomycin, and no Phenol Red) and then transferred to a flask. The chamber was washed with the same volume of post-fusion media to obtain additional cells. The cells were incubated at room temperature for 25 min and then overnight at 37° C., 5% $CO_2$.

One day after fusion, the cells were diluted in pre-warmed seeding media (cIMDM plus 10% FBS containing 1× hypoxanthine-aminopterin-thymidine) to the desired density (35,000 cells/mL) and plated at 200 µL/well in 96-well microplates. The plates were incubated at 37° C., 5% $CO_2$ and fed with fresh medium weekly for 3-4 weeks.

Screening of Anti-CA9 mAbs:

B-cells from rabbit splenocytes were fused to fusion partner cells CBF7 to generate hybridomas as described herein. Four weeks after plating the cells, the supernatants from individual hybridoma cultures were collected and screened using a CA9-specific ELISA. The assay plates (Greiner Bio-One High Binding 384-well clear plate, cat #655081) were coated with 1 µg/ml CA9 ECD overnight at 4° C. and blocked with 1× Assay Buffer (PBS plus 1% BSA, containing 0.05% Tween-20). Then, 25 µL/well of supernatants and controls were added to the blocked plates and incubated overnight at 4° C. The assay plates were washed three times and 25 µL/well of secondary antibodies (HRP-conjugated goat anti-mouse IgG, Jackson #115-035-146) diluted 1:10,000 in Assay Buffer was added to the plates. After incubation at room temperature for one hour, the assay plates were washed three times and 25 µL/well of TMB Substrate (KPL #52-000-04) was added to the plates. After incubation at room temperature for 5 minutes, 25 µL/well of 1× Stop Solution (1:10 $H_2SO_4$, VWR #EM-SX1244-75) was added. Sample absorbance at 450 nm was measured by using Paradigm (Beckman) plate reader. The positive hits from the primary screen were confirmed by a second CA9-specific ELISA.

Cloning and Mutagenesis

Amplification of VH and Vκ Regions of CA9 and hTEM1 mAbs:

Hybridoma cells secreting rabbit mAbs of interest were lysed to extract RNA. RNA was then used for DNA amplification of variable kappa (Vκ) and heavy chain variable (VH) regions by using the reverse transcriptase-polymerase chain reaction (RT-PCR) method. One hundred to 10,000 cultured hybridoma cells were washed with ice cold PBS and lysed by adding 100 µL of Lysis/Binding Solution (Ambion, 8540G5) and pipetting. The lysed cells were quickly frozen on dry ice. RNA was isolated with Ambion RNAqueous Kit according to manufacture procedure. About 5 ng RNAs were subject to first round of RT-PCR using the primers listed on Table 2 in each reaction.

TABLE 2

Primers used for first round of RT-PCR

| | |
|---|---|
| Rabb.VHA1.F | 5'-CAGTCGCTGCTCGAGTCCGGGGGT-3' (SEQ ID NO: 9) |
| Rabb.VHB1.F | 5'-CTCTGGCACAGGAGCTC-3' (SEQ ID NO: 10) |
| Rabb.IgM_CH1.R | 5'-GGAGACGAGCGGGTACAGAGT-3' (SEQ ID NO: 11) |
| Rabb.IgG_Hinge.R | 5'-CGTGGGCTTGCTGCATGTCG-3' (SEQ ID NO: 12) |
| Rabb.Vκ.F | 5'-GTGATGACCCAGACTCCA-3' (SEQ ID NO: 13) |
| Rabb.Vκ1B4.R | 5'-ACAGTCACCCCTATTGAAGCTCTGG-3' (SEQ ID NO: 14) |
| Rabb.Vκ2B4.R | 5'-GCAGTCACCCCTGTTGAAGCTCTG-3' (SEQ ID NO: 15) |

The cycling parameters for the RT-PCR amplification were as follows: 55° C. 30 min; 95° C. 2 min; 30 cycles of (94° C. 1 min, 54° C. 50 sec, 68° C. 1.5 min); 68° C. 10 min.

The products from the first round RT-PCR were subjected to a second round of PCR amplification in separate reaction for heavy chain and light chain, using the primers listed in Table 3.

TABLE 3

Primers used for second round of PCR amplification

Heavy Chain

| | |
|---|---|
| ldr-Rabb.VHA1.F | gccaccggcgtgcactccCAGTCGGTGRAGGA GTCCRGGGG (SEQ ID NO: 16) |
| R-Rb-VH1-hu-gamma | gggcccttggtggatgcTGARGAGAYGGTGAC CAGGGTGCC (SEQ ID NO: 17) |

Light Chain

| | |
|---|---|
| ldr-Rabb.Vκ.F | gccaccggcgtgcactccGAGCTCGTGATGAC CCAGACTCCA (SEQ ID NO: 18) |
| R-Rb-Vκ1m-hu-kappa | agccacagttcgTTTGATCTCCAGCTCGGTCCC (SEQ ID NO: 19) |
| R-Rb-Vκ2-hu-kappa | agccacagttcgTTTGATTTCCACATTGGTGCC (SEQ ID NO: 20) |
| R-Rb-Vκ3-hu-kappa | agccacagttcgTTTGACSACCACCTCGGTCCC (SEQ ID NO: 21) |

The cycling parameters for the second round of PCR amplification were as follows: 95° C. 5 min; 40 cycles of (94° C. 1 min, 54° C. 50 sec, 68° C. 1.5 min); 68° C. 10 min; 4° C. Soak.

PCR products were then separated by electrophoresis on agarose gel. PCR products having the correct molecular sizes for the VL and VH products were purified by QIAquick® Gel Extraction Kit (Qiagen, Valencia, Calif.), and the fragments were subcloned into an expression plasmid containing a human gamma (Cγ) or kappa (Cκ) constant region using an InFusion HD cloning kit (Clontech). All clones were sequenced to confirm the presence and fidelity of the inserts.

Gene Synthesis:

Humanized VH domains and zu155D5LC-1, -huVK1-39, -huVK2-40, -huVK3-11, -huVK4-1, -huVK5-2, -huVK6-21, -huVK6D-41, -huVK7-3, zu1E4LC-1, and zu166B3LC-1 Vκ domains were codon-optimized for expression in human cells and were synthesized by DNA 2.0. The variable domains were synthesized with a Kozak sequence and an Ig leader sequence, and included 15 basepairs at the 5' and 3' ends homologous to the cloning site within the subcloning vector. Following excision from the DNA 2.0 vector, the fragments were subcloned into an expression plasmid containing a human Cγ or Cκ region using an InFusion HD cloning kit. All clones were sequenced to confirm the presence and fidelity of the inserts.

QuikChange:

Mutagenesis of the codon-optimized Vκ domains was performed using Stratagene's QuikChange XL according to the manufacturer's protocol. All clones were sequenced to confirm the presence of the mutation.

Cell Culture

Transfection and Stable Cell Line Generation:

One day prior to transfection, 293F cells were seeded at $6.0 \times 10^5$ cells/mL in 293FreeStyle medium (Thermo Fisher Scientific) in a shake flask and incubated at 37° C., 8% $CO_2$, with shaking at 125 rpm. On the day of transfection, cells were seeded at $1 \times 10^6$ cells/mL as above. Cells were transfected using PEI (25 kDa, linear; Polysciences) or ExpiFectamine (Thermo Fisher Scientific). For the PEI transfections, 166.7 ng HC plasmid, 166.7 ng LC plasmid, 2.2 µg PEI, and 50 µL OptiPro (Thermo Fisher Scientific) per mL of transfected cells were incubated for 15 min at 22° C. The DNA:PEI mixture was added to the cells while swirling and incubated at 37° C., 8% $CO_2$, shaking at 125 rpm. After 48-72 h, cells were fed at a final concentration of 10 g/L Yeastolate (BD Biosciences), 5 mM valeric acid (Sigma Aldrich), and 1:100 CD Lipid Concentrate (Thermo Fisher Scientific).

For each mL of cells to be transfected with ExpiFectamine, 333.3 ng HC plasmid and 333.3 ng LC plasmid were incubated for 10 min in 50 µL Opti-MEM (Thermo Fisher Scientific). Likewise, 2.67 µL ExpiFectamine was incubated in 50 µL Opti-MEM. The ExpiFectamine solution was added to the DNA mixture, and incubated for 30 min at 22° C. The DNA:ExpiFectamine mixture was added to the cells while swirling and incubated at 37° C., 8% $CO_2$, shaking at 125 rpm. The following day, 3 µL of enhancer 1 and 30 µL of enhancer 2 per mL of cells were added to the transfection with continued to incubate for another 7 or 10 days, depending on cell density.

Antibody-expressing stable pools were selected by adding 3 mL of transfectants to 12 mL DMEM in a T75 flask with 5 µg/mL blasticidin and 400 µg/mL zeocin (Thermo Fisher Scientific) one to three days after transfection. After drug-resistant cells grew to confluency, the medium was replaced with FreeStyle 293 expression medium. After 24 or 48 h, cells were physically dislodged by tapping the flask (trypsinization resulted in low viability; data not shown) and were then seeded at $6 \times 10^5$ cells/mL in 30 mL FreeStyle 293 expression medium in a 125-mL shake flask. Cultures were incubated at 37° C. in 8% $CO_2$ with shaking at 125 rpm.

mAb Production:

Antibody production from stable pools was performed by one of two methods:
1. Stable-transfected cell line pools were seeded at 0.6 to $1 \times 10^6$ cells/mL in 293FreeStyle medium. Two days after the culture reached a density of $1 \times 10^6$ cells/mL, cultures were fed as described herein; or
2. Stable-transfected cell line pools were centrifuged at 1000 rpm in a Beckman Allegra 6 centrifuge for 5 min. The supernatant was removed, and the cells were resuspended in 1 L expi293 medium (Gibco) at 0.5-0.8×10⁶ cells/mL in a 2.8-L shake flask. Cells were incubated at 37° C., 8% $CO_2$, shaking at 125 rpm.

For both methods, the cultures were incubated at 37° C. in 8% $CO_2$ with shaking at 125 rpm for 7-10 days, depending on when cell viability dropped to about 50%, at which time the cultures were centrifuged for 1 h at 8000 rpm in a Beckman MA8.1000 rotor. The supernatant was then filtered through a 0.2 μm PES filter and stored at 4° C. or −20° C. until purification.

mAb Purification

Antibody Purification by Protein A Affinity Chromatography:

Using an ÄKTA Explorer (GE Healthcare), a protein A column (GE Healthcare) was equilibrated with 10 column volumes (CV) of 20 mM sodium phosphate, 10 mM EDTA, pH 7.2. The sample was then loaded, followed by washing unbound material with 10 CV of equilibration buffer. The sample was eluted using 5 CV of 0.1 M Glycine pH 2.9. The fractions containing the mAb were pooled and dialyzed in Dulbecco's phosphate buffer (DPBS) using a MWCO 20K Slide-A-Lyzer (Thermo Fisher Scientific).

Cysteine Decapping:

Using an ÄKTA Explorer (GE Healthcare), a protein A column (GE Healthcare) was equilibrated with 10 CV of 20 mM sodium phosphate, 10 mM EDTA, pH 7.2 (equilibration buffer). The sample was then loaded, followed by washing unbound material with 10 CV of equilibration buffer. The column was washed with 16 CV of 20 mM sodium phosphate, 10 mM EDTA, 5 mM cysteine, pH 7.2 at 0.5 mL/min for 16 h at 4° C. to remove capping group. The column was then washed with 60 CV of 20 mM Tris, pH 7.5 at 0.5 mL/min for 60 h at 4° C. The sample was eluted using 5 CV of 0.1 M glycine pH 2.9 and immediately neutralized using 5% volume of 2M Tris, pH 9.0. The fractions containing mAb were pooled and dialyzed in DPBS using a MWCO 20K Slide-A-Lyzer (Thermo Fisher Scientific).

LC-MS/MS Cysteinylation and Disulfide Bond Mapping Analyses

The mAb was buffer-exchanged to 50 mM ammonium bicarbonate buffer, pH 7.8 using a Zeba spin desalting column (Thermo-Fisher). The concentration was adjusted to 1 mg/mL and RapiGest (Waters) was added to 0.1%. The mAb was then digested with Glu-C (New England BioLabs) (25:1 w/w) at 37° C. for 4 h, followed by digestion with Asp-N(New England BioLabs) (25:1 w/w) at 37° C. for 18 h. Following digestion, 5% trifluoroacetic acid (TFA) was added to 0.5% and incubated at 37° C. for 90 min. The sample was centrifuged at 13,000 rpm for 30 min to remove pellets and analyzed by LC-MS/MS using $MS^E$ methodology in the second ionization phase. $MS^E$ methodology uses a ramped voltage rather than a fixed voltage in the second ionization phase to generate a more complete ion profile. Samples were analyzed using a Waters Acquity UPLC and Q-Tof Premier mass spectrometer. Samples were injected onto a Waters BEH 300 C18, 1.7 μm pore size, 2.1×100 mm, eluted from the column with a 3 min equilibration in 97% of mobile phase A (0.1% formic acid in $H_2O$), a 55 min linear gradient (3-45% mobile phase B (0.1% formic acid in acetonitrile)), a 5 min linear gradient (45%-90% mobile phase B), a 5 min isocratic phase (90% mobile phase B), a 5 min linear gradient (90%-3% mobile phase B), and a 5 min re-equilibration in 97% of mobile phase A, at 0.05 mL/min. The Q-Tof mass spectrometer was run in positive ion, V-mode with detection in the range of 200-2000 m/z. The source parameters were as follows: capillary voltage, 3.0 kV, sampling cone voltage, 40 V; source temperature, 120° C.; desolvation temperature, 250° C.; desolvation gas flow, 600 L/hr. Lockspray mass reference standard was glu-fib. $MS^E$ method was as follows: acquisition time, 3-70 mins; data range, 200-2000 m/z; scan time, 1.5 sec; expression, low energy 6V, ramp high energy from 10-30V.

The antibody aggregation was analyzed by size-exclusion, high-performance liquid chromatography method (SEC-HPLC) using an Agilent 1100. The mAb was diluted to 1 mg/mL in DPBS. The antibody (20 μL) was injected onto a TSKgel SuperSW guard column (4.6 mm×3.5 cm, 4 μm pore size, Tosoh Bioscience), followed by a TSKgel SuperSW3000 column (4.6 mm×30 cm, 4 μm pore size), eluted from the column with 0.1 M PBS containing 0.15 M NaCl and 0.05% $NaN_3$, at pH 7.4, at a flow rate of 0.3 mL/min for 20 min. All data were analyzed using Agilent ChemStation software. Percent aggregation was calculated as $[PA_{aggregate}/PA_{total}]*100$, where PA=integrated peak area.

UPLC/ESI-MS Analysis of Malemide-Biotin: mAb Conjugation

Purified antibodies were diluted to 1 mg/mL in DPBS (samples were left at original concentration if below 1.0 mg/mL). Maleimide-PEG2-Biotin ((mal)-PEG2-Biotin) (Thermo Fisher Scientific) was dissolved in DPBS to yield a 20 mM stock solution, followed by dilution to 1 mM in DPBS. Mal-PEG2-Biotin was added to 1 mL of decapped mAb at a 5:1 conjugation ratio and incubated at 22° C. with gentle rotating for 2 hr. The reaction was desalted using a Zeba spin desalting column. The mAbs were then deglycosylated using PNGase F (New England BioLabs). G7 buffer (10 μL) and PNGase F (2 μL) were added to the mAb (90 μL). The reaction was incubated in a Discover microwave (CEM) for 2 cycles: 1) microwave power 10 W, 37° C., 10 min, followed by a 5-min pause; and 2) microwave power 2 W, 37° C., 10 min. A portion of the sample was reduced by adding dithiothreitol (DTT) to a final concentration of 20 mM, followed by incubation at 60° C. for 3 min.

Samples were then analyzed using a Waters Acquity UPLC and Q-Tof Premier mass spectrometer. Samples (0.5-2 μg each) were injected onto a MassPrep micro desalting column at 65° C., eluted from the column with a 5 min equilibration in 95% of mobile phase A, a 10 min gradient (5-90% B), and a 10 min re-equilibration in 95% of mobile phase A, at 0.05 mL/min. Mobile phase A was 0.1% formic acid in water. Mobile phase B was 0.1% formic acid in acetonitrile. The Q-Tof mass spectrometer was run in positive ion, V-mode with detection in the range of 500-4000 m/z. The source parameters were as follows: capillary voltage, 2.25 kV (intact antibody)-2.50 kV (reduced antibody); sampling cone voltage, 65.0 V (intact antibody) or 50.0 V (reduced antibody); source temperature, 100° C.; desolvation temperature, 250° C.; desolvation gas flow, 550 L/hr. The protein peak was deconvoluted using the MassLynx MaxEnt 1 function. Conjugation efficiency was calculated as $[I_{biotinylated}/(I_{biotinylated}+I_{unmodified})]*100$ of the deconvoluted mass spectrum, where I=mass peak intensity.

BIAcore Analysis of mAb: Antigen Affinity

Antibody concentrations were adjusted to generate 30-40 RU signal when bound to the antigen. Humanized mAbs purified by standard protein A affinity chromatography or by the decapping method were injected over an anti-human IgG sensor on a BIAcore T100 (GE Healthcare) for 1 min at a flow rate of 10 μL/min. The sensor surface was washed by injecting HBS-P buffer for 1 min at a flow rate of 50 μL/min. To record the antigen association to the captured mAb, a series of increasing concentrations of antigen was injected for 60 sec at a flow rate of 50 μL/min. The dissociation of antigen was monitored for 30 min at the same flow rate. The sensor surface was regenerated by injecting 3 M MgCl$_2$ for 1 min and then 30 sec at a flow rate of 30 μL/min. Sensograms were analyzed with Biacore T100 Evaluation Software using a 1:1 Langmuir binding model.

Bivalent/Bispecific Fab Preparation mAb-derived Fab fragments were prepared separately using immobilized papain, followed by isolation of the pure Fab fragments from Fc/undigested mAb using Protein A chromatography. Maleimido-PEG4-azide was synthesized by combining NHS-maleimide and azido-PEG4-amine in DMSO for 1 hr in a 1:1 molar ratio. Unreacted NHS was quenched by the addition of Tris-HCl buffer to prevent homodimerization. Fabs were conjugated to either maleimido-PEG4-azide or maleimido-PEG4-dibenzocyclooctyne (DBCO) at a 5:1 molar ratio of maleimide:Fab and reacted for 4 hr at 22° C. The modified Fab fragments were desalted twice each in DPBS to remove all unreacted products, and the Fab fragments were combined at a molar ratio of 1:1 at 2 mg/mL final concentration and allowed to form dimers overnight at 22° C. The reaction was analyzed by SDS-PAGE and dimerization efficiency was estimated at 20%. The dimer preparation was purified from unreacted monomer by S-200 gel filtration chromatography.

Bivalent/Bispecific Octet Assay

Biotinylated human CA9 was captured on streptavidin Biosensor tips (Pall) for 4 min. Following incubation in PBS for 2 min, the tips were incubated with the bivalent/bispecific Fabs, mAb alone, or Fab alone for 5 min. Following incubation in PBS for 2 min, the tips were incubated with human endosialin/TEM-1 for 5 min. Finally, the tips were incubated in PBS for another 2 min. Association and disassociation protein to the tips was measured throughout.

Example 2—Cys80 Conjugation

Objective

Site-specific conjugation technologies are desirable to produce a homogeneous product with a defined drug-to-antibody ratio (DAR). The VK domain of a rabbit mAb, such as that derived from *Oryctolagus cuniculus*, may contain a cysteine in position 80 (referred to as "Cys80") (FIG. 1A) and the CK region may contain a cysteine in position 171 ("Cys171") (FIG. 1B). In-silico modelling predicted that Cys80 and Cys171 might be forming a disulfide bond, as the two S atoms are predicted to be approximately 1.6 Å apart (FIG. 2A). Human mAbs have proline, serine, or alanine residues in position 80 (FIG. 1A), and serine in position 171 (FIG. 1B), thus there is no disulfide bridge between the variable and constant region (FIG. 2B).

The crystal structure closest to rabbit or human VK and CK sequences was identified using BLAST pdb database and used as a template for modeling 155D5 mAb structure. Models were generated using Discovery Studio's "Build Homology Models" tool (Accelrys). The model with the lowest total energy was selected, typed with the CHARMm forcefield, and the energy was further minimized through two rounds of energy minimization using the "Minimize" tool. The CDR loops were then refined using the "Model Antibody Loops" tool. The model with the lowest total energy was selected, typed with the CHARMm forcefield, and the energy was further minimized as above. The proximity of Cys80 and Cys171 (FIG. 2A) predicts that these cysteines may be forming a disulfide bond. The "Build Mutants" tool was used to represent this disulfide bond.

Since disulfide bonds are critical for maintaining secondary and tertiary structural integrity, which in turn is necessary for an antibody's biological activity, it was important to prove whether the predicted Cys80-Cys171 bond actually existed. Therefore, ad hoc experiments were conducted that unequivocally demonstrated that the rabbit mAbs contained such a bond (Table 4).

TABLE 4

Demonstration of the existence of Cys80-Cys171 disulfide bond

| Peptide Sequence (position) | Predicted mass(Da)- | Observed mass (Da) |
|---|---|---|
| DCTYNLSSTLSLTK (170-183) (SEQ ID NO: 22) | 1545.7465 | Not observed |
| FTLTITGVQCD (71-81) (SEQ ID NO: 23) | 1197.582 | Not observed |
| DCTYNLSSTLSLTK = FTLTITGVQCD (SEQ ID NO: 22) (SEQ ID NO: 23) (disulfide-linked peptides as above) | 2741.3285 | 2740.2659 |

LC-MS/MS analysis was performed on a Glu-C/Asp-N digest of rabbit 155D5 MAb (from NZW rabbit). Only masses corresponding to disulfide-linked cys80-cys171 were found, indicating that cys80 forms a disulfide bond with cys171 in rabbit IgG. A similar analysis was performed using 1-55-2 mAb (from b9 rabbit).

A species-human chimerized mAb is made through the fusion between: i) the variable region from the species where the mAb was generated; and ii) the human constant region. This process is called chimerization. A humanized mAb is mostly made of human variable and constant regions, except for those residues necessary for antigen binding, which are from the same species of the host from which the mAb was generated. This process is called humanization. To engineer human chimerized or humanized mAbs, whereby the mAbs were generated in hosts belonging to the species *Oryctolagus cuniculus* the entire constant domains as well as most of the variable regions (if humanized) were genetically replaced with the human variable and human constant sequences. After either chimerization or humanization, the Cys80 in the VK no longer formed a disulfide bond with position 171 in the CK ((FIG. 2C), and is therefore unpaired.

Germline NZW rabbit VK families have a cysteine at position 80 as shown in FIG. 3 (the CDR regions were deleted, and frameworks (FWR) 1, 2, and 3 were aligned).

Discovery and Characterization of an Unpaired Cysteine at Position 80

Rabbit constant regions of 155D5 and 1E4 (anti-CA9), 1-55-2 (anti-hTEM1), as well as 33O11 (anti-MSLN), all of which contain Cys80 and generated as described in Example 1, were replaced with the human constant regions of an IgG1κ to generate rabbit/human chimerized mAb, as described elsewhere herein. Specifically, the rabbit VH region of 155D5 was fused with the human Cγ region to generate xi155D5HC, and the rabbit Vκ region of 155D5 was fused with the human Cκ region to generate xi155D5LC. The rabbit/human chimerized 155D5 mAb with the unpaired Cys80 is referred to herein as xi155D5.

VH region of 1-55-2 was fused with the human Cγ region to generate xi1-55-2H, and the rabbit Vκ region of 1-55-2 was fused with the human Cκ region to generate xi1-55-2LC. The rabbit/human chimerized 1-55-2 mAb with the unpaired Cys80 is referred to herein as xi1-55-2.

The rabbit VH region of 1E4 was fused with the human Cγ region to generate xi1E4HC, and the rabbit Vκ region of 1E4 was fused with the human Cκ region to generate xi1E4LC. The rabbit/human chimerized 1E4 mAb with the unpaired Cys80 is referred to herein as xi1E4.

The rabbit VH region of 33O11 was fused with the human Cγ region to generate xi33O11HC, and the rabbit Vκ region of 33O11 was fused with the human Cκ region to generate xi33O11LC. The rabbit/human chimerized 33O11 mAb (xi33O11) with the unpaired Cys80 is referred to herein as xi33O11.

Figure 4:
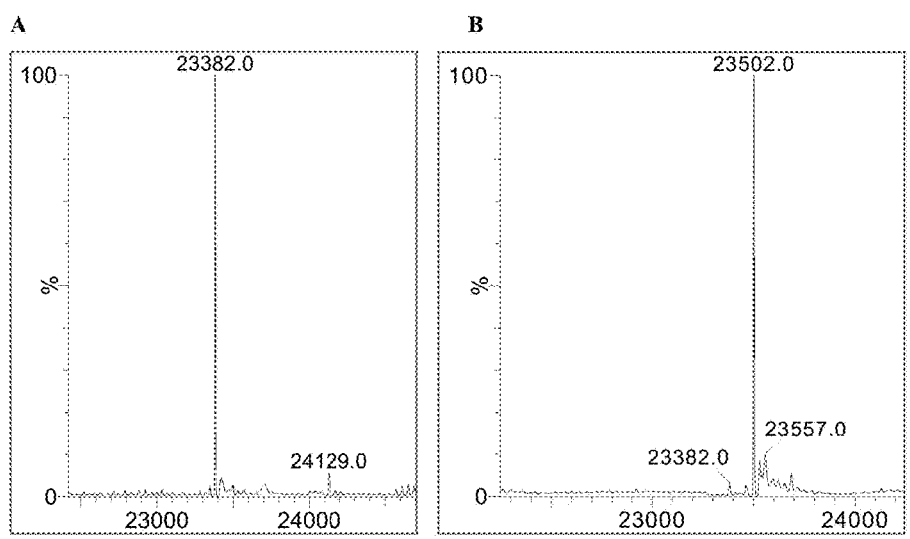
FIG. 4 illustrates an exemplary mass spectrometry analysis of xi155D5 light chain when (A) reduced using harsh conditions (20 mM DTT, 60° C., 5 minutes) and (B) reduced using mild conditions (100 μM DTT, 22° C., 30 minutes).

Because the Cys171 was substituted with Ser171 during chimerization, the chimerized antibodies (xi155D5, xi1-55-2, xi1E4, and xi33O11) contained an unpaired cysteine at position 80 in the Vκ (referred to as "Cys80"). When reduced using harsh conditions (20 mM DTT at 60° C. for 5 min), the molecular weight (mass) of the protein A-purified mAb xi155D5 light chain was 23,382 Da (FIG. 4A). However, when subjected to mild reducing conditions (100 μM DTT, RT, 30 min) the mass increased by 120 Da (FIG. 4B). This mass increase suggested that Cys80 might be forming a disulfide bond with a free cysteine, referred to as "capping" cysteine. This molecular structure, which results from a reaction called "cysteinylation", is referred to as "capped" Cys80. To confirm this hypothesis, xi155D5 mAb was digested with Asp-N and Glu-C, and the masses of the peptides were analyzed. Mass spectrometry analysis of peptide fragments corresponding to residues 71 through Cys80 (FTLTITGVQC) (SEQ ID N0:24) indicated an increased molecular weight by 119 Da (Table 5), thereby confirming that Cys80 was capped.

TABLE 5

Mass spectrometry of xi155D5 peptide 71-Cys80 fragments

| Peptide Sequence | Fragment mass (DA) | Observed mass (DA) | Δmass (DA) |
| --- | --- | --- | --- |
| FTLTITGVQC (SEQ ID NO: 24) | 1082.555 | 1201.5544 | 118.9994 |
| TLTITGVQC (SEQ ID NO: 25) | 935.4866 | 1054.4946 | 119.008 |
| LTITGVQC (SEQ ID NO: 26) | 834.4389 | 953.4397 | 119.0008 |
| TITGVQC (SEQ ID NO: 27) | 721.3549 | 840.3552 | 119.0003 |
| ITGVQC (SEQ ID NO: 28) | 620.3072 | 739.3067 | 118.9995 |

TABLE 5-continued

Mass spectrometry of xi155D5 peptide 71-Cys80 fragments

| Peptide Sequence | Fragment mass (DA) | Observed mass (DA) | Δmass (DA) |
| --- | --- | --- | --- |
| TGVQC (SEQ ID NO: 29) | 507.2231 | 626.2235 | 119.0004 |
| GVQC (SEQ ID NO: 30) | 405.47 | 525.1809 | 119.7109 |
| QC (SEQ ID NO: 31) | 249.28 | 369.0883 | 119.8083 |

Figure 5:
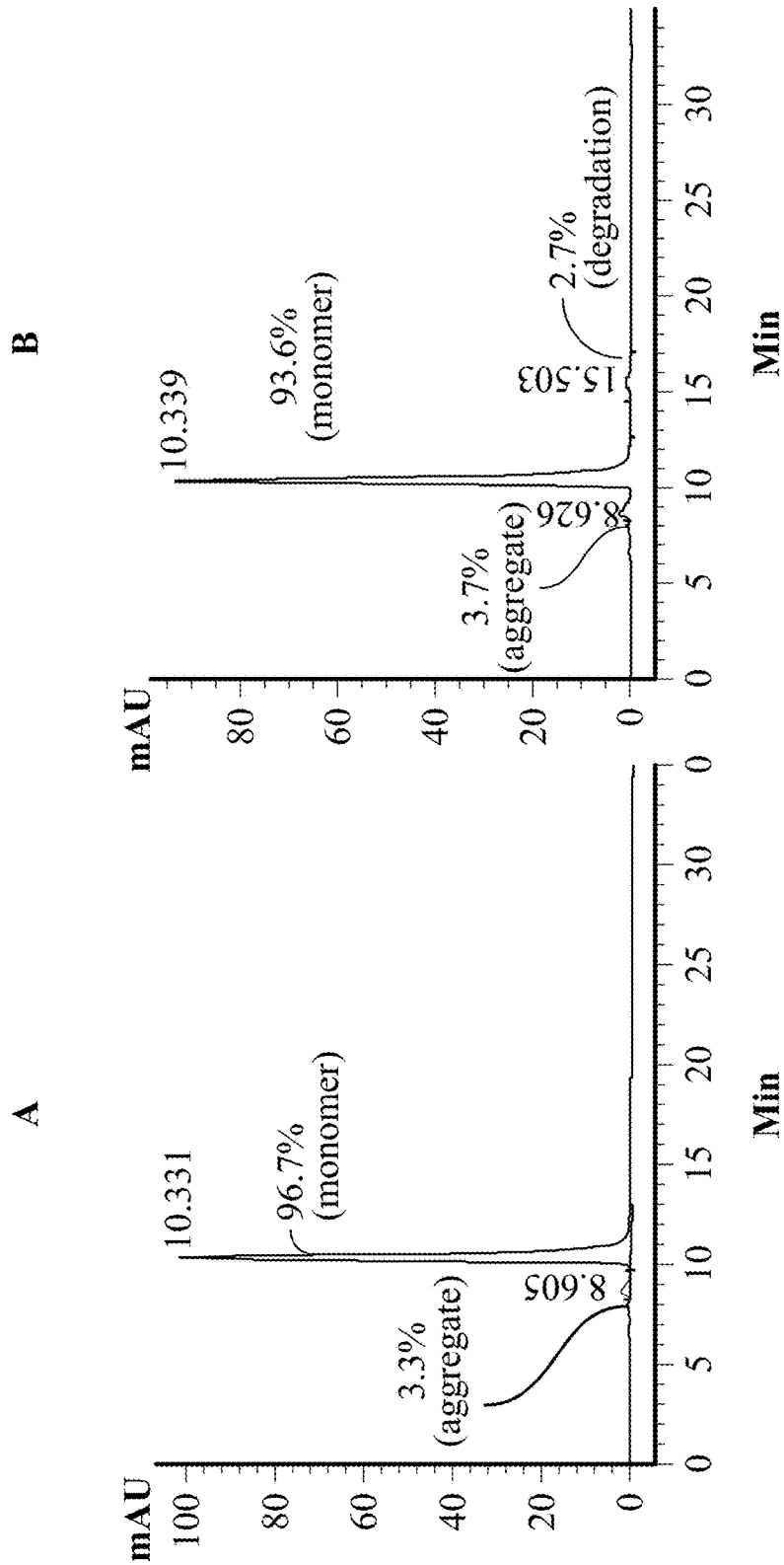
FIG. 5 illustrates an exemplary SE-HPLC analysis of the stability of xi155D5. (A) Stability of xi155D5 stored at −80° C. (B) Stability of xi155D5 stored at 37° C. for 1 week. Only a very slight increase in formation of aggregates or degradation products was observed. Y axis, mAU; x axis, retention time (minutes).

Because the lack of the Cys80-Cys171 disulfide bond could have led to antibody instability, disruption of antigen binding, or both, antibody stability and antigen binding tests were conducted. The stability of xi155D5 was tested using a SE-HPLC assay. This assay tests whether the lack of Cys80-Cys171 disulfide bond could lead to aggregation (due to possible intermolecular Cys80-Cys80 bonds), or degradation (due to increased sensitivity to proteases). Purified antibody at 1 mg/mL in 1×PBS was stored at −80° C. or 37° C. for 1 week. Ten μL of xi155D5 was injected onto a SuperSW3000 column (TOSOH Biosciences, 4.6 mm×30 cm, 4 μm particle size) equipped with an in-line TSKgel 4.6 mm×3.5 cm guard column at a flow rate at 0.3 mL/min with 0.1 M sodium phosphate, 0.15 M NaCl, 0.05% $NaN_3$ as mobile phase. No significant change in aggregation was observed between the two storage conditions (FIGS. 5A and 5B). The level of aggregation was in the 3-4% range and hence within the normal range of a typical human IgG1 (data not shown). Little or no degradation products were observed in any storage conditions (FIG. 5). These results suggest that xi155D5 lacking the Cys80-Cys171 disulfide bond is a stable protein under the storage conditions tested.

To determine if chimerization, and therefore the loss of Cys80-Cys171 disulfide bond, results in structural perturbations leading to loss of antigen binding, the binding affinity of mAbs 155D5, xi155D5, 1-55-2, and xi1-55-2 by surface plasmon resonance was evaluated. Biotinylated ligand (biotin-hTEM1 for 1-55-2, biotin-CA9 for 155D5) was captured on a coated biotin CAP BIAcore chip (GE Healthcare, Piscataway, N.J.) using HBS-EP as running buffer. Final antigen capture levels were 130 RU and 280 RU, respectively, for biotin-TEM1 and biotin-CA9. Serial dilutions of antibody (120 μL of 0-50 nM) were passed over the ligand-coated chip. Dissociation was observed for 25 min. The chip surface was regenerated with 6 M GuHCl, 250 mM NaOH. Sensograms were double referenced and kinetic parameters were determined using BIAEvaluations software (ver. 4.1). Little or no loss of binding affinity was observed due to chimerization of two different mAb (Table 6), suggesting that the lack of the Cys80-Cys171 disulfide bond does not lead to disruption of the binding region.

TABLE 6

Kinetic constants of chimerized and rabbit mAbs

| mAb | $k_a$ ($M^{-1}sec^{-1}$) | $k_d$ ($sec^{-1}$) | $K_D$ (M) |
| --- | --- | --- | --- |
| 1-55-2 | $3.7 \times 10^6$ | $5.8 \times 10^{-5}$ | $1.5 \times 10^{-11}$ |
| xi1-55-2 | $1.5 \times 10^6$ | $7.1 \times 10^{-5}$ | $4.6 \times 10^{-11}$ |
| 155D5 | $5.1 \times 10^5$ | $2.1 \times 10^{-5}$ | $4.1 \times 10^{-11}$ |
| xi155D5 | $4.6 \times 10^5$ | $2.4 \times 10^{-5}$ | $5.1 \times 10^{-11}$ |

Assessment of the Utility of Cys80 for Conjugations of Functional Agents

After having established that the lack of Cys80-Cys171 disulfide bond does not lead to structural perturbations, the possibility of replacing the capping cysteine with a thiol-reactive compound was explored. A thiol-reactive group can be attached to a linker, which in turn can be attached to a molecule of diagnostic or therapeutic utility, referred to herein as "functional agent." Functional agents may include fluorophores, fluorescent dyes, polypeptides, immunoglobulins, antibiotics, nucleic acids, radionuclides, chemical linkers, small molecules (such as chemotherapeutic agents), chelators, lipids, and drugs.

Figure 6:
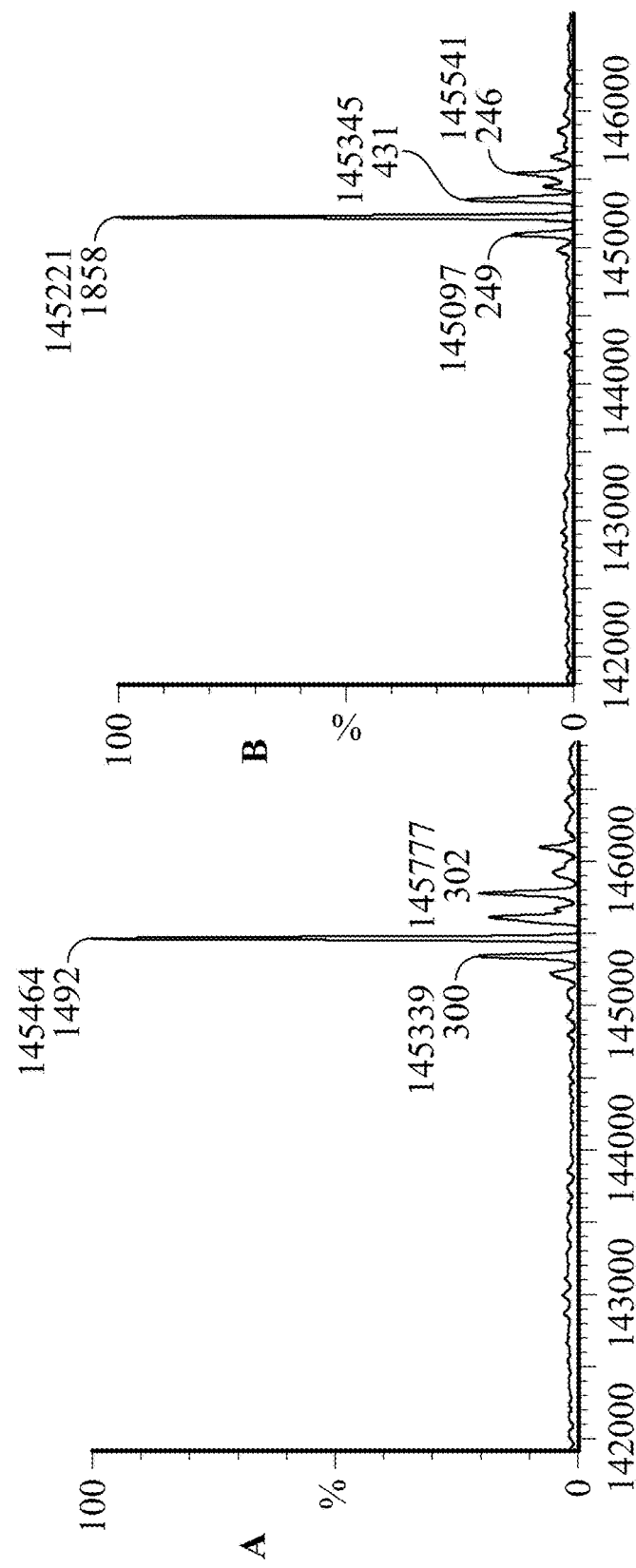
FIG. 6 represents an exemplary decapping experiment showing that the cysteine capping Cys80 can be removed by mild reducing conditions (buffer containing 5 mM cysteine for 16 hours followed by washing with a cysteine-free Tris-containing buffer for 60 hours; all incubations carried out at 4° C.). The mass of xi155D5 before (A) and after (B) decapping was 145,464 and 145,221 Da, respectively. The difference (243 Da) corresponding approximately to two free cysteines.

To substitute the capping cysteine with a functional agent, the capping cysteine was first removed. Exposing purified mAbs to reducing conditions could break the disulfide bond between Cys80 and the capping cysteine, referred to herein as "decapping." However, suboptimal reducing conditions, for example harsh reducing conditions, could also break the inter- and intra-chain disulfide bonds, thereby compromising the mAb structure and activity. Therefore, a decapping method involving removal of the capping cysteine using mild reduction, followed by reoxidation with Tris-containing buffer that does not alter the mAb structure and activity, while still allowing removal of the capping cysteine, was developed. A number of reducing agents were initially evaluated, including reduced glutathione, cysteine, TCEP, and DTT. Glutathione did not efficiently remove the capping cysteine (data not shown). Both DTT and TCEP efficiently removed the capping cysteine, but higher concentrations also resulted in the near-complete breakage of inter-chain disulfides and likely some intra-chain disulfides as well (data not shown). The mild reductant cysteine efficiently removed the capping cysteine and only limited inter-chain breakage was observed. Reoxidation was examined using phosphate buffer, Tris buffer, and the strong oxidant $CuSO_4$. No reoxidation of the disrupted inter-chain disulfides was observed with phosphate buffer, while $CuSO_4$ efficiently and rapidly reformed the disulfides, but was not evaluated further, due to its inherent toxicity compared with Tris. Optimized conditions were adapted to a column format to allow for sequential purification and decapping from feedstock. With this method, the antibody was bound to protein A resin and incubated with limited flow (0.5 mL/min) with a buffer containing 5 mM cysteine for 16 h to reduce (break) the Cys80-cysteine disulfide bond, followed by washing with a cysteine-free Tris-containing buffer for 60 h to remove the cysteines released by this treatment and re-oxidize any reduced interchain disulfide bonds. The mAb was then eluted in a low pH glycine buffer. In an exemplary experiment whereby the decapping method was applied to xi155D5, the mass of the non-reduced, purified mAb was determined and ~99% of the mAb was found decapped, as demonstrated by the drop in mass equivalent to two free cysteines (FIGS. 6A and 6B). Free thiol assay confirmed the presence of two thiol groups per mAb, also demonstrating efficient reoxidation (data not shown).

Decapped Cys80 can be Conjugated to Maleimide

Figure 7:
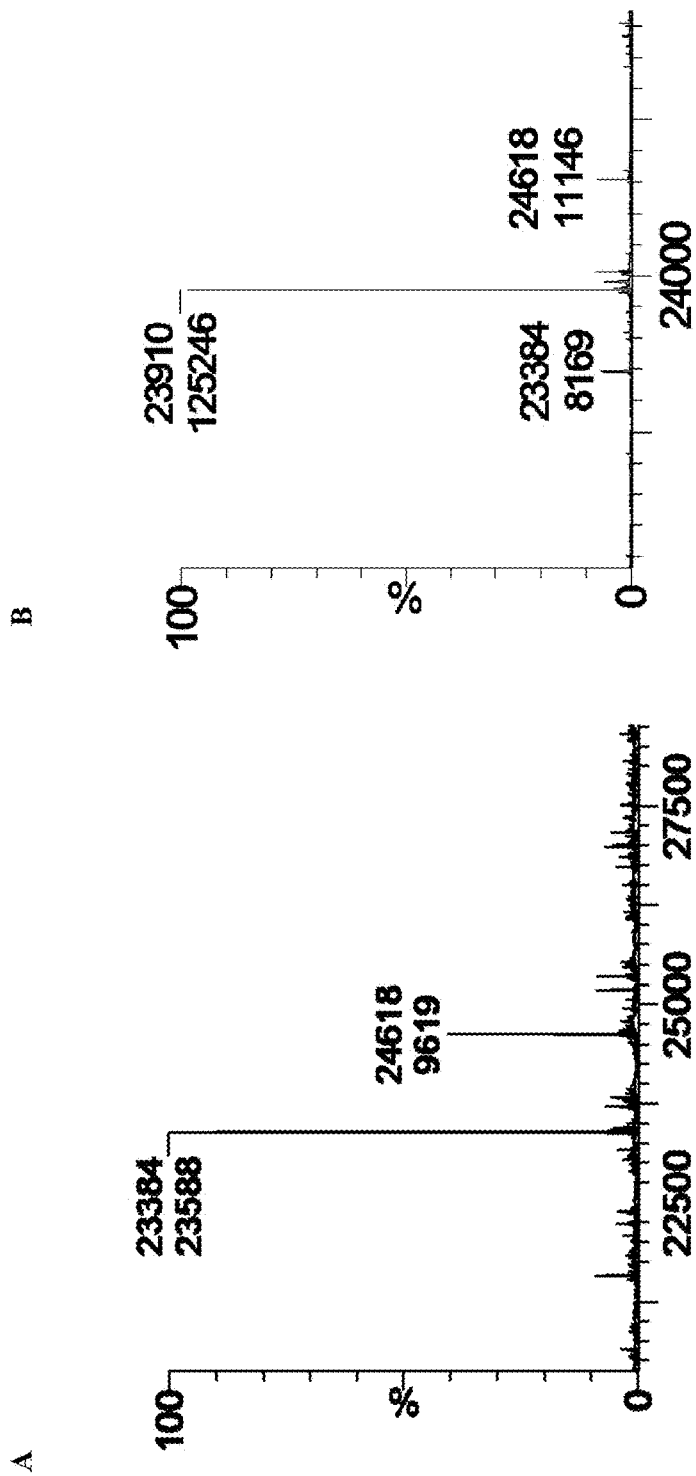
FIG. 7 represents an exemplary conjugation experiment showing that an uncapped Cys80 can be conjugated to maleimide-PEG2-biotin. (A) The light chain of reduced xi155D5 (predicted mass of 23,399 Da) had a mass of 23,384 Da, and (B) after incubation with maleimide-PEG2-biotin, 94% of the product showed a mass increase by 526 Da (23,910 Da). Asterisks denote non-light chain peaks.

Cysteine is an α-amino acid with a nonpolar side chain (thiol; —SH). The reduced thiol side chain in an unpaired cysteine could serve as a nucleophile that can react with an electrophile molecule such as maleimide, a chemical compound with the formula $H_2C_2(CO)_2NH$. The electrophile double bond in maleimide readily reacts with the nucleophile thiol group found on cysteine to form a stable carbon-sulfur thioether bond. The nonpolarity of the thiol side chain, depending on the surrounding residues, might confer a hydrophobic property to a cysteine that may prevent solvent exposure necessary for chemical modifications. In addition, the location of the cysteine in the context of the secondary structure of the peptide in which it is located may further prevent access of thiol-reactive molecule. Experimental testing to determine whether Cys80 could react with a thiol-reactive molecule after decapping was performed. The decapped xi155D5 was incubated with maleimide-PEG2-biotin as described elsewhere herein. Mass spectrometry analysis showed that 94% of the mAb was conjugated with maleimide-PEG2-biotin as indicated by an increase in molecular mass by 526 Da (FIG. 7), corresponding to the functional agent mass. As each light chain was found conjugated (single mass peak, FIG. 7), the maleimide-PEG2-biotin to xi155D5 ratio was homogeneously equal to 2:1. One maleimide-PEG2-biotin was conjugated to a Cys80 in each of the two light chains in the chimerized mAb ($Cys80^1$ and $Cys80^2$).

These results demonstrate that Cys80 and Cys171 form a disulfide bond that links the Vκ and Cκ regions of a rabbit mAb. When rabbit mAbs were chimerized, Cys171 was substituted by Ser171 present in the human Cκ region. This substitution abolished the Cys80-Cys171 disulfide bond. When the effects of losing this disulfide bridge on the structural stability and activity of the resulting chimerized mAb compared with the parental rabbit mAb were evaluated, it was observed that the chimerized mAb was stable and active. It was discovered that both $Cys80^1$ and $Cys80^2$, which remained unpaired in the chimerized mAb, were capped by a free cysteine (capping cysteine). Subsequently, a method to remove the capping cysteine (decapping), while maintaining structural stability and activity of the resulting chimera mAb, was developed. Additionally, it was demonstrated that high yields of mAb conjugated to maleimide-PEG2-biotin could be achieved with a functional agent to mAb ratio equal to 2:1.

Humanization of Rabbit mAbs

Chimerized mAbs could be immunogenic when administered to humans and therefore it is desirable to humanize rabbit mAbs by substituting rabbit sequences with human sequences in the Vκ and VH regions. The amino acid sequence of mAb 155D5 was analyzed using a BLAST search against a human variable domain database at http://www.ncbi.nlm.nih.gov/igblast/to identify the human sequence with highest homology to the rabbit sequence. IGHV3-64*04 and IGKV1-5*03 were identified as the best sequences for humanization, as their use would result in the least number of rabbit residue substitutions (FIG. 8).

The 155D5 sequences corresponding to the antigen binding domains as identified by Kabat and Chothia CDRH1, Chothia CDRH2, CDRH3, CDRL1, CDRL2, and CDRL3 were inserted into the framework (FWR) regions of human IGHV3-64*04 or IGKV1-5*03 to generate the humanized 155D5 mAb, named zu155D5-1 (Table 7 and Table 8).

Figure 9:
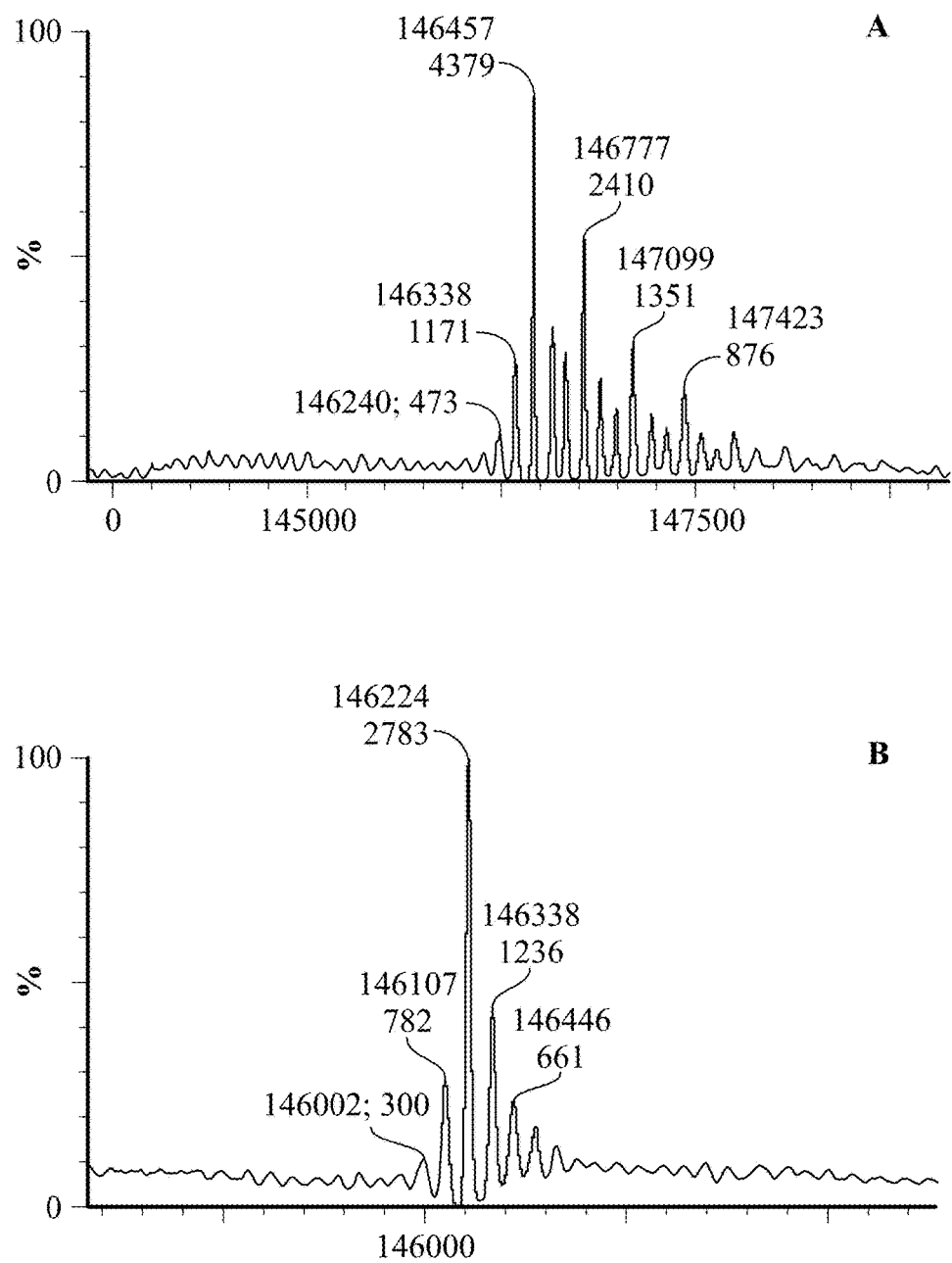
FIG. 9 illustrates an exemplary standard protein A purification of zu155D5-1. zu155D5-1 was found capped (A), as evidenced by the change of mass after decapping (B) by 233 Da, approximately corresponding to two capping cysteines.
Figure 10:
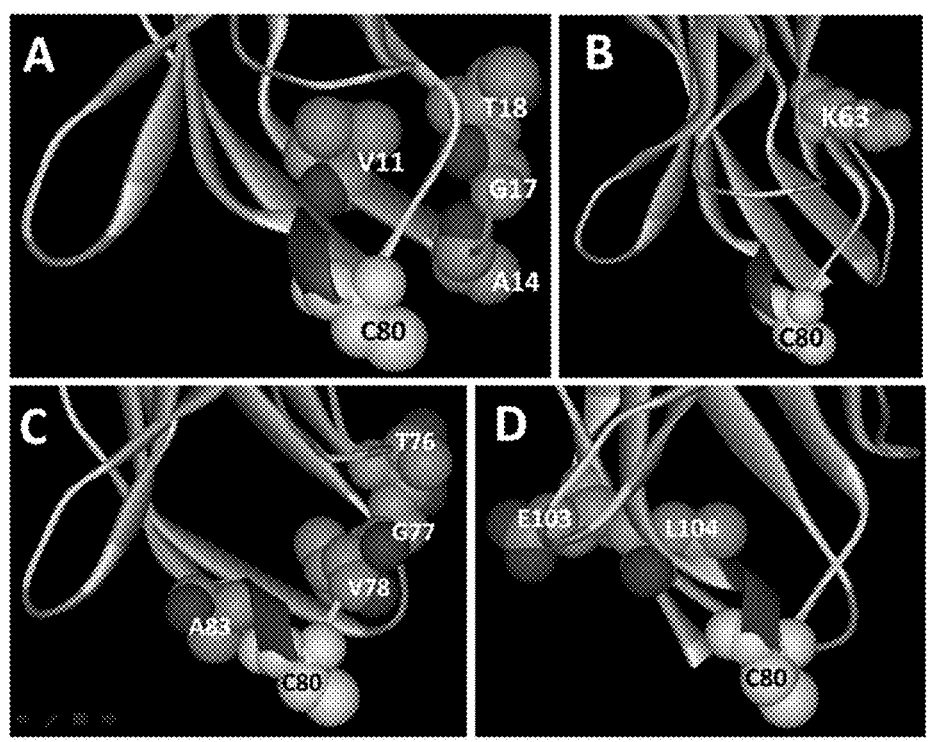
FIG. 10 illustrates exemplary structural models of chimerized xi155D5. Modelling to determine Cys80 proximity was conducted as in FIG. 2. The residues differing between xi155D5 and zu155D5-1 were highlighted and the distance to Cys80 was measured for each. (A) Residues Val11, Ala14, Gly17, Thr18; (B) Lys63; (C) Thr76, Gly77, Val78, Ala83; and (D) Glu103 and Leu104, are within 11 Å of Cys80, except for Lys63 (18 Å). These residues were changed back to the rabbit amino acids in the presence of Cys80.

During the humanization of 155D5LC (zu155D5LC), Cys80 was maintained, which was unpaired since the human kappa sequence has Ser171 as opposed to Cys171. zu155D5-1 was produced and purified using standard protein A purification, and found to be capped, as evidenced by the change of mass after decapping by 233 Da, approximately corresponding to two capping cysteines (FIG. 9). As observed with xi155D5, zu155D5-1 could also be decapped with efficiency close to 100% (Table 9). However, the decapping led to massive levels of aggregation (70%) versus only 14% in xi155D5. When zu155D5-1 was reacted with maleimide-PEG2-biotin, 0% conjugation was observed while xi155D5 was 93% conjugated (Table 9). These results were surprising, as they suggest that: 1) having a cysteine in position 80, although necessary, is not sufficient to allow for site-specific conjugation of a functional agent; and 2) in some conditions, attempting conjugation on Cys80 could lead to high aggregation not compatible with drug manufacturability. However, since the disclosed studies, which characterized xi155D5, demonstrated that at least in some conditions conjugation of a functional agent on Cys80 could be very efficient, it was next investigated how residues surrounding Cys80 may influence conjugation efficiency. Consequently, structural models of chimerized xi155D5 were generated (FIG. 10), which indicated that residues Val11, Ala14, Gly17, Thr18, Lys63, Thr76, Gly77, Val78, Ala83, Glu103, and Leu104 were in close proximity (within 18 Å) to Cys80 and therefore could potentially be affecting the efficiency of its conjugation.

Two versions of FWR1 (FWR1a-b), one version of FWR2, three versions of FWR3 (FWR3a-c), and two version of FWR4 (FWR4a-b) were designed based on the aforementioned residues (Table 7).

ping. It is noted that the zu155D5-4 antibody has a propensity to aggregate independently of decapping, which may account for the observed results. These data suggested that Phe83 is involved in causing high aggregation after decapping and is not conducive to conjugation on Cys80.

TABLE 9

Aggregation levels and conjugation efficiency of xi155D5 versus different variants of zu155D5

| mAb name | % Aggregates ProA | Decapped | % Decapped | % Conjugated | aa 80-83 |
|---|---|---|---|---|---|
| xi155D5   | ND     | 14.20%    | 100.00% | 93.90%    | CXXA |
| zu155D5-1 | 1.10%  | 70.10%| 100.00% | 0.00% | CXXF |
| zu155D5-2 | 10.10% | 44.50%| 100.00% | 0.00% | CXXF |
| zu155D5-3 | 0.00%  | 17.30%    | 100.00% | 80.10%    | CXXA |
| zu155D5-4 | 10.80% | 28.30%| 100.00% | 25.90%| CXXA |
| zu155D5-5 | 7.40%  | 13.30%    | 100.00% | 86.90%    | CXXA |

TABLE 7

Versions of frameworks derived from human Vκ family IGKV1-5

| human Vκ family | FWR version code | FWR1 | FWR2 | FWR3 | FWR4 |
|---|---|---|---|---|---|
| IGKV1-5 | A | DIQMTQSPSTLSA SVGDRVTITC (SEQ ID NO: 32) | WYQQKPGKAP KLLIY (SEQ ID NO: 33) | GVPSRFSGSGSGTEFTL TISSLQCDDFATYYC (SEQ ID NO: 34) | FGGGTKVEIK (SEQ ID NO: 35) |
| IGKV1-5 | B | DIQMTQSPSTVSA AVGGTVTITC (SEQ ID NO: 36) | n/a | GVPSRFSGSGSGTEFTL TITGVQCDDFATYYC (SEQ ID NO: 37) | FGGGTELEIK (SEQ ID NO: 38) |
| IGKV1-5 | C | n/a | n/a | GVPSRFKGSGSGTEFT LTITGVQCDDAATYYC (SEQ ID NO: 39) | n/a |

Residues in bold font indicate differences between the framework variants. n/a, not applicable.

A series of humanized 155D5 variants were generated that contained combinations of these frameworks and either Cys80-Xaa$_1$-Xaa$_2$-Phe83 (also referred to as C-X-X-F or CXXF) or Cys80-Xaa$_1$-Xaa$_2$-Ala83 (also referred to as C-X-X-A or CXXA), whereby "Xaa" or "X" indicates amino acids in position 81 and 82 (Table 8).

TABLE 8

Humanized 155D5 variants derived from human Vκ family IGKV1-5

| mAb name | FWR combination | aa 80-83 |
|---|---|---|
| zu155D5-1 | FWR1a, FWR2a, FWR3a, FWR4a | CXXF |
| zu155D5-2 | FWR1a, FWR2a, FWR3b, FWR4a | CXXF |
| zu155D5-3 | FWR1a, FWR2a, FWR3a, FWR4a | CXXA |
| zu155D5-4 | FWR1a, FWR2a, FWR3b, FWR4a | CXXA |
| zu155D5-5 | FWR1a, FWR2a, FWR3c, FWR4a | CXXA |
| zu155D5-6 | FWR1b, FWR2a, FWR3b, FWR4a | CXXA |
| zu155D5-7 | FWR1a, FWR2a, FWR3b, FWR4b | CXXA |

It was observed that, irrespective of the FWR version used, humanized mAbs having the C-X-X-F motif showed high aggregation (after decapping) and poor conjugation (Table 9). Conversely, 4 of the 5 mAb variants containing C-X-X-A motif, and irrespective of the FWR version used, showed high percent of conjugation efficiency (≥80%) and low aggregation (after decapping) of <18% (Table 9). zu155D5-4 is an outlier that exhibited a low percentage of conjugation efficiency and a high aggregation after decap- TABLE 9-continued Aggregation levels and conjugation efficiency of xi155D5 versus different variants of zu155D5

| mAb name | % Aggregates ProA | Decapped | % Decapped | % Conjugated | aa 80-83 |
|---|---|---|---|---|---|
| zu155D5-6 | 1.60% | 6.70%  | 100.00% | 88.20% | CXXA |
| zu155D5-7 | 4.90% | 12.30% | 100.00% | 89.30% | CXXA |

In bold are indicated the C-X-X-F motif and values not meeting the conjugation specifications.

It is desirable to achieve aggregation of 25% or less as a starting point of downstream process optimization, whereby further optimization of fermentation parameters, purification conditions and drug formulations can achieve a more desirable aggregation level of 5% or less. It is also desirable to achieve 70% or higher conjugation efficiency to minimize product waste, cost of goods, and maximize product homogeneity. Henceforth, the investigation focused on meeting and exceeding these specifications by extrapolating rules to apply to the humanization methods of rabbit mAbs.

155D5-1 was generated by following a standard practice, which involves utilizing the human germline sequences most homologous to the parent sequence. Because of this practice, the human Vκ subfamily IGKV1-5 was used for humanizing 155D5, having a percent identity of 70.5% (data not shown) and containing Phe83. The alternative Vκ subfamilies, which have similar percent of identity (data not shown), also contained Phe83 (FIG. 8). As this residue appeared to negatively influence Cys80 conjugation efficiency and cause high aggregation, the presence or absence of Phe83 in other human Vκ families was evaluated, despite the fact that the highest identity found in these Vκ families was lower (68.4%) and therefore they would not typically be used for humanizing 155D5. Since all of the human Vκ families except IGKV4, IGKV5, and IGKV7 have multiple subfamilies, all subfamilies were aligned within their family (data not shown). After removal of redundant sequences, only one sequence remained for each of the IGKV-4, -5, -6, -6D, and -7 families, which could be used for humanization. For families IGKV-1, -2, and -3, the subfamily with closest homology to the consensus was chosen as the framework to humanize 155D5. A preliminary analysis indicated that while some of these Vκ families contained Phe83 others did not (and Table 10).

To study the effect of the presence or absence of Phe83 in the context of these Vκ families, the CDR regions of 155D5 were genetically grafted onto the human frameworks IGKV1-39*01, IGKV2-40*01, IGKV3-11*01, IGKV4-1*01, IGKV5-2*01, IGKV6-21*01, IGKV6D-41*01, and IGKV7-3*01. IGKV5-2*01 Asn20, which contains an N-linked glycosylation site at residues 20, and its Thr20 variant were not included in this analysis because the former could not be analyzed by mass spectrometry due to heterogeneity, and the latter did not express well. IGKV7-3*01 Asn81 was not included in the analysis because it could not be analyzed by mass spectrometry. However, the variant IGKV7-3*01-Glu81 was included in the analysis. The following results were obtained from the analysis (Table 10):

1. The humanized mAb with the huIGKV1-39 sequence and containing Phe83 showed an aggregation increase from 0 to 26% after decapping; the conjugation efficiency was borderline acceptable (68%) but aggregation being >25% was not;
2. The humanized mAb with the huIGKV2-40 sequence contained a human germline Val83; this mAb showed aggregation <25% after decapping (11%) and conjugation efficiency >70% (92%). These parameters were acceptable, suggesting that the human germline Val83 is conducive to pairing with Cys80 to allow Cys80 conjugation;
3. The humanized mAb with the huIGKV3-11 sequence contained a human germline Phe83; while aggregation was below 25%, conjugation efficiency was 55%, therefore not meeting the criterion of >70%;
4. The humanized mAb with the huIGKV4-1 sequence contained a human germline Val83; this mAb showed aggregation <25% after decapping (6%) and conjugation efficiency >70% (82%). These parameters were acceptable, suggesting that the human Val83 is conducive to pairing with Cys80 to allow Cys80 conjugation, as seen with the huIGKV2-40 sequence;
5. The humanized mAbs with the huIGKV6-21 or huIGKV6D-41 sequences both contained a human germline Ala83; these mAbs showed aggregation <25% after decapping and conjugation efficiency >70%. These parameters were acceptable, suggesting that the human germline Ala83 is conducive to pairing with Cys80 to allow Cys80 conjugation, as seen with the xi155D5 sequence; and
6. The humanized mAb with the huIGKV7-3-Glu81 sequence contain a human germline Thr83; this mAb showed aggregation <25% after decapping (6%) and conjugation efficiency close to 100%. These parameters were acceptable, suggesting that the human germline Thr83 is conducive to pairing with Cys80 to allow Cys80 conjugation.

TABLE 10

Aggregation levels and conjugation efficiency of different variants of zu155D5 generated by using various human Vκ subfamilies

| humanized mAb | aa 80-83 | % Aggregates ProA | Decapped | % Decapped | % Conjugated |
|---|---|---|---|---|---|
| zu155D5-1 (huVK1-5) | CXXF | 1.10% | 70.10% | 100.00% | 0.00% |
| zu155D5-huVK1-39 | CXXF | 0.00% | 26.00% | 100.00% | 68.70% |
| zu155D5-huVK2-40 | CXXV | 9.60% | 11.70% | 100.00% | 92.70% |
| zu155D5-huVK3-11 | CXXF | 6.20% | 16.50% | 100.00% | 55.00% |
| zu155D5-huVK4-1 | CXXV | 0.00% | 6.30% | 100.00% | 82.70% |
| zu155D5-huVK6-21 | CXXA | 13.80% | 15.00% | 61.70% | 81.50% |
| zu155D5-huVK6D-41 | CXXA | 9.30% | 11.90% | 62.00% | 79.80% |
| zu155D5-huVK7-3-Glu81 | CXXT | 0.00% | 6.30% | 100.00% | 100.00% |

In bold are indicated the C-X-X-F motif and values not meeting the conjugation specifications.

These results support the discovery that position 83 influences Cys80 conjugation efficiency negatively when occupied by phenylalanine, and indicate that, in addition to alanine, valine and threonine can substitute Phe83 to allow Cys80 conjugation.

To confirm that, in the context of other mAbs, Phe83 is involved with causing high aggregation after decapping and is not conducive to conjugation on Cys80, humanized mAb variants of 1E4 (anti-CA9), 166B3 (anti-CA9), and 33O11 (anti-MSLN) were generated containing either C-X-X-F or C-X-X-A.

Monoclonal antibody variants having C-X-X-F motif met the conjugation specifications but not the aggregation specifications, whereas all humanized mAb variants having C-X-X-A showed aggregation less than 25% and conjugation efficiency greater than 70% (Tables 11 and 12). These studies demonstrate that the C-X-X-(non) F or K is a motif that allows meeting conjugation specifications.

TABLE 11

Aggregation levels and conjugation efficiency of different variants of humanized mAbs comparing C-X-X-F versus C-X-X-A and C-X-X-I motifs

| humanized mAb | % Aggregates ProA | Decapped | % Decapped | % Conjugated |
|---|---|---|---|---|
| zu155D5-CXXF (zu155D5-1) | 1.10% | 70.10% | 100.00% | 0.00% |
| zu155D5-CXXA (zu155D5-3) | 0.00% | 17.30% | 100.00% | 80.10% |
| zu166B3-CXXF | 22.10% | 51.50% | 77.70% | 34.70% |
| zu166B3-CXXA | 2.30% | 6.90% | 100.00% | 89.90% |
| zu33O11-CXXF | 2.10% | 27.50% | 100.00% | 76.10% |
| zu33O11-CXXA | 1.50% | 4.30% | 100.00% | 93.20% |
| zu33O11-CXXI | 1.40% | 4.30% | 100.00% | 100.00% |

In bold are indicated the C-X-X-F motif and values not meeting the conjugation specifications.

TABLE 12

Aggregation levels and conjugation efficiency of different variants of zu1E4 mAbs comparing C-X-X-F versus C-X-X-(non)F or K motifs

| Antibody | Protein A | | Decapped | | | | fold increase aggregation |
|---|---|---|---|---|---|---|---|
| | % Aggregates | % Monomer | % Aggregates | % Monomer | % Decapping | % Conjugated | |
| 1E4-CXXG | 7.10% | 93.00% | ND* | ND* | ND* | ND* | |
| 1E4-CXXA | 13.20% | 86.80% | 21.90% | 78.10% | 100.00% | 71.00% | 1.66 |
| 1E4-CXXL | 8.30% | 91.70% | 13.10% | 86.90% | 100.00% | 88.30% | 1.59 |
| 1E4-CXXV | 12.10% | 87.90% | 18.00% | 82.00% | 100.00% | 95.60% | 1.49 |
| 1E4-CXXP | 11.60% | 88.40% | 23.30% | 76.70% | 100.00% | 87.50% | 2.01 |
| 1E4-CXXM | 10.70% | 89.30% | 17.60% | 82.40% | 100.00% | 91.10% | 1.65 |
| 1E4-CXXF | 22.10% | 77.90% | 47.20% | 52.80% | 77.70% | 43.60% | 2.14 |
| 1E4-CXXY | 7.20% | 92.80% | 16.40% | 83.70% | 100.00% | 90.90% | 2.28 |
| 1E4-CXXW | 11.50% | 88.50% | 19.50% | 80.50% | 100.00% | 89.80% | 1.7 |
| 1E4-CXXS | 9.90% | 90.10% | 14.60% | 85.40% | 100.00% | 97.20% | 1.48 |
| 1E4-CXXT | 7.10% | 92.90% | 11.70% | 88.40% | 100.00% | 97.20% | 1.64 |
| 1E4-CXXN | 7.30% | 92.70% | 13.40% | 86.70% | 100.00% | 96.60% | 1.82 |
| 1E4-CXXQ | 11.10% | 88.90% | 12.80% | 87.20% | 100.00% | 93.40% | 1.15 |
| 1E4-CXXD | 10.60% | 89.40% | 14.90% | 85.10% | 100.00% | 73.00% | 1.4 |
| 1E4-CXXE | 7.80% | 92.20% | 13.20% | 86.80% | 100.00% | 70.60% | 1.69 |
| 1E4-CXXK | 8.40% | 91.70% | 15.10% | 84.90% | 50.00% | 43.70% | 1.81 |
| 1E4-CXXR | 12.60% | 87.40% | 20.50% | 79.50% | 100.00% | 87.10% | 1.63 |
| 1E4-CXXH | 11.20% | 88.80% | 16.30% | 83.70% | 100.00% | 83.70% | 1.45 |

In bold are indicated the C-X-X-F and C-X-X-K motifs and values not meeting the aggregation or conjugation specifications.

In addition to Ala83, Val83, and Thr83, which can be found in Vκ sequences belonging to huIGKV1-7 germline subfamilies, Ile83 can also be found, albeit rarely, in the huIGKV1 germline family. Because Ala83, Val83 and Thr83 were already found conducive for Cys80 conjugation (Table 9, and Table 11), it remained to be determined whether Ile83 would be a favorable or unfavorable residue with respect to Cys80 conjugation. Hence, the humanized mAb variant of 33O11 was generated containing the Cys80-Xaa$_1$-Xa$_2$-Ile83 (also referred to as C-X-X-I or CXXI) motif, which showed aggregation less than 25% and conjugation efficiency greater than 70% (Table 11), consistent with previous C-X-X-(non)F motifs tested. This result supports the discovery that, in addition to Ala83, Val83 and Thr83, Ile83 can also substitute Phe83 to allow Cys80 conjugation while meeting conjugation specifications.

Figure 11:
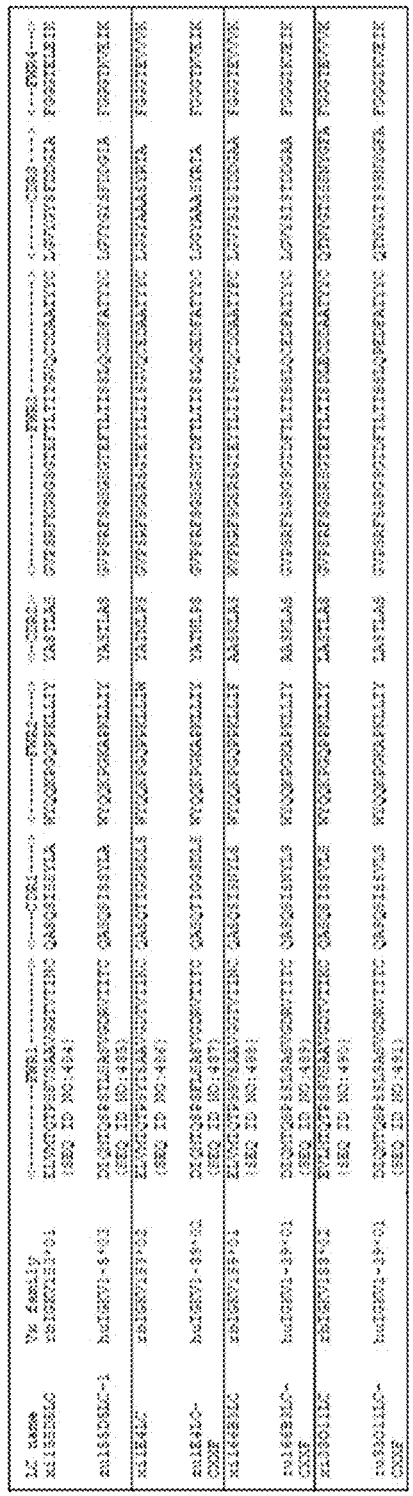
FIG. 11 illustrates exemplary humanized mAbs of 155D5, 1E4, 166B3, and 33O11 light chain sequences.

The disclosed studies indicate that, while chimerized rabbit mAbs are suitable for site-specific conjugation on Cys80 only after applying the disclosed decapping method as discussed above, humanized rabbit mAbs having the C-X-X-F motif or C-X-X-K motif are not well suited for such modifications due to high aggregation after decapping and/or low conjugation efficiency. It was hypothesized that the residues surrounding Cys80 may play a role in this phenomenon. Because the Vκ region encompasses more than 100 residues, understanding the interplay between key surrounding residues and Cys80 required the use of structural modelling paired with experimental testing. It was discovered that among the residues in close proximity to Cys80, Phe83 exerted a negative effect on Cys80 conjugation efficiency. It was also observed that all of the rabbit mAbs contained Phe83 after humanization using a classical humanization approach (FIG. 11), despite the fact that human Vκ sequences can also contain other amino acids in position 83, including alanine, threonine, valine, and isoleucine. When these Vκ families were used for humanization, it was confirmed that Phe83 and Lys83 are sufficient to endow the humanized mAb with undesirable properties, such as high aggregation and/or low conjugation efficiency, while the remaining amino acid residues (with the exception of Cys, which was not tested due to the desire to obtain a single Cys for conjugation) were conducive to Cys80 conjugation.

These results suggest that the C-X-X-F motif and C-X-X-K motif are to be avoided when conjugating at Cys80. Using a C-X-X-(not)F or K motif, for example the motif C-X-X-A, C-X-X-T, C-X-X-V, and C-X-X-I through the substitution of Phe83, chimerized as well as humanized mAbs were generated that met the desired conjugation specifications.

Affinity of xi155D5 and the Humanized Variants xi155D5 and the humanized variants were purified by standard protein A chromatography or the decapping method, and their affinity was analyzed using BIAcore (Table 13). There was less than a 2-fold difference in the KD between chimeric and humanized 155D5, and little difference between the samples purified by the two different methods.

TABLE 13

BIAcore analysis of antigen binding of humanized and chimeric 155D5 mAbs

| Antibodies | ProA | | | Decapped | | |
|---|---|---|---|---|---|---|
| | ka (1/Ms) | kd (1/s) | KD (M) | ka (1/Ms) | kd (1/s) | Kd (M) |
| xi155D5 | 4.58E+05 | 1.49E−04 | 3.24E−10 | | | |
| zu155D5-1 | 1.01E+06 | 4.95E−04 | 4.98E−10 | 7.70E+05 | 3.55E−04 | 5.00E−10 |
| zu155D5-2 | 6.63E+05 | 3.76E−04 | 5.69E−10 | 4.58E+05 | 2.70E−04 | 5.89E−10 |

TABLE 13-continued

BIAcore analysis of antigen binding of humanized and chimeric 155D5 mAbs

| | ProA | | | Decapped | | |
|---|---|---|---|---|---|---|
| Antibodies | ka (1/Ms) | kd (1/s) | KD (M) | ka (1/Ms) | kd (1/s) | Kd (M) |
| zu155D5-3 | 7.27E+05 | 4.01E−04 | 5.62E−10 | 7.26E+05 | 3.51E−04 | 5.07E−10 |
| zu155D5-4 | 5.77E+05 | 3.82E−04 | 6.64E−10 | 6.41E+05 | 3.78E−04 | 5.90E−10 |
| zu155D5-5 | 5.87E+05 | 3.73E−04 | 6.39E−10 | 5.72E+05 | 2.73E−04 | 4.78E−10 |
| zu155D5-6 | 8.98E+05 | 4.77E−04 | 5.33E−10 | 5.58E+05 | 3.19E−04 | 5.68E−10 |
| zu155D5-7 | 8.69E+05 | 4.58E−04 | 5.34E−10 | 4.85E+05 | 3.19E−04 | 6.80E−10 |

Example 3—Generation of Mesothelin-Auristatin Conjugated Monoclonal Antibodies

Mesothelin (MSLN) is a cell-surface protein expressed in cancer, including certain ovarian, lung, pancreatic, and mesothelioma tumors. To improve the potency of agents targeting MSLN, de novo anti-MSLN rabbit monoclonal antibodies (mAbs) were developed and subsequently engineered and conjugated with auristatin F (AuF) at Cys80 to generate a panel of MSLN-AuF conjugated mAbs.

Generation and Characterization of Rabbit Anti-MSLN mAbs

Figure 12:
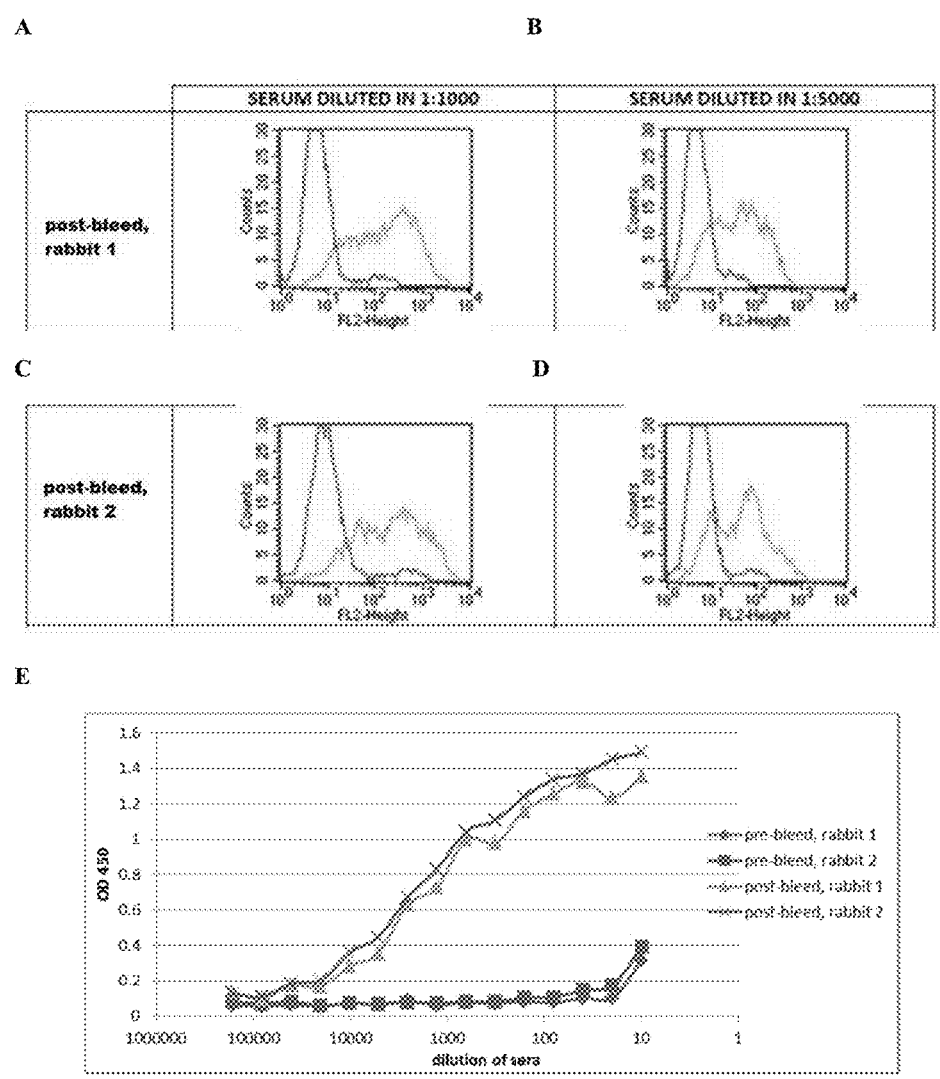
FIG. 12 represents (A-D) flow cytometry screening of sera from immunized animals and (E) ELISA screening of sera from immunized animals. (A-D) Cells were incubated with post-immunization bleed sera at the indicated dilutions (A: post bleed, rabbit 1 serum diluted in 1:1000; B: post bleed, rabbit 1 serum diluted in 1:5000; C: post bleed, rabbit 2 serum diluted in 1:1000; and D: post bleed, rabbit 2 serum diluted in 1:5000). Signal from cells transiently expressing human MSLN (+MSLN) and that from MSLN-negative cells (−MSLN) are shown. (E) ELISA plates were coated with 1 μg/mL of human MSLN at 4° C. overnight and blocked using 1% BSA in PBS with 0.01% Tween (PBST) for 2 hours at room temperature. After blocking buffer was removed, serial diluted samples of pre- and post-immunization bleeds were added to wells. The plate was incubated for 2 hours at room temperature and then washed three times with PBST. HRP-conjugated goat anti-rabbit antibody was added in blocking buffer and incubated for 1 hour. The plate was washed three times and TMB substrate was added. The reaction was stopped and absorbance was measured at 450 nm.

New Zealand rabbits (*Oryctolagus cuniculus*) were immunized at Aldevron (Germany) using plasmid DNA encoding the human MSLN protein ("MSLN"). On day 52, animal sera were collected and later tested for MSLN binding by flow cytometry using mammalian cells transiently expressing human MSLN. FIG. 12-D shows that sera from both animals contained MSLN-binding antibodies. An ELISA assay later confirmed this result (FIG. 12E). Then, animals were sacrificed and PBMCs from blood as well as the lymphocytes from spleens and lymph nodes were collected and cryopreserved.

The lymphocytes from lymph nodes previously frozen were recovered and treated with DNase I and Pokeweed mitogen for one hour at 37° C./5% $CO_2$. Cells were counted and seeded at 5 cells/40 μL/well in complete IMDM medium containing 10% fetal bovine serum (FBS) and cytokines (IL-2 and IL-21 at 10.5 ng/mL) in 384-well plates pre-seeded with CHO-K1 cells expressing CD154 as feeder cells. Cells were fed again by adding 20 μL/well of the same medium as above after one week. Two weeks after seeding, B cell culture supernatants were collected for screening to identify clones with specific reactivity to human MSLN. The plates with cells were frozen and stored at −80° C. for future RNA isolation and gene amplification. B cell culture supernatants were first screened for IgG production by rabbit IgG FRET assay. IgG-producing clones (5,775) were selected and screened by using ELISA to determine binding to human MSLN (1$^{st}$ screening). Some of the anti-MSLN-reactive clones were re-tested (2$^{nd}$ screening) for reactivity to MSLN but not to a control antigen (human CD73). Five mAbs were selected and are shown in Table 14.

TABLE 14

Clones with specific reactivity to human MSLN

| | 1$^{st}$ screening Reading (Optical Density) | | 2$^{nd}$ screening Reading (Optical Density) | |
|---|---|---|---|---|
| rabbit mAb name | IgG production | Anti-MSLN reactivity | Anti-MSLN reactivity | Anti-CD73 reactivity |
| 33O11 | 0.524 | 0.2821 | 0.5039 | 0.0818 |
| 178F16 | 1.534 | 0.9661 | 1.879 | 0.1411 |
| 237N18 | 0.586 | 0.362 | 0.6683 | 0.0918 |
| 324O5 | 2.207 | 1.3982 | 2.218 | 0.0801 |
| 383I18 | 0.586 | 0.249 | 0.2965 | 0.0744 |

The plates containing the selected mAbs were thawed, and the B cells were lysed to isolate RNAs using RNAqueous Kit (Ambion). The RNAs were used to set up RT-PCR reactions to amplify the antibody variable regions. The resulting DNAs were sequenced, and primers were designed for compatibility with the InFusion HD® cloning system as described by the manufacturer (Clontech, Mountain View, Calif.). The variable region PCR fragments were cloned into an expression plasmid containing either a human gamma or kappa constant region. These plasmids were transfected using the FreeStyle 293 expression system (Thermo Fisher Scientific) to produce mAbs as described elsewhere herein.

Generation and Characterization of MSLN-AuF Cys80 Conjugated mAbs

Chimerized mAbs were generated as disclosed in Example 2, wherein xi33O11 is one of the five anti-MSLN mAbs and the other four mAbs were chimerized following the same method. Hence, these anti-MSLN mAbs contain unpaired Cys80, specifically, the motif C-X-X-A. They are herein referred to as xi324O5, xi178F16, xi237N18, xi33O11, and xi383I18.

After their production, the selected five chimerized mAbs were conjugated to auristatin F (AuF) according to the following methods to generate MSLN-AuF Cys80 conjugated mAbs.

Antibody Purification with "Decapping":

Decapping rabbit/human mAbs is a step required for conjugation to Cys80. Using an ÄKTA Explorer (GE Healthcare), a protein A column (GE Healthcare) was equilibrated with 10 CV of 20 mM sodium phosphate, 10 mM EDTA, pH 7.2. The sample was then loaded, followed by washing unbound material with 10 CV of equilibration buffer. The column was washed with 16 CV of 20 mM sodium phosphate, 10 mM EDTA, 5 mM cysteine, pH 7.2 at 0.5 mL/min for 16 h. The column was then washed with 60 CV of 20 mM Tris, pH 7.5 at 0.5 mL/min for 60 h. The sample was eluted using 5 CV of 0.1 M Glycine pH 2.9. The fractions containing the mAb were pooled and dialyzed in DPBS using a MWCO 20K Slide-A-Lyzer (Thermo Fisher Scientific). Protein recovery was determined by BCA assay.

Auristatin F Conjugation:

Purified and decapped chimerized MSLN-mAbs containing the C-X-X-A motif were incubated with maleimido-PEG2-auristatin F (mal-PEG2-AuF) (structure shown below), diluted from a 10 mM stock in DMSO (Concortis Biosystems, San Diego, Calif.) at a 5:1 molar ratio (AuF:MAb) at a final antibody concentration of 5 mg/mL in 1×PBS. Conjugation was performed for 2 hr at 22° C. Unreacted mal-PEG2-AuF was removed by desalting purification on an AKTA FPLC fitted with a 26/10 desalting column (GE Healthcare) using 1×PBS as running buffer. Antibody-containing fractions were pooled and protein concentration determined by BCA assay.

Maleimido-PEG2-Auristatin F:

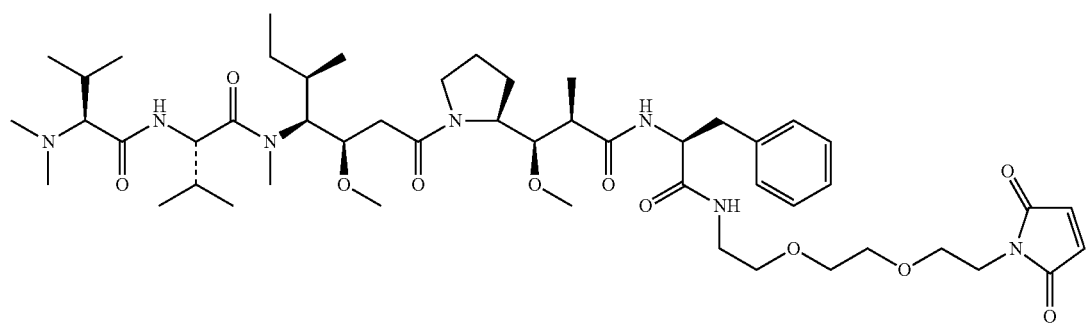 [SMILES: CC[C@@H](C)[C@@H]([C@@H](CC(=O)N1CCC[C@H]1[C@H](OC)[C@@H](C)C(=O)N[C@@H](Cc1ccccc1)C(=O)NCCOCCOCCN1C(=O)C=CC1=O)OC)N(C)C(=O)[C@@H](NC(=O)[C@H](C(C)C)N(C)C)C(C)C]

Figure 13:
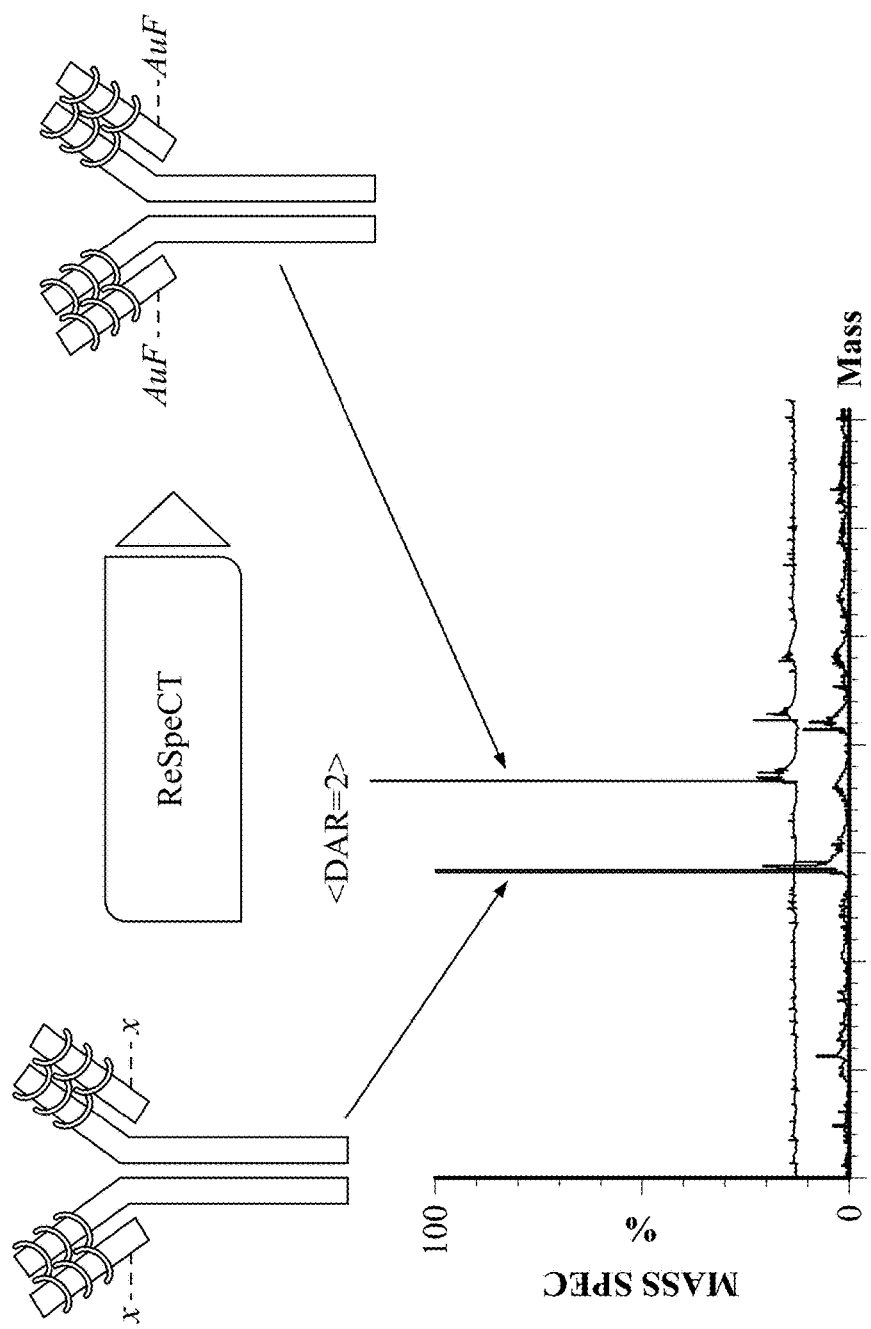
FIG. 13 represents an exemplary protein peak of deconvoluted mass spectrometry analysis before and after conjugation of maleimido-PEG2-auristatin F (AuF) to Cys80.

UPLC/ESI-MS Analysis:

Samples were reduced by adding DTT to a final concentration of 20 mM, followed by incubation at 60° C. for 3 min. Samples were then analyzed using a Waters Acquity UPLC and Q-Tof Premier mass spectrometer. Samples (0.5-2 μg each) were injected onto a MassPrep micro desalting column at 65° C., eluted from the column with a 5 min equilibration in 95% of mobile phase A, a 10 min gradient (5-90% B), and a 10 min re-equilibration in 95% of mobile phase A, at 0.05 mL/min. Mobile phase A was 0.1% formic acid in water. Mobile phase B was 0.1% formic acid in acetonitrile. The Q-Tof mass spectrometer was run in positive ion, V-mode with detection in the range of 500-4000 m/z. The source parameters were as follows: capillary voltage, 2.25 kV (intact antibody)-2.50 kV (reduced antibody); sampling cone voltage, 65.0 V (intact antibody) or 50.0 V (reduced antibody); source temperature, 100° C.; desolvation temperature, 250° C.; desolvation gas flow, 550 L/hr. The protein peak was deconvoluted using the MassLynx MaxEnt 1 function. A representative analysis is shown in FIG. 13. Typically, ≥90% of conjugated mAbs had an antibody-to-functional agent ratio of 2, signifying that each chimerized anti-MSLN mAbs carried an AuF molecule conjugated to each of Cys80$^1$ and Cys80$^2$.

In Vitro Cytotoxicity

A431-MSLN are cells derived from A431 cells (ATCC® CRL-1555™) that stably express human MSLN. A431-MSLN cells were sub-cultured and seeded in 96-well plates at 10,000 cells/well/100 μL in RPMI medium containing 10% FBS and incubated at 37° C., 5% $CO_2$ for 16 hour. MSLN-AuF Cys80 conjugated mAbs were serially diluted 1:4 in 2 mL deep-well dilution plates. Diluted compounds (100 μL) were added to the cell plates, with final concentrations ranging 0.28-75 μg/mL. Mal-PEG2-AuF was used at an equimolar concentration of the conjugated mAbs. For example, 10 μg/mL of MSLN-AuF Cys80 conjugated mAb (DAR=2) equates to 0.14 μg/mL of mal-PEG2-AuF. Plates were incubated at 37° C., 5% $CO_2$ for an additional 48 hours. Medium was discarded, plates were washed once with 200 μL DPBS, stained with 50 μL of 0.2% crystal violet solution at 22° C. for 15 minutes, and then washed extensively with tap water. Plates were air-dried, and crystal violet was dissolved with 200 μL of 1% SDS solution. Colorimetric optical density was determined at 570 nm. Excel was used to extrapolate cell number from optical densities and GraphPad Prism 6 was used to plot the percent cytotoxicity.

When MSLN-negative A431 cells were treated with MSLN-AuF Cys80 conjugated mAbs, no significant cytotoxicity was observed, while mal-PEG2-AuF was cytotoxic only at the highest concentration tested (FIG. 14A). When MSLN-positive A431-MSLN cells were treated with MSLN-AuF Cys80 conjugated mAbs, significant cytotoxicity was observed. Based on the dose-response curves (FIG. 14B), MSLN-AuF Cys80 conjugated mAbs could be categorized into 2 groups: Medium cytotoxicity—xi324O5-AuF, and xi178F16-AuF; and High cytotoxicity—xi237N18-AuF, xi33O11-AuF, and xi383I18-AuF.

In Vivo Evaluation—Initial Selection of MSLN-AuF Cys80 Conjugated mAbs

The in vivo efficacy of the MSLN-AuF Cys80 conjugated mAbs was tested against tumor expressing MSLN, with the objective of selecting a few compounds with high efficacy and low toxicity.

The A431-MSLN cells were propagated in cell culture, suspended in serum-free growth medium, mixed 1:1 with Matrigel™, and 5 million cells/0.2 mL/mouse were implanted subcutaneously (s.c.) into athymic NCr nu/nu mice. Tumor volume was determined by caliper measurements (mm) and using the formula for an ellipsoid sphere: Length×Width$^2$/2=Volume (mm$^3$). When tumor volume ranged 100-250 mm$^3$, mice were randomized into treatment groups. The animal body weights and tumor size were recorded twice weekly. The overall design of this study is summarized in Table 15. The MSLN-AuF Cys80 conjugated mAbs were administered intravenously (i.v.) Q7D starting on randomization day (day 1), two doses total.

TABLE 15

Study design

| group | # mice | treatment | Dose (mg/kg) | Regimen |
|---|---|---|---|---|
| 1 | 8 | saline | 0 | Q7D × 2 |
| 2 | 8 | xi33O11-AuF | 10 | Q7D × 2 |
| 3 | 8 | xi324O5-AuF | 10 | Q7D × 2 |

TABLE 15-continued

Study design

| group | # mice | treatment | Dose (mg/kg) | Regimen |
|---|---|---|---|---|
| 4 | 8 | xi178F16-AuF | 10 | Q7D × 2 |
| 5 | 8 | xi237N18-AuF | 10 | Q7D × 2 |
| 6 | 8 | xi383I18-AuF | 10 | Q7D × 2 |
| 7 | 8 | mal-PEG2-AuF | 10 | Q7D × 2 |

Figure 15:
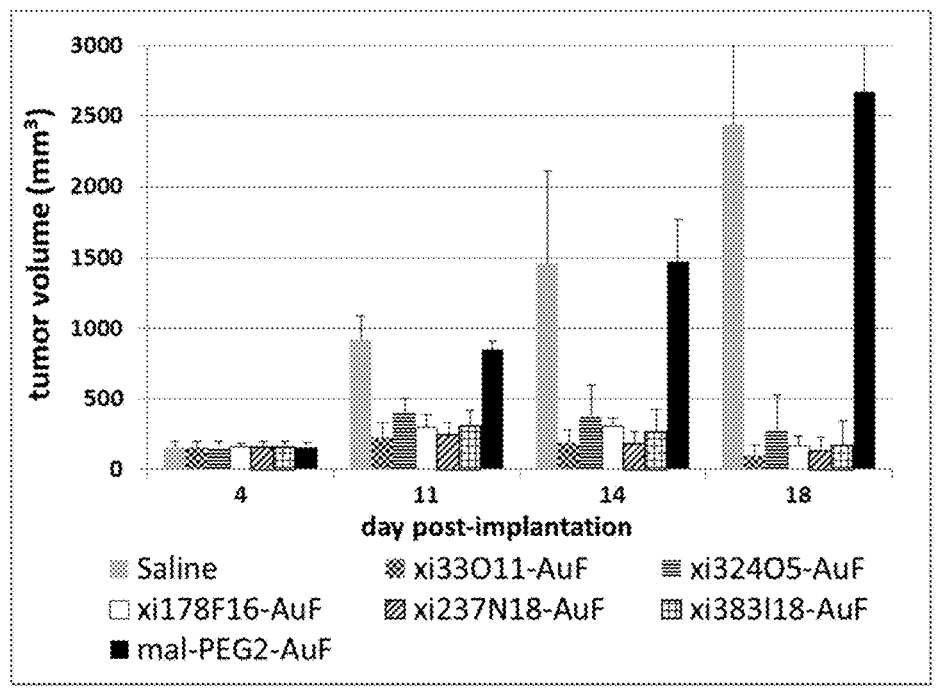
FIG. 15 represents the average tumor volumes among different treatment groups.

FIG. 15 shows the average tumor volumes among different treatment groups, up to day 18 post-implantation, when 3 of 8 animals had to be euthanized in the saline-treated group due to high tumor burden and/or tumor ulceration. Day 4 post-implantation corresponds to the day when mice were randomized into different treatment groups, with average tumor volume ranging 157-160 mm$^3$ across all groups. On this day, the first dose of MSLN-AuF Cys80 conjugated mAbs was administered followed by a second dose on day 11.

All MSLN-AuF Cys80 conjugated mAbs showed anti-tumor response, as evidenced by the fact that the tumor volume on day 18 was 20% or less compared to the saline-treated group (Table 16). In contrast, mal-PEG2-AuF showed no anti-tumor response.

TABLE 16

Percent of tumor volume vs. saline group

| Treatment | % tumor volume vs. saline group | Number of on-study animals on day 18 |
|---|---|---|
| Saline | 100% | 8 |
| xi33O11-AuF | 4% | 8 |
| xi324O5-AuF | 11% | 6 |
| xi178F16-AuF | 7% | 6 |
| xi237N18-AuF | 6% | 6 |
| xi383I18-AuF | 7% | 6 |
| mal-PEG2-AuF | 109% | 7 |

Toxicity was also evaluated by observing any body weight loss on day 18 (based on average weight of on-study animals in each group) compared to day 4, as well as by observing any dead or moribund animals (Table 17). In the xi324O5-AuF-treated group, a body weight loss of 11% was observed in surviving animals as well as two dead/moribund animals. In the xi178F16-AuF, xi237N18-AuF, and xi383I18-AuF-treated groups, no significant body loss was observed, but one or two dead/moribund animals were observed. All the other treatment groups showed neither body weight loss nor dead/moribund animals.

TABLE 17

Assessment of gross toxicity

| Treatment | % body weight change on day 18 vs. day 4 | Number of mice dead or moribund on day 18 |
|---|---|---|
| Saline | 106% | 0 |
| xi33O11-AuF | 102% | 0 |
| xi324O5-AuF | 89% | 2 |
| xi178F16-AuF | 104% | 1 |
| xi237N18-AuF | 96% | 2 |
| xi383I18-AuF | 107% | 1 |
| mal-PEG2-AuF | 111% | 0 |

Based on the anti-tumor responses as well as the minimal toxicity, mAbs xi33O11-AuF and xi237N18-AuF were chosen for further evaluation.

Assessment of Target Specificity of Anti-Tumor Activity Mediated by MSLN-AuF Cys80 Conjugated mAbs The method used for this study was the same as described above (In vivo evaluation—Initial selection of MSLN-AuF Cys80 conjugated mAbs). In addition to A431-MSLN cells, which were implanted on the left flank of each mouse on Day 4, MSLN-negative A431 cells were implanted in the same mouse on the opposite (right) flank on Day 1. The former cells grow tumors faster than the latter, and hence were implanted 3 days later so that the first dose of test drug were given when the tumor in both flanks were similar in volume. The overall design of this study is summarized in Table 18.

TABLE 18

Study Design

| group | # mice | treatment | Dose (mg/kg) | Regimen |
|---|---|---|---|---|
| 1 | 8 | saline | 0 | Q7D × 2 |
| 2 | 8 | xi33O11-AuF | 10 | Q7D × 2 |
| 3 | 8 | xi237N18-AuF | 10 | Q7D × 2 |
| 4 | 8 | xi1-55-2-AuF | 10 | Q7D × 2 |
| 5 | 8 | mal-PEG2-AuF | 0.14 | Q7D × 2 |

MSLN-Positive Tumors:

FIG. 16A shows the average tumor volumes among different treatment groups, up to day 18 post-implantation, when 4 of 8 animals had to be euthanized in the saline-treated group due to high tumor burden and/or tumor ulceration. Day 4 post-implantation corresponds to the day when mice were randomized into different treatment groups, with average A431-MSLN tumor volume ranging 169-178 mm$^3$ across all groups. On this day, the first dose of MSLN-AuF Cys80 conjugated mAbs was administered followed by a second dose on day 11.

xi33O11-AuF mediated anti-tumor responses that reduced tumor volume on day 18 to 12% compared to the saline-treated group (Table 19). xi237N18-AuF mediated anti-tumor responses that reduced tumor volume to 24% compared to the saline-treated group (Table 19). An unpaired, two-tailed t test indicated a p value of 0.00039 and 0.00197, respectively, suggesting that these anti-tumor responses versus saline-treated group were statistically significant. In contrast, mal-PEG2-AuF or xi1-55-2-AuF, which targets endosialin/TEM1, showed no significant anti-tumor responses.

TABLE 19

Percent of A431-MSLN tumor volume vs. saline group

| Treatment | % Tumor Volume on Day 18 vs. Saline Group | Number of Mice on Study on Day 18 |
|---|---|---|
| Saline | 100% | 6 |
| xi33O11-AuF | 12% | 5 |
| xi237N18-AuF | 24% | 6 |
| xi1-55-2-AuF | 108% | 5 |
| mal-PEG2-AuF | 104% | 8 |

MSLN-Negative Tumors:

FIG. 16B shows the average tumor volumes among different treatment groups, up to day 21 post-implantation;

this day corresponds to Day 18 of A431-MSLN post-implantation, as described above, and Day 7 post-implantation corresponds to the day when mice were randomized into different treatment groups, with average A431 tumor volume ranging 174-184 mm$^3$ across all groups. xi33O11-AuF mediated anti-tumor responses that reduced tumor volume on day 21 to 78% compared to the saline-treated group (Table 20). xi237N18-AuF Cys80 conjugated mAb mediated anti-tumor responses that reduced tumor volume on day 21 to 64% compared to the saline-treated group (Table 20). An unpaired, two-tailed t test indicated a p value of 0.317 and 0.091, respectively, suggesting that these anti-tumor responses versus saline-treated group were not statistically significant. These responses were similar to those observed with mal-PEG2-AuF or xi1-55-2-AuF.

TABLE 20

Percent of A431 (MSLN-negative) tumor volume vs. saline group

| Treatment | % Tumor Volume on Day 21 vs. Saline Group | Number of Mice on Study on Day 21 |
|---|---|---|
| Saline | 100% | 6 |
| xi33O11-AuF | 78% | 5 |
| xi237N18-AuF | 64% | 6 |
| xi1-55-2-AUF | 76% | 5 |
| mal-PEG2-AuF | 78% | 8 |

Toxicity was also evaluated by observing any body weight loss on Day 21 post implantation of A431 cells compared to Day 7, as well as by observing any dead or moribund animals (Table 21). No body weight loss ≥10% was observed in any of the treatment groups. Two deaths were observed in both xi33O11-AuF and xi237N18-AuF-treated group.

TABLE 21

Assessment of gross toxicity

| Treatment | % Body Weight Change on Day 21 vs. Day 7 | Number of Mice Dead or Moribund on Day 21 |
|---|---|---|
| Saline | 100% | 0 |
| xi33O11-AuF | 97% | 2 |
| xi237N18-AuF | 92% | 2 |
| xi1-55-2-AUF | 107% | 0 |
| mal-PEG2-AuF | 103% | 0 |

Conclusion

MSLN-AuF Cys80 conjugated mAb were generated and screened based on in vitro cytotoxicity and in vivo anti-tumor activity. The in vitro cytotoxicity analysis indicated that these compounds were targeting and killing MSLN-positive but not MSLN-negative tumor cells.

All MSLN-AuF Cys80 conjugated mAbs tested had anti-tumor activity, some of which appeared to be potentially more toxic than others. The nature of this toxicity was not further characterized. It was observed that both the MSLN-AuF Cys80 conjugated mAbs tested in vivo could target MSLN-positive tumors and inhibit their growth, whereas no significant effect was observed against MSLN-negative tumors in the opposite flank. While the toxicity profile of xi237N18 was similar in both studies, xi33O11-AuF treatment showed no toxicity in the first study but was associated with two deaths in the second study. The nature of this toxicity was not further characterized; however, as xi33O11-AuF-treated mice still carried a large MSLN-negative tumor on the other flank and were therefore sicker than the animals in the first study, these mice may have been more sensitive to the effect of the massive tumor cell lysis against the MSLN-positive tumor.

Example 4—Generation of Antibody-Fluorescent Dye Conjugates

The xi155D5 mAb containing the C-X-X-A motif was conjugated to the 800CW dye (LI-COR Biotechnology, Lincoln, Nebr.) to generate a xi155D5-800CW Cys80 conjugated mAb having two dye molecules conjugated to Cys80$_1$ and Cys80$_2$.

Figure 17:
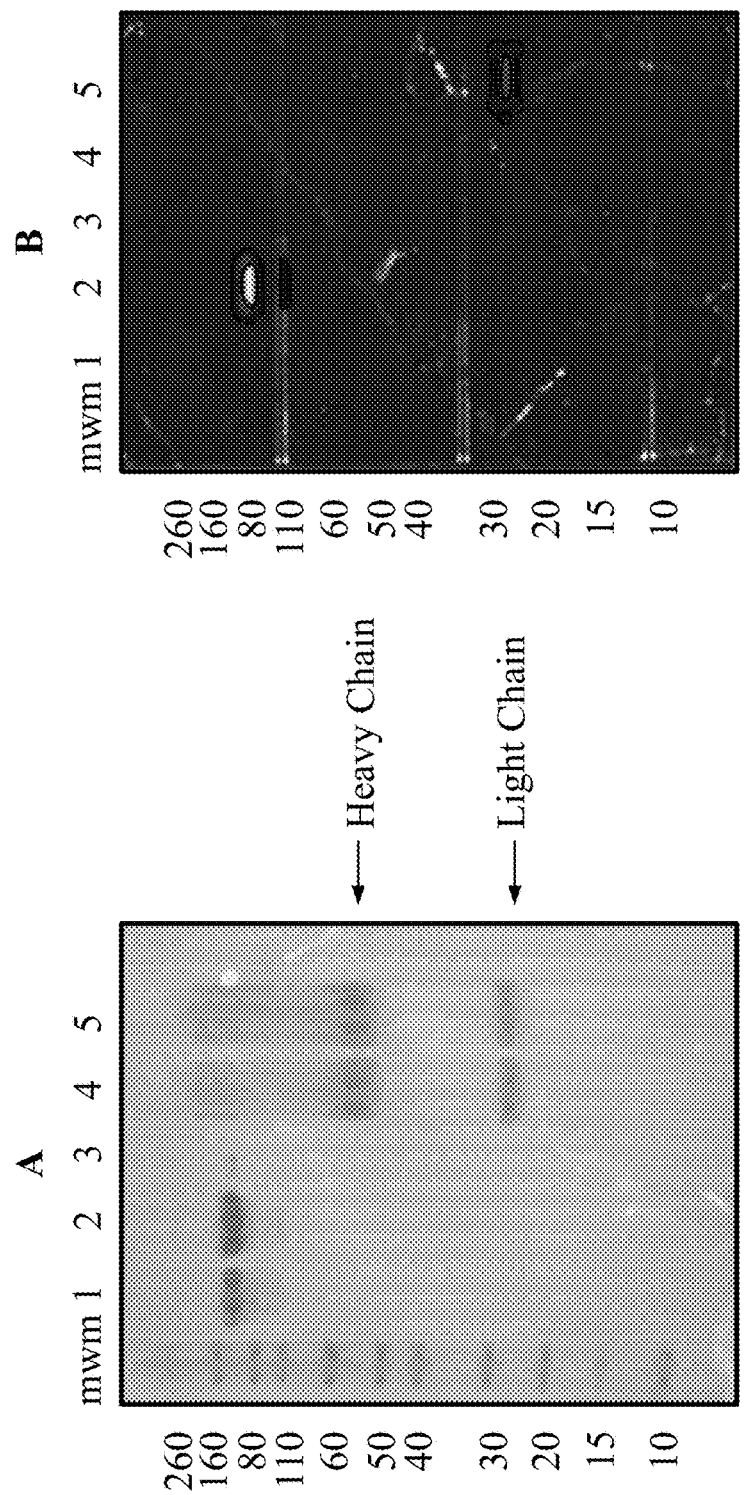
FIG. 17 represents an SDS-PAGE analysis of an exemplary xi155D5-800CW conjugated antibody. (A) mwm, molecular weight marker; lane 1, xi155D5, unconjugated, non-reduced; lane 2, xi155D5, xi155D5-800CW, non-reduced; lane 3, blank; lane 4, unconjugated xi155D5, reduced; lane 5, xi155D5, xi155D5-800CW, reduced. All lanes contain 5 μg protein, Coomassie-stained. (B) Same gel as in A, imaged on IVIS system. Results indicate that IRDye 800CW is conjugated only on the light chain of xi155D5. ELISA analysis of xi155D5-800CW indicates that full binding to CA9 is retained (data not shown).

Conjugation of 800CW onto Cys80 was carried out using maleimide-(CH$_2$)$_2$—800CW (LiCor), whereby (CH$_2$)$_2$ is an alkyl linker. Briefly, maleimide-(CH$_2$)$_2$—800CW was dissolved into 100% DMSO at a final concentration of 10 mM. Maleimide-(CH$_2$)$_2$—800CW was added to xi155D5 (5 mg/ml in 1×PBS) at a 5:1 molar ratio of dye:MAb and incubated for 4 hr at room temp. Unincorporated dye was removed by desalting on PD-10 columns (Millipore). xi155D5-800CW was further polished via size-exclusion chromatography on Superdex 75. Void volume material was pooled, aliquotted, and frozen at −80 until use. SDS-PAGE and imaging analyses of reduced xi155D5-800CW indicated that the dye was conjugated only on the light chain but not the heavy chain (FIG. 17).

Figure 18:
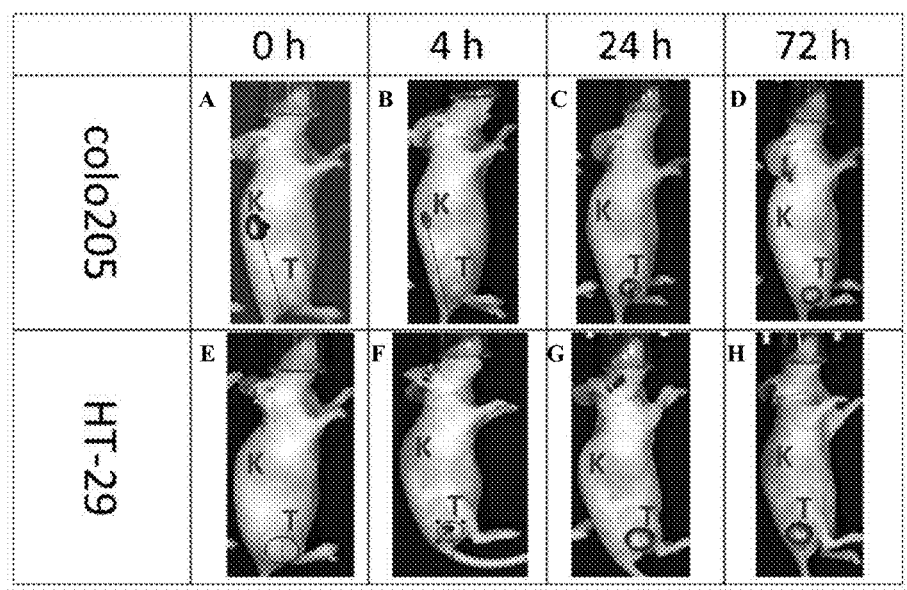
FIG. 18 illustrates the tumor-specific localization of an exemplary DyeIR 800CW-conjugated antibody (xi155D5-800CW). Human colo205 (A-D) and HT-29 (E-H) cells were grafted into nude mice, which were later injected with xi155D5-800CW. Fluorescent signal (orange-red) was monitored at various times including 0 hr (A and E), 4 hr (B and F), 24 hr (C and G) and 72 hr (D and H) (shown only 0-72 hours and right flank). Approximate location of kidney (K) and tumor (T) is shown.

NCR-nude female mice were injected with either colo205 or HT-29 human tumor cells subcutaneously to the right hind limbs. Tumor growth was monitored by caliper measurement. When the tumor volume was 200-300 mm$^3$, xi155D5-800CW was injected through the tail veils at 0.1 mg/200$4$/mouse. For monitoring xi155D5-800CW distribution via fluorescent living imaging, animals were placed into an anesthesia chamber for approximately 3-4 minutes using isofluorane/O$_2$ until the animals were unconscious. Animals were imaged using the fluorescence setting of 745 excitation and 840 emission in a IVIS® Lumina II-Kinetic instrument (PerkinElmer, Waltham, Mass.). Images of the dorsal, right, ventral, and left side were taken at different time points as indicated in FIG. 18. After each successive image the animal were allowed to regain consciousness in a recovery chamber receiving 100% oxygen flush followed by normal air.

Using the colo205 or HT-29 models, it was observed that xi155D5-800CW efficiently targeted human tumors, as demonstrated by the tumor-specific localization of its fluorescent signal (FIG. 18).

These results demonstrated that a mAb containing the C-X-X-(not)F, K, or C motif can be conjugated to a dye and that the conjugated mAb can be used to identify and monitor tumor status.

Example 5—Generation of Bivalent/Bispecific Antigen-Binding Molecules

When a mAb containing the C-X-X-(not)F, K, or C motif is digested with papain, or is recombinantly expressed as a Fab fragment, it will contain a single unpaired Cys80 since the Fab contains only one Vκ region. Using orthogonal conjugation chemistry, Cys80-containing Fabs can be used to generate chemically-conjugated bivalent/bispecific antigen-binding molecules, such as bivalent/bispecific Fab-Fab, that can be utilized for targeting two independent disease-relevant targets, including two ligands (cytokines, chemokines), two membrane receptors, or ligand/receptor combinations, to name a few.

Figure 19:
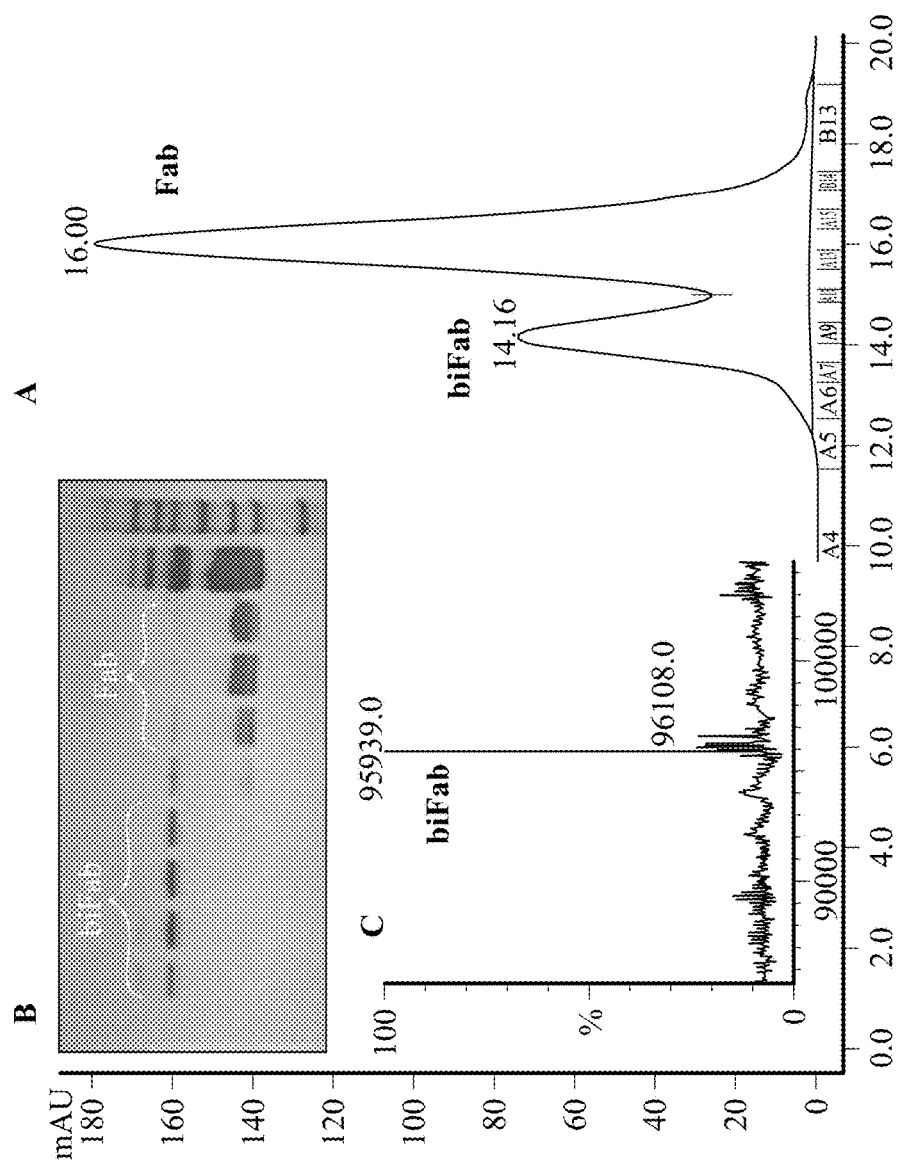
FIG. 19 illustrates an exemplary purification of a xi155D5/xi1-55-2 bivalent/bispecific antigen-binding molecule. Gel-filtration chromatography graph showing the peak corresponding to the xi155D5/xi1-55-2 bivalent/bispecific antigen-binding molecule (referred to as "biFab") (A). Fraction's molecular size was analyzed by SDS-PAGE (B). The fractions containing the xi155D5/xi1-55-2 bivalent/bispecific antigen-binding molecule (biFab) were pooled and the mass was determined by mass spectrometry (C).

As an example, Fabs were generated from xi155D5 and xi1-55-2 using limited papain digestion, followed by protein A chromatography to remove the Fc fragments and undigested mAb. Fabs were shown to be fully decapped using mass spectrometry (data not shown). Subsequently, xi155D5 and xi1-55-2 Fabs were conjugated separately using maleimido-PEG4-dibenzylcyclooctyne (DBCO) and maleimido-PEG4-azide, respectively. Unconjugated compound was removed by desalting chromatography and complete occupancy of the Cys80 sites was confirmed by mass spectrometry (data not shown). Then, xi155D5-maleimido-PEG4-DBCO and xi1-55-2-maleimido-PEG4-azide fragments were conjugated to each other via strain-promoted copper-free click chemistry by incubation in PBS at 22° C. for 16 hours. Conjugated products were fractionated by using gel-filtration chromatography (FIG. 19A) and the different species were identified by SDS-PAGE based on their expected molecular size (FIG. 19B). Fractions containing the xi155D5/xi1-55-2 bivalent/bispecific antigen-binding molecule were pooled and the xi155D5/xi1-55-2 bivalent/bispecific antigen-binding molecule identity was confirmed by mass spectrometry based on its expected mass (95,939 Da, FIG. 19C).

Figure 20:
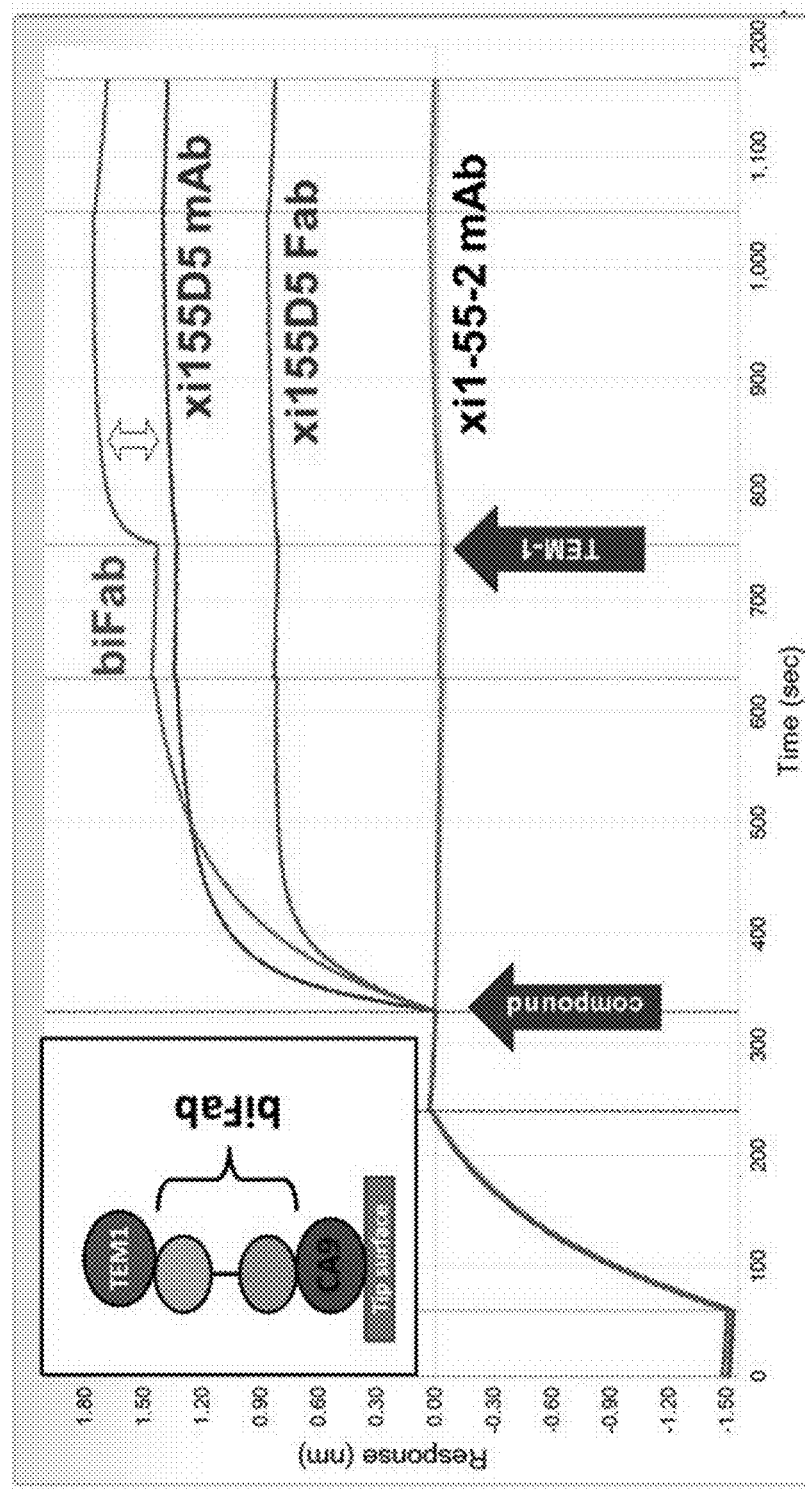
FIG. 20 illustrates the bispecificity of an exemplary xi155D5/xi1-55-2 bivalent/bispecific antigen-binding molecule (biFab). Biotinylated human CA9 was captured on streptavidin Octet biosensor tips. Compounds were added as indicated by the first arrow ("compound") and then allowed to bind. Subsequently, soluble human TEM-1 (second arrow; "TEM-1") was added and its binding to the captured CA9/compound complexes was measured. The response shift (double arrow), indicating capturing of the soluble TEM-1, was observed only with xi155D5/xi1-55-2 bivalent/bispecific antigen-binding molecule (biFab).

The bispecificity of xi155D5/xi1-55-2 bivalent/bispecific antigen-binding molecule was confirmed via biolayer inferometry (BLI) analysis using an inverse sandwich assay. This analysis demonstrated binding to immobilized human CA9 (bound by the xi155D5 Fab moiety) followed by binding of soluble TEM-1 (bound by xi1-55-2 Fab moiety) (FIG. 20). As expected, xi155D5 mAb, xi155D5 Fab, and the xi155D5/xi1-55-2 bivalent/bispecific antigen-binding molecule bound to immobilized CA9. Only the CA9-immobilized xi155D5/xi1-55-2 bivalent/bispecific antigen-binding molecule was able to bind also human endosialin/TEM-1, as demonstrated by the additional response shift observed (FIG. 20, double arrow). Surface plasmon resonance analysis demonstrated that the affinity of xi155D5/xi1-55-2 for CA9 or TEM-1 was the same or slightly reduced, respectively (Table 22).

These results demonstrate that: 1) a mAb containing the C-X-X-(not)Fcan be conjugated to polypeptides, such as an antibody fragment or a Fab; and 2) when two mAbs or Fabs, of different specificity, containing the C-X-X-(not)F are orthogonally conjugated, a bivalent/bispecific compound can be generated.

TABLE 22

Affinity of xi155D5/xi1-55-2 bivalent/bispecific antigen-binding molecule to CA9 and TEM-1

| Antibody | Flowell | Ligand | ka (1/Ms) | kd (1/s) | Rmax (RU) | KD (M) | Chi$^2$ (RU$^2$) |
|---|---|---|---|---|---|---|---|
| xi1-55-2 (Fab) | Fc3 | TEM1-Fc | 8.62E+05 | 3.29E−04 | 37.9 | 3.82E−10 | 6.42 |
|  | Fc4 | TEM1-Fc | 8.65E+05 | 3.26E−04 | 38 | 3.76E−10 | 5.89 |
| bivalent/bispecific | Fc3 | TEM1-Fc | 8.29E+05 | 2.57E−04 | 79.7 | 3.10E−10 | 6.65 |
|  | Fc4 | TEM1-Fc | 1.02E+06 | 1.89E−04 | 96.8 | 1.85E−10 | 31.6 |
| xi155D5 (Fab) | Fc3 | CA9 | 5.72E+05 | 2.19E−05 | 65.1 | 3.83E−11 | 8.86 |
|  | Fc4 | CA9 | 5.19E+05 | 2.59E−05 | 63.9 | 4.99E−11 | 8.24 |
| bivalent/bispecific | Fc3 | CA9 | 3.22E+05 | 3.91E−05 | 130.2 | 1.21E−10 | 31.3 |
|  | Fc4 | CA9 | 2.94E+05 | 4.40E−05 | 131.8 | 1.50E−10 | 24.3 |

Example 6—Generation of Antibody-Peptide Conjugates xi33O11 and xi1-55-2 mAbs containing the C-X-X-A motif were conjugated to azide-modified peptide Aβ(1-16) (SEQ ID NO:40) (Table 23).

TABLE 23

Aβ(1-16) Peptide Sequence

| Peptide name | Sequence | mass (Da) | Parent protein |
|---|---|---|---|
| Aβ(1-16) | NH2-DAEFRHDSGYEVHHQK(PEG8-N3)-COOH (SEQ ID NO: 40) | 2404 | human amyloid-beta peptide ACCESSION 1BA6_A |

Figure 21:
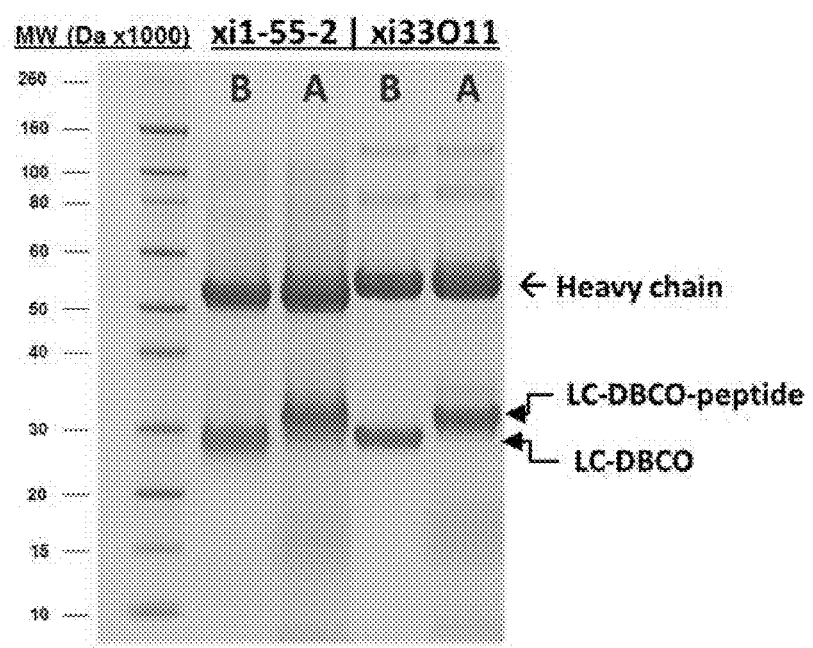
FIG. 21 illustrates an SDS-PAGE analysis of xi33O11-Aβ(1-16) Cys80 conjugated mAbs and xi1-55-2-Aβ(1-16) Cys80 conjugated mAbs. Shown are the products before (B) and after (A) conjugation of mAb-DBCO with peptide Aβ(1-16). MW, molecular weight marker. LC, light chain.
Figure 22:
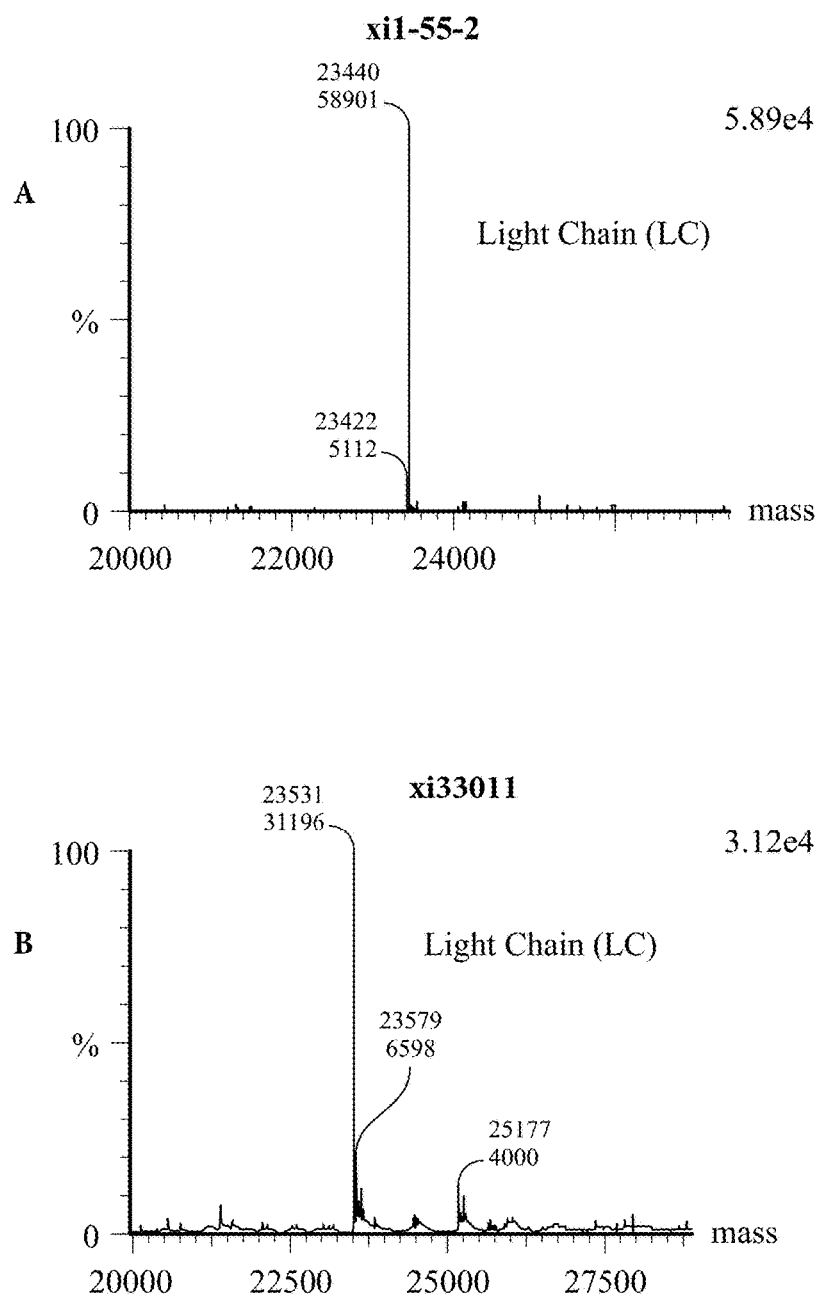
FIG. 22 illustrates an exemplary mass spectrometry analysis of xi1-55-2 and xi33O11 parental light chain (LC) (A and B, respectively), xi1-55-2-DBCO Cys80 conjugated LC and xi33O11-DBCO Cys80 conjugated LC (C and D, respectively), and xi1-55-2-Aβ(1-16) Cys80 conjugated LC and xi33O11-Aβ(1-16) Cys80 conjugated LC (E and F, respectively).
Figure 23:
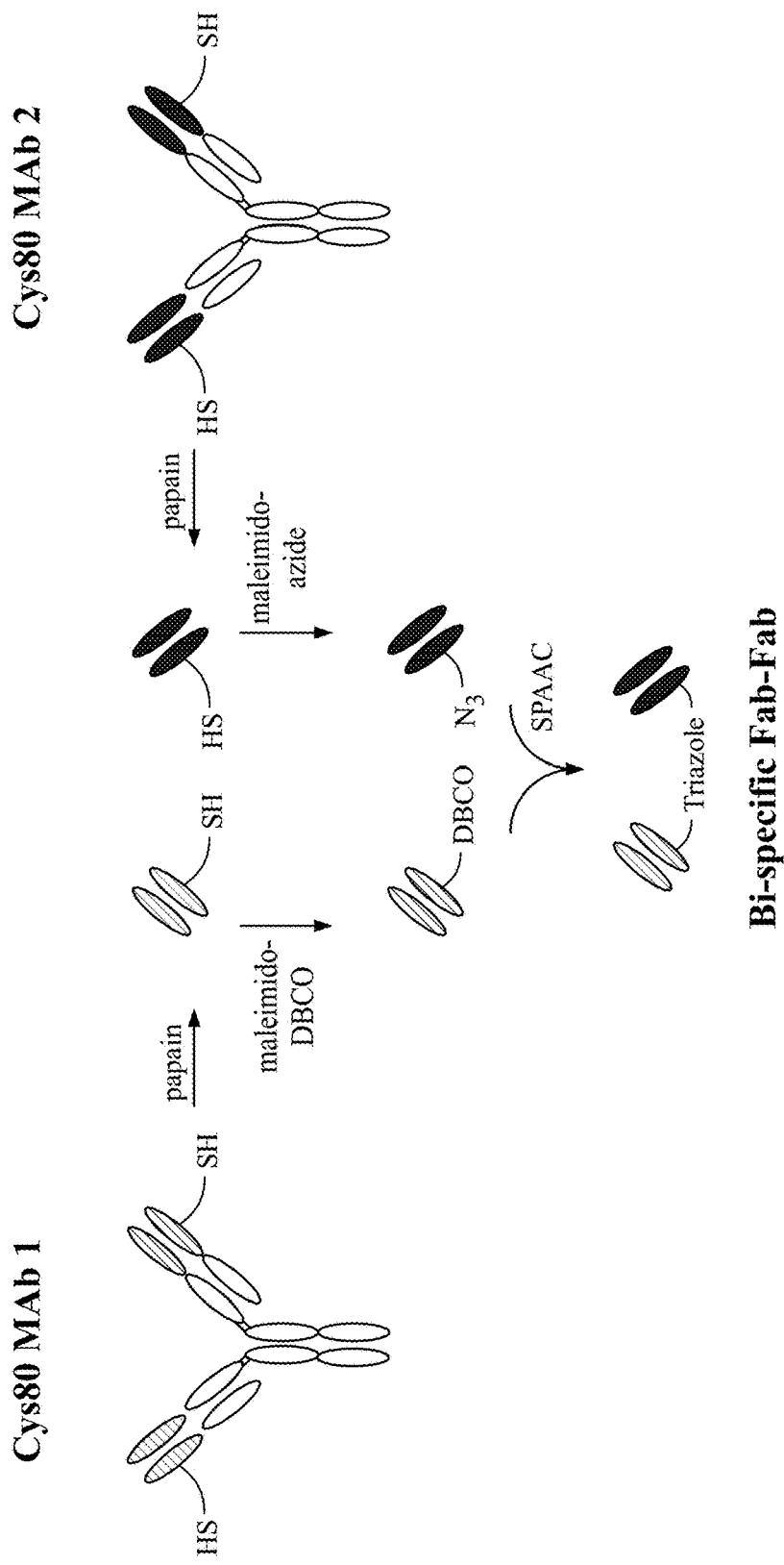
FIG. 23 illustrates an exemplary scheme for generating antigen binding molecules. Immunoglobulins derived from rabbit can be digested with papain to generate Fabs. A first Fab can be incubated with maleimido-DBCO and a second Fab can be incubated with maleimido-azide. The first and second Fabs can be combined to form a bi-specific-Fab-Fab binding molecule. SPAAC=strain promoted alkyne-azide conjugation.

Conjugation of peptide Aβ(1-16) onto Cys80 was carried out using a two-step conjugation procedure, whereby Cys80 was first conjugated with maleimido-dibenzylcyclooctyne (mal-DBCO). Azido-modified peptide Aβ(1-16) was then conjugated to the DBCO-modified mAbs using strain-promoted copper-free click chemistry. Briefly, mAb (20 mgs) was incubated with mal-DBCO (Click Chemistry Tools, cat A108) at a mal-DBCO:MAb molar ratio of 5:1 for 16 hrs at 22° C. in 1×DPBS. Unincorporated mal-DBCO was removed from conjugated mAb by desalting chromatography using a HiPrep 26/10 column with 1×DPBS as running buffer. Conjugation efficiency of 100% (no evidence of unconjugated light chain) was confirmed for both mAbs by LC-MS (FIG. 21 and Table 24). Each mAb (50 μL/each, 95 μg and 70 μg of xi1-55-2 and xi33O11, respectively) was incubated with peptide Aβ(1-16) at peptide:MAb molar ratio of 20:1 in 1×DPBS for 16 hrs at 22° C. Conjugations were analyzed by SDS-PAGE. Samples were run under reducing conditions, with 20 mM DTT as reductant and heating to 75° C. for 10 min prior to separation.

Analysis of the SDS-PAGE indicated retardation of the peptide-conjugated light chain migration accompanied by no detectable unconjugated light chain, indicating efficient conjugation (FIG. 21). No change in heavy chain mobility was observed. Conjugations were then desalted using 0.5 ml Zeba 40 k MWCO spin desalting columns (Thermo-Fisher) to remove unconjugated peptide and were analyzed by LC-MS. Mass spectrometry analysis (FIG. 22A-F) indicated that the peptide was conjugated to the light chains of xi1-55-2 and xi33O11 with efficiencies of 85%-100% (Table 24).

These results demonstrated that a mAb containing the C-X-X-(not)F, K, or C motif can be efficiently conjugated to peptides.

TABLE 24

Conjugation summary

|  | DBCO | DBCO-peptide Aβ(1-16) |
|---|---|---|
| predicted Δmass | +429 Da | +2833 Da |
| xi1-55-2 measured Δmass | +425 Da | +2829 Da |
| conjugation efficiency | 100% | 100% |
| xi33O11 measured Δmass | +432 Da | +2834 Da |
| conjugation efficiency | 100% | 85% |

TABLE 25

Monoclonal antibodies and corresponding LC and HC

| mAb name | LC name | HC name |
|---|---|---|
| 1-55-2 | 1-55-2LC | 1-55-2HC |
| xi1-55-2 | xi1-55-2LC | xi1-55-2HC |
|  | (SEQ ID NO: 108) | (SEQ ID NO: 56) |
| 155D5 | 155D5LC | 155D5HC |
| xi155D5 | xi155D5LC | xi155D5HC |
|  | (SEQ ID NO: 78) | (SEQ ID NO: 52) |
| zu155D5-1 | zu155D5LC-1 | zu155D5HC |
|  | (SEQ ID NO: 80) | (SEQ ID NO: 54) |
| zu155D5-2 | zu155D5LC-2 | zu155D5HC |
|  | (SEQ ID NO: 82) | (SEQ ID NO: 54) |
| zu155D5-3 | zu155D5LC-3 | zu155D5HC |
|  | (SEQ ID NO: 84) | (SEQ ID NO: 54) |
| zu155D5-4 | zu155D5LC-4 | zu155D5HC |
|  | (SEQ ID NO: 86) | (SEQ ID NO: 54) |
| zu155D5-5 | zu155D5LC-5 | zu155D5HC |
|  | (SEQ ID NO: 88) | (SEQ ID NO: 54) |
| zu155D5-6 | zu155D5LC-6 | zu155D5HC |
|  | (SEQ ID NO: 90) | (SEQ ID NO: 54) |
| zu155D5-7 | zu155D5LC-7 | zu155D5HC |
|  | (SEQ ID NO: 92) | (SEQ ID NO: 54) |
| zu155D5-huVK1-39 | zu155D5LC-huVK1-39 | zu155D5HC |
|  | (SEQ ID NO: 94) | (SEQ ID NO: 54) |
| zu155D5-huVK2-40 | zu155D5LC-huVK2-40 | zu155D5HC |
|  | (SEQ ID NO: 96) | (SEQ ID NO: 54) |
| zu155D5-huVK3-11 | zu155D5LC-huVK3-11 | zu155D5HC |
|  | (SEQ ID NO: 98) | (SEQ ID NO: 54) |
| zu155D5-huVK4-1 | zu155D5LC-huVK4-1 | zu155D5HC |
|  | (SEQ ID NO: 100) | (SEQ ID NO: 54) |
| zu155D5-huVK6-21 | zu155D5LC-huVK6-21 | zu155D5HC |
|  | (SEQ ID NO: 102) | (SEQ ID NO: 54) |
| zu155D5-huVK6D-41 | zu155D5LC-huVK6D-41 | zu155D5HC |
|  | (SEQ ID NO: 104) | (SEQ ID NO: 54) |
| zu155D5-huVK7-3-Glu81 | zu155D5LC-huVK7-3-Glu81 | zu155D5HC |
|  | (SEQ ID NO: 106) | (SEQ ID NO: 54) |
| xi1E4 | xi1E4LC | xi1E4HC |
|  | (SEQ ID NO: 110) | (SEQ ID NO: 58) |
| zu1E4-CXXF | zu1E4LC-CXXF | zu1E4HC |
|  | (SEQ ID NO: 112) | (SEQ ID NO: 60) |
| zu1E4-CXXA | zu1E4LC-CXXA | zu1E4HC |
|  | (SEQ ID NO: 114) | (SEQ ID NO: 60) |
| xi166B3 | xi166B3LC | xi166B3HC |
|  | (SEQ ID NO: 132) | (SEQ ID NO: 74) |
| zu166B3-CXXF | zu166B3LC-CXXF | zu166B3HC |
|  | (SEQ ID NO: 134) | (SEQ ID NO: 76) |
| zu166B3-CXXA | zu166B3LC-CXXA | zu166B3HC |
|  | (SEQ ID NO: 136) | (SEQ ID NO: 76) |
| xi33O11 | xi33O11LC | xi33O11HC |
|  | (SEQ ID NO: 116) | (SEQ ID NO: 62) |
| zu33O11-CXXF | zu33O11LC-CXXF | zu33O11HC |
|  | (SEQ ID NO: 118) | (SEQ ID NO: 64) |
| zu33O11-CXXA | zu33O11LC-CXXA | zu33O11HC |
|  | (SEQ ID NO: 120) | (SEQ ID NO: 64) |
| zu33O11-CXXI | zu33O11LC-CXXI | zu33O11HC |
|  | (SEQ ID NO: 122) | (SEQ ID NO: 64) |
| xi324O5 | xi324O5LC | xi324O5HC |
|  | (SEQ ID NO: 124) | (SEQ ID NO: 66) |
| xi178F16 | xi178F16LC | xi178F16HC |
|  | (SEQ ID NO: 126) | (SEQ ID NO: 68) |
| xi237N18 | xi237N18LC | xi237N18HC |
|  | (SEQ ID NO: 128) | (SEQ ID NO: 70) |
| xi383I18 | xi383I18LC | xi383I18HC |
|  | (SEQ ID NO: 130) | (SEQ ID NO: 72) |

TABLE 26

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| Human TEM1/ endosialin/ CD248 | ATGCTGCTGCGCCTGTTGCTGGCCTGGGCGGCCGCAGGGCC CACACTGGGCCAGGACCCCTGGGCTGCTGAGCCCCGTGCCG CCTGCGGCCCCAGCAGCTGCTACGCTCTCTTCCCACGGCGC CGCACCTTCCTGGAGGCCTGGCGGGCCTGCCGCGAGCTGGG GGGCGACCTGGCCACTCCTCGGACCCCCGAGGAGGCCCAGC GTGTGGACAGCCTGGTGGGTGCGGGCCCAGCCAGCCGGCTG CTGTGGATCGGGCTGCAGCGGCAGGCCCGGCAATGCCAGCT GCAGCGCCCACTGCGCGGCTTCACGTGGACCACAGGGGACC AGGACACGGCTTTCACCAACTGGGCCCAGCCAGCCTCTGGA GGCCCCTGCCCGGCCCAGCGCTGTGTGGCCCTGGAGGCAAG TGGCGAGCACCGCTGGCTGGAGGGCTCGTGCACGCTGGCTG TCGACGGCTACCTGTGCCAGTTTGGCTTCGAGGGCGCCTGC CCGGCGCTGCAAGATGAGGCGGGCCAGGCCGGCCCAGCCGT | MLLRLLLAWAAAGPTLGQD PWAAEPRAACGPSSCYALF PRRRTFLEAWRACRELGGD LATPRTPEEAQRVDSLVGA GPASRLLWIGLQRQARQCQ LQRPLRGFTWTTGDQDTAF TNWAQPASGGPCPAQRCVA LEASGEHRWLEGSCTLAVD GYLCQFGFEGACPALQDEA GQAGPAVYTTPFHLVSTEF EWLPFGSVAAVQCQAGRGA SLLCVKQPEGGVGWSRAGP LCLGTGCSPDNGGCEHECV | 1-51 | NA | NA |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GTATACCACGCCCTTCCACCTGGTCTCCACAGAGTTTGAGT<br>GGCTGCCCTTCGGCTCTGTGGCCGCTGTGCAGTGCCAGGCT<br>GGCAGGGGAGCCTCTCTGCTCTGCGTGAAGCAGCCTGAGGG<br>AGGTGTGGGCTGGTCACGGGCTGGGCCCCTGTGCCTGGGGA<br>CTGGCTGCAGCCCTGACAACGGGGGCTGCGAACACGAATGT<br>GTGGAGGAGGTGGATGGTCACGTGTCCTGCCGCTGCACTGA<br>GGGCTTCCGGCTGGCAGCAGACGGGCGCAGTTGCGAGGACC<br>CCTGTGCCCAGGCTCCGTGCGAGCAGCAGTGTGAGCCCGGT<br>GGGCCACAAGGCTACAGCTGCCACTGTCGCCTGGGTTTCCG<br>GCCAGCGGAGGATGATCCGCACCGTGTGTGGACACAGATG<br>AGTGCCAGATTGCCGGTGTGTGCCAGACAGATGTGTGTCAAC<br>TACGTTGGTGGCTTCGAGTGTTATTGTAGCGAGGGACATGA<br>GCTGGAGGCTGATGGCATCAGCTGCAGCCCTGCAGGGGCCA<br>TGGGTGCCCAGGCTTCCCAGGACCTCGGAGATGAGTTGCTG<br>GATGACGGGGAGGATGAGGAAGATGAAGACGAGGCCTGGAA<br>GGCCTTCAACGGTGGCTGGACGGAGATGCCTGGGATCCTGT<br>GGATGGAGCCTACGCAGCCGCCTGACTTTGCCCTGGCCTAT<br>AGACCGAGCTTCCAGAGGACAGAGAGCCACAGATACCCTA<br>CCCGGAGCCCACCTGGCCACCCCCGCTCAGTGCCCCCAGGG<br>TCCCCTACCACTCCTCAGTGCTCTCCGTCACCCGGCCTGTG<br>GTGGTCTCTGCCACGCATCCCACACTGCCTTCTGCCCACCA<br>GCCTCCTGTGATCCTGCCACACACCCAGCTTTGTCCCGTG<br>ACCACCAGATCCCCGTGATCGCAGCCAACTATCCAGATCTG<br>CCTTCTGCCTACCAACCCGGTATTCTCTCTGTCTCTCATTC<br>AGCACAGCCTCCTGCCCACCAGCCCCTATGATCTCAACCA<br>AATATCCGGAGCTCTTCCCTGCCCACCAGTCCCCCATGTTT<br>CCAGACACCCGGGTCGCTGGCACCCAGACCACCACTCATTT<br>GCCTGGAATCCCACCTAACCATGCCCCTCTGGTCACCACCC<br>TCGGTGCCCAGCTACCCCCTCAAGCCCCAGATGCCCTTGTC<br>CTCAGAACCCAGGCCACCCAGCTTCCCATTATCCCAACTGC<br>CCAGCCCTCTCTGACCACCACCTCCAGGTCCCCTGTGTCTC<br>CTGCCCATCAAATCTCTGTGCCTGCTGCCACCCAGCCCGCA<br>GCCCTCCCCACCCTCCTGCCCTCTCAGAGCCCCACTAACCA<br>GACCTCACCCATCAGCCCTACACATCCCCATTCCAAAGCCC<br>CCCAAATCCCAAGGGAAGATGGCCCCAGTCCCAAGTTGGCC<br>CTGTGGCTGCCCTCACCAGCTCCCACAGCAGCCCCAACAGC<br>CCTGGGGAGGCTGTCTTGCCGAGCACAGCCAGAGGGATG<br>ACCGGTGGCTGCTGGTGGCACTCCTGGTGCCAACGTGTGTC<br>TTTTGGTGGTCCTGCTTGCACTGGGCATCGTGTACTGCAC<br>CCGCTGTGGCCCCATGCACCCAACAAGCGCATCACTGACT<br>GCTATCGCTGGGTCATCCATGCTGGGAGCAAGAGCCCAACA<br>GAACCCATGCCCCCAGGGGCAGCCTCACAGGGGTGCAGAC<br>CTGCAGAACCAGCGTGTGA<br>(SEQ ID NO: 41) | EEVDGHVSCRCTEGFRLAA<br>DGRSCEDPCAQAPCEQQCE<br>PGGPQGYSCHCRLGFRPAE<br>DDPHRCVDTDECQIAGVCQ<br>QMCVNYVGGFECYCSEGHE<br>LEADGISCSPAGAMGAQAS<br>QDLGDELLDDGEDEEDEDE<br>AWKAFNGGWTEMPGILWME<br>PTQPPDFALAYRPSFPEDR<br>EPQIPYPEPTWPPPLSAPR<br>VPYHSSVLSVTRPVVVSAT<br>HPTLPSAHQPPVIPATHPA<br>LSRDHQIPVIAANYPDLPS<br>AYQPGILSVSHSAQPPAHQ<br>PPMISTKYPELFPAHQSPM<br>FPDTRVAGTQTTTHLPGIP<br>PNHAPLVTTLGAQLPPQAP<br>DALVLRTQATQLPIIPTAQ<br>PSLTTTSRSPVSPAHQISV<br>PAATQPAALPTLLPSQSPT<br>NQTSPISPTHPHSKAPQIP<br>REDGPSPKLALWLPSPAPT<br>AAPTALGEAGLAEHSQRDD<br>RWLLVALLVPTCVFLVLL<br>ALGIVYCTRCGPHAPNKRI<br>TDCYRWVIHAGSKSPTEPM<br>PPRGSLTGVQTCRTSV*<br>(SEQ ID NO: 42) | | | |
| human endosialin/<br>TEM1<br>extra-cellular domain fused to mouse IgG2b Fc | ATGCTGCTGCGCCTGTTGCTGGCCTGGGCGGCCGCAGGGCC<br>CACACTGGGCCAGGACCCCTGGCTGCTGAGCCCCGTGCCG<br>CCTGCGGCCCCAGCAGCTGCTACGCTCTCTTCCCACGCGC<br>CGCACCTTCCTGGAGGCCTGGCGGGCCTGCCGCGAGCTGGG<br>GGGCGACCTGGCCACTCCTCGGACCCCCGAGGAGGCCCAGC<br>GTGTGGACAGCCTGGTGGGTGCGGGCCAGCAGCCGGCTG<br>CTGTGGATCGGGCTGCAGCGGCAGGCCCGGCAATGCCAGCT<br>GCAGCGCCCACTGCGCGGCTTCACGTGGACCACAGGGGACC<br>AGGACACGGCTTTCACCAACTGGGCCCAGCCAGCCTCTGGA<br>GGCCCCTGCCCGGCCCAGCGCTGTGTGGCCCTGGAGGCAAG<br>TGGCGACACCGCTGGCTGGAGGGCTGCACGCTGGCTG<br>GAGTGGCTGCCCTTCGGTTCGGTTCGGGTGGCGCCTGC<br>TCGACGGCTACCTGTGCCAGTTTGGCTTCGAGGGCGCCTGC<br>CCGGCGCTGCAAGATGAGGCGGGCCAGGCCGGCCCAGCCGT<br>GTATACCACGCCCTTCCACCTGGTCTCCACAGAGTTTGAGT<br>GGCTGCCCTTCGGCTCTGTGGCCGCTGTGCAGTGCCAGGCT<br>GGCAGGGGAGCCTCTCTGCTCTGCGTGAAGCAGCCTGAGGG<br>AGGTGTGGGCTGGTCACGGGCTGGGCCCCTGTGCCTGGGGA<br>CTGGCTGCAGCCCTGACAACGGGGGCTGCGAACACGAATGT<br>GTGGAGGAGGTGGATGGTCACGTGTCCTGCCGCTGCACTGA<br>GGGCTTCCGGCTGGCAGCAGACGGGCGCAGTTGCGAGGACC<br>CCTGTGCCCAGGCTCCGTGCGAGCAGCAGTGTGAGCCCGGT<br>GGGCCACAAGGCTACAGCTGCCACTGTCGCCTGGGTTTCCG<br>GCCAGCGGAGGATGATCCGCACCGTGTGTGGACACAGATG<br>AGTGCCAGATTGCCGGTGTGTGCCAGACAGATGTGTGTCAAC<br>TACGTTGGTGGCTTCGAGTGTTATTGTAGCGAGGGACATGA<br>GCTGGAGGCTGATGGCATCAGCTGCAGCCCTGCAGGGGCCA<br>TGGGTGCCCAGGCTTCCCAGGACCTCGGAGATGAGTTGCTG<br>GATGACGGGGAGGATGAGGAAGATGAAGACGAGGCCTGGAA | MLLRLLLAWAAAGPTLGQD<br>PWAAEPRAACGPSSCYALF<br>PRRRTFLEAWRACRELGGD<br>LATPRTPEEAQRVDSLVGA<br>GPASRLLWIGLQRQARQCQ<br>LQRPLRGFTWTTGDQDTAF<br>TNWAQPASGGPCPAQRCVA<br>LEASGEHRWLEGSCTLAVD<br>GYLCQFGFEGACPALQDEA<br>GQAGPAVYTTPPHLVSTEF<br>EWLPFGSVAAVQCQAGRGA<br>SLLCVKQPEGGVGWSRAGP<br>LCLGTGCSPDNGGCEHECV<br>EEVDGHVSCRCTEGFRLAA<br>DGRSCEDPCAQAPCEQQCE<br>PGGPQGYSCHCRLGFRPAE<br>DDPHRCVDTDECQIAGVCQ<br>QMCVNYVGGFECYCSEGHE<br>LEADGISCSPAGAMGAQAS<br>QDLGDELLDDGEDEEDEDE<br>AWKAFNGGWTEMPGILWME<br>PTQPPDFALAYRPSFPEDR<br>EPQIPYPEPTWPPPLSAPR<br>VPYHSSVLSVTRPVVVSAT<br>HPTLPSAHQPPVIPATHPA<br>LSRDHQIPVIAANYPDLPS<br>AYQPGILSVSHSAQPPAHQ<br>PPMISTKYPELFPAHQSPM | 1-51 | NA | NA |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GGCCTTCAACGGTGGCTGGACGGAGATGCCTGGGATCCTGT GGATGGAGCCTACGCAGCCGCCTGACTTTGCCCTGGCCTAT AGACCGAGCTTCCCAGAGGACAGAGAGCCACAGATACCCTA CCCGGAGCCCACCTGGCCACCCCGCTCAGTGCCCCAGGG TCCCCTACCACTCCTCAGTGCTCTCCGTCACCCGGCCTGTG GTGGTCTCTGCCACGCATCCCACACTGCCTTCTGCCCACCA GCCTCCTGTGATCCCTGCCACACACCCAGCTTTGTCCCGTG ACCACCAGATCCCCGTGATCGCAGCCAACTATCCAGATCTG CCTTCTGCCTACCAACCCGGTATTCTCTCTGTCTCTCATTC AGCACAGCCTCCTGCCCACCAGCCCCCTATGATCTCAACCA AATATCCGGAGCTCTTCCCTGCCCACCAGTCCCCCATGTTT CCAGACACCCGGGTCGCTGGCACCCAGACCACCACTCATTT GCCTGGAATCCCACCTAACCATGCCCCTCTGGTCACCACCC TCGGTGCCCAGCTACCCCCTCAAGCCCCAGATGCCCTTGTC CTCAGAACCCAGGCCACCCAGCTTCCCATTATCCCAACTGC CCAGCCCTCTCTGACCACCACCTCCAGGTCCCCTGTGTCTC CTGCCCATCAAATCTCTGTGCCTGCTGCCACCCAGCCCGCA GCCCTCCCCACCCTCCTGCCCTCTCAGAGCCCCACTAACCA GACCTCACCCATCAGCCCTACACATCCCCATTCCAAAGCCC CCCAAATCCCAAGGGAAGATGGCCCCAGTCCCAAGTTGGCC CTGTGGCTGCCCTCACCAGCTCCCACAGCAGCCCCAACAGC CCTGGGGGAGGCTGGTCTTGCCGAGCACAGCCAGAGGGATG ACCGGGTTAACGACGACGACGACAAAGAGCCCAGCGGACCA ATTTCAACAATCAACCCCTCCTCCATCCAAGGAGTCTCA CAAAAGCCCAGCTCCTAACCTCGAGGGTGGACCATCCGTCT TCATCTTCCCTCCAAATATCAAGGATGTACTCATGATCTCC CTGACACCCAAGGTCACGTGTGTGGTGGTGGATGTGAGCGA GGATGACCCAGACGTCCAGATCAGCTGGTTTGTGAACAACG TGGAAGTACACACAGCYCAGACACAAACCCATAGAGAGGAT TACAACAGTACTATCCGGGTGGTCAGCACCCTCCCCATCCA GCACCAGGACTGGATGAGTGGCAAGGAGTTCAAATGCAAGG TCAACAACAAAGACCTCCCATCACCCATCGAGAGAACCATC TCAAAAATTAAAGGGCTAGTCAGAGCTCCACAAGTATACAT CTTGCCGCCACCAGCAGAGCAGTTGTCCAGGAAAGATGTCA GTCTCACTTGCCTGGTCGTGGGCTTCAACCCTGGAGACATC AGTGTGGAGTGGACCAGCAATGGGCATACAGAGGAGAACTA CAAGGACACCGCACCAGTCCTGGACTCTGACGGTTCTTACT TCATATATAGCAAGCTCAATATGAAAACAAGCAAGTGGGAG AAAACAGATTCCTTCTCATGCAACGTGAGACACGAGGGTCT GAAAAATTACTACCTGAAGAAGACCATCTCCCGGTCTCCGG GTAAATGA (SEQ ID NO: 43) | FPDTRVAGTQTTTHLPGIP PNHAPLVTTLGAQLPPQAP DALVLRTQATQLPIIPTAQ PSLTTTSRSPVSPAHQISV PAATQPAALPTLLPSQSPT NQTSPISPTHPHSKAPQIP REDGPSPKLALWLPSPAPT AAPTALGEAGLAEHSQRDD RVNDDDDKEPSGPISTINP SPPSKESHKSPAPNLEGGP SVFIFPPNIKDVLMISLTP KVTCVVVDVSEDDPDVQIS WFVNNVEVHTAQTQTHRED YNSTIRVVSTLPIQHQDWM SGKEFKCKVNNKDLPSPIE RTISKIKGLVRAPQVYILP PPAEQLSRKDVSLTCLVVG FNPGDISVEWTSNGHTEEN YKDTAPVLDSDGSYFIYSK LNMKTSKWEKTDSFSCNVR HEGLKNYYLKKTISRSPGK * (SEQ ID NO: 44) | | | |
| Human CA9 | ATGGCACCACTGTGCCCAAGCCCATGGCTGCCACTGCTGAT CCCAGCACCAGCACCAGGACTGACCGTGCAGCTGCTGCTGA GCCTGCTGCTGCTGGTGCCCGTGCACCCCCAGCGGCTGCCC CGGATGCAGGAGGACAGCCCCCTGGGCGGCAGCAGCGG CGAGGACGACCCCCTGGGCGAGGAGGACCTGCCCAGCGAGG AGGACAGCCCCCGGGAGGAGGACCCCCCGGAGAAGAGGAC CTGCCCGGCGAGGAGGACCTGCCAGGAGAGGAGGACCTGCC AGAGGTGAAGCCAAAGAGCGAGGAGGAGGGAAGCCTGAAGC TGGAGGACCTGCCAACCGTGGAGGCACCAGGCGACCCACAG GAGCCCCAGAACAACGCCCACCGGGACAAGGAGGGCGACGA CCAGAGCCACTGGAGATACGGAGGCGACCCACCATGGCCAC GGGTGAGCCCAGCATGCGCAGGACGGTTCCAGAGCCCCGTG GACATCCGGCCCCAGCTGGCCGCCTTCTGCCCCGCCCTGCG GCCCCTGGAGCTGCTGGGCTTCCAGCTGCCCCCCCTGCCCG AGCTGCGGCTGCGAACAACGGCCACAGCGTGCAGCTGACC CTGCCCCCCGGCCTGGAGATGGCCCTGGGCCCCGGCCGGGA GTACCGGGCCCTGCAGCTGCACCTGCACTGGGGCGCCGCCG GCCGGCCCGGCAGCGAGCACACCGTGGAGGGACACAGGTTC CCAGCAGAGATCCACGTGGTGCACCTGAGCACCGCATTCGC AAGGGTGGACGAGGCACTGGGAAGGCCAGGAGGACTGGCAG TGCTGGCCCTTCCTGGAGGAGGCCAGGAGGAGAACAGC GCATACGAGCAGCTGCTGAGCCGGCTGGAGGAGATCGCAGA GGAGGGAAGCGAGACCCAGGTGCAGGGCCTGGACATCAGCG CACTGCTGCCAAGCGACTTCAGCCGGTACTTCCAGTACGAG GGCAGCCTGACCACCCCCCCTGCGCCCCAGGGCGTGATCTG GACCGTGTTCAACCAGACCGTGATGCTGAGCGCAAAGCAGC TGCACACCCTGAGCGACACCGTGGGGACCAGGCGACAGC CGGCTGCAGCTGAACTTCAGGGCAACCCAGCCCCTGAACGG AAGAGTGATCGAGGCAAGCTTCCCAGCAGGAGTGGACAGCA GCCCAAGGGCAGCAGAGCCAGTGCAGCTGAACAGCTGCCTG | MAPLCPSPWLPLLIPAPAP GLTVQLLLSLLLLVPVHPQ RLPRMQEDSPLGGGSSGED DPLGEEDLPSEEDSPREED PGEEDLPGEEDLPGEEDL PEVKPKSEEEGSLKLEDLP TVEAPGDPQEPQNNAHRDK EGDDQSHWRYGGDPPWPRV SPACAGRFQSPVDIRPQLA AFCPALRPLELLGFQLPPL PELRLRNNGHSVQLTLPPG LEMALGPGREYRALQLHLH WGAAGRPGSEHTVEGHRFP AEIHVVHLSTAFARVDEAL GRPGGLAVLAAFLEEGPEE NSAYEQLLSRLEEIAEEGS ETQVPGLDISALLPSDFSR YFQYEGSLTTPPCAQGVIW TVFNQTVMLSAKQLHTLSD TLWGPGDSRLQLNFRATQP LNGRVIEASFPAGVDSSPR AAEPVQLNSCLAAGDILAL VFGLLFAVTSVAFLVQMRR QHRRGTKGGVSYRPAEVAE TGA* (SEQ ID NO: 46) | 1-111 | NA | NA |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GCAGCAGGCGACATCCTGGCACTGGTGTTCGGACTGCTGTT CGCAGTGACCAGCGTGGCCTTCCTGGTGCAGATGCGGCGGC AGCACCGGCGGGGCACCAAGGGCGGCGTGAGCTACCGGCCC GCCGAGGTGGCCGAGACCGGCGCCTGA (SEQ ID NO: 45) | | | | |
| Human CA9 extra-cellular domain | ATGGGCTGGAGCTGCATCATCCTGTTCCTGGTGGCAACCGC AACCGGAGTGCACAGCCAGAGGCTGCCACGGATGCAGGAGG ACAGCCCCCTGGGCGGCGGCAGCAGCGGCGAGGACGACCCC CTGGGCGAGGAGGACCTGCCCAGCGAGGAGGACAGCCCAAG GGAGGAGGAGGACCCACCAGGAGAGGAGGACCTGCCTGGCGAGG AGGACCTGCCTGGGGAGGAGGACCTGCCAGAGGTGAAGCCA AAGAGCGAAGAGGAGGGAAGCCTGAAGCTGGAGGACCTGCC AACCGTGGAGGCACCAGGCGACCCACAGGAGCCCCAGAACA ACGCCCACCGGGACAAGGAGGCGACGACCAGAGCCACTGG ATGCGCAGGACGGTTCCAGAGCCCCGTGGACATCCGGCCCC AGCTGGCCGCCTTCTGCCCCGCCCTGCGCCCCCTGGAGCTG CTGGGCTTCCAGCTGCCCCCCCTGCCCGAGCTGCGGCTGCG GAACAACGGCCACAGCGTGCAGCTGACCCTGCCCCCCGGCC TGGAGATGGCCCTGGGCCCCGGCCGGGAGTACCGGGCCCTG CAGCTGCACCTGCTGGGGCGCGCGGCCGGCCCGGCAG CGAGCACACCGTGGAGGGACACAGGTTCCCAGCAGAGATCC ACGTGGTGCACCTGAGCACCGCATTCGCAAGGGTGGACGAG GCACTGGGAAGGCCAGGAGGACTGGCAGTGCTGGCAGCCTT CCTGGAGGAGGGACCAGAGGAGAACAGCGCATACGAGCAGC TGCTGAGCCGGCTGGAGGAGATCGCAGAGGAGGGAAGCGAG ACCCAGGTGCCAGGCCTGGACATCAGCGCACTGCTGCCAAG CGACTTCAGCCGGTACTTCCAGTACGAGGGCAGCCTGACCA CCCCCCCCTGCGCCCAGGGCGTGATCTGGACCGTGTTCAAC CAGACCGTGATGCTGAGCGCAAAGCAGCTGCACACCCTGAG CGACACCCTGTGGGGACCAGGCGACAGCCGGCTGCAGCTGA ACTTCAGGGCAACCCAGCCCTGAACGGAAGAGTGATCGAG GCAAGCTTCCCAGCAGGAGTGGACAGCAGCCCAAGGGCAGC AGAGCCAGTGCAGCTGAACAGCTGCCTGGCCGGCCACCACC ACCACCACCACTGA (SEQ ID NO: 47) | MGWSCIILFLVATATGVHS QRLPRMQEDSPLGGGSSGE DDPLGEEDLPSEEDSPREE DPPGEEDLPGEEDLPGEED GEEDPPGEEDLPGEEDLPS E EVKPKSEEEGSLKLEDL PTVEAPGDPQEPQNNAHRD KEGDDQSHWRYGGDPPWPR VSPACAGRFQSPVDIRPQL AAFCPALRPLELLGFQLPP LPELRLNNGHSVQLTLPP GLEMALGPGREYRALQLHL HWAAGRPGSEHTVEGHRF PAEIHVVHLSTAFARVDEA LGRPGGLAVLAAFLEEGPE ENSAYEQLLSRLEEIAEEG SETQVPGLDISALLPSDFS RYFQYEGSLTTPPCAQGVI WTVFNQTVMLSAKQLHTLS DTLWGPGDSRLQLNFRATQ PLNGRVIEASFPAGVDSSP RAAEPVQLNSCLAGHHHHH H* (SEQ ID NO: 48) | 1-57 | NA | NA |
| MSLN | ATGGGATGGAGCTGTATCATCCTCTTCTTGGTAGCAACAGC TACAGGTGTACACAGCGAAGTGGAGAAGACAGCCTGTCCTT CAGGCAAGAAGGCCCGCGAGATAGACGAGAGCCTCATCTTC TACAAGAAGTGGGAGCTGGAAGCCTGCGTGGATGCGGCCCT GCTGGCCACCCAGATGGACCGCGTGAACGCCATCCCCTTCA CCTACGAGCAGCTGGACGTCCTAAAGCATAAACTGGATGAG CTCTACCCACAAGGTTACCCCGAGTCTGTGATCCAGCACCT GGGCTACCTCTTCCTCAAGATGAGCCCTGAGGACATTCGCA AGTGGAATGTGACGTCCCTGGAGACCCTGAAGGCTTTGCTT TGAAGTCAACAAAGGGCACGAAATGAGTCCTCAGGTGGCCAC CCTGATCGACCGCTTTGTGAAGGGAAGGGGCCAGCTAGACA AAGACACCCTAGACACCCTGACCGCCTTCTACCCTGGGTAC CTGTGCTCCCTCAGCCCCGAGGAGCTGAGCTCCGTGCCCCC CAGCAGCATCTGGGCGGTCAGGCCCCAGGACCTGGACACGT GTGACCCAAGGCAGCTGGACGTCCTCTATCCCAAGGCCCGC CTTGCTTTCCAGAACATGAACGGGTCCGAATACTTCGTGAA GATCCAGTCCTTCCTGGGTGGGCCCCCACGGAGGATTTGA AGGCGCTCAGTCAGCAGAATGTGAGCATGGACTTGGCCACG TTCATGAAGCTGCGGACGGATGCGGTGCTGCCGTTGACTGT GGCTGAGGTGCAGAAACTTCTGGGACCCCACGTGGAGGGCC TGAAGGCGGAGGAGCGGCACCGCCCGGTGCGGGACTGGATC CTACGGCAGCGGCAGGACGACCTGGACACGCTGGGGCTGGG GCTACAGGGCGGCATCCCCAACGGCTACCTGGTCCTAGACC TCAGCATGCAAGAGGCCCTCTCGGGGACGCCCTGCCTCCTA GGACCTGGACCTGTTCTCACCGTCCTGGCACTGCTCCTAGC CTCCACCCTGGCCTGA (SEQ ID NO: 49) | MGWSCIILFLVATATGVHS EVEKTACPSGKKAREIDES LIFYKKWELEACVDAALLA TQMDRVNAIPFTYEQLDVL KHKLDELYPQGYPESVIQH LGYLFLKMSPEDIRKWNVT SLETLKALLEVNKGHEMSP QVATLIDRFVKGRGQLDKD TLDTLTAFYPGYLCSLSPE ELSSVPPSSIWAVRPQDLD TCDPRQLDVLYPKARLAFQ NMNGSEYFVKIQSFLGGAP TEDLKALSQQNVSMDLATF MKLRTDAVLPLTVAEVQKL LGPHVEGLKAEERHRPVRD WILRQRQDDLDTLGLGLQG GIPNGYLVLDLSMQEALSG TPCLLGPGPVLTVLALLLA STLA* (SEQ ID NO: 50) | 1-57 | NA | NA |
| xi155D5HC (rabbit Vh-human IgG1) (human CA9) | ATGGGCTGGTCCTGCATCATCCTGTTTCTGGTGGCCACCGC CACCGGCGTGCACAGCCAGTCGGTGAAGGAGTCCGGGGGTC GCCTGGTCACGCCTGGGACACCCCTGACACTCACCTGCACA TCTGTCTGGATTCTCCCTCAATAGCTATGCGATGATCTGGGT CCGCCAGGCTCCAGGGAAGGGGCTGGAATACATCGGATTCA TTACTACTGGTGGTACCACATACTACGCGAGCTGGCAAAA GGCCGATTCACCATCTCCAGAACCTCGACCACGGTGGATCT | MGWSCIILFLVATATGVHS QSVKESGGRLVTPGTPLTL TCTVSGFSLNSYAMIWVRQ APGEGLEYIGFITTGGTTY YASWAKGRFTISRTSTTVD LKLTRPTTEDTATYFCARD RVKSYDDYGDLDAFEPWGP | 1-57 | 58-423 | 424-1416 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GAAGCTCACCCGTCCGACAACCGAGGACACGGCCACCTATT<br>TCTGTGCCAGAGATCGGGTTAAAAGCTACGATGACTATGGT<br>GATTTAGATGCTTTCGAGCCCTGGGGCCCAGGCACCCTGGT<br>CACCGTCTCCTCAGCATCCACCAAGGGCCCATCGGTCTTCC<br>CCCTGGCACCCTCCTCCAAGAGCACCTCTGGGGGCACAGCG<br>GCCCTGGGCTGCCTGGTCAAGGACTACTTCCCCGAACCGGT<br>GACGGTGTCGTGGAACTCAGGCGCCCTGACCAGCGGCGTGC<br>ACACCTTCCCGGCTGTCCTACAGTCCTCAGGACTCTACTCC<br>CTCAGCAGCGTGGTGACCGTGCCCTCCAGCAGCTTGGGCAC<br>CCAGACCTACATCTGCAACGTGAATCACAAGCCCAGCAACA<br>CCAAGGTGGACAAGAAAGTTGAGCCCAAATCTTGTGACAAA<br>ACTCACACATGCCCACCGTGCCCAGCACCTGAACTCCTGGG<br>GGGACCGTCAGTCTTCCTCTTCCCCCCAAAACCCAAGGACA<br>CCCTCATGATCTCCCGGACCCCTGAGGTCACATGCGTGGTG<br>GTGGACGTGAGCCACGAAGACCCTGAGGTCAAGTTCAACTG<br>GTACGTGGACGGCGTGGAGGTGCATAATGCCAAGACAAAGC<br>CGCGGGAGGAGCAGTACAACAGCACGTACCGTGTGGTCAGC<br>GTCCTCACCGTCCTGCACCAGGACTGGCTGAATGGCAAGGA<br>GTACAAGTGCAAGGTCTCCAACAAAGCCCTCCCAGCCCCCA<br>TCGAGAAAACCATCTCCAAAGCCAAAGGGCAGCCCCGAGAA<br>CCACAGGTGTACACCCTGCCCCCATCCCGGGATGAGCTGAC<br>CAAGAACCAGGTCAGCCTGACCTGCCTGGTCAAAGGCTTCT<br>ATCCCAGCGACATCGCCGTGGAGTGGGAGAGCAATGGGCAG<br>CCGGAGAACAACTACAAGACCACGCCTCCCGTGCTGGACTC<br>CGACGGCTCCTTCTTCTTATATTCAAAGCTCACCGTGGACA<br>AGAGCAGGTGGCAGCAGGGGAACGTCTTCTCATGCTCCGTG<br>ATGCATGAGGCTCTGCACAACCACTACACGCAGAAGAGCCT<br>CTCCCTGTCTCCGGGAAATGA<br>(SEQ ID NO: 51) | GTLVTISSASTKGPSVFPL<br>APSSKSTSGGTAALGCLVK<br>DYFPEPVTVSWNSGALTSG<br>VHTFPAVLQSSGLYSLSSV<br>VTVPSSSLGTQTYICNVNH<br>KPSNTKVDKKVEPKSCDKT<br>HTCPPCPAPELLGGPSVFL<br>FPPKPKDTLMISRTPEVTC<br>VVVDVSHEDPEVKFNWYVD<br>GVEVHNAKTKPREEQYNST<br>YRVVSVLTVLHQDWLNGKE<br>YKCKVSNKALPAPIEKTIS<br>KAKGQPREPQVYTLPPSRD<br>ELTKNQVSLTCLVKGFYPS<br>DIAVEWESNGQPENNYKTT<br>PPVLDSDGSFFLYSKLTVD<br>KSRWQQGNVFSCSVMHEAL<br>HNHYTQKSLSLSPGK*<br>(SEQ ID NO: 52) | | | |
| zu155D5HC<br>(human Vh-<br>human IgG1)<br>(human CA9) | ATGGGTTGGAGTTGCATCATTCTGTTCCTGGTGGCCACAGC<br>TACTGGCGTGCACTCACAGGTGCAGCTGGTGGAGTCCGGAG<br>GAGGACTGGTGCAGCCAGGTGGCTCTCTGCGACTGTCTTGT<br>AGTGCTTCAGGCTTTTCCCTGAACAGCTACGCTATGATCTG<br>GGTCAGGCAGGCACCTGGCAAGGGCCTGGAATATATCGGAT<br>TCATTACCACAGGAGGGACTACCTACTATGCCGACTCCGTG<br>AAGGGGAGATTCACTATCTCTCGCGATAACAGTAAGAATAC<br>CCTGTACCTGCAGATGAATAGCCTGAGAGCAGAGGACACAG<br>CCGTGTACTATTGCGCCAGGGATCGGGTGAAATCTTACGAC<br>GATTATGGAGACCTGGATGCTTTCGAACCATGGGGACAGGG<br>GACCCTGGTGACAGTGTCCAGCGCATCCACCAAGGGCCCAT<br>CGGTCTTCCCCCTGGCACCCTCCTCCAAGAGCACCTCTGGG<br>GGCACAGCGGCCCTGGGCTGCCTGGTCAAGGACTACTTCCC<br>CGAACCGGTGACGGTGTCGTGGAACTCAGGCGCCCTGACCA<br>GCGGCGTGCACACCTTCCCGGCTGTCCTACAGTCCTCAGGA<br>CTCTACTCCCTCAGCAGCGTGGTGACCGTGCCCTCCAGCAG<br>CTTGGGCACCCAGACCTACATCTGCAACGTGAATCACAAGC<br>CCAGCAACACCAAGGTGGACAAGAAAGTTGAGCCCAAATCT<br>TGTGACAAAACTCACACATGCCCACCGTGCCCAGCACCTGA<br>ACTCCTGGGGGGACCGTCAGTCTTCCTCTTCCCCCCAAAAC<br>CCAAGGACACCCTCATGATCTCCCGGACCCCTGAGGTCACA<br>TGCGTGGTGGTGGACGTGAGCCACGAAGACCCTGAGGTCAA<br>GTTCAACTGGTACGTGGACGGCGTGGAGGTGCATAATGCCA<br>AGACAAAGCCGCGGGAGGAGCAGTACAACAGCACGTACCGT<br>GTGGTCAGCGTCCTCACCGTCCTGCACCAGGACTGGCTGAA<br>TGGCAAGGAGTACAAGTGCAAGGTCTCCAACAAAGCCCTCC<br>CAGCCCCCATCGAGAAAACCATCTCCAAAGCCAAAGGGCAG<br>CCCCGAGAACCACAGGTGTACACCCTGCCCCCATCCCGGGA<br>TGAGCTGACCAAGAACCAGGTCAGCCTGACCTGCCTGGTCA<br>AAGGCTTCTATCCCAGCGACATCGCCGTGGAGTGGGAGAGC<br>AATGGGCAGCCGGAGAACAACTACAAGACCACGCCTCCCGT<br>GCTGGACTCCGACGGCTCCTTCTTCTTATATTCAAAGCTCA<br>CCGTGGACAAGAGCAGGTGGCAGCAGGGGAACGTCTTCTCA<br>TGCTCCGTGATGCATGAGGCTCTGCACAACCACTACACGCA<br>GAAGAGCCTCTCCCTGTCTCCGGGAAATGA<br>(SEQ ID NO: 53) | MGWSCIILFLVATATGVHS<br>QVQLVESGGGLVQPGGSLR<br>LSCSASGFSLNSYAMIWVR<br>QAPGKGLEYIGFITTGGTT<br>YYADSVKGRFTISRDNSKN<br>TLYLQMNSLRAEDTAVYYC<br>ARDRVKSYDDYGDLDAFEP<br>WGQGTLVTVSSASTKGPSV<br>FPLAPSSKSTSGGTAALGC<br>LVKDYFPEPVTVSWNSGAL<br>TSGVHTFPAVLQSSGLYSL<br>SSVVTVPSSSLGTQTYICN<br>VNHKPSNTKVDKKVEPKSC<br>DKTHTCPPCPAPELLGGPS<br>VFLFPPKPKDTLMISRTPE<br>VTCVVVDVSHEDPEVKFNW<br>YVDGVEVHNAKTKPREEQY<br>NSTYRVVSVLTVLHQDWLN<br>GKEYKCKVSNKALPAPIEK<br>TISKAKGQPREPQVYTLPP<br>SRDELTKNQVSLTCLVKGF<br>YPSDIAVEWESNGQPENNY<br>KTTPPVLDSDGSFFLYSKL<br>TVDKSRWQQGNVFSCSVMH<br>EALHNHYTQKSLSLSPGK*<br>(SEQ ID NO: 54) | 1-57 | 58-432 | 433-1425 |
| xi1-55-2HC<br>(rabbit Vh-<br>human IgG1)<br>(human TEM1) | ATGGGCTGGTCCTGCATCATCCTGTTTCTGGTGGCCACCGC<br>CACCGGCGTGCACTCCCAGTCGGTGGAGGAGTCCGGGGGAG<br>ACCTGGTCAAGCCTGAGGGATCCCTGACACTCACCTGCACA<br>GCCTCTGGATTCTCCTTCAGTAGCAGCTACTGGGGATGCTG<br>GGTCCGCCAGGCTCCAGGGAAGGGGCCTGAGTGGATCGCAT<br>GCATTTATGGTGGTAGTAGTGGTACCACTTATTACCCGAAC<br>TGGGCGAAAGGCCGATTCACCATCTCCAAAACCTCG | MGWSCIILFLVATATGVHS<br>QSVEESGGDLVKPEGSLTL<br>TCTASGFSFSSSYWGCWVR<br>QAPGKGPEWIACIYGGSSG<br>TTYYPNWAKGRFSISKTSS<br>TVTLQMASLTAADTATYF | 1-57 | 58-417 | 418-1410 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | TGGGCGAAAGGCCGATTCTCCATCTCCAAAACCTCGTCGAC<br>CACGGTGACTCTGCAAATGGCCAGTCTGACAGCCGCGGACA<br>CGGCCACCTATTTCTGTGCGAGAGTGACTAATGGTGGTGAT<br>TGGGATTTTAAATTGTGGGGCCCAGGCACCCTGGTCACCAT<br>CTCCTCAGCATCCACCAAGGGCCCATCGGTCTTCCCCCTGG<br>CACCCTCCTCCAAGAGCACCTCTGGGGGCACAGCGGCCCTG<br>GGCTGCCTGGTCAAGGACTACTTCCCCGAACCGGTGACGGT<br>GTCGTGGAACTCAGGCGCCCTGACCAGCGGCGTGCACACCT<br>TCCCGGCTGTCCTACAGTCCTCAGGACTCTACTCCCTCAGC<br>AGCGTGGTGACCGTGCCCTCCAGCAGCTTGGGCACCCAGAC<br>CTACATCTGCAACGTGAATCACAAGCCCAGCAACACCAAGG<br>TGGACAAGAAAGTTGAGCCCAAATCTTGTGACAAAACTCAC<br>ACATGCCCACCGTGCCCAGCACCTGAACTCCTGGGGGGACC<br>GTCAGTCTTCCTCTTCCCCCCAAAACCCAAGGACACCCTCA<br>TGATCTCCCGGACCCCTGAGGTCACATGCGTGGTGGTGGAC<br>GTGAGCCACGAAGACCCTGAGGTCAAGTTCAACTGGTACGT<br>GGACGGCGTGGAGGTGCATAATGCCAAGACAAAGCCGCGGG<br>AGGAGCAGTACAACAGCACGTACCGTGTGGTCAGCGTCCTC<br>ACCGTCCTGCACCAGGACTGGCTGAATGGCAAGGAGTACAA<br>GTGCAAGGTCTCCAACAAAGCCCTCCCAGCCCCCATCGAGA<br>AAACCATCTCCAAAGCCAAAGGGCAGCCCCGAGAACCACAG<br>GTGTACACCCTGCCCCCATCCCGGGATGAGCTGACCAAGAA<br>CCAGGTCAGCCTGACCTGCCTGGTCAAAGGCTTCTATCCCA<br>GCGACATCGCCGTGGAGTGGGAGAGCAATGGGCAGCCGGAG<br>AACAACTACAAGACCACGCCTCCCGTGCTGGACTCCGACGG<br>CTCCTTCTTCTTATATTCAAAGCTCACCGTGGACAAGAGCA<br>GGTGGCAGCAGGGGAACGTCTTCTCATGCTCCGTGATGCAT<br>GAGGCTCTGCACAACCACTACACGCAGAAGAGCCTCTCCCT<br>GTCTCCCGGGAAATGA<br>(SEQ ID NO: 55) | CARVTNGGDWDFKLWGPGT<br>LVTISSASTKGPSVFPLAP<br>SSKSTSGGTAALGCLVKDY<br>FPEPVTVSWNSGALTSGVH<br>TFPAVLQSSGLYSLSSVVT<br>VPSSSLGTQTYICNVNHKP<br>SNTKVDKKVEPKSCDKTHT<br>CPPCPAPELLGGPSVFLFP<br>PKPKDTLMISRTPEVTCVV<br>VDVSHEDPEVKFNWYVDGV<br>EVHNAKTKPREEQYNSTYR<br>VVSVLTVLHQDWLNGKEYK<br>CKVSNKALPAPIEKTISKA<br>KGQPREPQVYTLPPSRDEL<br>TKNQVSLTCLVKGFYPSDI<br>AVEWESNGQPENNYKTTPP<br>VLDSDGSFFLYSKLTVDKS<br>RWQQGNVFSCSVMHEALHN<br>HYTQKSLSLSPGK*<br>(SEQ ID NO: 56) | | | |
| xi1E4HC (rabbit Vh-human IgG1) (human CA9) | ATGGGCTGGTCCTGCATCATCCTGTTTCTGGTGGCCACCGC<br>CACCGGCGTGCACAGCCAGTCGGTGGAGGAGTCCAGGGGTC<br>GCCTGGTCACGCCTGGGACACCCCTGACACTCACCTGCACA<br>GTCTCTGGAATCGACCTCAGTAATTATGCAATGACCTGGGT<br>CCGCCAGGCTCCAGGGAAGGGGCTGGAATGGATCGGAATCA<br>TTAGTAGTAATGATAAGACATGGTACGCGAGCTGGGTGAAA<br>GGCCGGTTCACCATCTCAAAAACCTCGTCGACCACGGTGGA<br>TCTGAAAATGACCAGTCTGACAACCGAGGACACGGCCACCT<br>ATTTCTGTGCCAGAGCTGCTATGCCTGGTGGTTTAAAGAAT<br>GCTTTCGATCCCTGGGGCCCAGGCACCCTGGTCACCGTCTC<br>TTCAGCATCCACCAAGGGCCCATCGGTCTTCCCCCTGGCAC<br>CCTCCTCCAAGAGCACCTCTGGGGGCACAGCGGCCCTGGGC<br>TGCCTGGTCAAGGACTACTTCCCCGAACCGGTGACGGTGTC<br>GTGGAACTCAGGCGCCCTGACCAGCGGCGTGCACACCTTCC<br>CGGCTGTCCTACAGTCCTCAGGACTCTACTCCCTCAGCAGC<br>GTGGTGACCGTGCCCTCCAGCAGCTTGGGCACCCAGACCTA<br>CATCTGCAACGTGAATCACAAGCCCAGCAACACCAAGGTGG<br>ACAAGAAAGTTGAGCCCAAATCTTGTGACAAAACTCACACA<br>TGCCCACCGTGCCCAGCACCTGAACTCCTGGGGGGACCGTC<br>AGTCTTCCTCTTCCCCCCAAAACCCAAGGACACCCTCATGA<br>TCTCCCGGACCCCTGAGGTCACATGCGTGGTGGTGGACGTG<br>AGCCACGAAGACCCTGAGGTCAAGTTCAACTGGTACGTGGA<br>CGGCGTGGAGGTGCATAATGCCAAGACAAAGCCGCGGGAGG<br>AGCAGTACAACAGCACGTACCGTGTGGTCAGCGTCCTCACC<br>GTCCTGCACCAGGACTGGCTGAATGGCAAGGAGTACAAGTG<br>CAAGGTCTCCAACAAAGCCCTCCCAGCCCCCATCGAGAAAA<br>CCATCTCCAAAGCCAAAGGGCAGCCCCGAGAACCACAGGTG<br>TACACCCTGCCCCCATCCCGGGATGAGCTGACCAAGAACCA<br>GGTCAGCCTGACCTGCCTGGTCAAAGGCTTCTATCCCAGCG<br>ACATCGCCGTGGAGTGGGAGAGCAATGGGCAGCCGGAGAAC<br>AACTACAAGACCACGCCTCCCGTGCTGGACTCCGACGGCTC<br>CTTCTTCTTATATTCAAAGCTCACCGTGGACAAGAGCAGGT<br>GGCAGCAGGGGAACGTCTTCTCATGCTCCGTGATGCATGAG<br>GCTCTGCACAACCACTACACGCAGAAGAGCCTCTCCCTGTC<br>TCCCGGGAAATGA<br>(SEQ ID NO: 57) | MGWSCIILFLVATATGVHS<br>QSVEESRGRLVTPGTPLTL<br>TCTVSGIDLSNYAMTWVRQ<br>APGKGLEWIGIISSNDKTW<br>YASWVKGRFTISKTSSTTV<br>DLKMTSLTTEDTATYFCAR<br>AAMPGGLKNAFDPWGPGTL<br>VTVSSASTKGPSVFPLAPS<br>SKSTSGGTAALGCLVKDYF<br>PEPVTVSWNSGALTSGVHT<br>FPAVLQSSGLYSLSSVVTV<br>PSSSLGTQTYICNVNHKPS<br>NTKVDKKVEPKSCDKTHTC<br>PPCPAPELLGGPSVFLFPP<br>KPKDTLMISRTPEVTCVVV<br>DVSHEDPEVKFNWYVDGVE<br>VHNAKTKPREEQYNSTYRV<br>VSVLTVLHQDWLNGKEYKC<br>KVSNKALPAPIEKTISKAK<br>GQPREPQVYTLPPSRDELT<br>KNQVSLTCLVKGFYPSDIA<br>VEWESNGQPENNYKTTPPV<br>LDSDGSFFLYSKLTVDKSR<br>WQQGNVFSCSVMHEALHNH<br>YTQKSLSLSPGK*<br>(SEQ ID NO: 58) | 1-57 | 58-414 | 415-1407 |
| zu1E4HC (human Vh-human IgG1) (human CA9) | ATGGGCTGGTCCTGCATCATCCTGTTTCTGGTGGCCACCGC<br>CACCGGCGTGCACAGCGAGGTCCAGCTGGTGGAATCAGGGG<br>GAGGACTGGTGCAGCCCGGAGGGTCACTGCGACTGTCTTGT<br>GCCGCTTCAGGCATTGATCTGTCTAACTACGCTATGACTTG<br>GGTGAGGCAGGCACCCGGCAAGGGACTGGAGTGGGTCGGAA | MGWSCIILFLVATATGVHS<br>EVQLLESGGGLVQPGGSLR<br>LSCAASGIDLSNYAMTWVR<br>QAPGKGLEWVGIISSNDKT<br>WYADSVKGRFTISRDNSKN | 1-57 | 58-420 | 421-1413 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | TCATTAGCTCCAATGACAAGACCTGGTACGCCGATTCAGTG<br>AAAGGCCGGTTCACCATCTCTAGAGACAACAGTAAGAATAC<br>ACTGTATCTGCAGATGAACAGCCTGCGGGCAGAAGATACAG<br>CCGTCTACTATTGCGCTAAAGCCGCTATGCCTGGCGGACTG<br>AAGAACGCATTTGATCCTTGGGGACAGGGAACTCTGGTCAC<br>CGTCTCATCTGCATCCACCAAGGGCCCATCGGTCTTCCCCC<br>TGGCACCCTCCTCCAAGAGCACCTCTGGGGGCACAGCGGCC<br>CTGGGCTGCCTGGTCAAGGACTACTTCCCCGAACCGGTGAC<br>GGTGTCGTGGAACTCAGGCGCCCTGACCAGCGGCGTGCACA<br>CCTTCCCGGCTGTCCTACAGTCCTCAGGACTCTACTCCCTC<br>AGCAGCGTGGTGACCGTGCCCTCCAGCAGCTTGGGCACCCA<br>GACCTACATCTGCAACGTGAATCACAAGCCCAGCAACACCA<br>AGGTGGACAAGAAAGTTGAGCCCAAATCTTGTGACAAAACT<br>CACACATGCCCACCGTGCCCAGCACCTGAACTCCTGGGGGG<br>ACCGTCAGTCTTCCTCTTCCCCCCAAAACCCAAGGACACCC<br>TCATGATCTCCCGGACCCCTGAGGTCACATGCGTGGTGGTG<br>GACGTGAGCCACGAAGACCCTGAGGTCAAGTTCAACTGGTA<br>CGTGGACGGCGTGGAGGTGCATAATGCCAAGACAAAGCCGC<br>GGGAGGAGCAGTACAACAGCACGTACCGTGTGGTCAGCGTC<br>CTCACCGTCCTGCACCAGGACTGGCTGAATGGCAAGGAGTA<br>CAAGTGCAAGGTCTCCAACAAAGCCCTCCCAGCCCCCATCG<br>AGAAAACCATCTCCAAAGCCAAAGGGCAGCCCCGAGAACCA<br>CAGGTGTACACCCTGCCCCCATCCCGGGATGAGCTGACCAA<br>GAACCAGGTCAGCCTGACCTGCCTGGTCAAAGGCTTCTATC<br>CCAGCGACATCGCCGTGGAGTGGGAGAGCAATGGGCAGCCG<br>GAGAACAACTACAAGACCACGCCTCCCGTGCTGGACTCCGA<br>CGGCTCCTTCTTCCTCTATATTCAAAGCTCACCGTGGACAAGA<br>GCAGGTGGCAGCAGGGGAACGTCTTCTCATGCTCCGTGATG<br>CATGAGGCTCTGCACAACCACTACACGCAGAAGAGCCTCTC<br>CCTGTCTCCGGGAAATGA<br>(SEQ ID NO: 59) | TLYLQMNSLRAEDTAVYC<br>AKAAMPGGLKNAFDPWGQG<br>TLVTVSSASTKGPSVFPLA<br>PSSKSTSGGTAALGCLVKD<br>YFPEPVTVSWNSGALTSGV<br>HTFPAVLQSSGLYSLSSVV<br>TVPSSSLGTQTYICNVNHK<br>PSNTKVDKKVEPKSCDKTH<br>TCPPCPAPELLGGPSVFLF<br>PPKPKDTLMISRTPEVTCV<br>VVDVSHEDPEVKFNWYVDG<br>VEVHNAKTKPREEQYNSTY<br>RVVSVLTVLHQDWLNGKEY<br>KCKVSNKALPAPIEKTISK<br>AKGQPREPQVYTLPPSRDE<br>LTKNQVSLTCLVKGFYPSD<br>IAVEWESNGQPENNYKTTP<br>PVLDSDGSFFLYSKLTVDK<br>SRWQQGNVFSCSVMHEALH<br>NHYTQKSLSLSPGK*<br>(SEQ ID NO: 60) | | | |
| xi33011HC<br>(rabbitVh-<br>human IgG1)<br>(human MSLN) | ATGGGCTGGTCCTGCATCATCCTGTTTCTGGTGGCCACCGC<br>CACCGGCGTGCACTCCCAGTCGGTGGAGGAGTCCGGGGGTC<br>GCCTGGTCACGCCTGGGACCCCTGACACTCACCTGCACC<br>GTCTCTGGAATCTCCCTCAGTAGCGATGCAATAAGCTGGGT<br>CCGCCAGGCTCCAGGGAAGGGGCTCGAATACATCGGAATCA<br>TTAATGGTGGTGGTAACACATACTACGCGAGCTGGGCGAAA<br>GGCCGATTCACCATCTCCAAAACCTCGACCACGGTGGATCT<br>GAAAATCACCAGTCCGACAACCGAGGACACGGCCACCTATT<br>TCTGTGCCAGAGGCATTCAACATGGTGGTGGTAATAGTGAT<br>TATTATTATTACGGCATGGACCTCTGGGGCCCAGGCACCCT<br>GGTCACTGTCTCTTCAGCATCCACCAAGGGCCCATCGGTCT<br>TCCCCCTGGCACCCTCCTCCAAGAGCACCTCTGGGGGCACA<br>GCGGCCCTGGGCTGCCTGGTCAAGGACTACTTCCCCGAACC<br>GGTGACGGTGTCGTGGAACTCAGGCGCCCTGACCAGCGGCG<br>TGCACACCTTCCCGGCTGTCCTACAGTCCTCAGGACTCTAC<br>TCCCTCAGCAGCGTGGTGACCGTGCCCTCCAGCAGCTTGGG<br>CACCCAGACCTACATCTGCAACGTGAATCACAAGCCCAGCA<br>ACACCAAGGTGGACAAGAAAGTTGAGCCCAAATCTTGTGAC<br>AAAACTCACACATGCCCACCGTGCCCAGCACCTGAACTCCT<br>GGGGGGACCGTCAGTCTTCCTCTTCCCCCCAAAACCCAAGG<br>ACACCCTCATGATCTCCCGGACCCCTGAGGTCACATGCGTG<br>GTGGTGGACGTGAGCCACGAAGACCCTGAGGTCAAGTTCAA<br>CTGGTACGTGGACGGCGTGGAGGTGCATAATGCCAAGACAA<br>AGCCGCGGGAGGAGCAGTACAACAGCACGTACCGTGTGGTC<br>AGCGTCCTCACCGTCCTGCACCAGGACTGGCTGAATGGCAA<br>GGAGTACAAGTGCAAGGTCTCCAACAAAGCCCTCCCAGCCC<br>CCATCGAGAAAACCATCTCCAAAGCCAAAGGGCAGCCCCGA<br>GAACCACAGGTGTACACCCTGCCCCCATCCCGGGATGAGCT<br>GACCAAGAACCAGGTCAGCCTGACCTGCCTGGTCAAAGGCT<br>TCTATCCCAGCGACATCGCCGTGGAGTGGGAGAGCAATGGG<br>CAGCCGGAGAACAACTACAAGACCACGCCTCCCGTGCTGGA<br>CTCCGACGGCTCCTTCTTCTTATATTCAAAGCTCACCGTGG<br>ACAAGAGCAGGTGGCAGCAGGGGAACGTCTTCTCATGCTCC<br>GTGATGCATGAGGCTCTGCACAACCACTACACGCAGAAGAG<br>CCTCTCCCTGTCTCCGGGAAATGA<br>(SEQ ID NO: 61) | MGWSCIILFLVATATGVHS<br>QSVEESGGRLVTPGTPLTL<br>TCTVSGISLSSDAISWVRQ<br>APGKGLEYIGIINGGGNTY<br>YASWAKGRFTISKTSTTVD<br>LKITSPTTEDTATYFCARG<br>IQHGGGNSDYYYYGMDLWG<br>PGTLVTVSSASTKGPSVFP<br>LAPSSKSTSGGTAALGCLV<br>KDYFPEPVTVSWNSGALTS<br>GVHTFPAVLQSSGLYSLSS<br>VVTVPSSSLGTQTYICNVN<br>HKPSNTKVDKKVEPKSCDK<br>THTCPPCPAPELLGGPSVF<br>LFPPKPKDTLMISRTPEVT<br>CVVVDVSHEDPEVKFNWYV<br>DGVEVHNAKTKPREEQYNS<br>TYRVVSVLTVLHQDWLNGK<br>EYKCKVSNKALPAPIEKTI<br>SKAKGQPREPQVYTLPPSR<br>DELTKNQVSLTCLVKGFYP<br>SDIAVEWESNGQPENNYKT<br>TPPVLDSDGSFFLYSKLTV<br>DKSRWQQGNVFSCSVMHEA<br>LHNHYTQKSLSLSPGK*<br>(SEQ ID NO: 62) | 1-57 | 58-426 | 427-1419 |
| zu33011HC<br>(humanVh-<br>human IgG1)<br>(human MSLN) | ATGGGCTGGTCCTGCATCATCCTGTTTCTGGTGGCCACCGC<br>CACCGGCGTGCACAGCGAAGTCCAACTGGTGGAAAGCGGGG<br>GAGGACTGGTGCAGCCGGGCGGATCCCTCCGGCTGTCATGT<br>GCTGCATCGGGAATTTCCCTCTCCTCCGACGCGATTAGCTG | MGWSCIILFLVATATGVHS<br>EVQLVESGGGLVQPGGSLR<br>LSCAASGISLSSDAISWVR<br>QAPGKGLEYIGIINGGGNT | 1-57 | 58-435 | 436-1428 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GGTCAGACAGGCCCCCGGAAAGGGGCTGGAGTACATCGGTA<br>TCATCAACGGCGGCGAAACACCTACTACGCCTCCTGGGCC<br>AAGGGCCGCTTCACCATCTCGCGGCATAATTCCAAGAACAC<br>TCTGTACTTGCAAATGAACTCCCTGAGGGCCGAGGACACCG<br>CCGTGTACTACTGCGCGCGCGGCATCCAGCACGGTGGTGGA<br>AACAGCGACTACTACTACTATGGGATGGATCTGTGGGGCCA<br>GGGAACTCTTGTGACCGTGTCGTCAGCATCCACCAAGGGCC<br>CATCGGTCTTCCCCCTGGCACCCTCCTCAAGAGCACCTCT<br>GGGGGCACAGCGGCCCTGGGCTGCCTGGTCAAGGACTACTT<br>CCCCGAACCGGTGACGGTGTCGTGGAACTCAGGCGCCCTGA<br>CCAGCGGCGTGCACACCTTCCCGGCTGTCCTACAGTCCTCA<br>GGACTCTACTCCTCAGCAGCGTGGTGACCGTGCCCTCCAG<br>CAGCTTGGGCACCCAGACCTACATCTGCAACGTGAATCACA<br>AGCCCAGCAACACCAAGGTGGACAAGAAAGTTGAGCCCAAA<br>TCTTGTGACAAAACTCACACATGCCCACCGTGCCCAGCACC<br>TGAACTCCTGGGGGGACCGTCAGTCTTCCTCTTCCCCCCAA<br>AACCCAAGGACACCCTCATGATCTCCCGGACCCCTGAGGTC<br>ACATGCGTGGTGGTGGACGTGAGCCACGAAGACCCTGAGGT<br>CAAGTTCAACTGGTACGTGGACGGCGTGGAGGTGCATAATG<br>CCAAGACAAAGCCGCGGGAGGAGCAGTACAACAGCACGTAC<br>CGTGTGGTCAGCGTCCTCACCGTCCTGCACCAGGACTGGCT<br>GAATGGCAAGGAGTACAAGTGCAAGGTCTCCAACAAAGCCC<br>TCCCAGCCCCCATCGAGAAAACCATCTCCAAAGCCAAAGGG<br>CAGCCCCGAGAACCACAGGTGTACACCCTGCCCCCATCCCG<br>GGATGAGCTGACCAAGAACCAGGTCAGCCTGACCTGCCTGG<br>TCAAAGGCTTCTATCCCAGCGACATCGCCGTGGAGTGGGAG<br>AGCAATGGGCAGCCGGAGAACAACTACAAGACCACGCCTCC<br>CGTGCTGGACTCCGACGGCTCCTTCTTCTTATATTCAAAGC<br>TCACCGTGGACAAGAGCAGGTGGCAGCAGGGGAACGTCTTC<br>TCATGCTCCGTGATGCATGAGGCTCTGCACAACCACTACAC<br>GCAGAAGAGCCTCTCCCTGTCTCCCGGGAAATGA<br>(SEQ ID NO: 63) | YYASWAKGRFTISRHNSKN<br>TLYLQMNSLRAEDTAVYYC<br>ARGIQHGGGNSDYYYYGMD<br>LWGQGTLVTVSSASTKGPS<br>VFPLAPSSKSTSGGTAALG<br>CLVKDYFPEPVTVSWNSGA<br>LTSGVHTFPAVLQSSGLYS<br>LSSVVTVPSSSLGTQTYIC<br>NVNHKPSNTKVDKKVEPKS<br>CDKTHTCPPCPAPELLGGP<br>SVFLFPPKPKDTLMISRTP<br>EVTCVVVDVSHEDPEVKFN<br>WYVDGVEVHNAKTKPREEQ<br>YNSTYRVVSVLTVLHQDWL<br>NGKEYKCKVSNKALPAPIE<br>KTISKAKGQPREPQVYTLP<br>PSRDELTKNQVSLTCLVKG<br>FYPSDIAVEWESNGQPENN<br>YKTTPPVLDSDGSFFLYSK<br>LTVDKSRWQQGNVFSCSVM<br>HEALHNHYTQKSLSLSPGK<br>*<br>(SEQ ID NO: 64) | | | |
| xi32405HC<br>(rabbitVh-<br>human IgG1)<br>(human MSLN) | ATGGGCTGGTCCTGCATCATCCTGTTTCTGGTGGCCACCGC<br>CACCGGCGTGCACTCCCAGTCGCTGGAGGAGTCCGGGGGTC<br>GCCTGGTCACGCCTGGGACACCCCTGACACTCACCTGCACA<br>GCCTCTGGATTCTCCCTCAGTAACTATGCAATGACCTGGGT<br>CCGCCAGGCTCCAGGGAAGGGGCTAGAATACATCGGAATCA<br>TTAGTACTGGCGGTATCACATACTATATGGACTCGGCAAAA<br>GGCCGATTCACCATCTCCAGAACCTCGACCACGGTGGATCT<br>GAAAATGACCAGTCTGACAACCGAGGACACGGCCACCTATT<br>TCTGTGGCAGAAATGCTGGTGGTAGTTATATTTTCTATTAT<br>TTTGACTTGTGGGGCCAAGGCACCCTGGTCACTGTCTCTTC<br>AGCATCCACCAAGGGCCCATCGGTCTTCCCCCTGGCACCCT<br>CCTCCAAGAGCACCTCTGGGGGCACAGCGGCCCTGGGCTGC<br>CTGGTCAAGGACTACTTCCCCGAACCGGTGACGGTGTCGTG<br>GAACTCAGGCGCCCTGACCAGCGGCGTGCACACCTTCCCGG<br>CTGTCCTACAGTCCTCAGGACTCTACTCCCTCAGCAGCGTG<br>GTGACCGTGCCCTCCAGCAGCTTGGGCACCCAGACCTACAT<br>CTGCAACGTGAATCACAAGCCCAGCAACACCAAGGTGGACA<br>AGAAAGTTGAGCCCAAATCTTGTGACAAAACTCACACATGC<br>CCACCGTGCCCAGCACCTGAACTCCTGGGGGGACCGTCAGT<br>CTTCCTCTTCCCCCCAAAACCCAAGGACACCCTCATGATCT<br>CCCGGACCCCTGAGGTCACATGCGTGGTGGTGGACGTGAGC<br>CACGAAGACCCTGAGGTCAAGTTCAACTGGTACGTGGACGG<br>CGTGGAGGTGCATAATGCCAAGACAAAGCCGCGGGAGGAGC<br>AGTACAACAGCACGTACCGTGTGGTCAGCGTCCTCACCGTC<br>CTGCACCAGGACTGGCTGAATGGCAAGGAGTACAAGTGCAA<br>GGTCTCCAACAAAGCCCTCCCAGCCCCCATCGAGAAAACCA<br>TCTCCAAAGCCAAAGGGCAGCCCCGAGAACCACAGGTGTAC<br>ACCCTGCCCCCATCCCGGGATGAGCTGACCAAGAACCAGGT<br>CAGCCTGACCTGCCTGGTCAAAGGCTTCTATCCCAGCGACA<br>TCGCCGTGGAGTGGGAGAGCAATGGGCAGCCGGAGAACAAC<br>TACAAGACCACGCCTCCCGTGCTGGACTCCGACGGCTCCTT<br>CTTCCTTATATTCAAAGCTCACCGTGGACAAGAGCAGGTGGC<br>AGCAGGGGAACGTCTTCTCATGCTCCGTGATGCATGAGGCT<br>CTGCACAACCACTACACGCAGAAGAGCCTCTCCCTGTCTCC<br>CGGGAAATGA<br>(SEQ ID NO: 65) | MGWSCIILFLVATATGVHS<br>QSLEESGGRLVTPGTPLTL<br>TCTASGFSLSNYAMTWVRQ<br>APGKGLEYIGIISTGGITY<br>YMDSAKGRFTISRTSTVD<br>LKMTSLTTEDTATYFCGRN<br>AGGSYIFYYFDLWGQGTLV<br>TVSSASTKGPSVFPLAPSS<br>KSTSGGTAALGCLVKDYFP<br>EPVTVSWNSGALTSGVHTF<br>PAVLQSSGLYSLSSVVTVP<br>SSSLGTQTYICNVNHKPSN<br>TKVDKKVEPKSCDKTHTCP<br>PCPAPELLGGPSVFLFPPK<br>PKDTLMISRTPEVTCVVVD<br>VSHEDPEVKFNWYVDGVEV<br>HNAKTKPREEQYNSTYRVV<br>SVLTVLHQDWLNGKEYKCK<br>VSNKALPAPIEKTISKAKG<br>QPREPQVYTLPPSRDELTK<br>NQVSLTCLVKGFYPSDIAV<br>EWESNGQPENNYKTTPPVL<br>DSDGSFFLYSKLTVDKSRW<br>QQGNVFSCSVMHEALHNHY<br>TQKSLSLSPGK*<br>(SEQ ID NO: 66) | 1-57 | 58-411 | 412-1404 |
| xi178F16HC<br>(rabbitVh-<br>human IgG1) | ATGGGCTGGTCCTGCATCATCCTGTTTCTGGTGGCCACCGC<br>CACCGGCGTGCACTCCCAGTCGTTGGAGGAGTCCGGGGGTC<br>GCCTGGTCACGCCTGGGACACCCCTGACACTCACCTGCACA | MGWSCIILFLVATATGVHS<br>QSLEESGGRLVTPGTPLTL<br>TCTASGFSLSNYAMTWVRQ | 1-57 | 58-411 | 412-1404 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| (human MSLN) | GCCTCTGGATTCTCCCTCAGTAACTATGCAATGACCTGGGT CCGCCAGGCTCCAGGGAAGGGGCTAGAATACATCGGAATCA TTAGTACTGGCGGTATCACATACTATATGGACTCGGCAAAA GGCCGATTCACCATCTCCAGAACCTCGACCACGGTGGATCT GAAAATGACCAGTCTGACAACCGAGGACACGGCCACCTATT TCTGTGGCAGAAATGCTGGTAGTTATATTTTCTATTAT TTCGACTTGTGGGGCCAAGGGACCCTCGTCACTGTCTCTTC AGCATCCACCAAGGGCCCATCGGTCTTCCCCCTGGCACCCT CCTCCAAGAGCACCTCTGGGGGCACAGCGGCCCTGGGCTGC CTGGTCAAGGACTACTTCCCCGAACCGGTGACGGTGTCGTG GAACTCAGGCGCCCTGACCAGCGGCGTGCACACCTTCCCGG CTGTCCTACAGTCCTCAGGACTCTACTCCCTCAGCAGCGTG GTGACCGTGCCCTCCAGCAGCTTGGGCACCCAGACCTACAT CTGCAACGTGAATCACAAGCCCAGCAACACCAAGGTGGACA AGAAAGTTGAGCCCAAATCTTGTGACAAAACTCACACATGC CCACCGTGCCCAGCACCTGAACTCCTGGGGGGACCGTCAGT CTTCCTCTTCCCCCCAAAACCCAAGGACACCCTCATGATCT CCCGGACCCCTGAGGTCACGTGCGTGGTGGTGGACGTGAGC CACGAAGACCCTGAGGTCAAGTTCAACTGGTACGTGGACGG CGTGGAGGTGCATAATGCCAAGACAAAGCCGCGGGAGGAGC AGTACAACAGCACGTACCGTGTGGTCAGCGTCCTCACCGTC CTGCACCAGGACTGGCTGAATGGCAAGGAGTACAAGTGCAA GGTCTCCAACAAAGCCCTCCCAGCCCCCATCGAGAAAACCA TCTCCAAAGCCAAAGGGCAGCCCCGAGAACCACAGGTGTAC ACCCTGCCCCCATCCCGGGATGAGCTGACCAAGAACCAGGT CAGCCTGACCTGCCTGGTCAAAGGCTTCTATCCCAGCGACA TCGCCGTGGAGTGGGAGAGCAATGGGCAGCCGGAGAACAAC TACAAGACCACGCCTCCCGTGCTGGACTCCGACGGCTCCTT CTTCTTATATTCAAAGCTCACCGTGGACAAGAGCAGGTGGC AGCAGGGGAACGTCTTCTCATGCTCCGTGATGCATGAGGCT CTGCACAACCACTACACGCAGAAGAGCCTCTCCCTGTCTCC CGGGAAATGA (SEQ ID NO: 67) | APGKGLEYIGIISTGGITY YMDSAKGRFTISRTSTTVD LKMTSLTTEDTATYFCGRN AGGSYIFYYFDLWGQGTLV TVSSASTKGPSVFPLAPSS KSTSGGTAALGCLVKDYFP EPVTVSWNSGALTSGVHTF PAVLQSSGLYSLSSVVTVP SSSLGTQTYICNVNHKPSN TKVDKKVEPKSCDKTHTCP PCPAPELLGGPSVFLFPPK PKDTLMISRTPEVTCVVVD VSHEDPEVKFNWYVDGVEV HNAKTKPREEQYNSTYRVV SVLTVLHQDWLNGKEYKCK VSNKALPAPIEKTISKAKG QPREPQVYTLPPSRDELTK NQVSLTCLVKGFYPSDIAV EWESNGQPENNYKTTPPVL DSDGSFFLYSKLTVDKSRW QQGNVFSCSVMHEALHNHY TQKSLSLSPGK* (SEQ ID NO: 68) | | | |
| xi237N18HC (rabbitVh-human IgG1) (human MSLN) | ATGGGCTGGTCCTGCATCATCCTGTTTCTGGTGGCCACCGC CACCGGCGTGCACTCCCAGTCGCTGGAGGAGTCCGGGGGTC GCCTGGTCGCGCCTGGGACACCCCTGACACTCACCTGCACA GTCTCTGGATTCTCCCTCAGTAGTTACCACATGAGCTGGGT CCGCCAGGCTCCAGGGAAGGGCTGGAATGGATCGGAGGCA TACGCCTCATGGGCGAAGGGATGGAAAGCCGCTTCACCATC TCCAAAACCTCGACGGTCGGAGGCGAAAG CCGCCAAAGCTGGCGGCTGGAAAACATGACGACGGCCAAA CTAATCAGTCCGACAACCGAGGACACGGCCACCTATT TCTGTGCCAGGGAACCTGGTTTTGTTAGTAACATCTGGGGC CCAGGCACCCTGGTCACCGTCTCCTTAGCATCCACCAAGGG CCCATCGGTCTTCCCCCTGGCACCCTCCTCCAAGAGCACCT CTGGGGGCACAGCGGCCCTGGGCTGCCTGGTCAAGGACTAC TTCCCCGAACCGGTGACGGTGTCGTGGAACTCAGGCGCCCT GACCAGCGGCGTGCACACCTTCCCGGCTGTCCTACAGTCCT CAGGACTCTACTCCCTCAGCAGCGTGGTGACCGTGCCCTCC AGCAGCTTGGGCACCCAGACCTACATCTGCAACGTGAATCA CAAGCCCAGCAACACCAAGGTGGACAAGAAAGTTGAGCCCA AATCTTGTGACAAAACTCACACATGCCCACCGTGCCCAGCA CCTGAACTCCTGGGGGGACCGTCAGTCTTCCTCTTCCCCCC AAAACCCAAGGACACCCTCATGATCTCCCGGACCCCTGAGG TCACATGCGTGGTGGTGGACGTGAGCCACGAAGACCCTGAG GTCAAGTTCAACTGGTACGTGGACGGCGTGGAGGTGCATAA TGCCAAGACAAAGCCGCGGGAGGAGCAGTACAACAGCACGT ACCGTGTGGTCAGCGTCCTCACCGTCCTGCACCAGGACTGG CTGAATGGCAAGGAGTACAAGTGCAAGGTCTCCAACAAAGC CCTCCCAGCCCCCATCGAGAAAACCATCTCCAAAGCCAAAG GGCAGCCCCGAGAACCACAGGTGTACACCCTGCCCCCATCC CGGGATGAGCTGACCAAGAACCAGGTCAGCCTGACCTGCCT GGTCAAAGGCTTCTATCCCAGCGACATCGCCGTGGAGTGGG AGAGCAATGGGCAGCCGGAGAACAACTACAAGACCACGCCT CCCGTGCTGGACTCCGACGGCTCCTTCTTCTTATATTCAAA GCTCACCGTGGACAAGAGCAGGTGGCAGCAGGGGAACGTCT TCTCATGCTCCGTGATGCATGAGGCTCTGCACAACCACTAC ACGCAGAAGAGCCTCTCCCTGTCTCCGGGAAATGA (SEQ ID NO: 69) | MGWSCIILFLVATATGVHS QSLEESGGRLVAPGTPLTL TCTVSGFSLSSYHMSWVRQ APGEGLEWIGGITAMSRTY YASWAKGRFTISKTSTTVH LKITSPTTEDTATYFCARE PGFVSNIWGPGTLVTVSLA STKGPSVFPLAPSSKSTSG GTAALGCLVKDYFPEPVTV SWNSGALTSGVHTFPAVLQ SSGLYSLSSVVTVPSSSLG TQTYICNVNHKPSNTKVDK KVEPKSCDKTHTCPPCPAP ELLGGPSVFLFPPKPKDTL MISRTPEVTCVVVDVSHED PEVKFNWYVDGVEVHNAKT KPREEQYNSTYRVVSVLTV LHQDWLNGKEYKCKVSNKA LPAPIEKTISKAKGQPREP QVYTLPPSRDELTKNQVSL TCLVKGFYPSDIAVEWESN GQPENNYKTTPPVLDSDGS FFLYSKLTVDKSRWQQGNV FSCSVMHEALHNHYTQKSL SLSPGK* (SEQ ID NO: 70) | 1-57 | 58-396 | 397-1389 |
| xi383118HC (rabbitVh-human IgG1) | ATGGGCTGGTCCTGCATCATCCTGTTTCTGGTGGCCACCGC CACCGGCGTGCACTCCCAGTCGGTGGAGGAGTCCGGGGGTC GCCTGGTCACGCCTGGGACACCCCTGACACTCACCTGCACA | MGWSCIILFLVATATGVHS QSVEESGGRLVTPGTPLTL TCTVSGFSLSSYAMGWVRQ | 1-57 | 58-411 | 412-1404 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| (human MSLN) | GTCTCTGGATTCTCCCTCAGTAGCTATGCAATGGGCTGGGT CCGCCAGGCTCCAGGGGAGGGGCTGGAATGGATCGGAACCA TTAGTACTGGTGGTATTACATACTACGCGAGCTGGGCGAAA GGCCGATTCACCATCTCCAAAACCTCGACCACGGTGGATCT GAAAATCACCAGTCCGACAACCGAGGACACGGCCACCTATT TCTGTGCCAGAGTGGGTAGTAGTGGTTATCTTTTCTACTTC TTTAACTTGTGGGGCCAAGGCACCCTCGTCACTGTCTCCTC AGCATCCACCAAGGGCCCATCGGTCTTCCCCCTGGCACCCT CCTCCAAGAGCACCTCTGGGGGCACAGCGGCCCTGGGCTGC CTGGTCAAGGACTACTTCCCCGAACCGGTGACGGTGTCGTG GAACTCAGGCGCCCTGACCAGCGGCGTGCACACCTTCCCGG CTGTCCTACAGTCCTCAGGACTCTACTCCCTCAGCAGCGTG GTGACCGTGCCCTCCAGCAGCTTGGGCACCCAGACCTACAT CTGCAACGTGAATCACAAGCCCAGCAACACCAAGGTGGACA AGAAAGTTGAGCCCAAATCTTGTGACAAAACTCACACATGC CCACCGTGCCCAGCACCTGAACTCCTGGGGGGACCGTCAGT CTTCCTCTTCCCCCCAAAACCCAAGGACACCCTCATGATCT CCCGGACCCCTGAGGTCACGTGCGTGGTGGTGGACGTGAGC CACGAAGACCCTGAGGTCAAGTTCAACTGGTACGTGGACGG CGTGGAGGTGCATAATGCCAAGACAAAGCCGCGGGAGGAGC AGTACAACAGCACGTACCGTGTGGTCAGCGTCCTCACCGTC CTGCACCAGGACTGGCTGAATGGCAAGGAGTACAAGTGCAA GGTCTCCAACAAAGCCCTCCCAGCCCCCATCGAGAAAACCA TCTCCAAAGCCAAAGGGCAGCCCCGAGAACCACAGGTGTAC ACCCTGCCCCCATCCCGGGATGAGCTGACCAAGAACCAGGT CAGCCTGACCTGCCTGGTCAAAGGCTTCTATCCCAGCGACA TCGCCGTGGAGTGGGAGAGCAATGGGCAGCCGGAGAACAAC TACAAGACCACGCCTCCCGTGCTGGACTCCGACGGCTCCTT CTTCTTATATTCAAAGCTCACCGTGGACAAGAGCAGGTGGC AGCAGGGGAACGTCTTCTCATGCTCCGTGATGCATGAGGCT CTGCACAACCACTACACGCAGAAGAGCCTCTCCCTGTCTCC CGGGAAATGA (SEQ ID NO: 71) | APGEGLEWIGTISTGGITY YASWAKGRFTISKTSTTVD LKITSPTTEDTATYFCARV GSSGYLFYFFNLWGQGTLV TVSSASTKGPSVFPLAPSS KSTSGGTAALGCLVKDYFP EPVTVSWNSGALTSGVHTF PAVLQSSGLYSLSSVVTVP SSSLGTQTYICNVNHKPSN TKVDKKVEPKSCDKTHTCP PCPAPELLGGPSVFLFPPK PKDTLMISRTPEVTCVVVD VSHEDPEVKFNWYVDGVEV HNAKTKPREEQYNSTYRVV SVLTVLHQDWLNGKEYKCK VSNKALPAPIEKTISKAKG QPREPQVYTLPPSRDELTK NQVSLTCLVKGFYPSDIAV EWESNGQPENNYKTTPPVL DSDGSFFLYSKLTVDKSRW QQGNVFSCSVMHEALHNHY TQKSLSLSPGK* (SEQ ID NO: 72) | | | |
| xi166B3HC (rabbitVh-human IgG1) (human CA9) | ATGGGCTGGTCCTGCATCATCCTGTTTCTGGTGGCCACCGC CACCGGCGTGCACAGCCAGTCGGTGAAGGAGTCCAGGGGTC GCCTGGTCACGCCTGGGACACCCCTGACACTCACCTGCACA GTCTCTGGATTCTCCCTCAGTAGGTATACATTGATCTGGGT CCGCCAGGCTCCAGGGAAGGGCTGGAATGGATCGGAATCA TAGATAGTAGTAGTAGTGCATACTACGCGAGGTGGGCGAAA GGCCGATTCACCATCTCCAAAACCTCGACCACGGTGGATCT TCTGTGCCAGAGACAGAGTCCTAAGCTACGATGGTGGT GATTTGCCCGATGGTTTCGATCCCTGGGGCCCAGGCACCCT GGTCACCGTCCTCAGCATCCACCAAGGGCCCATCGGTCT TCCCCCTGGCACCCTCCTCCAAGAGCACCTCTGGGGGCACA GCGGCCCTGGGCTGCCTGGTCAAGGACTACTTCCCCGAACC GGTGACGGTGTCGTGGAACTCAGGCGCCCTGACCAGCGGCG TGCACACCTTCCCGGCTGTCCTACAGTCCTCAGGACTCTAC TCCCTCAGCAGCGTGGTGACCGTGCCCTCCAGCAGCTTGGG CACCCAGACCTACATCTGCAACGTGAATCACAAGCCCAGCA ACACCAAGGTGGACAAGAAAGTTGAGCCCAAATCTTGTGAC AAAACTCACACATGCCCACCGTGCCCAGCACCTGAACTCCT GGGGGGACCGTCAGTCTTCCTCTTCCCCCCAAAACCCAAGG ACACCCTCATGATCTCCCGGACCCCTGAGGTCACATGCGTG GTGGTGGACGTGAGCCACGAAGACCCTGAGGTCAAGTTCAA CTGGTACGTGGACGGCGTGGAGGTGCATAATGCCAAGACAA AGCCGCGGGAGGAGCAGTACAACAGCACGTACCGTGTGGTC AGCGTCCTCACCGTCCTGCACCAGGACTGGCTGAATGGCAA GGAGTACAAGTGCAAGGTCTCCAACAAAGCCCTCCCAGCCC CCATCGAGAAAACCATCTCCAAAGCCAAAGGGCAGCCCCGA GAACCACAGGTGTACACCCTGCCCCCATCCCGGGATGAGCT GACCAAGAACCAGGTCAGCCTGACCTGCCTGGTCAAAGGCT TCTATCCCAGCGACATCGCCGTGGAGTGGGAGAGCAATGGG CAGCCGGAGAACAACTACAAGACCACGCCTCCCGTGCTGGA CTCCGACGGCTCCTTCTTCTTATATTCAAAGCTCACCGTGG ACAAGAGCAGGTGGCAGCAGGGGAACGTCTTCTCATGCTCC GTGATGCATGAGGCTCTGCACAACCACTACACGCAGAAGAG CCTCTCCCTGTCTCCCGGGAAATGA (SEQ ID NO: 73) | MGWSCIILFLVATATGVHS QSVKESRGRLVTPGTPLTL TCTVSGFSLSRYTLIWVRQ APGKGLEWIGIIDSSSSAY YARWAKGRFTISKTSTTVD LKITSPTTEDTATYFCARD RVLSYDDYGDLPDGFDPWG QGTLVTVSSASTKGPSVFP LAPSSKSTSGGTAALGCLV KDYFPEPVTVSWNSGALTS GVHTFPAVLQSSGLYSLSS VVTVPSSSLGTQTYICNVN HKPSNTKVDKKVEPKSCDK THTCPPCPAPELLGGPSVF LFPPKPKDTLMISRTPEVT CVVVDVSHEDPEVKFNWYV DGVEVHNAKTKPREEQYNS TYRVVSVLTVLHQDWLNGK EYKCKVSNKALPAPIEKTI SKAKGQPREPQVYTLPPSR DELTKNQVSLTCLVKGFYP SDIAVEWESNGQPENNYKT TPPVLDSDGSFFLYSKLTV DKSRWQQGNVFSCSVMHEA LHNHYTQKSLSLSPGK* (SEQ ID NO: 74) | 1-57 | 58-426 | 427-1419 |
| zu166B3HC (humanVh- | ATGGGCTGGTCCTGCATCATCCTGTTTCTGGTGGCCACCGC CACCGGCGTGCACAGCGAAGTGCAGCTGGTCGAATCTGGAG | MGWSCIILFLVATATGVHS EVQLVESGGGLVQPGGSLR | 1-57 | 58-435 | 436-1428 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| human IgG1) (human CA9) | GAGGACTGGTGCAGCCTGGAGGGAGCCTGAGACTGAGTTGC GCAGCAAGCGGGTTTAGCCTGTCCCGATACACCCTGATCTG GGTGAGACAGGCCCCCGGCAAGGGACTGGAGTGGGTCTCTA TCATTGACAGCTCCTCTAGTGCCTACTATGCTGATAGTGTG AAGGGCAGGTTCACCATTTCACGCGACAACGCTAAAAATAG CCTGTATCTGCAGATGAACTCCCTGCGGGCAGAAGACACAG CCGTGTACTATTGCGCACGGGATAGAGTCCTGAGCTACGAC GATTATGGGGACCTGCCTGACGGCTTTGATCCTTGGGGACA GGGAACTCTGGTGACAGTGAGCAGCGCATCCACCAAGGGCC CATCGGTCTTCCCCCTGGCACCCTCCTCCAAGAGCACCTCT GGGGGCACAGCGGCCCTGGGCTGCCTGGTCAAGGACTACTT CCCCGAACCGGTGACGGTGTCGTGGAACTCAGGCGCCCTGA CCAGCGGCGTGCACACCTTCCCGGCTGTCCTACAGTCCTCA GGACTCTACTCCCTCAGCAGCGTGGTGACCGTGCCCTCCAG CAGCTTGGGCACCCAGACCTACATCTGCAACGTGAATCACA AGCCCAGCAACACCAAGGTGGACAAGAAAGTTGAGCCCAAA TCTTGTGACAAAACTCACACATGCCCACCGTGCCCAGCACC TGAACTCCTGGGGGGACCGTCAGTCTTCCTCTTCCCCCCAA AACCCAAGGACACCCTCATGATCTCCCGGACCCCTGAGGTC ACATGCGTGGTGGTGGACGTGAGCCACGAAGACCCTGAGGT CAAGTTCAACTGGTACGTGGACGGCGTGGAGGTGCATAATG CCAAGACAAAGCCGCGGGAGGAGCAGTACAACAGCACGTAC CGTGTGGTCAGCGTCCTCACCGTCCTGCACCAGGACTGGCT GAATGGCAAGGAGTACAAGTGCAAGGTCTCCAACAAAGCCC TCCCAGCCCCCATCGAGAAAACCATCTCCAAAGCCAAAGGG CAGCCCCGAGAACCACAGGTGTACACCCTGCCCCCATCCCG GGATGAGCTGACCAAGAACCAGGTCAGCCTGACCTGCCTGG TCAAAGGCTTCTATCCCAGCGACATCGCCGTGGAGTGGGAG AGCAATGGGCAGCCGGAGAACAACTACAAGACCACGCCTCC CGTGCTGGACTCCGACGGCTCCTTCTTCCTATATTCAAAGC TCACCGTGGACAAGAGCAGGTGGCAGCAGGGGAACGTCTTC TCATGCTCCGTGATGCATGAGGCTCTGCACAACCACTACAC GCAGAAGAGCCTCTCCCTGTCTCCCGGGAAATGA (SEQ ID NO: 75) | LSCAASGFSLSRYTLIWVR QAPGKGLEWVSIIDSSSSA YYADSVKGRFTISRDNAKN SLYLQMNSLRAEDTAVYYC ARDRVLSYDDYGDLPDGFD PWGQGTLVTVSSASTKGPS VFPLAPSSKSTSGGTAALG CLVKDYFPEPVTVSWNSGA LTSGVHTFPAVLQSSGLYS LSSVVTVPSSSLGTQTYIC NVNHKPSNTKVDKKVEPKS CDKTHTCPPCPAPELLGGP SVFLFPPKPKDTLMISRTP EVTCVVVDVSHEDPEVKFN WYVDGVEVHNAKTKPREEQ YNSTYRVVSVLTVLHQDWL NGKEYKCKVSNKALPAPIE KTISKAKGQPREPQVYTLP PSRDELTKNQVSLTCLVKG FYPSDIAVEWESNGQPENN YKTTPPVLDSDGSFFLYSK LTVDKSRWQQGNVFSCSVM HEALHNHYTQKSLSLSPGK (SEQ ID NO: 76) | | | |
| xi155D5LC (rabbitVk-human kappa) (human CA9) | ATGGGCTGGTCCTGCATCATCCTGTTTCTGGTGGCCACCGC CACCGGCGTGCACAGCGAGCTCGTGATGACCCAGACTCCAT CCTCCGTGTCTGCAGCTGTGGGAGGCACAGTCACCATCAAT TGCCAGGCCAGTCAGAGTATTAGTAGCTACTTAGCCTGGTA TCAGCAGAAACCAGGGCAGCCTCCCAAGCTCCTGATCTATT ATGCATCCACTCTGGCGTCTGGGGTCCCATCGCGGTTCAAA GGCAGTGGCTCTGGGACAGAGTTCACTCTCACCATCACCGG CGTGCAGTGTGACGATGCTGCCACTTACTACTGTCTAGGTG TTTATGGTTATAGTTTTGATGATGGTATTGCTTTCGGCGGA GGGACCGAGCTGGAGATCAAACGAACTGTGGCTGCACCATC TGTCTTCATCTTCCCGCCATCTGATGAGCAGTTGAAATCTG GAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCA AGGACAGCACCTACAGCCTCAGCAGCACCCTGACGCTGAGC AAAGCAGACTACGAGAAACACAAAGTCTACGCCTGCGAAGT CACCCATCAGGGCCTGAGCTCGCCCGTCACAAAGAGCTTCA ACAGGGGAGAGTGTTGA (SEQ ID NO: 77) | MGWSCIILFLVATATGVHS ELVMTQTPSSVSAAVGGTV TINCQASQSISSYLAWYQQ KPGQPPKLLIYYASTLASG VPSRFKGSGSGTEFTLTIT MHSTLASGVPIRFKGVQCDDAATYYCLGVYGYS FDDGIAFGGGTELEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 78) | 1-57 | 58-390 | 391-714 |
| zu155D5LC-1 (humanVk-human kappa) (human | ATGGGGTGGTCTTGCATCATTCTGTTCCTGGTGGCAACCGC CACAGGTGTGCACTCCGACATCCAGATGACTCAGAGTCCAT CAACCCTGTCCGCTAGCGTGGGAGATAGAGTGACTATCACC TGTCAGGCCTCTCAGAGTATTTCCAGCTACCTGGCTTGGTA TCAGCAGAAGCCAGGCAAAGCACCCAAGCTGCTGATCTACT ATGCTAGTACACTGGCATCAGGAGTGCCTTCCCGCTTCTCA GGTTCCGGCAGCGGAACTGAGTTTACACTGACTATTTCTAG TCTGCAGCCTGACGATTTCGCTACCTACTATTGCCTGGGGG TGTACGGTTATTCTTTCGACGATGGCATCGCATTTGGCGGA GGGACAAAGGTGGAGATTAAGAGACTGTGGCTGCACCATCCCAG TGTGTTCATTTTTCCCCCTAGCGACGAACAGCTGAAAAGCG GACAGCCTCTGTGGTGTGTCTGCTGAACAATTTTTACCCT CGGGAGGCAAAGTGCAGTGGAAGGTGGATAACGCTCTGCA GTCTGGCAATAGTCAGGAGTCAGTGACCGAACAGGACTCCA AAGATAGCACATATTCTCTGTCATCCACCCTGACACTGTCC AAGGCAGACTACGAGAAGCACAAAGTGTATGCCTGCGAAGT | MGWSCIILFLVATATGVHS DIQMTQSPSTLSASVGDRV TITCQASQSISSYLAWYQQ KPGKAPKLLIYYASTLASG VPSRFSGSGSGTEFTLTIS SLQCDDFATYYCLGVYGYS FDDGIAFGGGTKVEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 80) | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GACTCATCAGGGCCTGAGCTCTCCCGTGACCAAGAGCTTTA<br>ACAGGGGAGAATGTTGA<br>(SEQ ID NO: 79) | | | | |
| zu155D5LC-2<br>(humanVk-<br>human kappa)<br>(human CA9) | ATGGGGTGGTCTTGCATCATTCTGTTCCTGGTGGCAACCGC<br>CACAGGTGTGCACTCCGACATCCAGATGACTCAGAGTCCAT<br>CAACCCTGTCCGCTAGCGTGGGAGATAGAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCTCA<br>GGTTCCGGCAGCGGAACTGAGTTTACACTGACTATTACTGG<br>TGTGCAGTGCGACGATTTCGCTACCTACTATTGCCTGGGGG<br>TGTACGGTTATTCTTTCGACGATGGCATCGCATTTGGCGGA<br>GGGACAAAAGTGGAGATTAAGAGGACTGTGGCCGCTCCCAG<br>TGTGTTCATTTTTCCCCCTAGCGACGAACAGCTGAAAAGCG<br>GGACAGCCTCTGTGGTGTGTCTGCTAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 81) | MGWSCIILFLVATATGVHS<br>DIQMTQSPSTLSASVGDRV<br>TITCQASQSISSYLAWYQQ<br>KPGKAPKLLIYYASTLASG<br>VPSRFSGSGSGTEFTLTIT<br>GVQCDDFATYYCLGVYGYS<br>FDDGIAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 82) | 1-57 | 58-390 | 391-714 |
| zu155D5LC-3<br>(humanVk-<br>human kappa)<br>(human CA9) | ATGGGGTGGTCTTGCATCATTCTGTTCCTGGTGGCAACCGC<br>CACAGGTGTGCACTCCGACATCCAGATGACTCAGAGTCCAT<br>CAACCCTGTCCGCTAGCGTGGGAGATAGAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCTCA<br>GGTTCCGGCAGCGGAACTGAGTTTACACTGACTATTTCTAG<br>TCTGCAGTGCGACGATGCCGCTACCTACTATTGCCTGGGGG<br>TGTACGGTTATTCTTTCGACGATGGCATCGCATTTGGCGGA<br>GGGACAAAAGTGGAGATTAAGAGGACTGTGGCCGCTCCCAG<br>TGTGTTCATTTTTCCCCCTAGCGACGAACAGCTGAAAAGCG<br>GGACAGCCTCTGTGGTGTGTCTGCTAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 83) | MGWSCIILFLVATATGVHS<br>DIQMTQSPSTLSASVGDRV<br>TITCQASQSISSYLAWYQQ<br>KPGKAPKLLIYYASTLASG<br>VPSRFSGSGSGTEFTLTIS<br>SLQCDDAATYYCLGVYGYS<br>FDDGIAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 84) | 1-57 | 58-390 | 391-714 |
| zu155D5LC-4<br>(humanVk-<br>human kappa)<br>(human CA9) | ATGGGGTGGTCTTGCATCATTCTGTTCCTGGTGGCAACCGC<br>CACAGGTGTGCACTCCGACATCCAGATGACTCAGAGTCCAT<br>CAACCCTGTCCGCTAGCGTGGGAGATAGAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCTCA<br>GGTTCCGGCAGCGGAACTGAGTTTACACTGACTATTACTGG<br>TGTGCAGTGCGACGATGCCGCTACCTACTATTGCCTGGGGG<br>TGTACGGTTATTCTTTCGACGATGGCATCGCATTTGGCGGA<br>GGGACAAAAGTGGAGATTAAGAGGACTGTGGCCGCTCCCAG<br>TGTGTTCATTTTTCCCCCTAGCGACGAACAGCTGAAAAGCG<br>GGACAGCCTCTGTGGTGTGTCTGCTAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 85) | MGWSCIILFLVATATGVHS<br>DIQMTQSPSTLSASVGDRV<br>TITCQASQSISSYLAWYQQ<br>KPGKAPKLLIYYASTLASG<br>VPSRFSGSGSGTEFTLTIT<br>GVQCDDAATYYCLGVYGYS<br>FDDGIAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 86) | 1-57 | 58-390 | 391-714 |
| zu155D5LC-5<br>(humanVk-<br>human kappa)<br>(human CA9) | ATGGGGTGGTCTTGCATCATTCTGTTCCTGGTGGCAACCGC<br>CACAGGTGTGCACTCCGACATCCAGATGACTCAGAGTCCAT<br>CAACCCTGTCCGCTAGCGTGGGAGATAGAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCAAA<br>GGTTCCGGCAGCGGAACTGAGTTTACACTGACTATTACTGG<br>TGTGCAGTGCGACGATGCCGCTACCTACTATTGCCTGGGGG<br>TGTACGGTTATTCTTTCGACGATGGCATCGCATTTGGCGGA | MGWSCIILFLVATATGVHS<br>DIQMTQSPSTLSASVGDRV<br>TITCQASQSISSYLAWYQQ<br>KPGKAPKLLIYYASTLASG<br>VPSRFKGSGSGTEFTLTIT<br>GVQCDDAATYYCLGVYGYS<br>FDDGIAFGGGTKVEIKRTV<br>AAPSVFIFPPSDEQLKSGT<br>ASVVCLLNNFYPREAKVQW | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GGGACAAAAGTGGAGATTAAGAGGACTGTGGCCGCTCCCAG<br>TGTGTTCATTTTTCCCCCTAGCGACGAACAGCTGAAAAGCG<br>GGACAGCCTCTGTGGTGTGTCTGCTGAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 87) | KVDNALQSGNSQESVTEQD<br>SKDSTYSLSSTLTLSKADY<br>EKHKVYACEVTHQGLSSPV<br>TKSFNRGEC*<br>(SEQ ID NO: 88) | | | |
| zu155D5LC-6 (humanVk-human kappa) (human CA9) | ATGGGGTGGTCTTGCATCATTCTGTTCCTGGTGGCAACCGC<br>CACAGGTGTGCACTCCGACATCCAGATGACTCAGAGTCCAT<br>CAACCGTGTCCGCTGCAGTGGGAGGTACAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCTCA<br>GGTTCCGGCAGCGGAACTGAGTTTACACTGACTATTACTGG<br>TGTCAGTGCGACGATGCCGCTACCTACTATTGCCTGGGGG<br>TGTACGGTTATTCTTTCGACGATGGCATCGCATTTGGCGGA<br>GGGACAAAAGTGGAGATTAAGAGGACTGTGGCCGCTCCCAG<br>TGTGTTCATTTTTCCCCCTAGCGACGAACAGCTGAAAAGCG<br>GACAGCCTCTGTGGTGTGTCTGCTGAACAATTTTTACCCT<br>GGACAGCCTCTGTGGTGTGTCTGCTGAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 89) | MGWSCIILFLVATATGVHS<br>DIQMTQSPSTVSAAVGGTV<br>TITCQASQSISSYLAWYQQ<br>KPGKAPKLLIYYASTLASG<br>VPSRFSGSGSGTEFTLTIT<br>GVQCDDAATYYCLGVYGYS<br>FDDGIAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 90) | 1-57 | 58-390 | 391-714 |
| zu155D5LC-7 (humanVk-human kappa) (human CA9) | ATGGGGTGGTCTTGCATCATTCTGTTCCTGGTGGCAACCGC<br>CACAGGTGTGCACTCCGACATCCAGATGACTCAGAGTCCAT<br>CAACCCTGTCCGCTAGCGTGGGAGATAGAGTGACTATCACC<br>TGTCAGGCCTCTCAGAGTATTTCCAGCTACCTGGCTTGGTA<br>TCAGCAGAAGCCAGGCAAAGCACCCAAGCTGCTGATCTACT<br>ATGCTAGTACACTGGCATCAGGAGTGCCTTCCCGCTTCTCA<br>GGTTCCGGCAGCGGAACTGAGTTTACACTGACTATTACTGG<br>TGTCAGTGCGACGATGCCGCTACCTACTATTGCCTGGGGG<br>TGTACGGTTATTCTTTCGACGATGGCATCGCATTTGGCGGA<br>GGGACAGAGCTGGAGATTAAGAGGACTGTGGCCGCTCCCAG<br>TGTGTTCATTTTTCCCCCTAGCGACGAACAGCTGAAAAGCG<br>GGACAGCCTCTGTGGTGTGTCTGCTGAACAATTTTTACCCT<br>CGGGAGGCCAAAGTGCAGTGGAAGGTGGATAACGCTCTGCA<br>GTCTGGCAATAGTCAGGAGTCAGTGACCGAACAGGACTCCA<br>AAGATAGCACATATTCTCTGTCATCCACCCTGACACTGTCC<br>AAGGCAGACTACGAGAAGCACAAAGTGTATGCCTGCGAAGT<br>GACTCATCAGGGCCTGAGCTCTCCCGTGACCAAGAGCTTTA<br>ACAGGGGAGAATGTTGA<br>(SEQ ID NO: 91) | MGWSCIILFLVATATGVHS<br>DIQMTQSPSTLSASVGDRV<br>TITCQASQSISSYLAWYQQ<br>KPGKAPKLLIYYASTLASG<br>VPSRFSGSGSGTEFTLTIT<br>GVQCDDAATYYCLGVYGYS<br>FDDGIAFGGGTELEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 92) | 1-57 | 58-390 | 391-714 |
| zu155D5LC-huVK1-39 (humanVk-human kappa) (human CA9) | ATGGGCTGGTCCTGCATCATCCTGTTTCTGGTGGCCACCGC<br>CACCGGCGTGCACAGCGACATTCAGATGACTCAGTCCCCT<br>CCTCCCTTTCGGCCTCCGTCGGCGACCGCGTGACCATTACC<br>TGTCAAGCCAGCCAGTCCATCTCATCTCCTACTTGGCCTGGTA<br>CCAACAGAAGCCAGGAAAAGCTCCTAAGCTGCTCATCTACT<br>ACGCCTCCACTCTGGCGTCTGGTGTCCCGTCACGGTTCAGC<br>SLQCEDFATYYCLGVYGYS<br>GGTCCGGATCAGGAACTGACTTCACCCTGACGATCAGCAG<br>CCTCCAGTGCGAGGATTTTGCGACCTACTACTGCCTGGGGG<br>TGTATGGTTACTCGTTCGACGATGGAATCGCATTCGGCTCG<br>GGCACCAAGGTGGAAATCAAAGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAAGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 93) | MGWSCIILFLVATATGVHS<br>DIQMTQSPSSLSASVGDRV<br>TITCQASQSISSYLAWYQQ<br>KPGKAPKLLIYYASTLASG<br>VPSRFSGSGSGTDFTLTIS<br>FDDGIAFGSGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 94) | 1-57 | 58-390 | 391-714 |
| zu155D5LC-huVK2-40 | ATGGGCTGGTCCTGCATCATCCTGTTTCTGGTGGCCACCGC<br>CACCGGCGTGCACAGCGACATTGTGATGACCCAGACTCCTC | MGWSCIILFLVATATGVHS<br>DIVMTQTPLSLPVTPGEPA | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| (humanVk-human kappa) (human CA9) | TCTCCCTGCCCGTGACTCCTGGAGAACCCGCCTCGATCTCA TGTCAAGCGTCGCAGAGCATCTCCTCATACTTGGCTTGGTA CCTCCAAAAGCCGGGCCAGAGCCCACAGCTTCTGATCTATT ACGCCTCCACCCTGGCCTCGGGCGTGCCGGATCGGTTTTCC GGTTCTGGAAGCGGAACCGACTTCACCCTGAAAATCTCCCG CGTGGAGTGCGAGGACGTGGGCGTGTACTACTGCCTGGGAG TCTACGGGTACTCCTTCGATGACGGCATTGCATTCGGGTCC GGTACCAAGGTCGAAATCAAACGAACTGTGGCTGCACCATC TGTCTTCATCTTCCCGCCATCTGATGAGCAGTTGAAATCTG GAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCA AGGACAGCACCTACAGCCTCAGCAGCACCCTGACGCTGAGC AAAGCAGACTACGAGAAACACAAAGTCTACGCCTGCGAAGT CACCCATCAGGGCCTGAGCTCGCCCGTCACAAAGAGCTTCA ACAGGGGAGAGTGTTGA (SEQ ID NO: 95) | SISCQASQSISSYLAWYLQ KPGQSPQLLIYYASTLASG VPDRFSGSGSGTDFTLKIS RVECEDVGVYYCLGVYGYS FDDGIAFGSGTKVEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 96) | | | |
| zu155D5LC-huVK3-11 (humanVk-human kappa) (human CA9) | ATGGGCTGGTCCTGCATCATCCTGTTTCTGGTGGCCACCGC CACCGGCGTGCACAGCGAAATTGTGCTCACTCAATCCCCTG CCACCCTTTCCTTGTCCCCCGGCGAAAGAGCCACTCTGTCA TGTCAAGCCAGCCAGTCAATCTCCTCTTACCTGGCTTGGTA CCAGCAGAAGCCAGGACAGGCACCGCGCCTGCTGATCTACT ACGCGTCGACCCTCGCCTCGGGAATCCCGGCCCGGTTCAGC GGATCAGGCTCCGGTACCGACTTCACTCTGACCATTAGCTC CCTGGAGTGCGAGGACTTCGCGGTGTATTACTGCCTGGGGG TGTACGGCTACTCCTTCGATGACGGAATCGCCTTTGGGAGC GGTACCAAGGTCGAGATCAAACGAACTGTGGCTGCACCATC TGTCTTCATCTTCCCGCCATCTGATGAGCAGTTGAAATCTG GAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCA AGGACAGCACCTACAGCCTCAGCAGCACCCTGACGCTGAGC AAAGCAGACTACGAGAAACACAAAGTCTACGCCTGCGAAGT CACCCATCAGGGCCTGAGCTCGCCCGTCACAAAGAGCTTCA ACAGGGGAGAGTGTTGA (SEQ ID NO: 97) | MGWSCIILFLVATATGVHS EIVLTQSPATLSLSPGERA TLSCQASQSISSYLAWYQQ KPGQAPRLLIYYASTLASG IPARFSGSGSGTDFTLTIS SLECEDFAVYYCLGVYGYS FDDGIAFGSGTKVEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 98) | 1-57 | 58-390 | 391-714 |
| zu155D5LC-huVK4-1 (humanVk-human kappa) (human CA9) | ATGGGCTGGTCCTGCATCATCCTGTTTCTGGTGGCCACCGC CACCGGCGTGCACAGCGATATCGTGATGACCCAAAGCCCTG ACTCCCTTGCCGTGTCACTCGGAGAACGCGCCACCATCAAC TGTCAAGCGTCGCAGTCCATCTCCTCATACCTGGCCTGGTA TCAGCAGAAACCGGGGCAGCCGCCAAAGCTGCTGATCTACT ACGCTTCCACTCTGGCCTCCGGCGTGCCCGATCGGTTCTCC GGATCGGGCTCCGGCACCGACTTTACTCTGACCATTAGCAG CCTCCAGTGCGAGGACGTGGCGGTGTACTACTGCTTGGGTG TCTACGGATACTCCTTCGACGACGGGATCGCATTCGGTTCG GGAACCAAGGTCGAGATTAAACGAACTGTGGCTGCACCATC TGTCTTCATCTTCCCGCCATCTGATGAGCAGTTGAAATCTG GAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCA AGGACAGCACCTACAGCCTCAGCAGCACCCTGACGCTGAGC AAAGCAGACTACGAGAAACACAAAGTCTACGCCTGCGAAGT CACCCATCAGGGCCTGAGCTCGCCCGTCACAAAGAGCTTCA ACAGGGGAGAGTGTTGA (SEQ ID NO: 99) | MGWSCIILFLVATATGVHS DIVMTQSPDSLAVSLGERA TINCQASQSISSYLAWYQQ KPGQPPKLLIYYASTLASG VPDRFSGSGSGTDFTLTIS SLQCEDVAVYYCLGVYGYS FDDGIAFGSGTKVEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 100) | 1-57 | 58-390 | 391-714 |
| zu155D5LC-huVK6-21 (humanVk-human kappa) (human CA9) | ATGGGCTGGTCCTGCATCATCCTGTTTCTGGTGGCCACCGC CACCGGCGTGCACAGCGAAATTGTTCTGACCCAAAGCCCTG ACTTCCAATCCGTGACCCCCAAGGAAAAGGTCACCATCACG TGTCAGGCCTCCCAGTCAATTTCCTCGTACCTTGCGTGGTA CCAGCAGAAGCCAGACCAGTCCCCGAAGCTCCTGATTAAGT ACGCATCCACCCTGGCTCCAGGCGTCCCAGTCCGGTTCTCG GGATCCGGCTCTGGAACTGACTTCACTCTGACCATCAACTC GCTCCAGTGCGAAGATGCCGCCACTTACTATTGCTTGGGGG TGTACGGGTACTCATTTGACGATGGCATCGCCTTCGGCTCC GGTACCAAAGGTCGAGATCAAACGAACTGTGGCTGCACCATC TGTCTTCATCTTCCCGCCATCTGATGAGCAGTTGAAATCTG GAACTGCCTCTGTTGTGTGCCTGCTGAATAACTTCTATCCC AGAGAGGCCAAAGTACAGTGGAAGGTGGATAACGCCCTCCA ATCGGGTAACTCCCAGGAGAGTGTCACAGAGCAGGACAGCA AGGACAGCACCTACAGCCTCAGCAGCACCCTGACGCTGAGC | MGWSCIILFLVATATGVHS EIVLTQSPDFQSVTPKEKV TITCQASQSISSYLAWYQQ KPDQSPKLLIKYASTLASG VPSRFSGSGSGTDFTLTIN SLECEDAATYYCLGVYGYS FDDGIAFGSGTKVEIKRTV AAPSVFIFPPSDEQLKSGT ASVVCLLNNFYPREAKVQW KVDNALQSGNSQESVTEQD SKDSTYSLSSTLTLSKADY EKHKVYACEVTHQGLSSPV TKSFNRGEC* (SEQ ID NO: 102) | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 101) | | | | |
| zu155D5LC-huVK6D-41 (humanVk-human kappa) (human CA9) | ATGGGCTGGTCCTGCATCATCCTGTTTCTGGTGGCCACCGC<br>CACCGGCGTGCACAGCGACGTCGTGATGACTCAAAGCCCCG<br>CATTCCTTTCCGTGACTCCTGGAGAAAAGGTCACCATCACC<br>TGTCAAGCCAGCCAGTCCATTTCGTCCTACTTGGCCTGGTA<br>TCAGCAGAAGCCAGACCAGGCCCCGAAGCTGCTGATTAAGT<br>ACGCCTCCACCCTGGCCAGCGGAGTGCCGTCACGGTTCTCC<br>GGGTCCGGCTCAGGAACCGACTTCACGTTCACCATCTCGTC<br>CCTCGAGTGCGAAGATGCTGCGACTTACTACTGCCTGGGCG<br>TGTACGGTTACTCGTTTGATGACGGCATCGCGTTCGGGTCT<br>GGAACCAAAGTGGAGATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 103) | MGWSCIILFLVATATGVHS<br>DVVMTQSPAFLSVTPGEKV<br>TITCQASQSISSYLAWYQQ<br>KPDQAPKLLIKYASTLASG<br>VPSRFSGSGSGTDFTFTIS<br>SLECEDAATYYCLGVYGYS<br>FDDGIAFGSGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 104) | 1-57 | 58-390 | 391-714 |
| zu155D5LC-huVK7-3-Glu81 (humanVk-human kappa) (human CA9) | ATGGGCTGGTCCTGCATCATCCTGTTTCTGGTGGCCACCGC<br>CACCGGCGTGCACAGCGATATCGTCCTCACTCAATCCCCCG<br>CTTCACTCGCCGTGTCCCCTGGTCAACGCGCCACCATTACG<br>TGTCAGGCGTCCCAGTCCATTTCGAGCTACCTTGCATGGTA<br>CCAGCAGAAGCCTGGACAGCCCCCGAAACTGCTGATCTATT<br>ACGCCTCCACCTTGGCCTCGGGAGTGCCAGCGCGGTTTAGC<br>GGTTCGGGCTCCGGCACTGACTTCACTCTGACCATCAACCC<br>GGTGGAGTGCGAAGATACCGCCAACTACTACTGCCTGGGGG<br>TGTACGGATACTCATTCGACGACGGGATCGCCTTCGGAAGC<br>GGCACCAAGGTCGAAATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 105) | MGWSCIILFLVATATGVHS<br>DIVLTQSPASLAVSPGQRA<br>TITCQASQSISSYLAWYQQ<br>KPGQPPKLLIYYASTLASG<br>VPARFSGSGSGTDFTLTIN<br>PVECEDTANYYCLGVYGYS<br>FDDGIAFGSGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 106) | 1-57 | 58-390 | 391-714 |
| xi1-55-2LC (rabbitVk-human kappa) (human TEM1) | ATGGGCTGGTCCTGCATCATCCTGTTTCTGGTGGCCACCGC<br>CACCGGCGTGCACAGCGAGCTCGTGATGACCCAGACTCCAG<br>CCTCTGTGGAGGTAGCTGTGGGAGGCACAGTCACCATCAAG<br>TGCCAGGCCAGTCAGAGCATTAATACCTACTTAGCCTGGTA<br>TCAGCAGAAACCAGGGCAGCCTCCCAAGCTCCTGATCTACA<br>GGGCATCCACTCTGGCATCTGGGGTCCCATCGCGGTTCAAA<br>GGCAGTGGATCTGGGACAGAGTTCACTCTCACCATTAGCGA<br>CCTGGAGTGTGCCGATGCTGCCACTTACTACTGTCAACAGA<br>GTGTTCGTGTTATTGATGTTGATAATACTTTCGGCGGAGGG<br>ACCGAGGTGGTGGTCAAACGAACTGTGGCTGCACCATCTGT<br>CTTCATCTTCCCGCCATCTGATGAGCAGTTGAAATCTGGAA<br>CTGCCTCTGTTGTGTGCCTGCTGAATAACTTCTATCCCAGA<br>GAGGCCAAAGTACAGTGGAAGGTGGATAACGCCCTCCAATC<br>GGGTAACTCCCAGGAGAGTGTCACAGAGCAGGACAGCAAGG<br>ACAGCACCTACAGCCTCAGCAGCACCCTGACGCTGAGCAAA<br>GCAGACTACGAGAAACACAAAGTCTACGCCTGCGAAGTCAC<br>CCATCAGGGCCTGAGCTCGCCCGTCACAAAGAGCTTCAACA<br>GGGGAGAGTGTTGA<br>(SEQ ID NO: 107) | MGWSCIILFLVATATGVHS<br>ELVMTQTPASVEVAVGGTV<br>TIKCQASQSINTYLAWYQQ<br>KPGQPPKLLIYRASTLASG<br>VPSRFKGSGSGTEFTLTIS<br>DLECADAATYYCQQSVRVI<br>DVDNTFGGGTEVVVKRTVA<br>APSVFIFPPSDEQLKSGTA<br>SVVCLLNNFYPREAKVQWK<br>VDNALQSGNSQESVTEQDS<br>KDSTYSLSSTLTLSKADYE<br>KHKVYACEVTHQGLSSPVT<br>KSFNRGEC*<br>(SEQ ID NO: 108) | 1-57 | 58-387 | 388-711 |
| xi1E4LC (rabbitVk-human kappa) (human CA9) | ATGGGCTGGTCCTGCATCATCCTGTTTCTGGTGGCCACCGC<br>CACCGGCGTGCACAGCGAGCTCGTGATGACCCAGACTCCAT<br>CCTACACGTCTGCAGCTGTGGGAGACACAGTCACCATCAAG<br>TGCCAGGCCAGTCAGACCATTGGTGGTAGCGACTTATCCTG<br>GTATCAGCAGAAACCAGGGCAGCCTCCCAAACTCCTGATCT<br>GGTATGCAACCAATCTGCCATCTGGGGTCCCATCGCGGTTC<br>AGTGGCAGTAGATCTGGGACAGAGTACACTCTCACCATCAG<br>CGGCGTGCAGTGTGAGGATGCTGCCACCTACTACTGTCTAG | MGWSCIILFLVATATGVHS<br>ELVMTQTPSYTSAAVGDTV<br>TIKCQASQTIGGSDLSWYQ<br>QKPGQPPKLLIWYATNLPS<br>GVPSRFSGSRSGTEYTLTI<br>SGVQCEDAATYYCLGGYAA<br>ASYRTAFGGGTEVVVKRTV<br>AAPSVFIFPPSDEQLKSGT | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | GTGGTTATGCTGCTGCTTCTTACAGAACTGCTTTCGGCGGA<br>GGGACCGAGGTGGTCGTCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 109) | ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 110) | | | |
| zu1E4LC-CXXF<br>(humanVk-human kappa)<br>(human CA9) | ATGGGCTGGTCCTGCATCATCCTGTTTCTGGTGGCCACCGC<br>CACCGGCGTGCACAGCGATATTCAGATGACTCAGAGCCCTT<br>CCTTCCTGTCAGCCAGCGTCGGGGATAGAGTCACAATCACT<br>TGCCAGGCCAGCCAGACCATTGGCGGGAGCGACCTGTCCTG<br>GTACCAGCAGAAGCCCGGAAAAGCCCCTAAGCTGCTGATCT<br>ACTATGCCACAAACCTGCCATCTGGCGTGCCCAGCCGGTTC<br>TCTGGAAGTGGCTCAGGGACTGACTTTACCCTGACAATTAG<br>CTCCCTGCAGTGCGAGGATTTCGCCACCTACTATTGTCTGG<br>GGGGCTATGCCGCCGCAAGCTACCGCACCGCCTTCGGAGGA<br>GGAACTAAAGTGGAAATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 111) | MGWSCIILFLVATATGVHS<br>DIQMTQSPSFLSASVGDRV<br>TITCQASQTIGGSDLSWYQ<br>QKPGKAPKLLIYYATNLPS<br>GVPSRFSGSGSGTDFTLTI<br>SSLQCEDFATYYCLGGYAA<br>ASYRTAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 112) | 1-57 | 58-390 | 391-714 |
| zu1E4LC-CXXA<br>(humanVk-human kappa)<br>(human CA9) | ATGGGCTGGTCCTGCATCATCCTGTTTCTGGTGGCCACCGC<br>CACCGGCGTGCACAGCGATATTCAGATGACTCAGAGCCCTT<br>CCTTCCTGTCAGCCAGCGTCGGGGATAGAGTCACAATCACT<br>TGCCAGGCCTCACAGACTATTGGCGGGAGCGACCTGTCCTG<br>GTACCAGCAGAAGCCCGGAAAAGCACCTAAGCTGCTGATCT<br>ACTATGCCACAAACCTGCCATCTGGCGTGCCCAGCCGGTTC<br>TCTGGAAGTGGCTCAGGGACTGACTTTACCCTGACAATTAG<br>CTCCCTGCAGTGCGAGGATGCCGCTACCTACTATTGTCTGG<br>GGGGCTACGCCGCCGCTTCATACAGGACCGCCTTCGGAGGA<br>GGAACTAAAGTGGAAATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 113) | MGWSCIILFLVATATGVHS<br>DIQMTQSPSFLSASVGDRV<br>TITCQASQTIGGSDLSWYQ<br>QKPGKAPKLLIYYATNLPS<br>GVPSRFSGSGSGTDFTLTI<br>SSLQCEDAATYYCLGGYAA<br>ASYRTAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 114) | 1-57 | 58-390 | 391-714 |
| xi33O11LC<br>(rabbitVk-human kappa)<br>(human MSLN) | ATGGGCTGGTCCTGCATCATCCTGTTTCTGGTGGCCACCGC<br>CACCGGCGTGCACTCCGAAGTGTTGATGACCCAGACTCCAT<br>CCTCCGTGTCTGCAGCTGTGGGAGACACAGTCACCATCAAG<br>TGCCAGGCCAGTCAGAGCATTAGTAGTGTCTTGTCCTGGTA<br>TCAGCAGAAACCAGGGCAGCCTCCCAAGCTCCTGATCTATC<br>TGGCATCCACTCTGGCATCTGGGGTCCCATCGCGGTTCAGC<br>GGCAGTAGATCTGGGACAGAGTTCACTCTCACCATCAGCGA<br>CCTGGAGTGTGACGATGCTGCCACTTACTACTGTCAAACCA<br>ATTATGGTACTAGTAGTAGTAATTATGGTTTTGCTTTCGGC<br>GGAGGGACCGAGGTGGTCGTCAAACGAACTGTGGCTGCACC<br>ATCTGTCTTCATCTTCCCGCCATCTGATGAGCAGTTGAAAT<br>CTGGAACTGCCTCTGTTGTGTGCCTGCTGAATAACTTCTAT<br>CCCAGAGAGGCCAAAGTACAGTGGAAGGTGGATAACGCCCT<br>CCAATCGGGTAACTCCCAGGAGAGTGTCACAGAGCAGGACA<br>GCAAGGACAGCACCTACAGCCTCAGCAGCACCCTGACGCTG<br>AGCAAAGCAGACTACGAGAAACACAAAGTCTACGCCTGCGA<br>AGTCACCCATCAGGGCCTGAGCTCGCCCGTCACAAAGAGCT<br>TCAACAGGGGAGAGTGTTGA<br>(SEQ ID NO: 115) | MGWSCIILFLVATATGVHS<br>EVLMTQTPSSVSAAVGDTV<br>TIKCQASQSISSVLSWYQQ<br>KPGQPPKLLIYLASTLASG<br>VPSRFSGSRSGTEFTLTIS<br>DLECDDAATYYCQTNYGTS<br>SSNYGFAFGGGTEVVVKRT<br>VAAPSVFIFPPSDEQLKSG<br>TASVVCLLNNFYPREAKVQ<br>WKVDNALQSGNSQESVTEQ<br>DSKDSTYSLSSTLTLSKAD<br>YEKHKVYACEVTHQGLSSP<br>VTKSFNRGEC*<br>(SEQ ID NO: 116) | 1-57 | 58-393 | 394-717 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| zu33011LC-CXXF (humanVk-human kappa) (human MSLN) | ATGGGCTGGTCCTGCATCATCCTGTTTCTGGTGGCCACCGC CACCGGCGTGCACAGCGACATTCAGATGACCCAGTCCCCAA GCTCGCTGTCCGCCTCCGTGGGCGACCGCGTGACCATCACG TGCCAGGCGTCCCAGTCAATTAGCAGCGTGCTCTCCTGGTA CCAACAGAAGCCGGGGAAAGCACCCAAGCTGCTGATCTACT TGGCCTCCACTCTGGCCTCGGGAGTGCCTTCACGGTTCTCC GGATCGGGATCTGGTACTGATTTCACCCTCACCATCTCGAG CCTTCAGTGCGAGGACTTCGCTACTTACTATTGTCAAACCA ACTACGGAACCTCCAGCTCCAACTACGGCTTTGCCTTCGGT GGCGGGACCAAGGTCGAAATCAAACGAACTGTGGCTGCACC ATCTGTCTTCATCTTCCCGCCATCTGATGAGCAGTTGAAAT CTGGAACTGCCTCTGTTGTGTGCCTGCTGAATAACTTCTAT CCCAGAGAGGCCAAAGTACAGTGGAAGGTGGATAACGCCCT CCAATCGGGTAACTCCCAGGAGAGTGTCACAGAGCAGGACA GCAAGGACAGCACCTACAGCCTCAGCAGCACCCTGACGCTG AGCAAAGCAGACTACGAGAAACACAAAGTCTACGCCTGCGA AGTCACCCATCAGGGCCTGAGCTCGCCCGTCACAAAGAGCT TCAACAGGGGAGAGTGTTGA (SEQ ID NO: 117) | MGWSCIILFLVATATGVHS DIQMTQSPSSLSASVGDRV TITCQASQSISSVLSWYQQ KPGKAPKLLIYLASTLASG VPSRFSGSGSGTDFTLTIS SLQCEDFATYYCQTNYGTS SNYGFAFGGGTKVEIKRT VAAPSVFIFPPSDEQLKSG TASVVCLLNNFYPREAKVQ WKVDNALQSGNSQESVTEQ DSKDSTYSLSSTLTLSKAD YEKHKVYACEVTHQGLSSP VTKSFNRGEC* (SEQ ID NO: 118) | 1-57 | 58-393 | 394-717 |
| zu33011LC-CXXA (humanVk-human kappa) (human MSLN) | ATGGGCTGGTCCTGCATCATCCTGTTTCTGGTGGCCACCGC CACCGGCGTGCACAGCGACATTCAGATGACCCAGTCCCCAA GCTCGCTGTCCGCCTCCGTGGGCGACCGCGTGACCATCACG TGCCAGGCGTCCCAGTCAATTAGCAGCGTGCTCTCCTGGTA CCAACAGAAGCCGGGGAAAGCACCCAAGCTGCTGATCTACT TGGCCTCCACTCTGGCCTCGGGAGTGCCTTCACGGTTCTCC GGATCGGGATCTGGTACTGATTTCACCCTCACCATCTCGAG CCTTCAGTGCGAGGACGCCGCTACTTACTATTGTCAAACCA ACTACGGAACCTCCAGCTCCAACTACGGCTTTGCCTTCGGT GGCGGGACCAAGGTCGAAATCAAACGAACTGTGGCTGCACC ATCTGTCTTCATCTTCCCGCCATCTGATGAGCAGTTGAAAT CTGGAACTGCCTCTGTTGTGTGCCTGCTGAATAACTTCTAT CCCAGAGAGGCCAAAGTACAGTGGAAGGTGGATAACGCCCT CCAATCGGGTAACTCCCAGGAGAGTGTCACAGAGCAGGACA GCAAGGACAGCACCTACAGCCTCAGCAGCACCCTGACGCTG AGCAAAGCAGACTACGAGAAACACAAAGTCTACGCCTGCGA AGTCACCCATCAGGGCCTGAGCTCGCCCGTCACAAAGAGCT TCAACAGGGGAGAGTGTTGA (SEQ ID NO: 119) | MGWSCIILFLVATATGVHS DIQMTQSPSSLSASVGDRV TITCQASQSISSVLSWYQQ KPGKAPKLLIYLASTLASG VPSRFSGSGSGTDFTLTIS SLQCEDAATYYCQTNYGTS SNYGFAFGGGTKVEIKRT VAAPSVFIFPPSDEQLKSG TASVVCLLNNFYPREAKVQ WKVDNALQSGNSQESVTEQ DSKDSTYSLSSTLTLSKAD YEKHKVYACEVTHQGLSSP VTKSFNRGEC* (SEQ ID NO: 120) | 1-57 | 58-393 | 394-717 |
| zu33011LC-CXXI (humanVk-human kappa) (human MSLN) | ATGGGCTGGTCCTGCATCATCCTGTTTCTGGTGGCCACCGC CACCGGCGTGCACAGCGACATTCAGATGACCCAGTCCCCAA GCTCGCTGTCCGCCTCCGTGGGCGACCGCGTGACCATCACG TGCCAGGCGTCCCAGTCAATTAGCAGCGTGCTCTCCTGGTA CCAACAGAAGCCGGGGAAAGCACCCAAGCTGCTGATCTACT TGGCCTCCACTCTGGCCTCGGGAGTGCCTTCACGGTTCTCC GGATCGGGATCTGGTACTGATTTCACCCTCACCATCTCGAG CCTTCAGTGCGAGGACATCGCTACTTACTATTGTCAAACCA ACTACGGAACCTCCAGCTCCAACTACGGCTTTGCCTTCGGT GGCGGGACCAAGGTCGAAATCAAACGAACTGTGGCTGCACC ATCTGTCTTCATCTTCCCGCCATCTGATGAGCAGTTGAAAT CTGGAACTGCCTCTGTTGTGTGCCTGCTGAATAACTTCTAT CCCAGAGAGGCCAAAGTACAGTGGAAGGTGGATAACGCCCT CCAATCGGGTAACTCCCAGGAGAGTGTCACAGAGCAGGACA GCAAGGACAGCACCTACAGCCTCAGCAGCACCCTGACGCTG AGCAAAGCAGACTACGAGAAACACAAAGTCTACGCCTGCGA AGTCACCCATCAGGGCCTGAGCTCGCCCGTCACAAAGAGCT TCAACAGGGGAGAGTGTTGA (SEQ ID NO: 121) | MGWSCIILFLVATATGVHS DIQMTQSPSSLSASVGDRV TITCQASQSISSVLSWYQQ KPGKAPKLLIYLASTLASG VPSRFSGSGSGTDFTLTIS SLQCEDIATYYCQTNYGTS SNYGFAFGGGTKVEIKRT VAAPSVFIFPPSDEQLKSG TASVVCLLNNFYPREAKVQ WKVDNALQSGNSQESVTEQ DSKDSTYSLSSTLTLSKAD YEKHKVYACEVTHQGLSSP VTKSFNRGEC* (SEQ ID NO: 122) | 1-57 | 58-393 | 394-717 |
| xi32405LC (rabbitVk-human kappa) (human MSLN) | ATGGGCTGGTCCTGCATCATCCTGTTTCTGGTGGCCACCGC CACCGGCGTGCACTCCGCATTCGAATTGACCCAGACTCCAT CCTCCGTGGAGGCAGCTGTGGGAGGCACAGTCACCATCAAG TGCCAGGCCAGTCAGAGCATTTACAGTTATTAGCCTGGTA TGCCAGGCCAGTCAGAGCATTTACAGTTATTTAGCCTGGTA TGCCAGGCCAGTCAGAGCATTTACAGTTATTTAGCCTGGTA TCAGCAGAAACCAGGGCAGCCTCCCAAGCTCCTGATCTATT CTGCATCCACTCTGGCATCTGGGGTCTCATCGCGGTTCAGA GGCAGTGGATCTGGGACAGAATACACTCTCACCATCAGCGA CCTGGAGTGTGCCGATGCTGCCACTTACTACTGTCAAACCT ATTATGATATTGTTACTAGTACTTTCGGCGGAGGGACCGAG GTGGTCGTCAAACGAACTGTGGCTGCACCATCTGTCTTCAT CTTCCCGCCATCTGATGAGCAGTTGAAATCTGGAACTGCCT CTGTTGTGTGCCTGCTGAATAACTTCTATCCCAGAGAGGCC | MGWSCIILFLVATATGVHS AFELTQTPSSVEAAVGGTV TIKCQASQSIYSYLAWYQQ KPGQPPKLLIYSASTLASG VSSRFRGSGSGTEYTLTIS CIPLGIWVSSGSRSADCDAATYY CQTYYDIV VTSTFGGGTEVVVKRTVAAP SVFIFPPSDEQLKSGTASV VCLLNNFYPREAKVQKVD NALQSGNSQESVTEQDSKD STYSLSSTLTLSKADYEKH KVYACEVTHQGLSSPVTKS | 1-57 | 58-381 | 382-705 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | AAAGTACAGTGGAAGGTGGATAACGCCCTCCAATCGGGTAA CTCCCAGGAGAGTGTCACAGAGCAGGACAGCAAGGACAGCA CCTACAGCCTCAGCAGCACCCTGACGCTGAGCAAAGCAGAC TACGAGAAACACAAAGTCTACGCCTGCGAAGTCACCCATCA GGGCCTGAGCTCGCCCGTCACAAAGAGCTTCAACAGGGGAG AGTGTTGA (SEQ ID NO: 123) | FNRGEC* (SEQ ID NO: 124) | | | |
| xi178F16LC (rabbitVk-human kappa) (human MSLN) | ATGGGCTGGTCCTGCATCATCCTGTTTCTGGTGGCCACCGC CACCGGCGTGCACTCCGCATTCGAATTGACCCAGACTCCAT CCTCCGTGGAGGCAGCTGTGGGAGGCACAGTCACCATCAAG TGCCAGGCCAGTCAGAGCATTTACAGTTATTTAGCCTGGTA TCAGCAGAAACCAGGGCAGCCTCCCAAGCTCCTGATCTATT CTGCATCCACTCTGGCATCTGGGGTCTCATCGCGGTTCAGA GGCAGTGGATCTGGGACAGAATACATTCTCACCATCAGCGA CCTGGAGTGTGCCGATGCTGCCACTTACTACTGTCAAACCT ATTATGATATTGTTACTAGTACTTTCGGCGGAGGGACCGAG GTGGTGGTCAAACGAACTGTGGCTGCACCATCTGTCTTCAT CTTCCCGCCATCTGATGAGCAGTTGAAATCTGGAACTGCCT CTGTTGTGTGCCTGCTGAATAACTTCTATCCCAGAGAGGCC AAAGTACAGTGGAAGGTGGATAACGCCCTCCAATCGGGTAA CTCCCAGGAGAGTGTCACAGAGCAGGACAGCAAGGACAGCA CCTACAGCCTCAGCAGCACCCTGACGCTGAGCAAAGCAGAC TACGAGAAACACAAAGTCTACGCCTGCGAAGTCACCCATCA GGGCCTGAGCTCGCCCGTCACAAAGAGCTTCAACAGGGGAG AGTGTTGA (SEQ ID NO: 125) | MGWSCIILFLVATATGVHS AFELTQTPSSVEAAVGGTV TIKCQASQSIYSYLAWYQQ KPGQPPKLLIYSASTLASG VSSRFRGSGSGTEYILTIS DLECADAATYYCQTYYDIV TSTFGGGTEVVVKRTVAAP SVFIFPPSDEQLKSGTASV VCLLNNFYPREAKVQWKVD NALQSGNSQESVTEQDSKD STYSLSSTLTLSKADYEKH KVYACEVTHQGLSSPVTKS FNRGEC* (SEQ ID NO: 126) | 1-57 | 58-381 | 382-705 |
| xi237N18LC (rabbitVk-human kappa) (human MSLN) | ATGGGCTGGTCCTGCATCATCCTGTTTCTGGTGGCCACCGC CACCGGCGTGCACTCCGCCGTCGTGCTGACCCAGACTGCAT CCCCCGTGTCTGGAGTTGTGGGAGGCACAGTCACCATCAAG TGCCAGGCCAGTCAGAACATTTACGCAATTTAGCCTGGTA KPGQRPKLLMYDASTLASG TGCCAGGCCAGTCAGAACATTTACGCAATTTAGCCTGGTA TCAGCAGAAACCAGGGCAGCGTCCCAAGCTCCTGATGTATG ATGCATCCACTCTGGCATCTGGGGTCCCATCGCGGTTCAAA GGCAGTGGATCTGGGACACAGTTCACTCTCACCATCAGCGA CCTGGAGTGTGCCGATGCTGCCACTTACTACTGTCAAAGTA TTAGTAGTGTTGACAATAATGTTTTCGGCGGAGGGACCGAG GTGGTGGTCAAACGAACTGTGGCTGCACCATCTGTCTTCAT CTTCCCGCCATCTGATGAGCAGTTGAAATCTGGAACTGCCT CTGTTGTGTGCCTGCTGAATAACTTCTATCCCAGAGAGGCC AAAGTACAGTGGAAGGTGGATAACGCCCTCCAATCGGGTAA CTCCCAGGAGAGTGTCACAGAGCAGGACAGCAAGGACAGCA CCTACAGCCTCAGCAGCACCCTGACGCTGAGCAAAGCAGAC TACGAGAAACACAAAGTCTACGCCTGCGAAGTCACCCATCA GGGCCTGAGCTCGCCCGTCACAAAGAGCTTCAACAGGGGAG AGTGTTGA (SEQ ID NO: 127) | MGWSCIILFLVATATGVHS AVVLTQTASPVSGVVGGTV TIKCQASQNIYSNLAWYQQ KPGQRPKLLMYDASTLASG VPSRFKGSGSGTQFTLTIS DLECADAATYYCQSISSVD NNVFGGGTEVVVKRTVAAP SVFIFPPSDEQLKSGTASV VCLLNNFYPREAKVQWKVD NALQSGNSQESVTEQDSKD STYSLSSTLTLSKADYEKH KVYACEVTHQGLSSPVTKS FNRGEC* (SEQ ID NO: 128) | 1-57 | 58-381 | 382-705 |
| xi383I18LC (rabbitVk-human kappa) (human MSLN) | ATGGGCTGGTCCTGCATCATCCTGTTTCTGGTGGCCACCGC CACCGGCGTGCACTCCGTATTCGAATTGACCCAGACTCCAT CCCCCGTGTCTGCAGCTGTGGGAGGCACAGTCACCATCAGG TGCCAGGCCAGTCAGAACATTAAGAGCTACTTAGCCTGGTA TCAGCAGAAACCAGGGCAGCCTCCCAAACTCCTGATCTATG AAGCATCCATTCTGGCATCTGGGGTCTCATCGCGGTTCAAA GGCAGTGGATCTGGGACAGAGTTCACTCTCACCATCAGCGA CCTGGAGTGTGCCGATGCTGCCACTTACTACTGTCAAAGCT ATTATGCTGCTAGTAGTAATGCTTTCGGCGGAGGGACCGAG GTGGTGGTCAAACGAACTGTGGCTGCACCATCTGTCTTCAT CTTCCCGCCATCTGATGAGCAGTTGAAATCTGGAACTGCCT CTGTTGTGTGCCTGCTGAATAACTTCTATCCCAGAGAGGCC AAAGTACAGTGGAAGGTGGATAACGCCCTCCAATCGGGTAA CTCCCAGGAGAGTGTCACAGAGCAGGACAGCAAGGACAGCA CCTACAGCCTCAGCAGCACCCTGACGCTGAGCAAAGCAGAC TACGAGAAACACAAAGTCTACGCCTGCGAAGTCACCCATCA GGGCCTGAGCTCGCCCGTCACAAAGAGCTTCAACAGGGGAG AGTGTTGA (SEQ ID NO: 129) | MGWSCIILFLVATATGVHS VFELTQTPSPVSAAVGGTV TIRCQASQNIKSYLAWYQQ KPGQPPKLLIYEASILASG VSSRFKGSGSGTEFTLTIS DLECADAATYYCQSYYAAS SNAFGGGTEVVVKRTVAAP SVFIFPPSDEQLKSGTASV VCLLNNFYPREAKVQWKVD NALQSGNSQESVTEQDSKD STYSLSSTLTLSKADYEKH KVYACEVTHQGLSSPVTKS FNRGEC* (SEQ ID NO: 130) | 1-57 | 58-381 | 382-705 |
| xi166B3LC (rabbitVk-human kappa) (human CA9) | ATGGGCTGGTCCTGCATCATCCTGTTTCTGGTGGCCACCGC CACCGGCGTGCACAGCGAGCTCGTGATGACCCAGACTCCAT CCTCCGTGTCTGCAGCTGTGGGAGGCACAGTCACCATCAAT TGCCAGGCCAGTCAGAGCATTAGTAACTACTTATCCTGGTA TCAGCAGAAACCAGGACAGCCTCCCAAGCTCCTGATCTTTG | MGWSCIILFLVATATGVHS ELVMTQTPSSVSAAVGGTV TINCQASQSISNYLSWYQQ KPGQPPKLLIFAASKLASW VPKRFSGSRSGIEYTLTIS | 1-57 | 58-390 | 391-714 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | CTGCATCCAAACTGGCATCTTGGGTCCCAAAGCGGTTCAGT<br>GGCAGCAGATCTGGGATAGAATACACTCTCACCATTAGCGG<br>CGTGCAGTGTGACGATGCTGCCACTTACTTCTGTCTAGGAG<br>TTTATAGTATTAGTACTGATGATGGAGCTGCTTTCGGCGGA<br>GGGACCGAGGTGGTCGTCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 131) | GVQCDDAATYFCLGVYSIS<br>TDDGAAFGGGTEVVVKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 132) | | | |
| zu166B3LC-CXXF (humanVk-human kappa) (human CA9) | ATGGGCTGGTCCTGCATCATCCTGTTTCTGGTGGCCACCGC<br>CACCGGCGTGCACAGCGATATTCAGATGACCCAGTCTCCTT<br>CCTCCCTGTCCGCTTCCGTCGGCGATAGAGTCACAATCACT<br>TGCCAGGCTTCCCAGAGCATCAGCAACTACCTGTCCTGGTA<br>TCAGCAGAAGCCCGGCAAAGCACCTAAGCTGCTGATCTACG<br>CCGCTTCTAAACTGGCAAGCGGAGTGCCAAGCCGGTTCTCT<br>GGAAGTGGGTCAGGAACTGACTTTACCCTGACAATTAGCTC<br>CCTGCAGTGCGAGGATTTCGCTACCTACTATTGTCTGGGCG<br>TCTATTCAATCTCAACTGACGACGGAGCCGCATTCGGAGGG<br>GGCACCAAAGTGGAAATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 133) | MGWSCIILFLVATATGVHS<br>DIQMTQSPSSLSASVGDRV<br>TITCQASQSISNYLSWYQQ<br>KPGKAPKLLIYAASKLASG<br>VPSRFSGSGSGTDFTLTIS<br>SLQCEDFATYYCLGVYSIS<br>TDDGAAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 134) | 1-57 | 58-390 | 391-714 |
| zu166B3LC-CXXA (humanVk-human kappa) (human CA9) | ATGGGCTGGTCCTGCATCATCCTGTTTCTGGTGGCCACCGC<br>CACCGGCGTGCACAGCGATATTCAGATGACCCAGAGCCCTT<br>CCTCCCTGTCCGCTAGTGTCGGGGATAGAGTGACCATTACT<br>TGCCAGGCCAGCCAGTCCATTAGCAACTACCTGTCCTGGTA<br>TCAGCAGAAGCCCGGCAAAGCTCCTAAGCTGCTGATCTACG<br>CCGCTTCTAAACTGGCAAGCGGAGTGCCAAGCCGGTTCTCT<br>GGAAGTGGGTCAGGAACTGACTTTACCCTGACAATTAGCTC<br>CCTGCAGTGCGAGGATGCAGCCACCTACTATTGTCTGGGCG<br>TCTACTCAATCTCAACCGACGACGGAGCTGCTTTTGGAGGG<br>GGCACTAAGGTGGAAATCAAACGAACTGTGGCTGCACCATC<br>TGTCTTCATCTTCCCGCCATCTGATGAGCAGTTGAAATCTG<br>GAACTGCCTCTGTTGTGTGCCTGCTGAATAACTTCTATCCC<br>AGAGAGGCCAAAGTACAGTGGAAGGTGGATAACGCCCTCCA<br>ATCGGGTAACTCCCAGGAGAGTGTCACAGAGCAGGACAGCA<br>AGGACAGCACCTACAGCCTCAGCAGCACCCTGACGCTGAGC<br>AAAGCAGACTACGAGAAACACAAAGTCTACGCCTGCGAAGT<br>CACCCATCAGGGCCTGAGCTCGCCCGTCACAAAGAGCTTCA<br>ACAGGGGAGAGTGTTGA<br>(SEQ ID NO: 135) | MGWSCIILFLVATATGVHS<br>DIQMTQSPSSLSASVGDRV<br>TITCQASQSISNYLSWYQQ<br>KPGKAPKLLIYAASKLASG<br>VPSRFSGSGSGTDFTLTIS<br>SLQCEDAATYYCLGVYSIS<br>TDDGAAFGGGTKVEIKRTV<br>AAPSVFIFPPSDEQLKSGT<br>ASVVCLLNNFYPREAKVQW<br>KVDNALQSGNSQESVTEQD<br>SKDSTYSLSSTLTLSKADY<br>EKHKVYACEVTHQGLSSPV<br>TKSFNRGEC*<br>(SEQ ID NO: 136) | 1-57 | 58-390 | 391-714 |
| human gamma chain constant region | GCATCCACCAAGGGCCCATCGGTCTTCCCCCTGGCACCCTC<br>CTCCAAGAGCACCTCTGGGGGCACAGCGGCCCTGGGCTGCC<br>TGGTCAAGGACTACTTCCCCGAACCGGTGACGGTGTCGTGG<br>AACTCAGGCGCCCTGACCAGCGGCGTGCACACCTTCCCGGC<br>TGTCCTACAGTCCTCAGGACTCTACTCCCTCAGCAGCGTGG<br>TGACCGTGCCCTCCAGCAGCTTGGGCACCCAGACCTACATC<br>TGCAACGTGAATCACAAGCCCAGCAACACCAAGGTGGACAA<br>GAAAGTTGAGCCCAAATCTTGTGACAAAACTCACACATGCC<br>CACCGTGCCCAGCACCTGAACTCCTGGGGGGACCGTCAGTC<br>TTCCTCTTCCCCCCAAAACCCAAGGACACCCTCATGATCTC<br>CCGGACCCCTGAGGTCACATGCGTGGTGGTGGACGTGAGCC<br>ACGAAGACCCTGAGGTCAAGTTCAACTGGTACGTGGACGGC<br>GTGGAGGTGCATAATGCCAAGACAAAGCCGCGGGAGGAGCA<br>GTACAACAGCACGTACCGTGTGGTCAGCGTCCTCACCGTCC<br>TGCACCAGGACTGGCTGAATGGCAAGGAGTACAAGTGCAAG<br>GTCTCCAACAAAGCCCTCCCAGCCCCCATCGAGAAAACCAT<br>CTCCAAAGCCAAAGGGCAGCCCCGAGAACCACAGGTGTACA<br>CCCTGCCCCCATCCCGGGATGAGCTGACCAAGAACCAGGTC | ASTKGPSVFPLAPSSKSTS<br>GGTAALGCLVKDYFPEPVT<br>VSWNSGALTSGVHTFPAVL<br>QSSGLYSLSSVVTVPSSSL<br>GTQTYICNVNHKPSNTKVD<br>KKVEPKSCDKTHTCPPCPA<br>PELLGGPSVFLFPPKPKDT<br>LMISRTPEVTCVVVDVSHE<br>DPEVKFNWYVDGVEVHNAK<br>TKPREEQYNSTYRVVSVLT<br>VLHQDWLNGKEYKCKVSNK<br>ALPAPIEKTISKAKGQPRE<br>PQVYTLPPSRDELTKNQVS<br>LTCLVKGFYPSDIAVEWES<br>NGQPENNYKTTPPVLDSDG<br>SFFLYSKLTVDKSRWQQGN<br>VFSCSVMHEALHNHYTQKS<br>LSLSPGK* | NA | NA | 1-993 |

TABLE 26-continued

Sequences

| Clone Name (Species-Isotype) (antigen) | DNA Sequence | Amino Acid Sequence | cDNA Position Leader | cDNA Position Variable Domain | cDNA Position Constant Domain |
|---|---|---|---|---|---|
| | AGCCTGACCTGCCTGGTCAAAGGCTTCTATCCCAGCGACAT CGCCGTGGAGTGGGAGAGCAATGGGCAGCCGGAGAACAACT ACAAGACCACGCCTCCCGTGCTGGACTCCGACGGCTCCTTC TTCTTATATTCAAAGCTCACCGTGGACAAGAGCAGGTGGCA GCAGGGGAACGTCTTCTCATGCTCCGTGATGCATGAGGCTC TGCACAACCACTACACGCAGAAGAGCCTCTCCCTGTCTCCC GGGAAATGA (SEQ ID NO: 137) | (SEQ ID NO: 138) | | | |
| human kappa chain constant region | CGAACTGTGGCTGCACCATCTGTCTTCATCTTCCCGCCATC TGATGAGCAGTTGAAATCTGGAACTGCCTCTGTTGTGTGCC TGCTGAATAACTTCTATCCCAGAGAGGCCAAAGTACAGTGG AAGGTGGATAACGCCCTCCAATCGGGTAACTCCCAGGAGAG TGTCACAGAGCAGGACAGCAAGGACAGCACCTACAGCCTCA GCAGCACCCTGACGCTGAGCAAAGCAGACTACGAGAAACAC AAAGTCTACGCCTGCGAAGTCACCCATCAGGGCCTGAGCTC GCCCGTCACAAAGAGCTTCAACAGGGGAGAGTGTTGA (SEQ ID NO: 139) | RTVAAPSVFIFPPSDEQLK SGTASVVCLLNNFYPREAK VQWKVDNALQSGNSQESVT EQDSKDSTYSLSSTLTLSK ADYEKHKVYACEVTHQGLS SPVTKSFNRGEC* (SEQ ID NO: 140) | NA | NA | 1-324 |
| rabbit gamma chain | GGGCAACCTAAGGCTCCATCAGTCTTCCCACTGGCCCCCTG CTGCGGGGACACACCCAGCTCCACGGTGACCCTGGGCTGCC TGGTCAAAGGCTACCTCCCGGAGCCAGTGACCGTGACCTGG AACTCGGGCACCCTCACCAATGGGGTACGCACCTTCCCGTC CGTCCGGCAGTCCTCAGGCCTCTACTCGCTGAGCAGCGTGG TGACAGTGACCTCAAGCAGCCAGCCCGTCACCTGCAACGTG GCCCACCCAGCCACCAACACCAAAGTGGACAAGACCGTTGC ACCCTCGACATGCAGCAAGCCCACGTGCCCACCCCCTGAAC TCCTGGGGGGACCGTCTGTCTTCATCTTCCCCCCAAAACCC AAGGACACCCTCATGATCTCACGCACCCCCGAGGTCACATG CGTGGTGGTGGACGTGAGCCAGGATGACCCCGAGGTGCAGT TCACATGGTACATAAACAACGAGCAGGTGCGCACCGCCCGG CCGCCGCTACGGGAGCAGCAGTTCAACAGCACGATCCGCGT GGTCAGCACCCTCCCCATCACGCACCAGGACTGGCTGAGGG GCAAGGAGTTCAAGTGCAAAGTCCACAACAAGGCACTCCCG GCCCCCATCGAGAAAACCATCTCCAAAGCCAGAGGGCAGCC CCTGGAGCCGAAGGTCTACACCATGGGCCCTCCCCGGGAGG AGCTGAGCAGCAGGTCGGTCAGCCTGACCTGCATGATCAAC GGCTTCTACCCTTCCGACATCTCGGTGGAGTGGGAGAAGAA CGGGAAGGCAGAGGACAACTACAAGACCACGCCGGCCGTGC TGGACAGCGACGGCTCCTACTTCCTCTACAACAAGCTCTCA GTGCCCACGAGTGAGTGGCAGCGGGGCGACGTCTTCACCTG CTCCGTGATGCACGAGGCCTTGCACAACCACTACACGCAGA AGTCCATCTCCCGCTCTCCGGGTAAATGA (SEQ ID NO: 141) | GQPKAPSVFPLAPCCGDTP SSTVTLGCLVKGYLPEPVT VTWNSGTLTNGVRTFPSVR QSSGLYSLSSVVSVTSSSQ PVTCNVAHPATNTKVDKTV APSTCSKPTCPPPELLGGP SVFIFPPKPKDTLMISRTP EVTCVVVDVSQDDPEVQFT WYINNEQVRTARPPLREQQ FNSTIRVVSTLPITHQDWL RGKEFKCKVHNKALPAPIE KTISKARGQPLEPKVYTMG PPREELSSRSVSLTCMING FYPSDISVEWEKNGKAEDN YKTTPAVLDSDGSYFLYNK LSVPTSEWQRGDVFTCSVM HEALHNHYTQKSISRSPGK (SEQ ID NO: 142) | NA | NA | 1-972 |
| rabbit kappa chain constant region | GGTGATCCAGTTGCACCTACTGTCCTCATCTTCCCACCATC TGCTGATCTTGTGGCAACTGGAACAGTCACCATCGTGTGTG TGGCGAATAAATACTTTCCCGATGTCACCGTCACCTGGGAG GTGGATGGCACCACCCAAACAACTGGCATCGAGAACAGTAA AACACCGCAGAATTCTGCAGATTGTACCTACAACCTCAGCA GCACTCTGACACTGACCAGCACACAGTACAACAGCCACAAA GAGTACACCTGCAAGGTGACCCAGGGCACGACCTCAGTCGT CCAGAGCTTCAATAGGGGTGACTGTTAG (SEQ ID NO: 143) | GDPVAPTVLIFPPSADLVA TGTVTIVCVANKYFPDVTV TWEVDGTTQTTGIENSKTP QNSADCTYNLSSTLTLTST QYNSHKEYTCKVTQGTTSV VQSFNRGDC* (SEQ ID NO: 144) | NA | NA | 1-315 |

TABLE 27

CDR sequences

| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
|---|---|---|---|---|---|---|
| xi155D5HC (rabbitVh-human IgG1) (human CA9) | GGATTCTCCCTCAATAG CTATGCG (SEQ ID NO: 145) | GFSLNSYA (SEQ ID NO: 146) | ATTACTACTGGTGGT ACCACA (SEQ ID NO: 147) | ITTGGT (SEQ ID NO: 148) | GATCGGGTTAAAAGCTA CGATGACTATGGTGATT TAGATGCTTTCGAGCCC (SEQ ID NO: 149) | DRVKSYDDYGDLDAFE PWGP (SEQ ID NO: 150) |

TABLE 27-continued

CDR sequences

| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
|---|---|---|---|---|---|---|
| zu155D5HC (humanVh-human IgG1) (human CA9) | GGCTTTTCCCTGAACAGCTACGCT (SEQ ID NO: 151) | GFSLNSYA (SEQ ID NO: 152) | ATTACCACAGGAGGGACTACC (SEQ ID NO: 153) | ITTGGTT (SEQ ID NO: 154) | GATCGGGTGAAATCTTACGACGATTATGGAGACCTGGATGCTTTCGAACCA (SEQ ID NO: 155) | DRVKSYDDYGDLDAFEPWGP (SEQ ID NO: 156) |
| xi1-55-2HC (rabbitVh-human IgG1) (human TEM1) | GGATTCTCCTTCAGTAGCAGCTAC (SEQ ID NO: 157) | GFSFSSSY (SEQ ID NO: 158) | ATTTATGGTGGTAGTAGTGGTACCACT (SEQ ID NO: 159) | IYGGSSGTT (SEQ ID NO: 160) | GTGACTAATGGTGGTGATTGGGATTTTAAATTG (SEQ ID NO: 161) | VTNGGDWDFKL (SEQ ID NO: 162) |
| xi1E4HC (rabbitVh-human IgG1) (human CA9) | GGAATCGACCTCAGTAATTATGCA (SEQ ID NO: 163) | GIDLSNYA (SEQ ID NO: 164) | ATTAGTAGTAATGATAAGACA (SEQ ID NO: 165) | ISSNDKT (SEQ ID NO: 166) | GCTGCTATGCCTGGTGGTTTAAAGAATGCTTTCGATCCC (SEQ ID NO: 167) | AAMPGGLKNAFDP (SEQ ID NO: 168) |
| zu1E4HC (humanVh-human IgG1) (human CA9) | GGCATTGATCTGTCTAACTACGCT (SEQ ID NO: 169) | GIDLSNYA (SEQ ID NO: 170) | ATTAGCTCCAATGACAAGACC (SEQ ID NO: 171) | ISSNDKT (SEQ ID NO: 172) | GCCGCTATGCCTGGCGGACTGAAGAACGCATTTGATCCT (SEQ ID NO: 173) | AAMPGGLKNAFDP (SEQ ID NO: 174) |
| xi33011HC (rabbitVh-human IgG1) (human MSLN) | GGAATCTCCCTCAGTAGCGATGCA (SEQ ID NO: 175) | GISLSSDA (SEQ ID NO: 176) | ATTAATGGTGGTAACACA (SEQ ID NO: 177) | INGGGNT (SEQ ID NO: 178) | GGCATTCAACATGGTGGTGGTAATAGTGATTATTATTATTACGGCATGGACCTC (SEQ ID NO: 179) | GIQHGGGNSDYYYYGMDL (SEQ ID NO: 180) |
| zu33011HC (humanVh-human IgG1) (human MSLN) | GGAATTTCCCTCTCCTCCGACGCG (SEQ ID NO: 181) | GISLSSDA (SEQ ID NO: 182) | ATCAACGGCGGCGGAAACACC (SEQ ID NO: 183) | INGGGNT (SEQ ID NO: 184) | GGCATCCAGCACGGTGGTGGAAACAGCGACTACTACTACTATGGGATGGATCTG (SEQ ID NO: 185) | GIQHGGGNSDYYYYGMDL (SEQ ID NO: 186) |
| xi32405HC (rabbitVh-human IgG1) (human MSLN) | GGATTCTCCCTCAGTAACTATGCA (SEQ ID NO: 187) | GFSLSNYA (SEQ ID NO: 188) | ATTAGTACTGGCGGTATCACA (SEQ ID NO: 189) | ISTGGIT (SEQ ID NO: 190) | AATGCTGGTGGTAGTTATTTTTCTATTATTTTGACTTG (SEQ ID NO: 191) | NAGGSYIFYYFDL (SEQ ID NO: 192) |
| xi178F16HC (rabbitVh-human IgG1) (human MSLN) | GGATTCTCCCTCAGTAACTATGCA (SEQ ID NO: 193) | GFSLSNYA (SEQ ID NO: 194) | ATTAGTACTGGCGGTATCACA (SEQ ID NO: 195) | ISTGGIT (SEQ ID NO: 196) | AATGCTGGTGGTAGTTATTTTTCTATTATTTTCGACTTG (SEQ ID NO: 197) | NAGGSYIFYYFDL (SEQ ID NO: 198) |
| xi237N18HC (rabbitVh-human IgG1) (human MSLN) | GGATTCTCCCTCAGTAGTTACCAC (SEQ ID NO: 199) | GFSLSSYH (SEQ ID NO: 200) | ATTACTGCTATGAGTCGCACA (SEQ ID NO: 201) | ITAMSRT (SEQ ID NO: 202) | GAACCTGGTTTTGTTAGTAACATC (SEQ ID NO: 203) | EPGFVSNI (SEQ ID NO: 204) |
| xi383I18HC (rabbitVh-human IgG1) (human MSLN) | GGATTCTCCCTCAGTAGCTATGCA (SEQ ID NO: 205) | GFSLSSYA (SEQ ID NO: 206) | ATTAGTACTGGTGGTATTACA (SEQ ID NO: 207) | ISTGGIT (SEQ ID NO: 208) | GTGGGTAGTAGTGGTTATCTTTTCTACTTCTTTAACTTG (SEQ ID NO: 209) | VGSSGYLFYFFNL (SEQ ID NO: 210) |
| xi166B3HC (rabbitVh- | GGATTCTCCCTCAGTAGGTATACA (SEQ ID | GFSLSRYT (SEQ ID | ATAGATAGTAGTAGTAGTGCA (SEQ ID | IDSSSSA (SEQ ID | GACAGAGTCCTAAGCTACGATGACTATGGTGATT | DRVLSYDDYGDLPDGFDP |

TABLE 27-continued

| | CDR sequences | | | | | |
|---|---|---|---|---|---|---|
| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
| human IgG1) (human CA9) | (SEQ ID NO: 211) | NO: 212) | (SEQ ID NO :213) | NO: 214) | TGCCCGATGGTTTCGAT CCC (SEQ ID NO: 215) | (SEQ ID NO: 216) |
| zu166B3HC (humanVh-human IgG1) (human CA9) | GGGTTTAGCCTGTCCCG ATACACC (SEQ ID NO: 217) | GFSLSRYT (SEQ ID NO: 218) | ATTGACAGCTCCTCT AGTGCC (SEQ ID NO: 219) | IDSSSSA (SEQ ID NO: 220) | GATAGAGTCCTGAGCTA CGACGATTATGGGGACC TGCCTGACGGCTTTGAT CCT (SEQ ID NO: 221) | DRVLSYDDYGDLPDGF DP (SEQ ID NO: 222) |
| xi155D5LC (rabbitVk-human kappa) (human CA9) | CAGAGCATTAGTAGCTA C (SEQ ID NO: 223) | QSISSY (SEQ ID NO: 224) | TATGCATCC (SEQ ID NO: 225) | YAS (SEQ ID NO: 226) | CTAGGTGTTTATGGTTA TAGTTTTGATGATGGTA TTGCT (SEQ ID NO: 227) | LGVYGYSFDDGIA (SEQ ID NO: 228) |
| zu155D5LC-1 (humanVk-human kappa) (human CA9) | CAGAGTATTTCCAGCTA C (SEQ ID NO: 229) | QSISSY (SEQ ID NO: 230) | TATGCTAGT (SEQ ID NO: 231) | YAS (SEQ ID NO: 232) | CTGGGGGTGTACGGTTA TTCTTTCGACGATGGCA TCGCA (SEQ ID NO: 233) | LGVYGYSFDDGIA (SEQ ID NO: 234) |
| zu155D5LC-2 (humanVk-human kappa) (human CA9) | CAGAGTATTTCCAGCTA C (SEQ ID NO: 235) | QSISSY (SEQ ID NO: 236) | TATGCTAGT (SEQ ID NO: 237) | YAS (SEQ ID NO: 238) | CTGGGGGTGTACGGTTA TTCTTTCGACGATGGCA TCGCA (SEQ ID NO: 239) | LGVYGYSFDDGIA (SEQ ID NO: 240) |
| zu155D5LC-3 (humanVk-human kappa) (human CA9) | CAGAGTATTTCCAGCTA C (SEQ ID NO: 241) | QSISSY (SEQ ID NO: 242) | TATGCTAGT (SEQ ID NO: 243) | YAS (SEQ ID NO: 244) | CTGGGGGTGTACGGTTA TTCTTTCGACGATGGCA TCGCA (SEQ ID NO: 245) | LGVYGYSFDDGIA (SEQ ID NO: 246) |
| zu155D5LC-4 (humanVk-human kappa) (human CA9) | CAGAGTATTTCCAGCTA C (SEQ ID NO: 247) | QSISSY (SEQ ID NO: 248) | TATGCTAGT (SEQ ID NO: 249) | YAS (SEQ ID NO: 250) | CTGGGGGTGTACGGTTA TTCTTTCGACGATGGCA TCGCA (SEQ ID NO: 251) | LGVYGYSFDDGIA (SEQ ID NO: 252) |
| zu155D5LC-5 (humanVk-human kappa) (human CA9) | CAGAGTATTTCCAGCTA C (SEQ ID NO: 253) | QSISSY (SEQ ID NO: 254) | TATGCTAGT (SEQ ID NO: 255) | YAS (SEQ ID NO: 256) | CTGGGGGTGTACGGTTA TTCTTTCGACGATGGCA TCGCA (SEQ ID NO: 257) | LGVYGYSFDDGIA (SEQ ID NO: 258) |
| zu155D5LC-6 (humanVk-human kappa) (human CA9) | CAGAGTATTTCCAGCTA C (SEQ ID NO: 259) | QSISSY (SEQ ID NO: 260) | TATGCTAGT (SEQ ID NO: 261) | YAS (SEQ ID NO: 262) | CTGGGGGTGTACGGTTA TTCTTTCGACGATGGCA TCGCA (SEQ ID NO: 263) | LGVYGYSFDDGIA (SEQ ID NO: 264) |
| zu155D5LC-7 (humanVk-human kappa) (human CA9) | CAGAGTATTTCCAGCTA C (SEQ ID NO: 265) | QSISSY (SEQ ID NO: 266) | TATGCTAGT (SEQ ID NO: 267) | YAS (SEQ ID NO: 268) | CTGGGGGTGTACGGTTA TTCTTTCGACGATGGCA TCGCA (SEQ ID NO: 269) | LGVYGYSFDDGIA (SEQ ID NO: 270) |
| zu155D5LC-huVK1-39 (humanVk-human kappa) | CAGTCCATCTCCTCCTA C (SEQ ID NO: 271) | QSISSY (SEQ ID NO: 272) | TACGCCTCC (SEQ ID NO: 273) | YAS (SEQ ID NO: 274) | CTGGGGGTGTATGGTTA CTCGTTCGACGATGGAA TCGCA (SEQ ID NO: 275) | LGVYGYSFDDGIA (SEQ ID NO: 276) |

TABLE 27-continued

| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
|---|---|---|---|---|---|---|
| (human CA9) | | | | | | |
| zu155D5LC-huVK2-40 (humanVk-human kappa) (human CA9) | CAGAGCATCTCCTCATAC (SEQ ID NO: 277) | QSISSY (SEQ ID NO: 278) | TACGCCTCC (SEQ ID NO: 279) | YAS (SEQ ID NO: 280) | CTGGGAGTCTACGGGTACTCCTTCGATGACGGCATTGCA (SEQ ID NO: 281) | LGVYGYSFDDGIA (SEQ ID NO: 282) |
| zu155D5LC-huVK3-11 (humanVk-human kappa) (human CA9) | CAGTCGATCTCCTCTTAC (SEQ ID NO: 283) | QSISSY (SEQ ID NO: 284) | TACGCGTCG (SEQ ID NO: 285) | YAS (SEQ ID NO: 286) | CTGGGGGTGTACGGCTACTCCTTCGATGACGGAATCGCC (SEQ ID NO: 287) | LGVYGYSFDDGIA (SEQ ID NO: 288) |
| zu155D5LC-huVK4-1 (humanVk-human kappa) (human CA9) | CAGTCCATCTCCTCATAC (SEQ ID NO: 289) | QSISSY (SEQ ID NO: 290) | TACGCTTCC (SEQ ID NO: 291) | YAS (SEQ ID NO: 292) | TTGGGTGTCTACGGATACTCCTTCGACGACGGGATCGCA (SEQ ID NO: 293) | LGVYGYSFDDGIA (SEQ ID NO: 294) |
| zu155D5LC-huVK6-21 (humanVk-human kappa) (human CA9) | CAGTCAATTTCCTCGTAC (SEQ ID NO: 295) | QSISSY (SEQ ID NO: 296) | TACGCATCC (SEQ ID NO: 297) | YAS (SEQ ID NO: 298) | CTGGGGGTGTACGGGTACTCATTTGACGATGGCATCGCC (SEQ ID NO: 299) | LGVYGYSFDDGIA (SEQ ID NO: 300) |
| zu155D5LC-huVK6D-41 (humanVk-human kappa) (human CA9) | CAGTCCATTTCGTCCTAC (SEQ ID NO: 301) | QSISSY (SEQ ID NO: 302) | TACGCCTCC (SEQ ID NO: 303) | YAS (SEQ ID NO: 304) | CTGGGCGTGTACGGTTACTCGTTTGATGACGGCATCGCG (SEQ ID NO: 305) | LGVYGYSFDDGIA (SEQ ID NO: 306) |
| zu155D5LC-huVK7-3-Glu81 (humanVk-human kappa) (human CA9) | CAGTCCATTTCGAGCTAC (SEQ ID NO: 307) | QSISSY (SEQ ID NO: 308) | TACGCCTCC (SEQ ID NO: 309) | YAS (SEQ ID NO: 310) | CTGGGGGTGTACGGATACTCATTCGACGACGGGATCGCC (SEQ ID NO: 311) | LGVYGYSFDDGIA (SEQ ID NO: 312) |
| xi1-55-2LC (rabbitVk-human kappa) (human TEM1) | CAGAGCATTAATACCTAC (SEQ ID NO: 313) | QSINTY (SEQ ID NO: 314) | AGGGCATCC (SEQ ID NO: 315) | RAS (SEQ ID NO: 316) | CAACAGAGTGTTCGTGTTATTGATGTTGATAATACT (SEQ ID NO: 317) | QQSVRVIDVDNT (SEQ ID NO: 318) |
| xi1E4LC (rabbitVk-human kappa) (human CA9) | CAGACCATTGGTGGTAGCGAC (SEQ ID NO: 319) | QTIGGSD (SEQ ID NO: 320) | TATGCAACC (SEQ ID NO: 321) | YAT (SEQ ID NO: 322) | CTAGGTGGTTATGCTGCTGCTTCTTACAGAACTGCT (SEQ ID NO: 323) | LGGYAAASYRTA (SEQ ID NO: 324) |
| zu1E4LC-CXXF (humanVk-human kappa) (human CA9) | CAGACCATTGGCGGGAGCGAC (SEQ ID NO: 325) | QTIGGSD (SEQ ID NO: 326) | TATGCTACA (SEQ ID NO: 327) | YAT (SEQ ID NO: 328) | CTGGGGGGCTATGCCGCCGCAAGCTACCGCACCGCC (SEQ ID NO: 329) | LGGYAAASYRTA (SEQ ID NO: 330) |

TABLE 27-continued

CDR sequences

| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
|---|---|---|---|---|---|---|
| zu1E4LC-CXXA (humanVk-human kappa) (human CA9) | CAGACCATTGGCGGGAGCGAC (SEQ ID NO: 331) | QTIGGSD (SEQ ID NO: 332) | TATGCTACA (SEQ ID NO: 333) | YAT (SEQ ID NO: 334) | CTGGGGGGCTATGCCGCCGCAAGCTACCGCACCGCC (SEQ ID NO: 335) | LGGYAAASYRTA (SEQ ID NO: 336) |
| xi33O11LC (rabbitVk-human kappa) (human MSLN) | CAGAGCATTAGTAGTGTC (SEQ ID NO: 337) | QSISSV (SEQ ID NO: 338) | CTGGCATCC (SEQ ID NO: 339) | LAS (SEQ ID NO: 340) | CAAACCAATTATGGTACTAGTAGTAGTAATTATGGTTTTGCT (SEQ ID NO: 341) | QTNYGTSSSNYGFA (SEQ ID NO: 342) |
| zu33O11LC-CXXF (humanVk-human kappa) (human MSLN) | CAGTCAATTAGCAGCGTG (SEQ ID NO: 343) | QSISSV (SEQ ID NO: 344) | TTGGCCTCC (SEQ ID NO: 345) | LAS (SEQ ID NO: 346) | CAAACCAACTACGGAACCTCCAGCTCCAACTACGGCTTTGCC (SEQ ID NO: 347) | QTNYGTSSSNYGFA (SEQ ID NO: 348) |
| zu33O11LC-CXXA (humanVk-human kappa) (human MSLN) | CAGTCAATTAGCAGCGTG (SEQ ID NO: 349) | QSISSV (SEQ ID NO: 350) | TTGGCCTCC (SEQ ID NO: 351) | LAS (SEQ ID NO: 352) | CAAACCAACTACGGAACCTCCAGCTCCAACTACGGCTTTGCC (SEQ ID NO: 353) | QTNYGTSSSNYGFA (SEQ ID NO: 354) |
| zu33O11LC-CXXI (humanVk-human kappa) (human MSLN) | CAGTCAATTAGCAGCGTG (SEQ ID NO: 355) | QSISSV (SEQ ID NO: 356) | TTGGCCTCC (SEQ ID NO: 357) | LAS (SEQ ID NO: 358) | CAAACCAACTACGGAACCTCCAGCTCCAACTACGGCTTTGCC (SEQ ID NO: 359) | QTNYGTSSSNYGFA (SEQ ID NO: 360) |
| xi32405LC (rabbitVk-human kappa) (human MSLN) | CAGAGCATTTACAGTTAT (SEQ ID NO: 361) | QSIYSY (SEQ ID NO: 362) | TCTGCATCC (SEQ ID NO: 363) | SAS (SEQ ID NO: 364) | CAAACCTATTATGATATTGTTACTAGTACT (SEQ ID NO: 365) | QTYYDIVTST (SEQ ID NO: 366) |
| xi178F16LC (rabbitVk-human kappa) (human MSLN) | CAGAGCATTTACAGTTAT (SEQ ID NO: 367) | QSIYSY (SEQ ID NO: 368) | TCTGCATCC (SEQ ID NO: 369) | SAS (SEQ ID NO: 370) | CAAACCTATTATGATATTGTTACTAGTACT (SEQ ID NO: 371) | QTYYDIVTST (SEQ ID NO: 372) |
| xi237N18LC (rabbitVk-human kappa) (human MSLN) | CAGAACATTTACAGCAAT (SEQ ID NO: 373) | QNIYSN (SEQ ID NO: 374) | GATGCATCC (SEQ ID NO: 375) | DAS (SEQ ID NO: 376) | CAAAGTATTAGTAGTGTTGACAATAATGTT (SEQ ID NO: 377) | QSISSVDNNV (SEQ ID NO: 378) |
| xi383I18LC (rabbitVk-human kappa) (human MSLN) | CAGAACATTAAGAGCTAC (SEQ ID NO: 379) | QNIKSY (SEQ ID NO: 380) | GAAGCATCC (SEQ ID NO: 381) | EAS (SEQ ID NO: 382) | CAAAGCTATTATGCTGCTAGTAGTAATGCT (SEQ ID NO: 383) | QSYYAASSNA (SEQ ID NO: 384) |
| xi166B3LC (rabbitVk-human kappa) | CAGAGCATTAGTAACTAC (SEQ ID NO: 385) | QSISNY (SEQ ID NO: 386) | GCTGCATCC (SEQ ID NO: 387) | AAS (SEQ ID NO: 388) | CTAGGAGTTTATAGTATTAGTACTGATGATGGAGCTGCT (SEQ ID NO: 389) | LGVYSISTDDGAA (SEQ ID NO: 390) |

TABLE 27-continued

CDR sequences

| Clone Name (Species-Isotype) (antigen) | CDR1 DNA Sequence | CDR1 Amino Acid Sequence | CDR2 DNA Sequence | CDR2 Amino Acid Sequence | CDR3 DNA Sequence | CDR3 Amino Acid Sequence |
|---|---|---|---|---|---|---|
| (human CA9) | | | | | | |
| zu166B3LC-CXXF (humanVk-human IgG1) (human CA9) | CAGAGCATCAGCAACTA C (SEQ ID NO: 391) | QSISNY (SEQ ID NO: 392) | GCCGCTTCT (SEQ ID NO: 393) | AAS (SEQ ID NO: 394) | CTGGGCGTCTATTCAAT CTCAACTGACGACGGAG CCGCA (SEQ ID NO: 395) | LGVYSISTDDGAA (SEQ ID NO: 396) |
| zu166B3LC-CXXA (humanVk-human IgG1) (human CA9) | CAGAGCATCAGCAACTA C (SEQ ID NO: 397) | QSISNY (SEQ ID NO: 398) | GCCGCTTCT (SEQ ID NO: 399) | AAS (SEQ ID NO: 400) | CTGGGCGTCTATTCAAT CTCAACTGACGACGGAG CCGCA (SEQ ID NO: 401) | LGVYSISTDDGAA (SEQ ID NO: 402) |

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

EMBODIMENTS

The following list of embodiments is intended to complement, rather than displace or supersede, the previous descriptions.

Embodiment 1

A method for generating a conjugated immunoglobulin, the method comprising:
decapping a cysteine at amino acid position 80 ("Cys80") in a light chain variable region of an immunoglobulin derived from rabbit, wherein the immunoglobulin comprises a heavy chain variable region and the light chain variable region; and
conjugating a thiol-reactive compound to the Cys80, wherein the thiol-reactive compound comprises a thiol-reactive group.

Embodiment 2

The method of embodiment 1, wherein the light chain variable region is a kappa light chain variable region.

Embodiment 3

The method of embodiment 1 or 2, wherein the light chain variable region is derived from *Oryctolagus cuniculus*.

Embodiment 4

The method of embodiment 1 or 2, wherein the light chain variable region is a human kappa light chain variable region of family IGKV-1.

Embodiment 5

The method of any one of the previous embodiments, wherein the decapping comprises incubating the immunoglobulin with a reducing buffer followed by incubating the immunoglobulin with an oxidizing buffer.

Embodiment 6

The method of embodiment 5, further comprising immobilizing the immunoglobulin on a matrix prior to the incubating with the reducing buffer and eluting the immunoglobulin from the matrix following the incubating with the oxidizing buffer.

Embodiment 7

The method of embodiment 6, wherein the matrix comprises Protein A.

Embodiment 8

The method of any one of the previous embodiments, wherein the thiol-reactive group is maleimide or haloacetyl.

Embodiment 9

The method of any one of the previous embodiments, wherein the thiol-reactive group is appended to a linker.

Embodiment 10

The method of embodiment 9, wherein the linker is a non-cleavable linker or a cleavable linker.

Embodiment 11

The method of embodiment 10, wherein the linker is a disulfide-containing linker, an acetal-based linker or a ketal-based linker.

Embodiment 12

The method of any one of the previous embodiments, wherein the thiol-reactive compound is attached to a functional agent.

Embodiment 13

The method of embodiment 12, wherein the functional agent comprises a fluorophore, fluorescent dye, polypeptide, immunoglobulin, antibiotic, nucleic acid, radionuclide, chemical linker, small molecule, chelator, lipid, or drug.

Embodiment 14

The method of any one of the previous embodiments, wherein the thiol-reactive compound is bound to a second thiol-reactive compound, the second thiol-reactive compound being bound to a second immunoglobulin having a second heavy chain variable region and a second light chain variable region, the second light chain variable region having a cysteine at amino acid position 80 ("Cys80$^2$"), wherein the second thiol-reactive compound comprises a second thiol-reactive group bound to the Cys80$^2$.

Embodiment 15

The method of embodiment 14, wherein the thiol-reactive compound is bound to the second thiol-reactive compound by click chemistry.

Embodiment 16

The method of any one of the previous embodiments, wherein Cys80 is unpaired.

Embodiment 17

The method of any one of the previous embodiments, wherein the immunoglobulin is a chimerized immunoglobulin.

Embodiment 18

The method of any one of embodiments 1-16, further comprising chimerizing the immunoglobulin prior to the decapping.

Embodiment 19

The method of any one of embodiments 1-16, wherein the immunoglobulin is a humanized immunoglobulin.

Embodiment 20

The method of any one of embodiments 1-16, further comprising humanizing the immunoglobulin.

Embodiment 21

The method of any one of the previous embodiments, further comprising substituting an amino acid at position 83 with an amino acid residue other than Phe, Lys, or Cys.

Embodiment 22

The method of embodiment 21, wherein the amino acid residue other than Phe, Lys, or Cys is a polar or hydrophobic residue.

Embodiment 23

A method for generating an antigen-binding molecule, the method comprising incubating a first conjugated immunoglobulin with a second conjugated immunoglobulin to generate the antigen-binding molecule, wherein:
the first conjugated immunoglobulin comprises a first heavy chain variable region and a first light chain variable region, the first light chain variable region having a cysteine at position 80 ("Cys80$^1$") wherein the Cys80$^1$ is conjugated to a first thiol-reactive compound comprising a first thiol-reactive group; and
the second conjugated immunoglobulin comprises a second heavy chain variable region and a second light chain variable region, the second light chain variable region having a cysteine at position 80 ("Cys80$^2$") wherein the Cys80$^2$ is conjugated to a second thiol-reactive compound comprising a second thiol-reactive group.

Embodiment 24

The method of embodiment 23, wherein the Cys80$^1$, the Cys80$^2$, or both, is unpaired.

Embodiment 25

The method of embodiment 23 or 24, further comprising, prior to the incubating step,
decapping the Cys80$^1$, Cys80$^2$, or both; and
conjugating a first thiol-reactive compound to the Cys80$^1$, a second thiol-reactive compound to the Cys80$^2$, or both, wherein the first thiol-reactive compound comprises a first thiol-reactive group and the second thiol-reactive compound comprises a second thiol-reactive group.

Embodiment 26

The method of any one of embodiments 23-25, wherein the decapping comprises incubating the first immunoglobulin, the second immunoglobulin, or both, with a reducing buffer followed by incubating the first immunoglobulin, the second immunoglobulin, or both, with an oxidizing buffer.

Embodiment 27

The method of embodiment 26, further comprising immobilizing the first immunoglobulin, the second immunoglobulin, or both on a matrix prior to the incubating with the reducing buffer and eluting the first immunoglobulin, the second immunoglobulin, or both from the matrix following the incubating with the oxidizing buffer.

Embodiment 28

The method of embodiment 27, wherein the matrix comprises Protein A.

Embodiment 29

The method of any one of embodiments 23-28, wherein the first immunoglobulin, the second immunoglobulin, or both, is chimerized.

Embodiment 30

The method of any one of embodiments 23-28, further comprising chimerizing the first immunoglobulin, the second immunoglobulin, or both, prior to the decapping.

Embodiment 31

The method of any one of embodiments 23-28, wherein the first immunoglobulin, the second immunoglobulin, or both, is humanized.

Embodiment 32

The method of any one of embodiments 23-28, further comprising humanizing the first immunoglobulin, the second immunoglobulin, or both.

Embodiment 33

The method of any one of embodiments 23-32, wherein the first thiol-reactive group, the second thiol-reactive group, or both, is maleimide or haloacetyl.

Embodiment 34

The method of any one of embodiments 23-33, wherein the first thiol-reactive compound is appended to a first linker, the second thiol-reactive compound is appended to a second linker, or both.

Embodiment 35

The method of embodiment 34, wherein the first linker, the second linker, or both, is a non-cleavable linker or a cleavable linker.

Embodiment 36

The method of embodiment 35, wherein the first linker, the second linker, or both, is a disulfide-containing linker, an acetal-based linker or a ketal-based linker.

Embodiment 37

The method of any one of embodiments 23-36, wherein the first thiol-reactive compound further comprises a first functional agent, the second thiol-reactive compound further comprises a second functional agent, or both.

Embodiment 38

The method of embodiment 37, wherein the first functional agent, the second functional agent, or both, is a chemical linker.

Embodiment 39

The method of embodiment 38, wherein the first thiol-reactive compound is maleimido-PEG4-azide or maleimido-PEG4-dibenzocyclooctyne.

Embodiment 40

The method of embodiment 38 or 39, wherein the second thiol-reactive compound is maleimido-PEG4-dibenzocyclooctyne or maleimido-PEG4-azide.

Embodiment 41

The method of any one of embodiments 23-40, wherein the first immunoglobulin and the second immunoglobulin are conjugated to each other by click chemistry.

Embodiment 42

The method of any one of embodiments 23-41, wherein the first immunoglobulin is a first Fab, the second immunoglobulin is a second Fab, or both.

Embodiment 43

The method of any one of embodiments 23-42, further comprising substituting an amino acid at position 83 of the first light chain variable region with an amino acid residue other than Phe, Lys, or Cys, substituting an amino acid at position 83 of the second light chain variable region with an amino acid residue other than Phe, Lys, or Cys, or both.

Embodiment 44

The method of embodiment 43, wherein amino acid residue other than Phe, Lys, or Cys is a polar or hydrophobic residue.

Embodiment 45

The method of any one of embodiments 23-44, wherein the first light chain variable region, the second light chain variable region, or both, is derived from *Oryctolagus cuniculus*.

Embodiment 46

The antigen-binding molecule produced according to the method of any one of embodiments 23-45.

Embodiment 47

An immunoglobulin comprising a heavy chain variable region and a light chain variable region, the light chain variable region having a cysteine at position 80 ("Cys80") and an amino acid other than Phe, Lys, or Cys at position 83.

Embodiment 48

The immunoglobulin of embodiment 47, wherein the light chain variable region is a kappa light chain variable region.

Embodiment 49

The immunoglobulin of embodiment 47 or 48, wherein the light chain variable region is derived from *Oryctolagus cuniculus*.

Embodiment 50

The immunoglobulin of any one of embodiments 47-49, wherein the amino acid other than Phe, Lys, or Cys is a polar or hydrophobic amino acid.

Embodiment 51

The immunoglobulin of any one of embodiments 47-50, wherein the Cys80 is unpaired.

Embodiment 52

The immunoglobulin of any one of embodiments 47-51, wherein the Cys80 is decapped.

Embodiment 53

The immunoglobulin of any one of embodiments 47-52, wherein the immunoglobulin is chimerized.

Embodiment 54

The immunoglobulin of any one of embodiments 47-53, wherein the immunoglobulin is humanized.

Embodiment 55

The immunoglobulin of any one of embodiments 47-54, wherein the immunoglobulin immunospecifically binds to human CA9.

Embodiment 56

The immunoglobulin of embodiment 55, comprising:
a. a heavy chain variable region having an amino acid sequence at least 90% identical to amino acids 20-141 of xi155D5HC (SEQ ID NO:52) and a light chain variable region having an amino acid sequence at least 90% identical to amino acids 20-130 of xi155D5LC (SEQ ID NO:78);
b. a heavy chain variable region having an amino acid sequence at least 90% identical to amino acids 20-144 of zu155D5HC (SEQ ID NO:54) and a light chain variable region having an amino acid sequence at least 90% identical to amino acids 20-130 of zu155D5LC-3 (SEQ ID NO:84), zu155D5LC-4 (SEQ ID NO:86), zu155D5LC-5 (SEQ ID NO:88), zu155D5LC-6 (SEQ ID NO:90), zu155D5LC-7 (SEQ ID NO:92), zu155D5LC-huVK2-40 (SEQ ID NO:96), zu155D5LC-huVK4-1 (SEQ ID NO:100), zu155D5LC-huVK6-21 (SEQ ID NO:102), zu155D5LC-huVK6D-41 (SEQ ID NO:104); or zu155D5LC-huVK7-3-Glu81 (SEQ ID NO:106);
c. a heavy chain variable region having an amino acid sequence at least 90% identical to amino acids 20-138 of xi1E4HC (SEQ ID NO:58) and a light chain variable region having an amino acid sequence at least 90% identical to amino acids 20-130 of xi1E4LC (SEQ ID NO:110);
d. a heavy chain variable region having an amino acid sequence at least 90% identical to amino acids 20-140 of zu1E4HC (SEQ ID NO:60) and a light chain variable region having an amino acid sequence at least 90% identical to amino acids 20-130 of zu1E4LC-CXXA (SEQ ID NO:114);
e. a heavy chain variable region having an amino acid sequence at least 90% identical to amino acids 20-142 of xi166B3HC (SEQ ID NO:74) and a light chain variable region having an amino acid sequence at least 90% identical to amino acids 20-130 of xi166B3LC (SEQ ID NO:132); or
f. a heavy chain variable region having an amino acid sequence at least 90% identical to amino acids 20-145 of zu166B3HC (SEQ ID NO:76) and a light chain variable region having an amino acid sequence at least 90% identical to amino acids 20-130 of zu166B3LC-CXXA (SEQ ID NO:136).

Embodiment 57

The immunoglobulin of embodiment 56, comprising:
a. a heavy chain CDR1, CDR2, and CDR3 of xi155D5HC as set forth as SEQ ID NO:146, 148, and 150, respectively, and a light chain CDR1, CDR2, and CDR3 of xi155D5LC as set forth as SEQ ID NO:224, 226, and 228, respectively;
b. a heavy chain CDR1, CDR2, and CDR3 of zu155D5HC as set forth as SEQ ID NO:152, 154, and 156, respectively, and a light chain CDR1, CDR2, and CDR3 of zu155D5LC-3 as set forth as SEQ ID NO:242, 244, and 246, respectively, zu155D5LC-4 as set forth as SEQ ID NO:248, 250, and 252, respectively, zu155D5LC-5 as set forth as SEQ ID NO:254, 256, and 258, respectively, zu155D5LC-6 as set forth as SEQ ID NO:260, 262, and 264, respectively, zu155D5LC-7 as set forth as SEQ ID NO:266, 268, and 270, respectively, zu155D5LC-huVK2-40 as set forth as SEQ ID NO 278, 280, and 282, respectively, zu155D5LC-huVK4-1 as set forth as SEQ ID NO 290, 292, and 294, respectively, zu155D5LC-huVK6-21 as set forth as SEQ ID NO 296, 298, and 300, respectively, zu155D5LC-huVK6D-41 as set forth as SEQ ID NO 302, 304, and 306, respectively; or zu155D5LC-huVK7-3-Glu81 as set forth as SEQ ID NO 308, 310, and 312, respectively;
c. a heavy chain CDR1, CDR2, and CDR3 of xi1E4HC as set forth as SEQ ID NO:164, 166, and 168, respectively, and a light chain CDR1, CDR2, and CDR3 of xi1E4LC as set forth as SEQ ID NO:320, 322, and 324, respectively;
d. a heavy chain CDR1, CDR2, and CDR3 of zu1E4HC as set forth as SEQ ID NO:170, 172, and 174, respectively, and a light chain CDR1, CDR2, and CDR3 of zu1E4LC-CXXA as set forth as SEQ ID NO:332, 334, and 336, respectively;
e. a heavy chain CDR1, CDR2, and CDR3 of xi166B3HC as set forth as SEQ ID NO:212, 214, and 216, respectively, and a light chain CDR1, CDR2, and CDR3 of xi166B3LC as set forth as SEQ ID NO:386, 388, and 390, respectively; or
f. a heavy chain CDR1, CDR2, and CDR3 of zu166B3HC as set forth as SEQ ID NO:218, 220, and 222, respectively, and a light chain CDR1, CDR2, and CDR3 of zu166B3LC-CXXA as set forth as SEQ ID NO:398, 400, and 402, respectively.

Embodiment 58

The immunoglobulin of any one of embodiments 46-54, wherein the immunoglobulin immunospecifically binds to human TEM1.

Embodiment 59

The immunoglobulin of embodiment 58, comprising:
a heavy chain variable region having an amino acid sequence at least 90% identical to amino acids 20-139 of xi1-55-2HC (SEQ ID NO:56) and a light chain variable region having an amino acid sequence at least 90% identical to amino acids 20-129 of xi1-55-2LC (SEQ ID NO:108).

Embodiment 60

The immunoglobulin of embodiment 59, comprising:
a heavy chain CDR1, CDR2, and CDR3 of xi1-55-2HC as set forth as SEQ ID NO:158, 160, and 162, respectively, and a light chain CDR1, CDR2, and CDR3 of xi1-55-2LC as set forth as SEQ ID NO:314, 316, and 318, respectively.

Embodiment 61

The immunoglobulin of any one of embodiments 46-54, wherein the immunoglobulin immunospecifically binds to human mesothelin.

Embodiment 62

The immunoglobulin of embodiment 61, comprising:
a. a heavy chain variable region having an amino acid sequence at least 90% identical to amino acids 20-142 of xi33O11HC (SEQ ID NO:62) and a light chain variable region having an amino acid sequence at least 90% identical to amino acids 20-131 of xi33O11LC (SEQ ID NO:116);
b. a heavy chain variable region having an amino acid sequence at least 90% identical to amino acids 20-145 of zu33O11HC (SEQ ID NO:64) and a light chain variable region having an amino acid sequence at least 90% identical to amino acids 20-131 of zu33O11LC-CXXA (SEQ ID NO:120) or zu33O11LC-CXXI (SEQ ID NO:122);
c. a heavy chain variable region having an amino acid sequence at least 90% identical to amino acids 20-137 of xi324O5HC (SEQ ID NO:66) and a light chain variable region having an amino acid sequence at least 90% identical to amino acids 20-127 of xi324O5LC (SEQ ID NO:124);
d. a heavy chain variable region having an amino acid sequence at least 90% identical to amino acids 20-137 of xi178F16HC (SEQ ID NO:68) and a light chain variable region having an amino acid sequence at least 90% identical to amino acids 20-127 of xi178F16LC (SEQ ID NO:126);
e. a heavy chain variable region having an amino acid sequence at least 90% identical to amino acids 20-132 of xi237N18HC (SEQ ID NO:70) and a light chain variable region having an amino acid sequence at least 90% identical to amino acids 20-127 of xi237N18LC (SEQ ID NO:128); or
f. a heavy chain variable region having an amino acid sequence at least 90% identical to amino acids 20-137 of xi383I18HC (SEQ ID NO:72) and a light chain variable region having an amino acid sequence at least 90% identical to amino acids 20-127 of xi383I18LC (SEQ ID NO:130).

Embodiment 63

The immunoglobulin of embodiment 62, comprising:
a. a heavy chain CDR1, CDR2, and CDR3 of xi33O11HC as set forth as SEQ ID NO: 176, 178, and 180, respectively, and a light chain CDR1, CDR2, and CDR3 of xi33O11LC as set forth in SEQ ID NO:338, 340, and 342, respectively;
b. a heavy chain CDR1, CDR2, and CDR3 of zu33O11HC as set forth as SEQ ID NO:182, 184, and 186, respectively, and a light chain CDR1, CDR2, and CDR3 of zu33O11LC-CXXA as set forth as SEQ ID NO:350, 352, and 354, respectively, or zu33O11LC-CXXI as set forth as SEQ ID NO:356, 358, and 360, respectively;
c. a heavy chain CDR1, CDR2, and CDR3 of xi324O5HC as set forth as SEQ ID NO:188, 190, and 192, respectively, and a light chain CDR1, CDR2, and CDR3 of xi324O5LC as set forth as SEQ ID NO:362, 364, and 366, respectively;
d. a heavy chain CDR1, CDR2, and CDR3 of xi178F16HC as set forth as SEQ ID NO:194, 196, and 198, respectively, and a light chain CDR1, CDR2, and CDR3 of xi178F16LC as set forth as SEQ ID NO:368, 370, and 372, respectively;
e. a heavy chain CDR1, CDR2, and CDR3 of xi237N18HC as set forth as SEQ ID NO:200, 202, and 204, respectively, and a light chain CDR1, CDR2, and CDR3 of xi237N18LC as set forth as SEQ ID NO:374, 376, and 378, respectively; or
f. a heavy chain CDR1, CDR2, and CDR3 of xi383I18HC as set forth as SEQ ID NO:206, 208, and 210, respectively, and a light chain CDR1, CDR2, and CDR3 of xi383I18LC as set forth as SEQ ID NO:380, 382, and 384, respectively.

Embodiment 64

A conjugated immunoglobulin comprising:
the immunoglobulin of any one of embodiments 46-63, wherein the cysteine at position 80 is conjugated to a thiol-reactive compound, the thiol-reactive compound comprising a thiol-reactive group.

Embodiment 65

The conjugated immunoglobulin of embodiment 64, wherein the thiol-reactive group is maleimide or haloacetyl.

Embodiment 66

The conjugated immunoglobulin of embodiment 64 or 65, wherein the thiol-reactive group is appended to a linker.

Embodiment 67

The conjugated immunoglobulin of embodiment 66, wherein the linker is a non-cleavable linker or a cleavable linker.

Embodiment 68

The conjugated immunoglobulin of embodiment 67, wherein the linker is a disulfide containing linker, an acetal-based linker or a ketal-based linker.

Embodiment 69

The conjugated immunoglobulin of any one of embodiments 64-68, wherein the thiol-reactive compound further comprises a functional agent.

Embodiment 70

The conjugated immunoglobulin of embodiment 69, wherein the functional agent comprises a fluorophore, fluorescent dye, polypeptide, immunoglobulin, antibiotic, nucleic acid, radionuclide, chemical linker, small molecule, chelator, lipid, or drug.

Embodiment 71

The conjugated immunoglobulin of embodiment 70, wherein the functional agent is auristatin F.

Embodiment 72

The conjugated immunoglobulin of any one of embodiments 69-71, wherein the conjugated immunoglobulin has an immunoglobulin:functional agent ratio of 2:1.

Embodiment 73

A method of treating cancer in a subject comprising administering to the subject a pharmaceutically effective amount of a conjugated mesothelin immunoglobulin, wherein the conjugated mesothelin immunoglobulin comprises:
the immunoglobulin of any one of embodiments 61-63, and a thiol-reactive compound comprising a thiol-reactive group, a linker, and a functional agent.

Embodiment 74

The method of embodiment 73, wherein the functional agent is auristatin F.

Embodiment 75

The method of embodiment 73 or 74, wherein the cancer is a mesothelin-expressing cancer.

Embodiment 76

A antigen-binding molecule comprising:
a first conjugated immunoglobulin comprising a first heavy chain variable region and a first light chain variable region, the first light chain variable region having a cysteine at position 80 ("Cys80$^1$"), wherein the Cys80$^1$ is conjugated to a first thiol-reactive compound comprising a first thiol-reactive group, and
a second conjugated immunoglobulin comprising a second heavy chain variable region and a second light chain variable region, the second light chain variable region having a cysteine at position 80 ("Cys80$^2$") wherein the Cys80$^2$ is conjugated to a second thiol-reactive compound comprising a second thiol-reactive group.

Embodiment 77

The antigen-binding molecule of embodiment 76, wherein the first light chain variable region, the second light chain variable region, or both, is derived from *Oryctolagus cuniculus*.

Embodiment 78

The antigen-binding molecule of embodiment 76 or 77, wherein Cys80$^1$, Cys80$^2$, or both, is unpaired.

Embodiment 79

The antigen-binding molecule of any one of embodiments 76-78, wherein the first immunoglobulin, the second immunoglobulin, or both, is chimerized.

Embodiment 80

The antigen-binding molecule of any one of embodiments 76-78, wherein the first immunoglobulin, the second immunoglobulin, or both, is humanized.

Embodiment 81

The antigen-binding molecule of any one of embodiments 76-80, wherein the amino acid at position 83 of the first immunoglobulin, the amino acid at position 83 of the second immunoglobulin, or both, is an amino acid residue other than Phe, Lys, or Cys.

Embodiment 82

The antigen-binding molecule of embodiment 81, wherein the amino acid residue other than Phe, Lys, or Cys is a polar or hydrophobic residue.

Embodiment 83

The antigen-binding molecule of any one of embodiments 76-82, wherein the first immunoglobulin and the second immunoglobulin bind to different antigens.

Embodiment 84

The antigen-binding molecule of any one of embodiments 76-83, wherein the first thiol-reactive group, the second thiol-reactive group, or both, is maleimide or haloacetyl.

Embodiment 85

The antigen-binding molecule of any one of embodiments 76-84, wherein the first thiol-reactive compound further comprises a first linker, the second thiol-reactive compound further comprises a second linker, or both.

Embodiment 86

The antigen-binding molecule of embodiment 85, wherein the first linker, the second linker, or both, is a cleavable linker or a non-cleavable linker.

Embodiment 87

The antigen-binding molecule of embodiment 86, wherein the first linker, the second linker, or both, is a disulfide containing linker, an acetal-based linker or a ketal-based linker.

Embodiment 88

The antigen-binding molecule of any one of embodiments 76-87, wherein the first thiol-reactive compound further comprises a first functional agent, the second thiol-reactive compound further comprises a second functional agent, or both.

Embodiment 89

The antigen-binding molecule of embodiment 88, wherein the first functional agent, the second functional agent, or both, is a chemical linker.

Embodiment 90

The antigen-binding molecule of any one of embodiments 76-89, wherein the first thiol-reactive compound, the second thiol-reactive compound, or both, is maleimido-PEG4-azide or maleimido-PEG4-dibenzocyclooctyne.

Embodiment 91

The antigen-binding molecule of any one of embodiments 76-90, wherein the first thiol-reactive compound differs from the second thiol-reactive compound.

Embodiment 92

The antigen-binding molecule of any one of embodiments 76-91, wherein the first immunoglobulin, second immunoglobulin, or both is a Fab.

Embodiment 93

A light chain variable region for use in a conjugated immunoglobulin, the light chain variable region having a cysteine at amino acid position 80 ("Cys80") and an amino acid residue other than Phe, Lys, or Cys at amino acid position 83, wherein the Cys80 is unpaired.

Embodiment 94

The light chain variable region of embodiment 93, wherein the light chain variable region has a Cys80-$Xaa_1$-$Xaa_2$-$Xaa_3$ motif, wherein $Xaa_3$ is any amino acid other than Phe, Lys, or Cys.

Embodiment 95

The light chain variable region of embodiment 93 or 94, wherein the light chain variable region is derived from *Oryctolagus cuniculus*.

Embodiment 96

The light chain variable region of any one of embodiments 93-95, wherein the light chain variable region is chimerized.

Embodiment 97

The light chain variable region of any one of embodiments 93-95, wherein the light chain variable region is humanized.

Embodiment 98

A nucleic acid molecule encoding the immunoglobulin of any one of embodiments 47-63.

Embodiment 99

A host cell comprising the nucleic acid molecule of embodiment 98.

---

What is claimed:

1. A method for generating a conjugated immunoglobulin, the method comprising:
   incubating a chimeric or humanized rabbit immunoglobulin or antigen-binding fragment thereof with a mild reducing buffer comprising cysteine, dithiothreitol (DTT), or tris (2-carboxyethyl) phosphine (TCEP) to decap a cysteine at amino acid position 80 ("Cys80") in a light chain variable region of the immunoglobulin, the Cys80 based upon the Kabat or Chothia numbering system, wherein the immunoglobulin comprises a heavy chain variable region and the light chain variable region; and
   conjugating a thiol-reactive compound to the decapped Cys80, wherein the thiol-reactive compound comprises a thiol-reactive group.

2. The method of claim 1, further comprising incubating the immunoglobulin or antigen-binding fragment thereof with a Tris-based, glutamine-based, arginine-based, or primary amine-based oxidizing buffer after the incubating with the mild reducing buffer.

3. The method of claim 2, further comprising immobilizing the immunoglobulin or antigen-binding fragment thereof on a matrix prior to the incubating with the mild reducing buffer and eluting the immunoglobulin from the matrix following the incubating with the oxidizing buffer.

4. The method of claim 1, wherein the thiol-reactive compound is attached to a functional agent.

5. The method of claim 4, wherein the functional agent comprises a fluorophore, fluorescent dye, polypeptide, immunoglobulin, antibiotic, nucleic acid, radionuclide, chemical linker, small molecule, chelator, lipid, or drug.

6. The method of claim 1, wherein the thiol-reactive compound is bound to a second thiol-reactive compound, the second thiol-reactive compound being bound to amino acid position 80 in a light chain variable region of a second chimeric or humanized rabbit immunoglobulin or antigen-binding fragment thereof ("Cys80$^2$"), the Cys80$^2$ based upon the Kabat or Chothia numbering system.

7. The method of claim 1, wherein the Cys80 is unpaired with Cys171 of the light chain.

8. The method of claim 1, further comprising substituting an amino acid at position 83 with an amino acid residue other than Phe, Lys, or Cys, the position 83 based upon the Kabat or Chothia numbering system.

9. A method for generating an antigen-binding molecule, the method comprising incubating a first conjugated immunoglobulin with a second conjugated immunoglobulin to generate the antigen-binding molecule, wherein:
   the first conjugated immunoglobulin comprises a first heavy chain variable region and a first light chain variable region, the first light chain variable region having a cysteine at position 80 ("Cys80$^1$") wherein the Cys80$^1$ is conjugated to a first thiol-reactive compound comprising a first thiol-reactive group, and wherein the immunoglobulin is a chimeric or humanized rabbit immunoglobulin or antigen-binding fragment thereof and the Cys80$^1$ is based upon the Kabat or Chothia numbering system; and
   the second conjugated immunoglobulin comprises a second heavy chain variable region and a second light chain variable region, the second light chain variable region having a cysteine at position 80 ("Cys80$^2$") wherein the Cys80$^2$ is conjugated to a second thiol-reactive compound comprising a second thiol-reactive group, and wherein the immunoglobulin is a chimeric or humanized rabbit immunoglobulin or antigen-binding fragment thereof and the Cys80$^2$ is based upon the Kabat or Chothia numbering system.

10. The method of claim 9, wherein the Cys80$^1$ is unpaired with Cys171$^1$ of the first light chain and/or the Cys80$^2$ is unpaired with Cys171$^2$ of the second light chain.

11. The method of claim 9, further comprising, prior to the incubating step,
   incubating a first chimeric or humanized rabbit immunoglobulin or antigen-binding fragment thereof with a mild reducing buffer comprising cysteine, dithiothreitol (DTT), or tris (2-carboxyethyl) phosphine (TCEP) to decap the Cys80$^1$ and/or incubating a second chimeric or humanized rabbit immunoglobulin or antigen-binding fragment thereof with a mild reducing buffer comprising cysteine, dithiothreitol (DTT), or tris (2-carboxyethyl) phosphine (TCEP) to decap the Cys80$^2$; and conjugating a first thiol-reactive compound to the decapped Cys80$^1$ and/or a second thiol-reactive compound to the decapped Cys80$^2$, wherein the first thiol-reactive compound comprises a first thiol-reactive group and the second thiol-reactive compound comprises a second thiol-reactive group.

12. The method of claim 9, wherein the first thiol-reactive compound further comprises a first functional agent and/or the second thiol-reactive compound further comprises a second functional agent.

13. The method of claim 9, wherein the first chimeric or humanized rabbit immunoglobulin or antigen-binding fragment thereof is a first Fab and/or the second chimeric or humanized rabbit immunoglobulin or antigen-binding fragment thereof is a second Fab.

14. The method of claim 9, further comprising substituting an amino acid at position 83 of the first light chain variable region with an amino acid residue other than Phe, Lys, or Cys, and/or substituting an amino acid at position 83 of the second light chain variable region with an amino acid residue other than Phe, Lys, or Cys, the position 83 based upon the Kabat or Chothia numbering system.

15. An antigen-binding molecule produced according to the method of claim 9.

* * * * *

SEQUENCE LISTING

<160> NUMBER OF SEQ ID NOS: 491

<210> SEQ ID NO 1
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatcaagctt gccgccacca tgggctggtc ctgcatcatc ctgtttctgg tggcggccgc    60
caccggcgtg cactcc                                                    76

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgcctttgg ctggcctgar gagayggtga ccagggtgcc         40

<210> SEQ ID NO 3
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatcaagctt gccgccacca tgggctggtc ctgcatcatc ctgtttctgg tggcggccgc         60
caccggcgtg cactcc         76

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatcggcgcg cctcacttgc cggggctccg g         31

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccaccggcg tgcactccca gtcggtgrag gagtccrggg g         41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggcccttgg tggatgctga rgagayggtg accagggtgc c         41

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccaccggcg tgcactccga gctcgtgatg acccagactc ca         42

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agccacagtt cgtttgacsa ccacctcggt ccc                                33

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagtcgctgc tcgagtccgg gggt                                          24

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctctggcaca ggagctc                                                  17

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggagacgagc gggtacagag t                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgtgggcttg ctgcatgtcg                                               20

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgatgaccc agactcca                                                 18

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acagtcaccc ctattgaagc tctgg                                        25

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcagtcaccc ctgttgaagc tctg                                         24

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccaccggcg tgcactccca gtcggtgrag gagtccrggg g                      41

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggcccttgg tggatgctga rgagayggtg accagggtgc c                      41

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccaccggcg tgcactccga gctcgtgatg acccagactc ca                     42

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agccacagtt cgtttgatct ccagctcggt ccc                               33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agccacagtt cgtttgattt ccacattggt gcc                               33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
agccacagtt cgtttgacsa ccacctcggt ccc        33

<210> SEQ ID NO 22
<211> LENGTH: 14
<212> TYPE: PRT
<213> ORGANISM: Oryctolagus cuniculus

<400> SEQUENCE: 22

Asp Cys Thr Tyr Asn Leu Ser Ser Thr Leu Ser Leu Thr Lys
1               5                   10

<210> SEQ ID NO 23
<211> LENGTH: 11
<212> TYPE: PRT
<213> ORGANISM: Oryctolagus cuniculus

<400> SEQUENCE: 23

Phe Thr Leu Thr Ile Thr Gly Val Gln Cys Asp
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Phe Thr Leu Thr Ile Thr Gly Val Gln Cys
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Thr Leu Thr Ile Thr Gly Val Gln Cys
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Leu Thr Ile Thr Gly Val Gln Cys
1               5

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Ile Thr Gly Val Gln Cys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Thr Gly Val Gln Cys
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Gly Val Gln Cys
1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Gln Cys
1

<210> SEQ ID NO 31
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Cys
1

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Tyr Gln Gln Lys Pro Gly Lys Ala Pro Lys Leu Leu Ile Tyr
1               5                   10                  15

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Val Pro Ser Arg Phe Ser Gly Ser Gly Ser Gly Thr Glu Phe Thr
1               5                   10                  15

Leu Thr Ile Ser Ser Leu Gln Cys Asp Asp Phe Ala Thr Tyr Tyr Cys
            20                  25                  30

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gly Gly Thr Lys Val Glu Ile Lys
1               5                   10

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Ile Gln Met Thr Gln Ser Pro Ser Thr Val Ser Ala Ala Val Gly
1               5                   10                  15

Gly Thr Val Thr Ile Thr Cys
            20

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Gly Val Pro Ser Arg Phe Ser Gly Ser Gly Ser Gly Thr Glu Phe Thr
1               5                   10                  15

Leu Thr Ile Thr Gly Val Gln Cys Asp Asp Phe Ala Thr Tyr Tyr Cys
            20                  25                  30

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Gly Gly Gly Thr Glu Leu Glu Ile Lys
1               5                   10

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Val Pro Ser Arg Phe Lys Gly Ser Gly Ser Gly Thr Glu Phe Thr
1               5                   10                  15

Leu Thr Ile Thr Gly Val Gln Cys Asp Asp Ala Ala Thr Tyr Tyr Cys
            20                  25                  30

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Ala Glu Phe Arg His Asp Ser Gly Tyr Glu Val His His Gln Lys
1               5                   10                  15

<210> SEQ ID NO 41
<211> LENGTH: 2274
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgctgctgc gcctgttgct ggcctgggcg ccgcagggc ccacactggg ccaggacccc      60
tgggctgctg agccccgtgc cgcctgcggc cccagcagct gctacgctct cttcccacgg     120
cgccgcacct tcctggaggc ctggcgggcc tgccgcgagc tggggggcga cctggccact     180
cctcggaccc ccgaggaggc ccagcgtgtg acagcctgg tgggtgcggg cccagccagc     240
cggctgctgt ggatcgggct gcagcggcag gcccggcaat gccagctgca gcgcccactg     300
cgcggcttca cgtggaccac aggggaccag gacacggctt tcaccaactg ggcccagcca     360
gcctctggag cccctgccc ggcccagcgc tgtgtggccc tggaggcaag tggcgagcac     420
cgctggctgg agggctcgtg cacgctggct gtcgacggct acctgtgcca gtttggcttc     480
```

```
gagggcgcct gcccggcgct gcaagatgag gcgggccagg ccggcccagc cgtgtatacc    540
acgcccttcc acctggtctc cacagagttt gagtggctgc ccttcggctc tgtggccgct    600
gtgcagtgcc aggctggcag gggagcctct ctgctctgcg tgaagcagcc tgagggaggt    660
gtgggctggt cacgggctgg gcccctgtgc ctggggactg gctgcagccc tgacaacggg    720
ggctgcgaac acgaatgtgt ggaggaggtg gatggtcacg tgtcctgccg ctgcactgag    780
ggcttccggc tggcagcaga cgggcgcagt tgcgaggacc cctgtgccca ggctccgtgc    840
gagcagcagt gtgagcccgg tgggccacaa ggctacagct gccactgtcg cctgggtttc    900
cggccagcgg aggatgatcc gcaccgctgt gtggacacag atgagtgcca gattgccggt    960
gtgtgccagc agatgtgtgt caactacgtt ggtggcttcg agtgttattg tagcgaggga   1020
catgagctgg aggctgatgg catcagctgc agccctgcag gggccatggg tgcccaggct   1080
tcccaggacc tcggagatga gttgctggat gacggggagg atgaggaaga tgaagacgag   1140
gcctggaagg ccttcaacgg tggctggacg gagatgcctg ggatcctgtg gatggagcct   1200
acgcagccgc ctgactttgc cctggcctat agaccgagct cccagagga cagagagcca   1260 cagatacccc tacccggagcc cacctggcca cccccgctca gtgcccccag ggtcccctac   1320
cactcctcag tgctctccgt cacccggcct gtggtggtct ctgccacgca tcccacactg   1380
ccttctgccc accagcctcc tgtgatccct gccacacacc cagctttgtc ccgtgaccac   1440
cagatccccg tgatcgcagc caactatcca gatctgcctt ctgcctacca acccggtatt   1500
ctctctgtct ctcattcagc acagcctcct gcccaccagc ccctatgat ctcaaccaaa   1560 tatccggagc tcttccctgc ccaccagtcc ccatgtttc cagacacccg ggtcgctggc   1620
acccagacca ccactcattt gcctggaatc ccacctaacc atgcccctct ggtcaccacc   1680
ctcggtgccc agctaccccc tcaagcccca gatgcccttg tcctcagaac ccaggccacc   1740
cagcttccca ttatcccaac tgcccagccc tctctgacca ccacctccag gtcccctgtg   1800
tctcctgccc atcaaatctc tgtgcctgct gccaccagc ccgcagccct ccccaccctc    1860
ctgccctctc agagccccac taaccagacc tcacccatca gccctacaca tccccattcc   1920
aaagcccccc aaatcccaag ggaagatggc cccagtccca agttggccct gtggctgccc   1980
tcaccagctc ccacagcagc cccaacagcc ctggggagg ctggtcttgc cgagcacagc   2040
cagagggatg accggtggct gctggtggca ctcctggtgc caacgtgtgt cttttggtg    2100 gtcctgcttg cactgggcat cgtgtactgc acccgctgtg gccccatgc acccaacaag    2160 cgcatcactg actgctatcg ctgggtcatc catgctggga gcaagagccc aacagaaccc    2220 atgccccca ggggcagcct cacaggggtg cagacctgca gaaccagcgt gtga           2274
```

<210> SEQ ID NO 42
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Leu Leu Arg Leu Leu Leu Ala Trp Ala Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Arg Thr Phe Leu Glu Ala Trp
        35                  40                  45

-continued

```
Arg Ala Cys Arg Glu Leu Gly Gly Asp Leu Ala Thr Pro Arg Thr Pro
 50                  55                  60

Glu Ala Gln Arg Val Asp Ser Leu Val Gly Ala Gly Pro Ala Ser
 65                  70                  75                  80

Arg Leu Leu Trp Ile Gly Leu Gln Arg Gln Ala Arg Gln Cys Gln Leu
                     85                  90                  95

Gln Arg Pro Leu Arg Gly Phe Thr Trp Thr Thr Gly Asp Gln Asp Thr
                100                 105                 110

Ala Phe Thr Asn Trp Ala Gln Pro Ala Ser Gly Gly Pro Cys Pro Ala
                115                 120                 125

Gln Arg Cys Val Ala Leu Glu Ala Ser Gly Glu His Arg Trp Leu Glu
                130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
                180                 185                 190

Leu Pro Phe Gly Ser Val Ala Ala Val Gln Cys Gln Ala Gly Arg Gly
                195                 200                 205

Ala Ser Leu Leu Cys Val Lys Gln Pro Glu Gly Gly Val Gly Trp Ser
210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Val Asp Gly His Val Ser Cys
                245                 250                 255

Arg Cys Thr Glu Gly Phe Arg Leu Ala Ala Asp Gly Arg Ser Cys Glu
                260                 265                 270

Asp Pro Cys Ala Gln Ala Pro Cys Glu Gln Cys Glu Pro Gly Gly
                275                 280                 285

Pro Gln Gly Tyr Ser Cys His Cys Arg Leu Gly Phe Arg Pro Ala Glu
                290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
                355                 360                 365

Leu Asp Asp Gly Glu Asp Glu Glu Asp Glu Asp Glu Ala Trp Lys Ala
                370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro
                420                 425                 430

Leu Ser Ala Pro Arg Val Pro Tyr His Ser Ser Val Leu Ser Val Thr
                435                 440                 445

Arg Pro Val Val Val Ser Ala Thr His Pro Thr Leu Pro Ser Ala His
450                 455                 460
```

```
Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
            485                 490                 495

Gln Pro Gly Ile Leu Ser Val Ser His Ser Ala Gln Pro Pro Ala His
        500                 505                 510

Gln Pro Pro Met Ile Ser Thr Lys Tyr Pro Glu Leu Phe Pro Ala His
    515                 520                 525

Gln Ser Pro Met Phe Pro Asp Thr Arg Val Ala Gly Thr Gln Thr Thr
530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
        595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Pro Thr Ala Leu Gly
            660                 665                 670

Glu Ala Gly Leu Ala Glu His Ser Gln Arg Asp Asp Arg Trp Leu Leu
        675                 680                 685

Val Ala Leu Leu Val Pro Thr Cys Val Phe Leu Val Val Leu Leu Ala
    690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
            740                 745                 750

Cys Arg Thr Ser Val
        755

<210> SEQ ID NO 43
<211> LENGTH: 2796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atgctgctgc gcctgttgct ggcctgggcg gccgcagggc ccacactggg ccaggacccc      60
tgggctgctg agccccgtgc cgcctgcggc cccagcagct gctacgctct cttcccacgg     120
cgccgcacct tcctggaggc ctggcgggcc tgccgcgagc tggggggcga cctggccact     180
cctcggaccc ccgaggaggc ccagcgtgtg acagcctggg tggtgcgggg ccagccagc     240 cggctgctgt ggatcgggct gcagcggcag gcccggcaat gccagctgca cgcccactg     300 cgcggcttca cgtggaccac agggaccag gacacggctt tcaccaactg ggcccagcca    360
```

```
gcctctggag gcccctgccc ggcccagcgc tgtgtggccc tggaggcaag tggcgagcac    420
cgctggctgg agggctcgtg cacgctggct gtcgacggct acctgtgcca gtttggcttc    480
gagggcgcct gcccggcgct gcaagatgag gcgggccagg ccggcccagc cgtgtatacc    540
acgcccttcc acctggtctc cacagagttt gagtggctgc ccttcggctc tgtggccgct    600
gtgcagtgcc aggctggcag gggagcctct ctgctctgcg tgaagcagcc tgagggaggt    660
gtgggctggt cacgggctgg gcccctgtgc ctggggactg gctgcagccc tgacaacggg    720
ggctgcgaac acgaatgtgt ggaggaggtg gatggtcacg tgtcctgccg ctgcactgag    780
ggcttccggc tggcagcaga cgggcgcagt tgcgaggacc cctgtgccca ggctccgtgc    840
gagcagcagt gtgagcccgg tgggccacaa ggctacagct gccactgtcg cctgggtttc    900
cggccagcgg aggatgatcc gcaccgctgt gtggacacag atgagtgcca gattgccggt    960
gtgtgccagc agatgtgtgt caactacgtt ggtggcttcg agtgttattg tagcgaggga   1020
catgagctgg aggctgatgg catcagctgc agccctgcag gggccatggg tgcccaggct   1080
tcccaggacc tcggagatga gttgctggat gacggggagg atgaggaaga tgaagacgag   1140
gcctggaagg ccttcaacgg tggctggacg gagatgcctg ggatcctgtg gatggagcct   1200
acgcagccgc ctgactttgc cctggcctat agaccgagct cccagagga cagagagcca   1260
cagataccct acccggagcc cacctggcca ccccgctca gtgcccccag ggtccctac    1320
cactcctcag tgctctccgt cacccggcct gtggtggtct ctgccacgca tcccacactg   1380
ccttctgccc accagcctcc tgtgatccct gccacacacc cagctttgtc ccgtgaccac   1440
cagatccccg tgatcgcagc caactatcca gatctgcctt ctgcctacca acccggtatt   1500
ctctctgtct tcattcagc acagcctcct gcccaccagc ccctatgat ctcaaccaaa    1560
tatccggagc tcttccctgc ccaccagtcc cccatgtttc agacacccg gtcgctggc    1620
acccagacca ccactcattt gcctggaatc ccacctaacc atgcccctct ggtcaccacc   1680
ctcggtgccc agctaccccc tcaagcccca gatgcccttg tcctcagaac ccaggccacc   1740
cagcttccca ttatcccaac tgcccagccc tctctgacca ccacctccag gtccctgtg    1800
tctcctgccc atcaaatctc tgtgcctgct gccacccagc ccgcagccct ccccaccctc   1860
ctgccctctc agagccccac taaccagacc tcacccatca gccctacaca tccccattcc   1920
aaagccccc aaatcccaag ggaagatggc cccagtccca gttggccct gtggctgccc    1980
tcaccagctc ccacagcagc cccaacagcc ctgggggagg ctggtcttgc cgagcacagc   2040
cagagggatg accgggttaa cgacgacgac gacaaagagc ccagcggacc aatttcaaca   2100
atcaacccct ctcctccatc caaggagtct cacaaaagcc cagctcctaa cctcgagggt   2160
ggaccatccg tcttcatctt ccctccaaat atcaaggatg tactcatgat ctccctgaca   2220
cccaaggtca cgtgtgtggt ggtggatgtg agcgaggatg acccagacgt ccagatcagc   2280
tggtttgtga caacgtgga agtacacaca gcycagacac aaacccatag agaggattac    2340
aacagtacta tccgggtggt cagcaccctc cccatccagc accaggactg gatgagtggc   2400
aaggagttca atgcaaggt caacaacaaa gacctcccat cacccatcga gagaaccatc    2460
tcaaaaatta aagggctagt cagagctcca caagtataca tcttgccgcc accagcagag   2520
cagttgtcca ggaaagatgt cagtctcact tgcctggtcg tgggcttcaa ccctggagac   2580
atcagtgtgg agtggaccag caatgggcat acagaggaga actacaagga caccgcacca   2640
gtcctggact ctgacggttc ttacttcata tatagcaagc tcaatatgaa aacaagcaag   2700
```

```
tgggagaaaa cagattcctt ctcatgcaac gtgagacacg agggtctgaa aaattactac    2760
ctgaagaaga ccatctcccg gtctccgggt aaatga                              2796
```

<210> SEQ ID NO 44
<211> LENGTH: 931
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Leu Leu Arg Leu Leu Leu Ala Trp Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Arg Thr Phe Leu Glu Ala Trp
        35                  40                  45

Arg Ala Cys Arg Glu Leu Gly Gly Asp Leu Ala Thr Pro Arg Thr Pro
    50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
        115                 120                 125

Gln Arg Cys Val Ala Leu Glu Ala Ser Gly Glu His Arg Trp Leu Glu
    130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Gly Val Gly Trp Ser
    210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Val Asp Gly His Val Ser Cys
                245                 250                 255

Arg Cys Thr Glu Gly Phe Arg Leu Ala Ala Asp Gly Arg Ser Cys Glu
            260                 265                 270

Asp Pro Cys Ala Gln Ala Pro Cys Glu Gln Cys Glu Pro Gly Gly
        275                 280                 285

Pro Gln Gly Tyr Ser Cys His Cys Arg Leu Gly Phe Arg Pro Ala Glu
    290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
```

```
                    340                 345                 350
Ala Gly Ala Met Gly Ala Gln Ala Ser Gln Asp Leu Gly Asp Glu Leu
            355                 360                 365

Leu Asp Asp Gly Glu Asp Glu Asp Glu Asp Glu Ala Trp Lys Ala
    370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
            435                 440                 445

Arg Pro Val Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
            500                 505                 510

Gln Pro Pro Met Ile Ser Thr Lys Tyr Pro Glu Leu Phe Pro Ala His
            515                 520                 525

Gln Ser Pro Met Phe Pro Asp Thr Arg Val Ala Gly Thr Gln Thr Thr
            530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
            595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
            660                 665                 670

Glu Ala Gly Leu Ala Glu His Ser Gln Arg Asp Asp Arg Val Asn Asp
            675                 680                 685

Asp Asp Asp Lys Glu Pro Ser Gly Pro Ile Ser Thr Ile Asn Pro Ser
    690                 695                 700

Pro Pro Ser Lys Glu Ser His Lys Ser Pro Ala Pro Asn Leu Glu Gly
705                 710                 715                 720

Gly Pro Ser Val Phe Ile Phe Pro Pro Asn Ile Lys Asp Val Leu Met
                725                 730                 735

Ile Ser Leu Thr Pro Lys Val Thr Cys Val Val Val Asp Val Ser Glu
            740                 745                 750

Asp Asp Pro Asp Val Gln Ile Ser Trp Phe Val Asn Asn Val Glu Val
            755                 760                 765
```

```
His Thr Ala Gln Thr Gln Thr His Arg Glu Asp Tyr Asn Ser Thr Ile
    770                 775                 780
Arg Val Val Ser Thr Leu Pro Ile Gln His Gln Asp Trp Met Ser Gly
785                 790                 795                 800
Lys Glu Phe Lys Cys Lys Val Asn Asn Lys Asp Leu Pro Ser Pro Ile
                805                 810                 815
Glu Arg Thr Ile Ser Lys Ile Lys Gly Leu Val Arg Ala Pro Gln Val
            820                 825                 830
Tyr Ile Leu Pro Pro Pro Ala Glu Gln Leu Ser Arg Lys Asp Val Ser
        835                 840                 845
Leu Thr Cys Leu Val Val Gly Phe Asn Pro Gly Asp Ile Ser Val Glu
    850                 855                 860
Trp Thr Ser Asn Gly His Thr Glu Glu Asn Tyr Lys Asp Thr Ala Pro
865                 870                 875                 880
Val Leu Asp Ser Asp Gly Ser Tyr Phe Ile Tyr Ser Lys Leu Asn Met
                885                 890                 895
Lys Thr Ser Lys Trp Glu Lys Thr Asp Ser Phe Ser Cys Asn Val Arg
            900                 905                 910
His Glu Gly Leu Lys Asn Tyr Tyr Leu Lys Lys Thr Ile Ser Arg Ser
        915                 920                 925
Pro Gly Lys
    930

<210> SEQ ID NO 45
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggcaccac tgtgcccaag cccatggctg ccactgctga tcccagcacc agcaccagga      60
ctgaccgtgc agctgctgct gagcctgctg ctgctggtgc ccgtgcaccc ccagcggctg     120
ccccggatgc aggaggacag ccccctgggc ggcggcagca cggcgagga cgaccccctg      180 ggcgaggagg acctgcccag cgaggaggac agccccgggg aggaggaccc cccggagaa      240 gaggacctgc ccggcgagga ggacctgcca ggagaggagg acctgccaga ggtgaagcca      300
aagagcgagg aggagggaag cctgaagctg gaggacctgc caaccgtgga ggcaccaggc      360
gacccacagg agccccagaa caacgcccac cgggacaagg agggcgacga ccagagccac      420
tggagatacg gaggcgaccc accatggcca cgggtgagcc cagcatgcgc aggacggttc      480
cagagccccg tggacatccg gccccagctg gccgccttct gccccgccct gcggcccctg      540
gagctgctgg gcttccagct gccccccctg cccgagctgc ggctgcggaa caacggccac      600
agcgtgcagc tgaccctgcc ccccggcctg gagatggccc tgggcccgg ccgggagtac      660 cgggccctgc agctgcacct gcactgggc ccgccggcc ggcccggcag cgagcacacc      720
gtggagggac acaggttccc agcagagatc cacgtggtgc acctgagcac cgcattcgca      780
agggtggacg aggcactggg aaggccagga ggactggcag tgctggcagc cttcctggag      840
gagggaccag aggagaacag cgcatacgag cagctgctga gccggctgga ggagatcgca      900
gaggagggaa gcgagaccca ggtgccaggc ctggacatca gcgcactgct gccaagcgac      960
ttcagccggt acttccagta cgagggcagc ctgaccaccc ccccctgcgc ccagggcgtg     1020
```

```
atctggaccg tgttcaacca gaccgtgatg ctgagcgcaa agcagctgca caccctgagc    1080
gacaccctgt ggggaccagg cgacagccgg ctgcagctga acttcagggc aacccagccc    1140
ctgaacggaa gagtgatcga ggcaagcttc ccagcaggag tggacagcag cccaagggca    1200
gcagagccag tgcagctgaa cagctgcctg gcagcaggcg acatcctggc actggtgttc    1260
ggactgctgt tcgcagtgac cagcgtggcc ttcctggtgc agatgcggcg gcagcaccgg    1320
cggggcacca agggcggcgt gagctaccgg cccgccgagg tggccgagac cggcgcctga    1380
```

<210> SEQ ID NO 46
<211> LENGTH: 459
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Ala Pro Leu Cys Pro Ser Pro Trp Leu Pro Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
        35                  40                  45

Leu Gly Gly Gly Ser Ser Gly Glu Asp Asp Pro Leu Gly Glu Glu Asp
50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Glu Gly Ser Leu Lys Leu Glu Asp
            100                 105                 110

Leu Pro Thr Val Glu Ala Pro Gly Asp Pro Gln Glu Pro Gln Asn Asn
        115                 120                 125

Ala His Arg Asp Lys Glu Gly Asp Asp Gln Ser His Trp Arg Tyr Gly
    130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
        195                 200                 205

Gly Leu Glu Met Ala Leu Gly Pro Gly Arg Glu Tyr Arg Ala Leu Gln
    210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
    290                 295                 300
```

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
            325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
            405                 410                 415

Ala Leu Val Phe Gly Leu Leu Phe Ala Val Thr Ser Val Ala Phe Leu
        420                 425                 430

Val Gln Met Arg Arg Gln His Arg Arg Gly Thr Lys Gly Gly Val Ser
    435                 440                 445

Tyr Arg Pro Ala Glu Val Ala Glu Thr Gly Ala
    450                 455

<210> SEQ ID NO 47
<211> LENGTH: 1203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgggctgga gctgcatcat cctgttcctg gtggcaaccg caaccggagt gcacagccag      60
aggctgccac ggatgcagga ggacagcccc ctgggcggcg gcagcagcgg cgaggacgac     120
ccctgggcg aggaggacct gcccagcgag gaggacagcc aagggagga ggaccacca      180
ggagaggagg acctgcctgg cgaggaggac ctgcctgggg aggaggacct gccagaggtg     240
aagccaaaga gcgaagagga gggaagcctg aagctggagg acctgccaac cgtggaggca     300
ccaggcgacc acaggagcc ccagaacaac gcccaccggg acaaggaggg cgacgaccag      360
agccactgga gatacggagg cgacccacca tggccacggg tgagcccagc atgcgcagga     420
cggttccaga gccccgtgga catccggccc cagctggccg ccttctgccc cgccctgcgg     480
cccctggagc tgctgggctt ccagctgccc cccctgcccg agctgcggct gcggaacaac     540
ggccacagcg tgcagctgac cctgccccc ggcctggaga tggccctggg ccccggccgg     600
gagtaccggg ccctgcagct gcacctgcac tggggcgccg ccggccggcc cggcagcgag     660
cacaccgtgg aggacacag gttcccagca gagatccacg tggtgcacct gagcaccgca     720
ttcgcaaggg tggacgaggc actgggaagg ccaggaggac tggcagtgct ggcagccttc     780
ctggaggagg gaccagagga gaacagcgca tacgagcagc tgctgagccg gctggaggag     840
atcgcagagg agggaagcga gacccaggtg ccaggcctgg acatcagcgc actgctgcca     900
agcgacttca gccggtactt ccagtacgag ggcagcctga ccacccccc ctgcgcccag     960
ggcgtgatct ggaccgtgtt caaccagacc gtgatgctga gcgcaaagca gctgcacacc    1020
ctgagcgaca ccctgtgggg accaggcgac agccggctgc agctgaactt cagggcaacc    1080
cagccccga cggaagagt gatcgaggca agcttcccag caggagtgga cagcagccca    1140
```

```
agggcagcag agccagtgca gctgaacagc tgcctggccg gccaccacca ccaccaccac    1200
tga                                                                  1203
```

<210> SEQ ID NO 48
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Met Gly Trp Ser Cys Ile Ile Leu Phe Leu Val Ala Thr Ala Thr Gly
1               5                   10                  15

Val His Ser Gln Arg Leu Pro Arg Met Gln Glu Asp Ser Pro Leu Gly
                20                  25                  30

Gly Gly Ser Ser Gly Glu Asp Asp Pro Leu Gly Glu Glu Asp Leu Pro
            35                  40                  45

Ser Glu Glu Asp Ser Pro Arg Glu Glu Asp Pro Pro Gly Glu Glu Asp
    50                  55                  60

Leu Pro Gly Glu Glu Asp Leu Pro Gly Glu Glu Asp Leu Pro Glu Val
65                  70                  75                  80

Lys Pro Lys Ser Glu Glu Glu Gly Ser Leu Lys Leu Glu Asp Leu Pro
                85                  90                  95

Thr Val Glu Ala Pro Gly Asp Pro Gln Glu Pro Gln Asn Asn Ala His
                100                 105                 110

Arg Asp Lys Glu Gly Asp Asp Gln Ser His Trp Arg Tyr Gly Gly Asp
            115                 120                 125

Pro Pro Trp Pro Arg Val Ser Pro Ala Cys Ala Gly Arg Phe Gln Ser
130                 135                 140

Pro Val Asp Ile Arg Pro Gln Leu Ala Ala Phe Cys Pro Ala Leu Arg
145                 150                 155                 160

Pro Leu Glu Leu Leu Gly Phe Gln Leu Pro Pro Leu Pro Glu Leu Arg
                165                 170                 175

Leu Arg Asn Asn Gly His Ser Val Gln Leu Thr Leu Pro Pro Gly Leu
            180                 185                 190

Glu Met Ala Leu Gly Pro Gly Arg Glu Tyr Arg Ala Leu Gln Leu His
        195                 200                 205

Leu His Trp Gly Ala Ala Gly Arg Pro Gly Ser Glu His Thr Val Glu
    210                 215                 220

Gly His Arg Phe Pro Ala Glu Ile His Val Val His Leu Ser Thr Ala
225                 230                 235                 240

Phe Ala Arg Val Asp Glu Ala Leu Gly Arg Pro Gly Gly Leu Ala Val
                245                 250                 255

Leu Ala Ala Phe Leu Glu Glu Gly Pro Glu Glu Asn Ser Ala Tyr Glu
            260                 265                 270

Gln Leu Leu Ser Arg Leu Glu Glu Ile Ala Glu Glu Gly Ser Glu Thr
        275                 280                 285

Gln Val Pro Gly Leu Asp Ile Ser Ala Leu Leu Pro Ser Asp Phe Ser
    290                 295                 300

Arg Tyr Phe Gln Tyr Glu Gly Ser Leu Thr Thr Pro Pro Cys Ala Gln
305                 310                 315                 320

Gly Val Ile Trp Thr Val Phe Asn Gln Thr Val Met Leu Ser Ala Lys
                325                 330                 335
```

```
Gln Leu His Thr Leu Ser Asp Thr Leu Trp Gly Pro Gly Asp Ser Arg
            340                 345                 350

Leu Gln Leu Asn Phe Arg Ala Thr Gln Pro Leu Asn Gly Arg Val Ile
        355                 360                 365

Glu Ala Ser Phe Pro Ala Gly Val Asp Ser Ser Pro Arg Ala Ala Glu
    370                 375                 380

Pro Val Gln Leu Asn Ser Cys Leu Ala Gly His His His His His
385                 390                 395                 400
```

<210> SEQ ID NO 49
<211> LENGTH: 1041
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
atgggatgga gctgtatcat cctcttcttg gtagcaacag ctacaggtgt acacagcgaa    60
gtggagaaga cagcctgtcc ttcaggcaag aaggcccgcg agatagacga gagcctcatc   120
ttctacaaga agtgggagct ggaagcctgc gtggatgcgg ccctgctggc cacccagatg   180
gaccgcgtga acgccatccc cttcacctac gagcagctgg acgtcctaaa gcataaactg   240
gatgagctct acccacaagg ttaccccgag tctgtgatcc agcacctggg ctacctcttc   300
ctcaagatga gccctgagga cattcgcaag tggaatgtga cgtccctgga gaccctgaag   360
gctttgcttg aagtcaacaa agggcacgaa atgagtcctc aggtggccac cctgatcgac   420
cgctttgtga agggaagggg ccagctagac aaagacaccc tagacaccct gaccgccttc   480
taccctgggt acctgtgctc cctcagcccc gaggagctga ctccgtgcc cccagcagc   540
atctgggcgg tcaggcccca ggacctggac acgtgtgacc caaggcagct ggacgtcctc   600
tatcccaagg cccgccttgc tttccagaac atgaacgggt ccgaatactt cgtgaagatc   660
cagtccttcc tgggtggggc ccccacggag gatttgaagg cgctcagtca gcagaatgtg   720
agcatggact tggccacgtt catgaagctg cggacggatg cggtgctgcc gttgactgtg   780
gctgaggtgc agaaacttct gggacccccac gtggagggcc tgaaggcgga ggagcggcac   840
cgcccggtgc gggactggat cctacggcag cggcaggacg acctggacac gctgggggctg   900
gggctacagg gcggcatccc caacggctac ctggtcctag acctcagcat gcaagaggcc   960
ctctcgggga cgccctgcct cctaggacct ggacctgttc tcaccgtcct ggcactgctc  1020
ctagcctcca ccctggcctg a                                            1041
```

<210> SEQ ID NO 50
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Met Gly Trp Ser Cys Ile Ile Leu Phe Leu Val Ala Thr Ala Thr Gly
1               5                   10                  15

Val His Ser Glu Val Glu Lys Thr Ala Cys Pro Ser Gly Lys Lys Ala
                20                  25                  30

Arg Glu Ile Asp Glu Ser Leu Ile Phe Tyr Lys Lys Trp Glu Leu Glu
            35                  40                  45
```

```
Ala Cys Val Asp Ala Ala Leu Leu Ala Thr Gln Met Asp Arg Val Asn
 50                  55                  60

Ala Ile Pro Phe Thr Tyr Glu Gln Leu Asp Val Leu Lys His Lys Leu
 65                  70                  75                  80

Asp Glu Leu Tyr Pro Gln Gly Tyr Pro Glu Ser Val Ile Gln His Leu
                 85                  90                  95

Gly Tyr Leu Phe Leu Lys Met Ser Pro Glu Asp Ile Arg Lys Trp Asn
            100                 105                 110

Val Thr Ser Leu Glu Thr Leu Lys Ala Leu Leu Glu Val Asn Lys Gly
        115                 120                 125

His Glu Met Ser Pro Gln Val Ala Thr Leu Ile Asp Arg Phe Val Lys
130                 135                 140

Gly Arg Gly Gln Leu Asp Lys Asp Thr Leu Asp Thr Leu Thr Ala Phe
145                 150                 155                 160

Tyr Pro Gly Tyr Leu Cys Ser Leu Ser Pro Glu Leu Ser Ser Val
                165                 170                 175

Pro Pro Ser Ser Ile Trp Ala Val Arg Pro Gln Asp Leu Asp Thr Cys
            180                 185                 190

Asp Pro Arg Gln Leu Asp Val Leu Tyr Pro Lys Ala Arg Leu Ala Phe
            195                 200                 205

Gln Asn Met Asn Gly Ser Glu Tyr Phe Val Lys Ile Gln Ser Phe Leu
        210                 215                 220

Gly Gly Ala Pro Thr Glu Asp Leu Lys Ala Leu Ser Gln Gln Asn Val
225                 230                 235                 240

Ser Met Asp Leu Ala Thr Phe Met Lys Leu Arg Thr Asp Ala Val Leu
                245                 250                 255

Pro Leu Thr Val Ala Glu Val Gln Lys Leu Leu Gly Pro His Val Glu
            260                 265                 270

Gly Leu Lys Ala Glu Glu Arg His Arg Pro Val Arg Asp Trp Ile Leu
        275                 280                 285

Arg Gln Arg Gln Asp Asp Leu Asp Thr Leu Gly Leu Gly Leu Gln Gly
290                 295                 300

Gly Ile Pro Asn Gly Tyr Leu Val Leu Asp Leu Ser Met Gln Glu Ala
305                 310                 315                 320

Leu Ser Gly Thr Pro Cys Leu Leu Gly Pro Gly Pro Val Leu Thr Val
                325                 330                 335

Leu Ala Leu Leu Leu Ala Ser Thr Leu Ala
            340                 345

<210> SEQ ID NO 51
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
atgggctggt cctgcatcat cctgtttctg gtggccaccg ccaccggcgt gcacagccag    60
tcggtgaagg agtccggggg tcgcctggtc acgcctggga cccccctgac actcacctgc   120
acagtctctg gattctccct caatagctat gcgatgatct gggtccgcca ggctccaggg   180
gaggggctgg aatacatcgg attcattact actggtggta ccacatacta cgcgagctgg   240
gcaaaaggcc gattcaccat ctccagaacc tcgaccacgg tggatctgaa gctcacccgt   300
ccgacaaccg aggacacggc cacctatttc tgtgccagag atcgggttaa aagctacgat   360
```

```
gactatggtg atttagatgc tttcgagccc tggggcccag gcaccctggt caccatctcc    420
tcagcatcca ccaagggccc atcggtcttc cccctggcac cctcctccaa gagcacctct    480
gggggcacag cggccctggg ctgcctggtc aaggactact tccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc   1020
aaggagtaca agtgcaaggt ctccaacaaa gccctcccag cccccatcga gaaaaccatc   1080
tccaaagcca agggcagccc cgagaaccag gtgtacaccc tgccccca atcccgggat   1140 gagctgacca gaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttctta tattcaaagc tcaccgtgga caagagcagg   1320
tggcagcagg ggaacgtctt ctcatgctcc gtgatgcatg aggctctgca caaccactac   1380
acgcagaaga gcctctccct gtctcccggg aaatga                              1416
```

<210> SEQ ID NO 52
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Gly Trp Ser Cys Ile Ile Leu Phe Leu Val Ala Thr Ala Thr Gly
1               5                   10                  15

Val His Ser Gln Ser Val Lys Glu Ser Gly Gly Arg Leu Val Thr Pro
            20                  25                  30

Gly Thr Pro Leu Thr Leu Thr Cys Thr Val Ser Gly Phe Ser Leu Asn
        35                  40                  45

Ser Tyr Ala Met Ile Trp Val Arg Gln Ala Pro Gly Glu Gly Leu Glu
    50                  55                  60

Tyr Ile Gly Phe Ile Thr Thr Gly Gly Thr Thr Tyr Ala Ser Trp
65                  70                  75                  80

Ala Lys Gly Arg Phe Thr Ile Ser Arg Thr Ser Thr Val Asp Leu
                85                  90                  95

Lys Leu Thr Arg Pro Thr Thr Glu Asp Thr Ala Thr Tyr Phe Cys Ala
            100                 105                 110

Arg Asp Arg Val Lys Ser Tyr Asp Asp Tyr Gly Asp Leu Asp Ala Phe
        115                 120                 125

Glu Pro Trp Gly Pro Gly Thr Leu Val Thr Ile Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu

```
            165                 170                 175
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly Lys
465                 470

<210> SEQ ID NO 53
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgggttgga gttgcatcat tctgttcctg gtggccacag ctactggcgt gcactcacag      60
gtgcagctgg tggagtccgg aggaggactg gtgcagccag gtggctctct gcgactgtct     120
tgtagtgctt caggcttttc cctgaacagc tacgctatga tctgggtcag gcaggcacct     180
ggcaagggcc tggaatatat cggattcatt accacaggag ggactaccta ctatgccgac     240
tccgtgaagg ggagattcac tatctctcgc gataacagta agaataccct gtacctgcag     300
```

```
atgaatagcc tgagagcaga ggacacagcc gtgtactatt gcgccaggga tcgggtgaaa    360
tcttacgacg attatggaga cctggatgct ttcgaaccat ggggacaggg gaccctggtg    420
acagtgtcca gcgcatccac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660
ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc ccccaaaac ccaaggacac cctcatgatc     840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcttat attcaaagct caccgtggac   1320
aagagcaggt ggcagcaggg gaacgtcttc tcatgctccg tgatgcatga ggctctgcac   1380
aaccactaca cgcagaagag cctctccctg tctcccggga atga                    1425
```

<210> SEQ ID NO 54
<211> LENGTH: 474
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 54

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Leu Val Gln
            20                  25                  30

Pro Gly Gly Ser Leu Arg Leu Ser Cys Ser Ala Ser Gly Phe Ser Leu
        35                  40                  45

Asn Ser Tyr Ala Met Ile Trp Val Arg Gln Ala Pro Gly Lys Gly Leu
    50                  55                  60

Glu Tyr Ile Gly Phe Ile Thr Thr Gly Gly Thr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Arg Val Lys Ser Tyr Asp Tyr Gly Asp Leu
        115                 120                 125

Asp Ala Phe Glu Pro Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 55
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgggctggt cctgcatcat cctgtttctg gtggccaccg ccaccggcgt gcactcccag      60
tcggtggagg agtccggggg agacctggtc aagcctgagg gatccctgac actcacctgc     120
acagcctctg gattctcctt cagtagcagc tactggggat gctgggtccg ccaggctcca     180
gggaaggggc tgagtggat cgcatgcatt tatggtggta gtagtggtac cacttattac     240

-continued

```
ccgaactggg cgaaaggccg attctccatc tccaaaacct cgtcgaccac ggtgactctg    300
caaatggcca gtctgacagc cgcggacacg gccacctatt tctgtgcgag agtgactaat    360
ggtggtgatt gggatttaa attgtggggc caggcaccc tggtcaccat ctcctcagca      420
tccaccaagg gcccatcggt cttccccctg gcacctcct ccaagagcac ctctgggggc     480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840
gtcacatgcg tggtggtgga cgtgagccac gaagaccctg aggtcaagtt caactggtac   900
gtggacggcg tggaggtgca taatgccaag acaaagccgc gggaggagca gtacaacagc   960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cttatattca aagctcaccg tggacaagag caggtggcag  1320
caggggaacg tcttctcatg ctccgtgatg catgaggctc tgcacaacca ctacacgcag  1380
aagagcctct ccctgtctcc cgggaaatga                                    1410
```

<210> SEQ ID NO 56
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Met Gly Trp Ser Cys Ile Ile Leu Phe Leu Val Ala Thr Ala Thr Gly
1               5                   10                  15

Val His Ser Gln Ser Val Glu Glu Ser Gly Gly Asp Leu Val Lys Pro
            20                  25                  30

Glu Gly Ser Leu Thr Leu Thr Cys Thr Ala Ser Gly Phe Ser Phe Ser
        35                  40                  45

Ser Ser Tyr Trp Gly Cys Trp Val Arg Gln Ala Pro Gly Lys Gly Pro
    50                  55                  60

Glu Trp Ile Ala Cys Ile Tyr Gly Gly Ser Gly Thr Thr Tyr Tyr
65                  70                  75                  80

Pro Asn Trp Ala Lys Gly Arg Phe Ser Ile Ser Lys Thr Ser Ser Thr
                85                  90                  95

Thr Val Thr Leu Gln Met Ala Ser Leu Thr Ala Ala Asp Thr Ala Thr
            100                 105                 110

Tyr Phe Cys Ala Arg Val Thr Asn Gly Gly Asp Trp Asp Phe Lys Leu
        115                 120                 125

Trp Gly Pro Gly Thr Leu Val Thr Ile Ser Ser Ala Ser Thr Lys Gly
    130                 135                 140
```

```
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 57
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgggctggt cctgcatcat cctgtttctg gtggccaccg ccaccggcgt gcacagccag      60
tcggtggagg agtccagggg tcgcctggtc acgcctggga cacccctgac actcacctgc     120
acagtctctg gaatcgacct cagtaattat gcaatgacct gggtccgcca ggctccaggg     180
```

```
aaggggctgg aatggatcgg aatcattagt agtaatgata agacatggta cgcgagctgg      240
gtgaaaggcc ggttcaccat ctcaaaaacc tcgtcgacca cggtggatct gaaaatgacc      300
agtctgacaa ccgaggacac ggccacctat ttctgtgcca gagctgctat gcctggtggt      360
ttaaagaatg ctttcgatcc ctggggccca ggcaccctgg tcaccgtctc ttcagcatcc      420
accaagggcc catcggtctt cccctggca ccctcctcca agagcacctc tgggggcaca       480
gcggccctgg gctgcctggt caaggactac ttccccgaac cggtgacggt gtcgtggaac      540
tcaggcgccc tgaccagcgg cgtgcacacc ttcccggctg tcctacagtc ctcaggactc      600
tactccctca gcagcgtggt gaccgtgccc tccagcagct gggcacccca gacctacatc      660
tgcaacgtga atcacaagcc cagcaacacc aaggtggaca agaaagttga gcccaaatct      720
tgtgacaaaa ctcacacatg cccaccgtgc ccagcacctg aactcctggg gggaccgtca      780
gtcttcctct tccccccaaa acccaaggac accctcatga tctcccggac ccctgaggtc      840
acatgcgtgg tggtggacgt gagccacgaa gaccctgagg tcaagttcaa ctggtacgtg      900
gacggcgtgg aggtgcataa tgccaagaca agccgcggg aggagcagta caacagcacg       960
taccgtgtgg tcagcgtcct caccgtcctg caccaggact ggctgaatgg caaggagtac     1020
aagtgcaagg tctccaacaa agccctccca gcccccatcg agaaaaccat ctccaaagcc     1080
aaagggcagc cccgagaacc acaggtgtac accctgcccc catcccggga tgagctgacc     1140
aagaaccagg tcagcctgac ctgcctggtc aaaggcttct atcccagcga catcgccgtg     1200
gagtgggaga gcaatgggca gccggagaac aactacaaga ccacgcctcc cgtgctggac     1260
tccgacggct ccttcttctt atattcaaag ctcaccgtgg acaagagcag gtggcagcag     1320
gggaacgtct tctcatgctc cgtgatgcat gaggctctgc acaaccacta cacgcagaag     1380
agcctctccc tgtctcccgg gaaatga                                         1407
```

<210> SEQ ID NO 58
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Gly Trp Ser Cys Ile Ile Leu Phe Leu Val Ala Thr Ala Thr Gly
1               5                   10                  15

Val His Ser Gln Ser Val Glu Glu Ser Arg Gly Arg Leu Val Thr Pro
            20                  25                  30

Gly Thr Pro Leu Thr Leu Thr Cys Thr Val Ser Gly Ile Asp Leu Ser
        35                  40                  45

Asn Tyr Ala Met Thr Trp Val Arg Gln Ala Pro Gly Lys Gly Leu Glu
    50                  55                  60

Trp Ile Gly Ile Ile Ser Ser Asn Asp Lys Thr Trp Tyr Ala Ser Trp
65                  70                  75                  80

Val Lys Gly Arg Phe Thr Ile Ser Lys Thr Ser Ser Thr Val Asp
                85                  90                  95

Leu Lys Met Thr Ser Leu Thr Thr Glu Asp Thr Ala Thr Tyr Phe Cys
            100                 105                 110

Ala Arg Ala Ala Met Pro Gly Gly Leu Lys Asn Ala Phe Asp Pro Trp
        115                 120                 125

Gly Pro Gly Thr Leu Val Thr Val Ser Ser Ala Ser Thr Lys Gly Pro
```

```
              130                 135                 140
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 59
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgggctggt cctgcatcat cctgtttctg gtggccaccg ccaccggcgt gcacagcgag      60
gtccagctgc tggaatcagg gggaggactg gtgcagcccg agggtcact gcgactgtct     120
```

```
tgtgccgctt caggcattga tctgtctaac tacgctatga cttgggtgag gcaggcaccc      180
ggcaagggac tggagtgggt cggaatcatt agctccaatg acaagacctg gtacgccgat      240
tcagtgaaag gccggttcac catctctaga caacagtaag aatacactg tatctgcag       300 atgaacagcc tgcgggcaga agatacagcc gtctactatt gcgctaaagc cgctatgcct      360
ggcggactga agaacgcatt tgatccttgg ggacagggaa ctctggtcac cgtctcatct      420
gcatccacca agggcccatc ggtcttcccc ctggcaccct cctccaagag cacctctggg      480
ggcacagcgg ccctgggctg cctggtcaag gactacttcc ccgaaccggt gacggtgtcg      540
tggaactcag gcgccctgac cagcggcgtg cacaccttcc cggctgtcct acagtcctca      600
ggactctact ccctcagcag cgtggtgacc gtgccctcca gcagcttggg cacccagacc      660
tacatctgca acgtgaatca caagcccagc aacaccaagg tggacaagaa agttgagccc      720
aaatcttgtg acaaaactca cacatgccca ccgtgcccag cacctgaact cctggggga       780 ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcgggagga gcagtacaac      960
agcacgtacc gtgtggtcag cgtcctcacc gtcctgcacc aggactggct gaatggcaag      1020
gagtacaagt gcaaggtctc caacaaagcc ctcccagccc ccatcgagaa aaccatctcc      1080
aaagccaaag ggcagccccg agaaccacag gtgtacaccc tgcccccatc ccgggatgag      1140
ctgaccaaga accaggtcag cctgacctgc ctggtcaaag gcttctatcc cagcgacatc      1200
gccgtggagt gggagagcaa tgggcagccg gagaacaact acaagaccac gcctcccgtg      1260
ctggactccg acggctcctt cttcttatat cagctca ccgtggacaa gagcaggtgg        1320
cagcagggga acgtcttctc atgctccgtg atgcatgagg ctctgcacaa ccactacacg      1380
cagaagagcc tctccctgtc tccgggaaa tga                                   1413
```

<210> SEQ ID NO 60
<211> LENGTH: 470
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Ile Asp Leu
        35                  40                  45

Ser Asn Tyr Ala Met Thr Trp Val Arg Gln Ala Pro Gly Lys Gly Leu
    50                  55                  60

Glu Trp Val Gly Ile Ile Ser Ser Asn Asp Lys Thr Trp Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Lys Ala Ala Met Pro Gly Gly Leu Lys Asn Ala Phe Asp
        115                 120                 125
```

Pro Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 61
<211> LENGTH: 1419
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgggctggt cctgcatcat cctgtttctg gtggccaccg ccaccggcgt gcactcccag    60

```
tcggtggagg agtccggggg tcgcctggtc acgcctggga cacccctgac actcacctgc    120
accgtctctg gaatctccct cagtagcgat gcaataagct gggtccgcca ggctccaggg    180
aaggggctcg aatacatcgg aatcattaat ggtggtggta acacatacta cgcgagctgg    240
gcgaaaggcc gattcaccat ctccaaaacc tcgaccacgg tggatctgaa aatcaccagt    300
ccgacaaccg aggacacggc cacctatttc tgtgccagag cattcaaca tggtggtggt     360 aatagtgatt attattatta cggcatggac ctctggggcc caggcaccct ggtcactgtc    420
tcttcagcat ccaccaaggg cccatcggtc ttcccctgg cacctcctc caagagcacc      480 tctgggggca gcggccct gggctgcctg gtcaaggact acttccccga accggtgacg       540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat    1020
ggcaaggagt acaagtgcaa ggtctccaac aaagccctcc cagccccat cgagaaaacc     1080 atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
cccgtgctgg actccgacgg ctccttcttc ttatattcaa agctcaccgt ggacaagagc    1320
aggtggcagc aggggaacgt cttctcatgc tccgtgatgc atgaggctct gcacaaccac    1380
tacacgcaga agagcctctc cctgtctccc gggaaatga                          1419
```

<210> SEQ ID NO 62
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Gly Trp Ser Cys Ile Ile Leu Phe Leu Val Ala Thr Ala Thr Gly
1               5                   10                  15

Val His Ser Gln Ser Val Glu Glu Ser Gly Gly Arg Leu Val Thr Pro
            20                  25                  30

Gly Thr Pro Leu Thr Leu Thr Cys Thr Val Ser Gly Ile Ser Leu Ser
        35                  40                  45

Ser Asp Ala Ile Ser Trp Val Arg Gln Ala Pro Gly Lys Gly Leu Glu
    50                  55                  60

Tyr Ile Gly Ile Ile Asn Gly Gly Asn Thr Tyr Tyr Ala Ser Trp
65                  70                  75                  80

Ala Lys Gly Arg Phe Thr Ile Ser Lys Thr Ser Thr Val Asp Leu
                85                  90                  95

Lys Ile Thr Ser Pro Thr Thr Glu Asp Thr Ala Thr Tyr Phe Cys Ala
            100                 105                 110

Arg Gly Ile Gln His Gly Gly Asn Ser Asp Tyr Tyr Tyr
    115                 120                 125
Met Asp Leu Trp Gly Pro Gly Thr Leu Val Thr Val Ser Ser Ala Ser
130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Gln Thr Tyr Ile
    210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Asp Glu Leu Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 63
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atgggctggt cctgcatcat cctgtttctg gtggccaccg ccaccggcgt gcacagcgaa      60
gtccaactgg tggaaagcgg gggaggactg gtgcagccgg gcggatccct ccggctgtca     120
tgtgctgcat cgggaatttc cctctcctcc gacgcgatta gctgggtcag acaggccccc     180
ggaaaggggc tggagtacat cggtatcatc aacggcggcg aaacaccta ctacgcctcc      240
tgggccaagg gccgcttcac catctcgcgg cataattcca agaacactct gtacttgcaa     300
atgaactccc tgagggccga ggacaccgcc gtgtactact gcgcgcgcgg catccagcac     360
ggtggtggaa acagcgacta ctactactat gggatggatc tgtggggcca gggaactctt     420
gtgaccgtgt cgtcagcatc caccaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
gaactcctgg ggggaccgtc agtcttcctc ttccccccaa acccaaggac acccctcatg     840
atctcccgga cccctgaggt cacatgcgtg gtggtggacg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggagta caagtgcaag gtctccaaca aagccctccc agcccccatc    1080
gagaaaacca tctccaaagc caaagggcag ccccgagaac acaggtgta caccctgccc     1140
ccatcccggg atgagctgac caagaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttct tatattcaa agctcaccgtg    1320
gacaagagca ggtggcagca ggggaacgtc ttctcatgct ccgtgatgca tgaggctctg    1380
cacaaccact acacgcagaa gagcctctcc ctgtctcccg ggaaatga                 1428
```

<210> SEQ ID NO 64
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Ile Ser Leu
            35                  40                  45

Ser Ser Asp Ala Ile Ser Trp Val Arg Gln Ala Pro Gly Lys Gly Leu
        50                  55                  60

Glu Tyr Ile Gly Ile Ile Asn Gly Gly Gly Thr Tyr Tyr Ala Ser
65                  70                  75                  80

Trp Ala Lys Gly Arg Phe Thr Ile Ser Arg His Asn Ser Lys Asn Thr
                85                  90                  95

Leu Tyr Leu Gln Met Asn Ser Leu Arg Ala Glu Asp Thr Ala Val Tyr

```
            100                 105                 110
Tyr Cys Ala Arg Gly Ile Gln His Gly Gly Gly Asn Ser Asp Tyr Tyr
            115                 120                 125
Tyr Tyr Gly Met Asp Leu Trp Gly Gln Gly Thr Leu Val Thr Val Ser
            130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                    165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
            195                 200                 205
Ser Leu Ser Ser Val Val Thr Val Pro Ser Ser Ser Leu Gly Thr Gln
            210                 215                 220
Thr Tyr Ile Cys Asn Val Asn His Lys Pro Ser Asn Thr Lys Val Asp
225                 230                 235                 240
Lys Lys Val Glu Pro Lys Ser Cys Asp Lys Thr His Thr Cys Pro Pro
                    245                 250                 255
Cys Pro Ala Pro Glu Leu Leu Gly Gly Pro Ser Val Phe Leu Phe Pro
                    260                 265                 270
Pro Lys Pro Lys Asp Thr Leu Met Ile Ser Arg Thr Pro Glu Val Thr
            275                 280                 285
Cys Val Val Val Asp Val Ser His Glu Asp Pro Glu Val Lys Phe Asn
            290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                    325                 330                 335
Leu His Gln Asp Trp Leu Asn Gly Lys Glu Tyr Lys Cys Lys Val Ser
                    340                 345                 350
Asn Lys Ala Leu Pro Ala Pro Ile Glu Lys Thr Ile Ser Lys Ala Lys
            355                 360                 365
Gly Gln Pro Arg Glu Pro Gln Val Tyr Thr Leu Pro Pro Ser Arg Asp
            370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                    405                 410                 415
Asn Asn Tyr Lys Thr Thr Pro Pro Val Leu Asp Ser Asp Gly Ser Phe
                    420                 425                 430
Phe Leu Tyr Ser Lys Leu Thr Val Asp Lys Ser Arg Trp Gln Gln Gly
                    435                 440                 445
Asn Val Phe Ser Cys Ser Val Met His Glu Ala Leu His Asn His Tyr
            450                 455                 460
Thr Gln Lys Ser Leu Ser Leu Ser Pro Gly Lys
465                 470                 475
```

<210> SEQ ID NO 65
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
atgggctggt cctgcatcat cctgtttctg gtggccaccg ccaccggcgt gcactcccag      60
tcgctggagg agtccggggg tcgcctggtc acgcctggga caccctgac actcacctgc     120
acagcctctg gattctccct cagtaactat gcaatgacct gggtccgcca ggctccaggg    180
aaggggctag aatacatcgg aatcattagt actggcggta tcacatacta tatggactcg    240
gcaaaaggcc gattcaccat ctccagaacc tcgaccacgg tggatctgaa aatgaccagt    300
ctgacaaccg aggacacggc cacctatttc tgtggcagaa atgctggtgg tagttatatt    360
ttctattatt ttgacttgtg gggccaaggc accctggtca ctgtctcttc agcatccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagccc aaatcttgt     720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcttata ttcaaagctc accgtggaca agagcaggtg gcagcagggg   1320
aacgtcttct catgctccgt gatgcatgag gctctgcaca accactacac gcagaagagc   1380
ctctccctgt ctcccgggaa atga                                          1404
```

<210> SEQ ID NO 66
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Met Gly Trp Ser Cys Ile Ile Leu Phe Leu Val Ala Thr Ala Thr Gly
1               5                   10                  15

Val His Ser Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Ala Met Thr Trp Val Arg Gln Ala Pro Gly Lys Gly Leu Glu
    50                  55                  60

Tyr Ile Gly Ile Ile Ser Thr Gly Gly Ile Thr Tyr Tyr Met Asp Ser
65                  70                  75                  80

Ala Lys Gly Arg Phe Thr Ile Ser Arg Thr Ser Thr Thr Val Asp Leu
                85                  90                  95
```

```
Lys Met Thr Ser Leu Thr Thr Glu Asp Thr Ala Thr Tyr Phe Cys Gly
            100                 105                 110

Arg Asn Ala Gly Gly Ser Tyr Ile Phe Tyr Tyr Phe Asp Leu Trp Gly
            115                 120                 125

Gln Gly Thr Leu Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 67
<211> LENGTH: 1404
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 67

| | | | | | |
|---|---|---|---|---|---|
| atgggctggt | cctgcatcat | cctgtttctg | gtggccaccg | ccaccggcgt | gcactcccag | 60 |
| tcgttggagg | agtccggggg | tcgcctggtc | acgcctggga | cacccctgac | actcacctgc | 120 |
| acagcctctg | gattctccct | cagtaactat | gcaatgacct | gggtccgcca | ggctccaggg | 180 |
| aaggggctag | aatacatcgg | aatcattagt | actggcggta | tcacatacta | tatggactcg | 240 |
| gcaaaaggcc | gattcaccat | ctccagaacc | tcgaccacgg | tggatctgaa | aatgaccagt | 300 |
| ctgacaaccg | aggacacggc | cacctatttc | tgtggcagaa | atgctggtgg | tagttatatt | 360 |
| ttctattatt | tcgacttgtg | gggccaaggg | accctcgtca | ctgtctcttc | agcatccacc | 420 |
| aagggcccat | cggtcttccc | cctggcaccc | tcctccaaga | gcacctctgg | gggcacagcg | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | aagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaag | 1020 |
| tgcaaggtct | ccaacaaagc | cctcccagcc | cccatcgaga | aaaccatctc | caaagccaaa | 1080 |
| gggcagcccc | gagaaccaca | ggtgtacacc | ctgcccccat | cccgggatga | gctgaccaag | 1140 |
| aaccaggtca | gcctgacctg | cctggtcaaa | ggcttctatc | ccagcgacat | cgccgtggag | 1200 |
| tgggagagca | atgggcagcc | ggagaacaac | tacaagacca | cgcctcccgt | gctggactcc | 1260 |
| gacggctcct | tcttcttata | ttcaaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctcccgggaa | atga | | | | 1404 |

<210> SEQ ID NO 68
<211> LENGTH: 467
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

Met Gly Trp Ser Cys Ile Ile Leu Phe Leu Val Ala Thr Ala Thr Gly
1               5                   10                  15

Val His Ser Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Asn Tyr Ala Met Thr Trp Val Arg Gln Ala Pro Gly Lys Gly Leu Glu
    50                  55                  60

Tyr Ile Gly Ile Ile Ser Thr Gly Gly Ile Thr Tyr Tyr Met Asp Ser
65                  70                  75                  80

-continued

Ala Lys Gly Arg Phe Thr Ile Ser Arg Thr Ser Thr Thr Val Asp Leu
             85                  90                  95
Lys Met Thr Ser Leu Thr Thr Glu Asp Thr Ala Thr Tyr Phe Cys Gly
        100                 105                 110
Arg Asn Ala Gly Gly Ser Tyr Ile Phe Tyr Tyr Phe Asp Leu Trp Gly
            115                 120                 125
Gln Gly Thr Leu Val Thr Val Ser Ser Ala Ser Thr Lys Gly Pro Ser
130                 135                 140
Val Phe Pro Leu Ala Pro Ser Ser Lys Ser Thr Ser Gly Gly Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Gln Thr Tyr Ile Cys Asn Val Asn His
    210                 215                 220
Lys Pro Ser Asn Thr Lys Val Asp Lys Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 69
<211> LENGTH: 1389
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 69

```
atgggctggt cctgcatcat cctgtttctg gtggccaccg ccaccggcgt gcactcccag    60
tcgctggagg agtccggggg tcgcctggtc gcgcctggga cacccctgac actcacctgc   120
acagtctctg gattctccct cagtagttac cacatgagct gggtccgcca ggctccaggg   180
gagggggctgg aatggatcgg aggcattact gctatgagtc gcacatacta cgcgagctgg   240
gcgaaaggcc gattcaccat ctccaaaacc tcgaccacgg tccatctgaa aatcaccagt   300
ccgacaaccg aggacacggc cacctatttc tgtgccaggg aacctggttt tgttagtaac   360
atctggggcc caggcaccct ggtcaccgtc tccttagcat ccaccaaggg cccatcggtc   420
ttccccctgg caccctcctc aagagcacc tctgggggca gcggccct gggctgcctg    480
gtcaaggact acttccccga accggtgacg gtgtcgtgga actcaggcgc cctgaccagc   540
ggcgtgcaca ccttcccggc tgtcctacag tcctcaggac tctactccct cagcagcgtg   600
gtgaccgtgc cctccagcag cttgggcacc cagacctaca tctgcaacgt gaatcacaag   660
cccagcaaca ccaaggtgga caagaaagtt gagcccaaat cttgtgacaa aactcacaca   720
tgcccaccgt gcccagcacc tgaactcctg ggggaccgt cagtcttcct cttcccccca    780
aaacccaagg acaccctcat gatctcccgg acccctgagg tcacatgcgt ggtggtggac   840
gtgagccacg aagaccctga ggtcaagttc aactggtacg tggacggcgt ggaggtgcat   900
aatgccaaga caaagccgcg ggaggagcag tacaacagca cgtaccgtgt ggtcagcgtc   960
ctcaccgtcc tgcaccagga ctggctgaat ggcaaggagt acaagtgcaa ggtctccaac  1020
aaagccctcc cagccccat cgagaaaacc atctccaaag ccaaagggca gccccgagaa  1080
ccacaggtgt acaccctgcc cccatcccgg gatgagctga ccaagaacca ggtcagcctg  1140
acctgcctgg tcaaaggctt ctatcccagc gacatcgccg tggagtggga gagcaatggg  1200
cagccggaga caactacaa gaccacgcct cccgtgctgg actccgacgg ctccttcttc  1260
ttatattcaa agctcaccgt ggacaagagc aggtggcagc aggggaacgt cttctcatgc  1320
tccgtgatgc atgaggctct gcacaaccac tacacgcaga agagcctctc cctgtctccc  1380
gggaaatga                                                          1389
```

<210> SEQ ID NO 70
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Gly Trp Ser Cys Ile Ile Leu Phe Leu Val Ala Thr Ala Thr Gly
1               5                   10                  15

Val His Ser Gln Ser Leu Glu Glu Ser Gly Gly Arg Leu Val Ala Pro
            20                  25                  30

Gly Thr Pro Leu Thr Leu Thr Cys Thr Val Ser Gly Phe Ser Leu Ser
        35                  40                  45

Ser Tyr His Met Ser Trp Val Arg Gln Ala Pro Gly Glu Gly Leu Glu
    50                  55                  60

Trp Ile Gly Gly Ile Thr Ala Met Ser Arg Thr Tyr Tyr Ala Ser Trp
```

65                  70                  75                  80
Ala Lys Gly Arg Phe Thr Ile Ser Lys Thr Ser Thr Thr Val His Leu
                    85                  90                  95

Lys Ile Thr Ser Pro Thr Thr Glu Asp Thr Ala Thr Tyr Phe Cys Ala
                100                 105                 110

Arg Glu Pro Gly Phe Val Ser Asn Ile Trp Gly Pro Gly Thr Leu Val
                115                 120                 125

Thr Val Ser Leu Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
                210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
                290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
                370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
        450                 455                 460

<210> SEQ ID NO 71
<211> LENGTH: 1404
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71

```
atgggctggt cctgcatcat cctgtttctg gtggccaccg ccaccggcgt gcactcccag      60
tcggtggagg agtccggggg tcgcctggtc acgcctggga cacccctgac actcacctgc    120
acagtctctg gattctccct cagtagctat gcaatgggct gggtccgcca ggctccaggg    180
gagggctgg aatggatcgg aaccattagt actggtggta ttacatacta cgcgagctgg     240
gcgaaaggcc gattcaccat ctccaaaacc tcgaccacgg tggatctgaa aatcaccagt    300
ccgacaaccg aggacacggc cacctatttc tgtgccagag tgggtagtag tggttatctt    360
ttctacttct taacttgtg gggccaaggc accctcgtca ctgtctcctc agcatccacc     420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcttata ttcaaagctc accgtggaca agagcaggtg gcagcagggg   1320
aacgtcttct catgctccgt gatgcatgag gctctgcaca accactacac gcagaagagc   1380
ctctccctgt ctcccgggaa atga                                           1404
```

<210> SEQ ID NO 72
<211> LENGTH: 467
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

Met Gly Trp Ser Cys Ile Ile Leu Phe Leu Val Ala Thr Ala Thr Gly
1               5                   10                  15

Val His Ser Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Gly Trp Val Arg Gln Ala Pro Gly Glu Gly Leu Glu
    50                  55                  60

Trp Ile Gly Thr Ile Ser Thr Gly Gly Ile Thr Tyr Tyr Ala Ser Trp
65                  70                  75                  80

```
Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Val Gly Ser Ser Gly Tyr Leu Phe Tyr Phe Asn Leu Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 73
<211> LENGTH: 1419
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
atgggctggt cctgcatcat cctgtttctg gtggccaccg ccaccggcgt gcacagccag      60
tcggtgaagg agtccagggg tcgcctggtc acgcctggga cccccctgac actcacctgc    120
acagtctctg gattctcccct cagtaggtat acattgatct gggtccgcca ggctccaggg   180
aaggggctgg aatggatcgg aatcatagat agtagtagta gtgcatacta cgcgaggtgg    240
gcgaaaggcc gattcaccat ctccaaaacc tcgaccacgg tggatctgaa aatcaccagt    300
ccgacaaccg aggacacggc cacctatttc tgtgccagag acagagtcct aagctacgat    360
gactatggtg atttgcccga tggtttcgat ccctggggcc aggcaccct ggtcaccgtc     420
tcctcagcat ccaccaaggg cccatcggtc ttccccctgg cacctcctc caagagcacc     480
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
gggggaccgt cagtcttcct cttccccccca aaacccaagg acaccctcat gatctcccgg    840
acccctgagg tcacatgcgt ggtggtggac gtgagccacg aagaccctga ggtcaagttc     900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct     1260
cccgtgctgg actccgacgg ctccttcttc ttatattcaa agctcaccgt ggacaagagc    1320
aggtggcagc aggggaacgt cttctcatgc tccgtgatgc atgaggctct gcacaaccac    1380
tacacgcaga agagcctctc cctgtctccc gggaaatga                           1419
```

<210> SEQ ID NO 74
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Met Gly Trp Ser Cys Ile Ile Leu Phe Leu Val Ala Thr Ala Thr Gly
1               5                   10                  15

Val His Ser Gln Ser Val Lys Glu Ser Arg Gly Arg Leu Val Thr Pro
            20                  25                  30

Gly Thr Pro Leu Thr Leu Thr Cys Thr Val Ser Gly Phe Ser Leu Ser
        35                  40                  45

Arg Tyr Thr Leu Ile Trp Val Arg Gln Ala Pro Gly Lys Gly Leu Glu
    50                  55                  60
```

```
Trp Ile Gly Ile Ile Asp Ser Ser Ser Ala Tyr Tyr Ala Arg Trp
 65                  70                  75                  80

Ala Lys Gly Arg Phe Thr Ile Ser Lys Thr Ser Thr Thr Val Asp Leu
                 85                  90                  95

Lys Ile Thr Ser Pro Thr Thr Glu Asp Thr Ala Thr Tyr Phe Cys Ala
                100                 105                 110

Arg Asp Arg Val Leu Ser Tyr Asp Asp Tyr Gly Asp Leu Pro Asp Gly
            115                 120                 125

Phe Asp Pro Trp Gly Pro Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Lys
465                 470
```

<210> SEQ ID NO 75
<211> LENGTH: 1428
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
atgggctggt cctgcatcat cctgtttctg gtggccaccg ccaccggcgt gcacagcgaa      60
gtgcagctgg tcgaatctgg aggaggactg gtgcagcctg agggagcct gagactgagt     120
tgcgcagcaa gcgggtttag cctgtcccga tacaccctga tctgggtgag acaggccccc    180
ggcaagggac tggagtgggt ctctatcatt gacagctcct ctagtgccta ctatgctgat    240
agtgtgaagg gcaggttcac catttcacgc gacaacgcta aaatagcct gtatctgcag     300
atgaactccc tgcgggcaga agacacagcc gtgtactatt gcgcacggga tagagtcctg    360
agctacgacg attatgggga cctgcctgac ggctttgatc cttggggaca gggaactctg    420
gtgacagtga gcagcgcatc caccaagggc ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa acccaaggga cacctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac acaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttct tatattcaaa gctcaccgtg   1320
gacaagagca ggtggcagca ggggaacgtc ttctcatgct ccgtgatgca tgaggctctg   1380
cacaaccact acacgcagaa gagcctctcc ctgtctcccg ggaaatga              1428
```

<210> SEQ ID NO 76
<211> LENGTH: 475
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Ser Arg Tyr Thr Leu Ile Trp Val Arg Gln Ala Pro Gly Lys Gly Leu
```

```
           50                  55                  60
Glu Trp Val Ser Ile Ile Asp Ser Ser Ser Ala Tyr Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
                100                 105                 110

Tyr Cys Ala Arg Asp Arg Val Leu Ser Tyr Asp Asp Tyr Gly Asp Leu
                115                 120                 125

Pro Asp Gly Phe Asp Pro Trp Gly Gln Gly Thr Leu Val Thr Val Ser
            130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475
```

<210> SEQ ID NO 77
<211> LENGTH: 714
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 77

```
atgggctggt cctgcatcat cctgtttctg gtggccaccg ccaccggcgt gcacagcgag    60
ctcgtgatga cccagactcc atcctccgtg tctgcagctg tgggaggcac agtcaccatc   120
aattgccagg ccagtcagag cattagtagc tacttagcct ggtatcagca gaaaccaggg   180
cagcctccca agctcctgat ctattatgca tccactctgg cgtctggggt cccatcgcgg   240
ttcaaaggca gtggctctgg gacagagttc actctcacca tcaccggcgt gcagtgtgac   300
gatgctgcca cttactactg tctaggtgtt tatggttata gttttgatga tggtattgct   360
ttcggcggag ggaccgagct ggagatcaaa cgaactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttga         714
```

<210> SEQ ID NO 78
<211> LENGTH: 237
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 78

```
Met Gly Trp Ser Cys Ile Ile Leu Phe Leu Val Ala Thr Ala Thr Gly
1               5                   10                  15

Val His Ser Glu Leu Val Met Thr Gln Thr Pro Ser Ser Val Ser Ala
            20                  25                  30

Ala Val Gly Gly Thr Val Thr Ile Asn Cys Gln Ala Ser Gln Ser Ile
        35                  40                  45

Ser Ser Tyr Leu Ala Trp Tyr Gln Gln Lys Pro Gly Gln Pro Pro Lys
    50                  55                  60

Leu Leu Ile Tyr Tyr Ala Ser Thr Leu Ala Ser Gly Val Pro Ser Arg
65                  70                  75                  80

Phe Lys Gly Ser Gly Ser Gly Thr Glu Phe Thr Leu Thr Ile Thr Gly
                85                  90                  95

Val Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Gly Thr Glu Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175
```

```
Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 79
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
atggggtggt cttgcatcat tctgttcctg gtggcaaccg ccacaggtgt gcactccgac      60
atccagatga ctcagagtcc atcaaccctg tccgctagcg tgggagatag agtgactatc     120
acctgtcagg cctctcagag tatttccagc tacctggctt ggtatcagca gaagccaggc     180
aaagcaccca agctgctgat ctactatgct agtacactgg catcaggagt gccttcccgc     240
ttctcaggtt ccggcagcgg aactgagttt acactgacta tttctagtct gcagtgcgac     300
gatttcgcta cctactattg cctgggggtg tacggttatt ctttcgacga tggcatcgca     360
tttggcggag ggacaaaagt ggagattaag aggactgtgg ccgctcccag tgtgttcatt     420
tttcccccta gcgacgaaca gctgaaaagc gggacagcct ctgtggtgtg tctgctgaac     480 aattttacc ctcgggaggc caaagtgcag tggaaggtgg ataacgctct gcagtctggc     540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga           714

<210> SEQ ID NO 80
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Ser Ser
                85                  90                  95

Leu Gln Cys Asp Asp Phe Ala Thr Tyr Tyr Cys Leu Gly Val Tyr Gly
            100                 105                 110
```

```
Tyr Ser Phe Asp Asp Gly Ile Ala Phe Gly Gly Gly Thr Lys Val Glu
            115                 120                 125

Ile Lys Arg Thr Val Ala Ala Pro Ser Val Phe Ile Phe Pro Pro Ser
        130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 81
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atggggtggt cttgcatcat tctgttcctg gtggcaaccg ccacaggtgt gcactccgac      60
atccagatga ctcagagtcc atcaaccctg tccgctagcg tgggagatag agtgactatc     120
acctgtcagg cctctcagag tatttccagc tacctggctt ggtatcagca gaagccaggc     180
aaagcaccca agctgctgat ctactatgct agtacactgg catcaggagt gccttcccgc     240
ttctcaggtt ccggcagcgg aactgagttt acactgacta ttactggtgt gcagtgcgac     300
gatttcgcta cctactattg cctgggggtg tacggttatt cttccgacga tggcatcgca     360
tttggcggag ggacaaaagt ggagattaag aggactgtgg ccgctcccag tgtgttcatt     420
tttccccta gcgacgaaca gctgaaaagc gggacagcct ctgtggtgtg tctgctgaac     480
aatttttacc ctcgggaggc caaagtgcag tggaaggtgg ataacgctct gcagtctggc     540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga           714
```

<210> SEQ ID NO 82
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45
```

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Thr Gly
                85                  90                  95

Val Gln Cys Asp Asp Phe Ala Thr Tyr Tyr Cys Leu Gly Val Tyr Gly
            100                 105                 110

Tyr Ser Phe Asp Asp Gly Ile Ala Phe Gly Gly Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 83
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atggggtggt cttgcatcat tctgttcctg gtggcaaccg ccacaggtgt gcactccgac      60
atccagatga ctcagagtcc atcaaccctg tccgctagcg tgggagatag agtgactatc     120
acctgtcagg cctctcagag tatttccagc tacctggctt ggtatcagca aaagccaggc     180
aaagcaccca agctgctgat ctactatgct agtacactgg catcaggagt gccttcccgc     240
ttctcaggtt ccggcagcgg aactgagttt acactgacta tttctagtct gcagtgcgac     300
gatgccgcta cctactattg cctgggggtg tacggttatt cttcgacga tggcatcgca     360 tttggcggag gcacaaaagt ggagattaag aggactgtgg ccgctcccag tgtgttcatt     420
tttcccccta gcgacgaaca gctgaaaagc gggacagcct ctgtggtgtg tctgctgaac     480
aatttttacc ctcgggaggc caaagtgcag tggaaggtgg ataacgctct gcagtctggc     540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga           714

<210> SEQ ID NO 84
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Ser Ser
                85                  90                  95

Leu Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 85
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
atggggtggt cttgcatcat tctgttcctg gtggcaaccg ccacaggtgt gcactccgac    60
atccagatga ctcagagtcc atcaaccctg tccgctagcg tgggagatag agtgactatc   120
acctgtcagg cctctcagag tatttccagc tacctggctt ggtatcagca gaagccaggc   180
aaagcaccca agctgctgat ctactatgct agtacactgg catcaggagt gccttcccgc   240
ttctcaggtt ccggcagcgg aactgagttt acactgacta ttactggtgt gcagtgcgac   300
gatgccgcta cctactattg cctgggggtg tacggttatt ctttcgacga tggcatcgca   360
tttggcggag ggacaaaagt ggagattaag aggactgtgg ccgctcccag tgtgttcatt   420
tttcccccta cgacgaaaca gctgaaaagc gggacagcct ctgtggtgtg tctgctgaac   480
aattttacc ctcgggaggc caaagtgcag tggaaggtgg ataacgctct gcagtctggc   540
aatagtcagg agtcagtgac cgaacaggac tccaaagata gcacatattc tctgtcatcc   600
```

```
accctgacac tgtccaaggc agactacgag aagcacaaag tgtatgcctg cgaagtgact    660
catcagggcc tgagctctcc cgtgaccaag agctttaaca ggggagaatg ttga          714
```

<210> SEQ ID NO 86
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Thr Gly
                85                  90                  95

Val Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 87
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
atggggtggt cttgcatcat tctgttcctg gtggcaaccg ccacaggtgt gcactccgac    60
atccagatga ctcagagtcc atcaaccctg tccgctagcg tgggagatag agtgactatc   120
acctgtcagg cctctcagag tatttccagc tacctggctt ggtatcagca gaagccaggc   180
aaagcaccca gctgctgat ctactatgct agtacactgg catcaggagt gccttcccgc    240
```

-continued

```
ttcaaaggtt ccggcagcgg aactgagttt acactgacta ttactggtgt gcagtgcgac      300
gatgccgcta cctactattg cctgggggtg tacggttatt ctttcgacga tggcatcgca      360
tttggcggag ggacaaaagt ggagattaag aggactgtgg ccgctcccag tgtgttcatt      420
tttcccccta cgacgaaca gctgaaaagc gggacagcct ctgtggtgtg tctgctgaac       480 aattttttacc ctcgggaggc caaagtgcag tggaaggtgg ataacgctct gcagtctggc    540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga            714
```

<210> SEQ ID NO 88
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Lys Gly Ser Gly Ser Gly Thr Glu Phe Thr Leu Thr Ile Thr Gly
                85                  90                  95

Val Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 89
<211> LENGTH: 714
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 89

```
atggggtggt cttgcatcat tctgttcctg gtggcaaccg ccacaggtgt gcactccgac      60
atccagatga ctcagagtcc atcaaccgtg tccgctgcag tgggaggtac agtgactatc     120
acctgtcagg cctctcagag tatttccagc tacctggctt ggtatcagca gaagccaggc     180
aaagcaccca agctgctgat ctactatgct agtacactgg catcaggagt gccttcccgc     240
ttctcaggtt ccggcagcgg aactgagttt acactgacta ttactggtgt gcagtgcgac     300
gatgccgcta cctactattg cctgggggtg tacggttatt ctttcgacga tggcatcgca     360
tttggcggag ggacaaaagt ggagattaag aggactgtgg ccgctcccag tgtgttcatt     420
tttcccccta gcgacgaaca gctgaaaagc gggacagcct ctgtggtgtg tctgctgaac     480
aatttttacc ctcgggaggc caaagtgcag tggaaggtgg ataacgctct gcagtctggc     540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga           714
```

<210> SEQ ID NO 90
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Val Ser Ala
            20                  25                  30

Ala Val Gly Gly Thr Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Thr Gly
                85                  90                  95

Val Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205
```

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 91
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atggggtggt cttgcatcat tctgttcctg gtggcaaccg ccacaggtgt gcactccgac      60
atccagatga ctcagagtcc atcaaccctg tccgctagcg tgggagatag agtgactatc     120
acctgtcagg cctctcagag tatttccagc tacctggctt ggtatcagca gaagccaggc     180
aaagcaccca gctgctgat ctactatgct agtacactgg catcaggagt gccttcccgc     240
ttctcaggtt ccggcagcgg aactgagttt acactgacta ttactggtgt gcagtgcgac     300
gatgccgcta cctactattg cctggggggtg tacggttatt ctttcgacga tggcatcgca     360
tttggcggag ggacagagct ggagattaag aggactgtgg ccgctcccag tgtgttcatt     420
tttcccccta cgacgaaca gctgaaaagc gggacagcct ctgtggtgtg tctgctgaac     480 aattttttacc ctcgggaggc caaagtgcag tggaaggtgg ataacgctct gcagtctggc     540
aatagtcagg agtcagtgac cgaacaggac tccaaagata gcacatattc tctgtcatcc     600
accctgacac tgtccaaggc agactacgag aagcacaaag tgtatgcctg cgaagtgact     660
catcagggcc tgagctctcc cgtgaccaag agctttaaca ggggagaatg ttga           714

<210> SEQ ID NO 92
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80

Phe Ser Gly Ser Gly Ser Gly Thr Glu Phe Thr Leu Thr Ile Thr Gly
                85                  90                  95

Val Gln Cys Asp Asp Ala Ala Thr Tyr Tyr Cys Leu Gly Val Tyr Gly
            100                 105                 110

Tyr Ser Phe Asp Asp Gly Ile Ala Phe Gly Gly Thr Glu Leu Glu
        115                 120                 125

Ile Lys Arg Thr Val Ala Ala Pro Ser Val Phe Ile Phe Pro Pro Ser
    130                 135                 140

```
Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 93
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
atgggctggt cctgcatcat cctgtttctg gtggccaccg ccaccggcgt gcacagcgac      60
attcagatga ctcagtcccc ctcctcccct tcggcctccg tcggcgaccg cgtgaccatt     120
acctgtcaag ccagccagtc catctcctcc tacttggcct ggtaccaaca gaagccagga     180
aaagctccta agctgctcat ctactacgcc tccactctgg cgtctggtgt cccgtcacgg     240
ttcagcgggt ccggatcagg aactgacttc accctgacga tcagcagcct ccagtgcgag     300
gattttgcga cctactactg cctgggggtg tatggttact cgttcgacga tggaatcgca     360
ttcggctcgg gcaccaaggt ggaaatcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct caatcgggt      540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714
```

<210> SEQ ID NO 94
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Gln Ala Ser Gln Ser Ile
        35                  40                  45

Ser Ser Tyr Leu Ala Trp Tyr Gln Gln Lys Pro Gly Lys Ala Pro Lys
    50                  55                  60

Leu Leu Ile Tyr Tyr Ala Ser Thr Leu Ala Ser Gly Val Pro Ser Arg
65                  70                  75                  80
```

Phe Ser Gly Ser Gly Ser Gly Thr Asp Phe Thr Leu Thr Ile Ser Ser
            85                  90                  95

Leu Gln Cys Glu Asp Phe Ala Thr Tyr Tyr Cys Leu Gly Val Tyr Gly
        100                 105                 110

Tyr Ser Phe Asp Asp Gly Ile Ala Phe Gly Ser Gly Thr Lys Val Glu
    115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 95
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgggctggt cctgcatcat cctgtttctg gtggccaccg ccaccggcgt gcacagcgac      60
attgtgatga cccagactcc tctctcccctg cccgtgactc ctggagaacc cgcctcgatc    120
tcatgtcaag cgtcgcagag catctcctca tacttggctt ggtacctcca aaagccgggc    180
cagagcccac agcttctgat ctattacgcc tccaccctgg cctcgggcgt gccggatcgg    240
ttttccggtt ctggaagcgg aaccgacttc accctgaaaa tctcccgcgt ggagtgcgag    300
gacgtgggcg tgtactactg cctgggagtc tacgggtact ccttcgatga cggcattgca    360
ttcgggtccg gtaccaaggt cgaaatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caagtacag tggaaggtgg ataacgccct caatcgggt     540 aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714

<210> SEQ ID NO 96
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Gly Trp Ser Cys Ile Ile Leu Phe Leu Val Ala Thr Ala Thr Gly
1               5                   10                  15

```
Val His Ser Asp Ile Val Met Thr Gln Thr Pro Leu Ser Leu Pro Val
         20                  25                  30

Thr Pro Gly Glu Pro Ala Ser Ile Ser Cys Gln Ala Ser Gln Ser Ile
     35                  40                  45

Ser Ser Tyr Leu Ala Trp Tyr Leu Gln Lys Pro Gly Gln Ser Pro Gln
 50                  55                  60

Leu Leu Ile Tyr Tyr Ala Ser Thr Leu Ala Ser Gly Val Pro Asp Arg
65                  70                  75                  80

Phe Ser Gly Ser Gly Ser Gly Thr Asp Phe Thr Leu Lys Ile Ser Arg
                 85                  90                  95

Val Glu Cys Glu Asp Val Gly Val Tyr Tyr Cys Leu Gly Val Tyr Gly
            100                 105                 110

Tyr Ser Phe Asp Asp Gly Ile Ala Phe Gly Ser Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 97
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
atgggctggt cctgcatcat cctgtttctg gtggccaccg ccaccggcgt gcacagcgaa      60
attgtgctca ctcaatcccc tgccaccctt tccttgtccc ccggcgaaag agccactctg     120
tcatgtcaag ccagccagtc gatctcctct tacctggctt ggtaccagca gaagccagga     180
caggcaccgc gcctgctgat ctactacgcg tcgaccctcg cctcgggaat cccggcccgg     240
ttcagcggat caggctccgg taccgacttc actctgacca ttagctccct ggagtgcgag     300
gacttcgcgg tgtattactg cctgggggtg tacggctact ccttcgatga cggaatcgcc     360
tttgggagcg gtaccaaggt cgagatcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga          714

<210> SEQ ID NO 98
```

```
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Gln Ala Ser Gln Ser Ile
        35                  40                  45

Ser Ser Tyr Leu Ala Trp Tyr Gln Gln Lys Pro Gly Gln Ala Pro Arg
    50                  55                  60

Leu Leu Ile Tyr Tyr Ala Ser Thr Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Cys Glu Asp Phe Ala Val Tyr Tyr Cys Leu Gly Val Tyr Gly
            100                 105                 110

Tyr Ser Phe Asp Asp Gly Ile Ala Phe Gly Ser Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 99
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
atgggctggt cctgcatcat cctgtttctg gtggccaccg ccaccggcgt gcacagcgat      60
atcgtgatga cccaaagccc tgactccctt gccgtgtcac tcggagaacg cgccaccatc    120
aactgtcaag cgtcgcagtc catctcctca tacctggcct ggtatcagca gaaaccgggg    180
cagccgccaa agctgctgat ctactacgct tccactctgg cctccggcgt gcccgatcgg    240
ttctccggat cgggctccgg caccgacttt actctgacca ttagcagcct ccagtgcgag    300
gacgtggcgg tgtactactg cttgggtgtc tacggatact ccttcgacga cgggatcgca    360
ttcggttcgg gaaccaaggt cgagattaaa cgaactgtgg ctgcaccatc tgtcttcatc    420
```

```
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714
```

<210> SEQ ID NO 100
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Gln Ala Ser Gln Ser Ile
        35                  40                  45

Ser Ser Tyr Leu Ala Trp Tyr Gln Gln Lys Pro Gly Gln Pro Pro Lys
    50                  55                  60

Leu Leu Ile Tyr Tyr Ala Ser Thr Leu Ala Ser Gly Val Pro Asp Arg
65                  70                  75                  80

Phe Ser Gly Ser Gly Ser Gly Thr Asp Phe Thr Leu Thr Ile Ser Ser
                85                  90                  95

Leu Gln Cys Glu Asp Val Ala Val Tyr Tyr Cys Leu Gly Val Tyr Gly
            100                 105                 110

Tyr Ser Phe Asp Asp Gly Ile Ala Phe Gly Ser Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 101
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
atgggctggt cctgcatcat cctgtttctg gtggccaccg ccaccggcgt gcacagcgaa    60
```

-continued

```
atcgtcttga cccaaagccc tgacttccaa tccgtgaccc ccaaggaaaa ggtcaccatc    120
acgtgtcagg cctcccagtc aatttcctcg taccttgcgt ggtaccagca gaagccagac    180
cagtccccga agctcctgat taagtacgca tccaccctgg ctagcggagt gccgagccgg    240
ttctcgggat ccggctctgg aactgacttc actctgacca tcaactcgct cgagtgcgaa    300
gatgccgcca cttactattg cctgggggtg tacgggtact catttgacga tggcatcgcc    360
ttcggctccg gtaccaaagt ggagatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714
```

<210> SEQ ID NO 102
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Asp Phe Gln Ser Val
            20                  25                  30

Thr Pro Lys Glu Lys Val Thr Ile Thr Cys Gln Ala Ser Gln Ser Ile
        35                  40                  45

Ser Ser Tyr Leu Ala Trp Tyr Gln Gln Lys Pro Asp Gln Ser Pro Lys
    50                  55                  60

Leu Leu Ile Lys Tyr Ala Ser Thr Leu Ala Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Cys Glu Asp Ala Ala Thr Tyr Tyr Cys Leu Gly Val Tyr Gly
            100                 105                 110

Tyr Ser Phe Asp Asp Gly Ile Ala Phe Gly Ser Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

```
<210> SEQ ID NO 103
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
atgggctggt cctgcatcat cctgtttctg gtggccaccg ccaccggcgt gcacagcgac     60
gtcgtgatga ctcaaagccc cgcattcctt tccgtgactc ctggagaaaa ggtcaccatc    120
acctgtcaag ccagccagtc catttcgtcc tacttggcct ggtatcagca gaagccagac    180
caggccccga agctgctgat taagtacgcc tccaccctgg ccagcggagt gccgtcacgg    240
ttctccgggt ccggctcagg aaccgacttc acgttcacca tctcgtccct cgagtgcgaa    300
gatgctgcga cttactactg cctgggcgtg tacggttact cgtttgatga cggcatcgcg    360
ttcgggtctg gaaccaaagt ggagatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714

<210> SEQ ID NO 104
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Gly Trp Ser Cys Ile Ile Leu Phe Leu Val Ala Thr Ala Thr Gly
1               5                   10                  15

Val His Ser Asp Val Val Met Thr Gln Ser Pro Ala Phe Leu Ser Val
            20                  25                  30

Thr Pro Gly Glu Lys Val Thr Ile Thr Cys Gln Ala Ser Gln Ser Ile
        35                  40                  45

Ser Ser Tyr Leu Ala Trp Tyr Gln Gln Lys Pro Asp Gln Ala Pro Lys
    50                  55                  60

Leu Leu Ile Lys Tyr Ala Ser Thr Leu Ala Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Glu Cys Glu Asp Ala Ala Thr Tyr Tyr Cys Leu Gly Val Tyr Gly
            100                 105                 110

Tyr Ser Phe Asp Asp Gly Ile Ala Phe Gly Ser Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
```

```
                    180                 185                 190
Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

<210> SEQ ID NO 105
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
atgggctggt cctgcatcat cctgtttctg gtggccaccg ccaccggcgt gcacagcgat    60
atcgtcctca ctcaatcccc cgcttcactc gccgtgtccc tggtcaacg cgccaccatt   120
acgtgtcagg cgtcccagtc catttcgagc taccttgcat ggtaccagca gaagcctgga   180
cagccccga aactgctgat ctattacgcc tccaccttgg cctcgggagt gccagcgcgg    240
tttagcggtt cgggctccgg cactgacttc actctgacca tcaacccggt ggagtgcgaa   300
gataccgcca actactactg cctggggtg tacggatact cattcgacga cgggatcgcc    360
ttcggaagcg gcaccaaggt cgaaatcaaa cgaactgtgg ctgcaccatc tgtcttcatc    420
ttcccgccat ctgatgagca gttgaaatct ggaactgcct ctgttgtgtg cctgctgaat   480
aacttctatc ccagagaggc caaagtacag tggaaggtgg ataacgccct caatcgggt    540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttga         714
```

<210> SEQ ID NO 106
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Ala Ser Leu Ala Val
            20                  25                  30

Ser Pro Gly Gln Arg Ala Thr Ile Thr Cys Gln Ala Ser Gln Ser Ile
        35                  40                  45

Ser Ser Tyr Leu Ala Trp Tyr Gln Gln Lys Pro Gly Gln Pro Pro Lys
    50                  55                  60

Leu Leu Ile Tyr Tyr Ala Ser Thr Leu Ala Ser Gly Val Pro Ala Arg
65                  70                  75                  80

Phe Ser Gly Ser Gly Ser Gly Thr Asp Phe Thr Leu Thr Ile Asn Pro
                85                  90                  95

Val Glu Cys Glu Asp Thr Ala Asn Tyr Tyr Cys Leu Gly Val Tyr Gly
            100                 105                 110

Tyr Ser Phe Asp Asp Gly Ile Ala Phe Gly Ser Gly Thr Lys Val Glu
```

```
                    115                 120                 125
Ile Lys Arg Thr Val Ala Ala Pro Ser Val Phe Ile Phe Pro Pro Ser
            130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

<210> SEQ ID NO 107
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
atgggctggt cctgcatcat cctgtttctg gtggccaccg ccaccggcgt gcactccgag    60
ctcgtgatga cccagactcc agcctctgtg gaggtagctg tgggaggcac agtcaccatc   120
aagtgccagg ccagtcagag cattaatacc tacttagcct ggtatcagca gaaaccaggg   180
cagcctccca agctcctgat ctacagggca tccactctgg catctggggt ccatcgcgg   240
ttcaaaggca gtggatctgg gacagagttc actctcacca ttagcgacct ggagtgtgcc   300
gatgctgcca cttactactg tcaacagagt gttcgtgtta ttgatgttga taatactttc   360
ggcggaggga ccgaggtggt ggtcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgcctccaa tcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgttg a            711
```

<210> SEQ ID NO 108
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Met Gly Trp Ser Cys Ile Ile Leu Phe Leu Val Ala Thr Ala Thr Gly
1               5                   10                  15

Val His Ser Glu Leu Val Met Thr Gln Thr Pro Ala Ser Val Glu Val
            20                  25                  30

Ala Val Gly Gly Thr Val Thr Ile Lys Cys Gln Ala Ser Gln Ser Ile
        35                  40                  45

Asn Thr Tyr Leu Ala Trp Tyr Gln Gln Lys Pro Gly Gln Pro Pro Lys
```

Leu Leu Ile Tyr Arg Ala Ser Thr Leu Ala Ser Gly Val Pro Ser Arg
 65                  70                  75                  80

Phe Lys Gly Ser Gly Ser Gly Thr Glu Phe Thr Leu Thr Ile Ser Asp
                 85                  90                  95

Leu Glu Cys Ala Asp Ala Ala Thr Tyr Tyr Cys Gln Gln Ser Val Arg
            100                 105                 110

Val Ile Asp Val Asp Asn Thr Phe Gly Gly Gly Thr Glu Val Val Val
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 109
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
atgggctggt cctgcatcat cctgtttctg gtggccaccg ccaccggcgt gcacagcgag      60
ctcgtgatga cccagactcc atcctacacg tctgcagctg tgggagacac agtcaccatc     120
aagtgccagg ccagtcagac cattggtggt agcgacttat cctggtatca gcagaaacca     180 ggcagcctc ccaaactcct gatctggtat gcaaccaatc tgccatctgg ggtcccatcg      240
cggttcagtg gcagtagatc tgggacagag tacactctca ccatcagcgg cgtgcagtgt     300
gaggatgctg ccacctacta ctgtctaggt ggttatgctg ctgcttctta cagaactgct     360
ttcggcggag ggaccgaggt ggtcgtcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714

<210> SEQ ID NO 110
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

| | | | | | | | | | | | | | | | |
|---|---|---|---|---|---|---|---|---|---|---|---|---|---|---|---|
|Met|Gly|Trp|Ser|Cys|Ile|Ile|Leu|Phe|Leu|Val|Ala|Thr|Ala|Thr|Gly|
|1| | | |5| | | | |10| | | | |15| |

Val His Ser Glu Leu Val Met Thr Gln Thr Pro Ser Tyr Thr Ser Ala
           20                  25                  30

Ala Val Gly Asp Thr Val Thr Ile Lys Cys Gln Ala Ser Gln Thr Ile
               35                  40                  45

Gly Gly Ser Asp Leu Ser Trp Tyr Gln Gln Lys Pro Gly Gln Pro Pro
    50                  55                  60

Lys Leu Leu Ile Trp Tyr Ala Thr Asn Leu Pro Ser Gly Val Pro Ser
65                  70                  75                  80

Arg Phe Ser Gly Ser Arg Ser Gly Thr Glu Tyr Thr Leu Thr Ile Ser
                85                  90                  95

Gly Val Gln Cys Glu Asp Ala Ala Thr Tyr Tyr Cys Leu Gly Gly Tyr
                100                 105                 110

Ala Ala Ala Ser Tyr Arg Thr Ala Phe Gly Gly Gly Thr Glu Val Val
            115                 120                 125

Val Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 111
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
atgggctggt cctgcatcat cctgtttctg gtggccaccg ccaccggcgt gcacagcgat     60
attcagatga cccagagccc ttccttcctg tcagccagcg tcggggatag agtcacaatc    120
acttgccagg ccagccagac cattggcggg agcgacctgt cctggtacca gcagaagccc    180
ggaaaagccc ctaagctgct gatctactat gctacaaacc tgccatctgg cgtgcccagc    240
cggttctctg gaagtggctc agggactgac tttaccctga caattagctc cctgcagtgc    300
gaggatttcg ccacctacta ttgtctgggg ggctatgccg ccgcaagcta ccgcaccgcc    360
ttcggaggag gaactaaagt ggaaatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccaga gagtgtcac agagcaggac agcaaggaca gcacctacag cctcagcagc    600
accctgacgc tgagcaaagc agactacgag aaacacaaag tctacgcctg cgaagtcacc    660
```
catcagggcc tgagctcgcc cgtcacaaag agcttcaaca ggggagagtg ttga          714

<210> SEQ ID NO 112
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Phe Leu Ser Ala
            20                  25                  30

Ser Val Gly Asp Arg Val Thr Ile Thr Cys Gln Ala Ser Gln Thr Ile
        35                  40                  45

Gly Gly Ser Asp Leu Ser Trp Tyr Gln Gln Lys Pro Gly Lys Ala Pro
    50                  55                  60

Lys Leu Leu Ile Tyr Tyr Ala Thr Asn Leu Pro Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Cys Glu Asp Phe Ala Thr Tyr Tyr Cys Leu Gly Gly Tyr
            100                 105                 110

Ala Ala Ala Ser Tyr Arg Thr Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 113
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
atgggctggt cctgcatcat cctgtttctg gtggccaccg ccaccggcgt gcacagcgat    60
attcagatga ctcagagccc ttccttcctg tccgcttccg tcgggatcg ggtcacaatc    120 acttgccagg cctcacagac tattggcggg agcgacctgt cctggtacca gcagaagccc   180
ggaaaagcac ctaagctgct gatctactat gccacaaacc tgccatctgg cgtgcccagc   240
cggttctctg gaagtggctc agggactgac tttaccctga caattagctc cctgcagtgc   300

| | | | | |
|---|---|---|---|---|
| gaggatgccg | ctacctacta | ttgtctgggg | ggctacgccg | ccgcttcata caggaccgcc | 360 |
| ttcggaggag | gaactaaagt | ggaaatcaaa | cgaactgtgg | ctgcaccatc tgtcttcatc | 420 |
| ttcccgccat | ctgatgagca | gttgaaatct | ggaactgcct | ctgttgtgtg cctgctgaat | 480 |
| aacttctatc | ccagagaggc | caaagtacag | tggaaggtgg | ataacgccct ccaatcgggt | 540 |
| aactcccagg | agagtgtcac | agagcaggac | agcaaggaca | gcacctacag cctcagcagc | 600 |
| accctgacgc | tgagcaaagc | agactacgag | aaacacaaag | tctacgcctg cgaagtcacc | 660 |
| catcagggcc | tgagctcgcc | cgtcacaaag | agcttcaaca | ggggagagtg ttga | 714 |

<210> SEQ ID NO 114
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Phe Leu Ser Ala
            20                  25                  30

Ser Val Gly Asp Arg Val Thr Ile Thr Cys Gln Ala Ser Gln Thr Ile
        35                  40                  45

Gly Gly Ser Asp Leu Ser Trp Tyr Gln Gln Lys Pro Gly Lys Ala Pro
    50                  55                  60

Lys Leu Leu Ile Tyr Tyr Ala Thr Asn Leu Pro Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Cys Glu Asp Ala Ala Thr Tyr Tyr Cys Leu Gly Gly Tyr
            100                 105                 110

Ala Ala Ala Ser Tyr Arg Thr Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 115
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
atgggctggt cctgcatcat cctgtttctg gtggccaccg ccaccggcgt gcactccgaa    60
gtgttgatga cccagactcc atcctccgtg tctgcagctg tgggagacac agtcaccatc   120
aagtgccagg ccagtcagag cattagtagt gtcttgtcct ggtatcagca gaaaccaggg   180
cagcctccca agctcctgat ctatctggca tccactctgg catctggggt cccatcgcgg   240
ttcagcggca gtagatctgg gacagagttc actctcacca tcagcgacct ggagtgtgac   300
gatgctgcca cttactactg tcaaaccaat tatggtacta gtagtagtaa ttatggtttt   360
gctttcggcg agggaccgag gtggtcgtc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660
acccatcagg gcctgagctc gcccgtcaca aagagcttca caggggaga gtgttga      717
```

<210> SEQ ID NO 116
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Met Gly Trp Ser Cys Ile Ile Leu Phe Leu Val Ala Thr Ala Thr Gly
1               5                   10                  15

Val His Ser Glu Val Leu Met Thr Gln Thr Pro Ser Ser Val Ser Ala
            20                  25                  30

Ala Val Gly Asp Thr Val Thr Ile Lys Cys Gln Ala Ser Gln Ser Ile
        35                  40                  45

Ser Ser Val Leu Ser Trp Tyr Gln Gln Lys Pro Gly Gln Pro Pro Lys
    50                  55                  60

Leu Leu Ile Tyr Leu Ala Ser Thr Leu Ala Ser Gly Val Pro Ser Arg
65                  70                  75                  80

Phe Ser Gly Ser Arg Ser Gly Thr Glu Phe Thr Leu Thr Ile Ser Asp
                85                  90                  95

Leu Glu Cys Asp Asp Ala Ala Thr Tyr Tyr Cys Gln Thr Asn Tyr Gly
            100                 105                 110

Thr Ser Ser Ser Asn Tyr Gly Phe Ala Phe Gly Gly Thr Glu Val
        115                 120                 125

Val Val Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

```
Leu Ser Ser Pro Val Thr Lys Ser Phe Asn Arg Gly Glu Cys
225                 230                 235
```

<210> SEQ ID NO 117
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
atgggctggt cctgcatcat cctgtttctg gtggccaccg ccaccggcgt gcacagcgac    60
attcagatga cccagtcccc aagctcgctg tccgcctccg tgggcgaccg cgtgaccatc   120
acgtgccagg cgtcccagtc aattagcagc gtgctctcct ggtaccaaca gaagccgggg   180
aaagcaccca agctgctgat ctacttggcc tccactctgg cctcgggagt gccttcacgg   240
ttctccggat cgggatctgg tactgatttc accctcacca tctcgagcct tcagtgcgag   300
gacttcgcta cttactattg tcaaaccaac tacggaacct ccagctccaa ctacggcttt   360
gccttcggtg cgggaccaa ggtcgaaatc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660 acccatcagg gcctgagctc gcccgtcaca aagagcttca caggggaga gtgttga     717
```

<210> SEQ ID NO 118
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Gln Ala Ser Gln Ser Ile
            35                  40                  45

Ser Ser Val Leu Ser Trp Tyr Gln Gln Lys Pro Gly Lys Ala Pro Lys
        50                  55                  60

Leu Leu Ile Tyr Leu Ala Ser Thr Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Cys Glu Asp Phe Ala Thr Tyr Tyr Cys Gln Thr Asn Tyr Gly
                100                 105                 110

Thr Ser Ser Ser Asn Tyr Gly Phe Ala Phe Gly Gly Thr Lys Val
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160
```

```
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235
```

<210> SEQ ID NO 119
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
atgggctggt cctgcatcat cctgtttctg gtggccaccg ccaccggcgt gcacagcgac      60
attcagatga cccagtcccc aagctcgctg tccgcctccg tgggcgaccg cgtgaccatc     120
acgtgccagg cgtcccagtc aattagcagc gtgctctcct ggtaccaaca gaagccgggg     180
aaagcaccca agctgctgat ctacttggcc tccactctgg cctcgggagt gccttcacgg     240
ttctccggat cgggatctgg tactgatttc accctcacca tctcgagcct tcagtgcgag     300
gacgccgcta cttactattg tcaaaccaac tacggaacct ccagctccaa ctacggcttt     360
gccttcggtg cgggaccaa ggtcgaaatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca caggggaga gtgttga       717
```

<210> SEQ ID NO 120
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Met Gly Trp Ser Cys Ile Ile Leu Phe Leu Val Ala Thr Ala Thr Gly
1               5                   10                  15
Val His Ser Asp Ile Gln Met Thr Gln Ser Pro Ser Ser Leu Ser Ala
            20                  25                  30
Ser Val Gly Asp Arg Val Thr Ile Thr Cys Gln Ala Ser Gln Ser Ile
        35                  40                  45
Ser Ser Val Leu Ser Trp Tyr Gln Gln Lys Pro Gly Lys Ala Pro Lys
    50                  55                  60
Leu Leu Ile Tyr Leu Ala Ser Thr Leu Ala Ser Gly Val Pro Ser Arg
65                  70                  75                  80
Phe Ser Gly Ser Gly Ser Gly Thr Asp Phe Thr Leu Thr Ile Ser Ser
                85                  90                  95
```

```
Leu Gln Cys Glu Asp Ala Ala Thr Tyr Tyr Cys Gln Thr Asn Tyr Gly
                100                 105                 110

Thr Ser Ser Ser Asn Tyr Gly Phe Ala Phe Gly Gly Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 121
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
atgggctggt cctgcatcat cctgtttctg gtggccaccg ccaccggcgt gcacagcgac      60
attcagatga cccagtcccc aagctcgctg tccgcctccg tgggcgaccg cgtgaccatc     120
acgtgccagg cgtcccagtc aattagcagc gtgctctcct ggtaccaaca gaagccgggg     180
aaagcaccca agctgctgat ctacttggcc tccactctgg cctcgggagt gccttcacgg     240
ttctccggat cgggatctgg tactgatttc accctcacca tctcgagcct tcagtgcgag     300
gacatcgcta cttactattg tcaaaccaac tacggaacct ccagctccaa ctacggcttt     360
gccttcggtg cgggaccaa ggtcgaaatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca caggggaga gtgttga       717

<210> SEQ ID NO 122
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30
```

Ser Val Gly Asp Arg Val Thr Ile Thr Cys Gln Ala Ser Gln Ser Ile
       35                  40                  45

Ser Ser Val Leu Ser Trp Tyr Gln Gln Lys Pro Gly Lys Ala Pro Lys
 50                  55                  60

Leu Leu Ile Tyr Leu Ala Ser Thr Leu Ala Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Cys Glu Asp Ile Ala Thr Tyr Tyr Cys Gln Thr Asn Tyr Gly
            100                 105                 110

Thr Ser Ser Asn Tyr Gly Phe Ala Phe Gly Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 123
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
atgggctggt cctgcatcat cctgtttctg gtggccaccg ccaccggcgt gcactccgca    60
ttcgaattga cccagactcc atcctccgtg gaggcagctg tgggaggcac agtcaccatc   120
aagtgccagg ccagtcagag catttacagt tatttagcct ggtatcagca gaaaccaggg   180
cagcctccca agctcctgat ctattctgca tccactctgg catctggggt ctcatcgcgg   240
ttcagaggca gtggatctgg gacagaatac actctcacca tcagcgacct ggagtgtgcc   300
gatgctgcca cttactactg tcaaacctat tatgatattg ttactagtac tttcggcgga   360
gggaccgagg tggtcgtcaa cgaactgtgg ctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag cacactgacg   600
ctgagcaaag cagactacga aaacacaaa gtctacgcct gcgaagtcac ccatcagggc   660
ctgagctcgc ccgtcacaaa gagcttcaac agggagagt gttga            705

<210> SEQ ID NO 124
<211> LENGTH: 234
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 124

| | | | | | | | | | | | | | | | |
|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 | |
| Val | His | Ser | Ala | Phe | Glu | Leu | Thr | Gln | Thr | Pro | Ser | Ser | Val | Glu | Ala |
| | | | 20 | | | | | 25 | | | | | 30 | | |
| Ala | Val | Gly | Gly | Thr | Val | Thr | Ile | Lys | Cys | Gln | Ala | Ser | Gln | Ser | Ile |
| | | | 35 | | | | | 40 | | | | | 45 | | |
| Tyr | Ser | Tyr | Leu | Ala | Trp | Tyr | Gln | Gln | Lys | Pro | Gly | Gln | Pro | Pro | Lys |
| | 50 | | | | | 55 | | | | | 60 | | | | |
| Leu | Leu | Ile | Tyr | Ser | Ala | Ser | Thr | Leu | Ala | Ser | Gly | Val | Ser | Ser | Arg |
| 65 | | | | | 70 | | | | | 75 | | | | | 80 |
| Phe | Arg | Gly | Ser | Gly | Ser | Gly | Thr | Glu | Tyr | Thr | Leu | Thr | Ile | Ser | Asp |
| | | | | 85 | | | | | 90 | | | | | 95 | |
| Leu | Glu | Cys | Ala | Asp | Ala | Ala | Thr | Tyr | Tyr | Cys | Gln | Thr | Tyr | Tyr | Asp |
| | | | 100 | | | | | 105 | | | | | 110 | | |
| Ile | Val | Thr | Ser | Thr | Phe | Gly | Gly | Thr | Glu | Val | Val | Val | Lys | Arg |
| | | | 115 | | | | | 120 | | | | | 125 | | |
| Thr | Val | Ala | Ala | Pro | Ser | Val | Phe | Ile | Phe | Pro | Pro | Ser | Asp | Glu | Gln |
| 130 | | | | | 135 | | | | | 140 | | | | | |
| Leu | Lys | Ser | Gly | Thr | Ala | Ser | Val | Val | Cys | Leu | Leu | Asn | Asn | Phe | Tyr |
| 145 | | | | | 150 | | | | | 155 | | | | | 160 |
| Pro | Arg | Glu | Ala | Lys | Val | Gln | Trp | Lys | Val | Asp | Asn | Ala | Leu | Gln | Ser |
| | | | | 165 | | | | | 170 | | | | | 175 | |
| Gly | Asn | Ser | Gln | Glu | Ser | Val | Thr | Glu | Gln | Asp | Ser | Lys | Asp | Ser | Thr |
| | | | 180 | | | | | 185 | | | | | 190 | | |
| Tyr | Ser | Leu | Ser | Ser | Thr | Leu | Thr | Leu | Ser | Lys | Ala | Asp | Tyr | Glu | Lys |
| | | | 195 | | | | | 200 | | | | | 205 | | |
| His | Lys | Val | Tyr | Ala | Cys | Glu | Val | Thr | His | Gln | Gly | Leu | Ser | Ser | Pro |
| | 210 | | | | | 215 | | | | | 220 | | | | |
| Val | Thr | Lys | Ser | Phe | Asn | Arg | Gly | Glu | Cys | | | | | | |
| 225 | | | | | 230 | | | | | | | | | | |

<210> SEQ ID NO 125
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
atgggctggt cctgcatcat cctgtttctg gtggccaccg ccaccggcgt gcactccgca      60
ttcgaattga cccagactcc atcctccgtg gaggcagctg tgggaggcac agtcaccatc     120
aagtgccagg ccagtcagag catttacagt tatttagcct ggtatcagca gaaaccaggg     180
cagcctccca agctcctgat ctattctgca tccactctgg catctggggt ctcatcgcgg     240
ttcagaggca gtggatctgg gacagaatac attctcacca tcagcgacct ggagtgtgcc     300
gatgctgcca cttactactg tcaaacctat tatgatattg ttactagtac tttcggcgga     360
gggaccgagg tggtggtcaa acgaactgtg gctgcaccat ctgtcttcat cttcccgcca     420
tctgatgagc agttgaaatc tggaactgcc tctgttgtgt gcctgctgaa taacttctat     480
```

```
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttga                    705
```

<210> SEQ ID NO 126
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

```
Met Gly Trp Ser Cys Ile Ile Leu Phe Leu Val Ala Thr Ala Thr Gly
1               5                   10                  15

Val His Ser Ala Phe Glu Leu Thr Gln Thr Pro Ser Ser Val Glu Ala
            20                  25                  30

Ala Val Gly Gly Thr Val Thr Ile Lys Cys Gln Ala Ser Gln Ser Ile
        35                  40                  45

Tyr Ser Tyr Leu Ala Trp Tyr Gln Gln Lys Pro Gly Gln Pro Pro Lys
    50                  55                  60

Leu Leu Ile Tyr Ser Ala Ser Thr Leu Ala Ser Gly Val Ser Ser Arg
65                  70                  75                  80

Phe Arg Gly Ser Gly Ser Gly Thr Glu Tyr Ile Leu Thr Ile Ser Asp
                85                  90                  95

Leu Glu Cys Ala Asp Ala Ala Thr Tyr Tyr Cys Gln Thr Tyr Tyr Asp
            100                 105                 110

Ile Val Thr Ser Thr Phe Gly Gly Gly Thr Glu Val Val Val Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 127
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
atgggctggt cctgcatcat cctgtttctg gtggccaccg ccaccggcgt gcactccgcc     60
gtcgtgctga cccagactgc atcccccgtg tctggagttg tgggaggcac agtcaccatc    120
```

```
aagtgccagg ccagtcagaa catttacagc aatttagcct ggtatcagca gaaaccaggg    180
cagcgtccca agctcctgat gtatgatgca tccactctgg catctggggt cccatcgcgg    240
ttcaaaggca gtggatctgg gacacagttc actctcacca tcagcgacct ggagtgtgcc    300
gatgctgcca cttactactg tcaaagtatt agtagtgttg acaataatgt tttcggcgga    360
gggaccgagg tggtggtcaa cgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga aaacacaaa gtctacgcct gcgaagtcac ccatcagggc    660
ctgagctcgc ccgtcacaaa gagcttcaac aggggagagt gttga                   705
```

```
<210> SEQ ID NO 128
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Gly Trp Ser Cys Ile Ile Leu Phe Leu Val Ala Thr Ala Thr Gly
1               5                   10                  15

Val His Ser Ala Val Val Leu Thr Gln Thr Ala Ser Pro Val Ser Gly
                20                  25                  30

Val Val Gly Gly Thr Val Thr Ile Lys Cys Gln Ala Ser Gln Asn Ile
            35                  40                  45

Tyr Ser Asn Leu Ala Trp Tyr Gln Gln Lys Pro Gly Gln Arg Pro Lys
        50                  55                  60

Leu Leu Met Tyr Asp Ala Ser Thr Leu Ala Ser Gly Val Pro Ser Arg
65                  70                  75                  80

Phe Lys Gly Ser Gly Ser Gly Thr Gln Phe Thr Leu Thr Ile Ser Asp
                85                  90                  95

Leu Glu Cys Ala Asp Ala Ala Thr Tyr Tyr Cys Gln Ser Ile Ser Ser
            100                 105                 110

Val Asp Asn Asn Val Phe Gly Gly Thr Glu Val Val Val Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 129
<211> LENGTH: 705
```

<210> SEQ ID NO 129
<211> LENGTH: 705
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
atgggctggt cctgcatcat cctgtttctg gtggccaccg ccaccggcgt gcactccgta    60
ttcgaattga cccagactcc atcccccgtg tctgcagctg tgggaggcac agtcaccatc   120
aggtgccagg ccagtcagaa cattaagagc tacttagcct ggtatcagca gaaaccaggg   180
cagcctccca aactcctgat ctatgaagca tccattctgg catctggggt ctcatcgcgg   240
ttcaaaggca gtggatctgg gacagagttc actctcacca tcagcgacct ggagtgtgcc   300
gatgctgcca cttactactg tcaaagctat tatgctgcta gtagtaatgc tttcggcgga   360
gggaccgagg tggtggtcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga aaacacaaa gtctacgcct gcgaagtcac ccatcagggc   660
ctgagctcgc ccgtcacaaa gagcttcaac aggggagagt gttga                  705
```

<210> SEQ ID NO 130
<211> LENGTH: 234
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Met Gly Trp Ser Cys Ile Ile Leu Phe Leu Val Ala Thr Ala Thr Gly
1               5                   10                  15

Val His Ser Val Phe Glu Leu Thr Gln Thr Pro Ser Pro Val Ser Ala
            20                  25                  30

Ala Val Gly Gly Thr Val Thr Ile Arg Cys Gln Ala Ser Gln Asn Ile
        35                  40                  45

Lys Ser Tyr Leu Ala Trp Tyr Gln Gln Lys Pro Gly Gln Pro Pro Lys
    50                  55                  60

Leu Leu Ile Tyr Glu Ala Ser Ile Leu Ala Ser Gly Val Ser Ser Arg
65                  70                  75                  80

Phe Lys Gly Ser Gly Ser Gly Thr Glu Phe Thr Leu Thr Ile Ser Asp
                85                  90                  95

Leu Glu Cys Ala Asp Ala Ala Thr Tyr Tyr Cys Gln Ser Tyr Tyr Ala
            100                 105                 110

Ala Ser Ser Asn Ala Phe Gly Gly Gly Thr Glu Val Val Val Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 131
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
atgggctggt cctgcatcat cctgtttctg gtggccaccg ccaccggcgt gcacagcgag      60
ctcgtgatga cccagactcc atcctccgtg tctgcagctg tgggaggcac agtcaccatc     120
aattgccagg ccagtcagag cattagtaac tacttatcct ggtatcagca gaaaccagga     180
cagcctccca agctcctgat ctttgctgca tccaaactgg catcttgggt cccaaagcgg     240
ttcagtggca gcagatctgg gatagaatac actctcacca ttagcggcgt gcagtgtgac     300
gatgctgcca cttacttctg tctaggagtt tatagtatta gtactgatga tggagctgct     360
ttcggcggag ggaccgaggt ggtcgtcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714

<210> SEQ ID NO 132
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Gly Trp Ser Cys Ile Ile Leu Phe Leu Val Ala Thr Ala Thr Gly
1               5                   10                  15

Val His Ser Glu Leu Val Met Thr Gln Thr Pro Ser Ser Val Ser Ala
            20                  25                  30

Ala Val Gly Gly Thr Val Thr Ile Asn Cys Gln Ala Ser Gln Ser Ile
        35                  40                  45

Ser Asn Tyr Leu Ser Trp Tyr Gln Gln Lys Pro Gly Gln Pro Pro Lys
    50                  55                  60

Leu Leu Ile Phe Ala Ala Ser Lys Leu Ala Ser Trp Val Pro Lys Arg
65                  70                  75                  80

Phe Ser Gly Ser Arg Ser Gly Ile Glu Tyr Thr Leu Thr Ile Ser Gly
                85                  90                  95

Val Gln Cys Asp Asp Ala Ala Thr Tyr Phe Cys Leu Gly Val Tyr Ser
            100                 105                 110

Ile Ser Thr Asp Asp Gly Ala Ala Phe Gly Gly Gly Thr Glu Val Val
        115                 120                 125

Val Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
            165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 133
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
atgggctggt cctgcatcat cctgtttctg gtggccaccg ccaccggcgt gcacagcgat      60
attcagatga cccagtctcc ttcctccctg tccgcttccg tcggcgatag agtcacaatc     120
acttgccagg cttcccagag catcagcaac tacctgtcct ggtatcagca gaagcccggc     180
aaagcaccta gctgctgat ctacgccgct tctaaactgg aagcggagt gccaagccgg       240 ttctctggaa gtgggtcagg aactgacttt accctgacaa ttagctccct gcagtgcgag     300
gatttcgcta cctactattg tctgggcgtc tattcaatct caactgacga cggagccgca     360
ttcggagggg gcaccaaagt ggaaatcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714

<210> SEQ ID NO 134
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Gln Ala Ser Gln Ser Ile
        35                  40                  45

Ser Asn Tyr Leu Ser Trp Tyr Gln Gln Lys Pro Gly Lys Ala Pro Lys
    50                  55                  60

```
Leu Leu Ile Tyr Ala Ala Ser Lys Leu Ala Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Cys Glu Asp Phe Ala Thr Tyr Tyr Cys Leu Gly Val Tyr Ser
            100                 105                 110

Ile Ser Thr Asp Asp Gly Ala Ala Phe Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 135
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
atgggctggt cctgcatcat cctgtttctg gtggccaccg ccaccggcgt gcacagcgat      60
attcagatga cccagagccc ttcctccctg tccgctagtg tcggggatag agtgaccatt     120
acttgccagg ccagccagag cattagcaac tacctgtcct ggtatcagca gaagcccggc     180
aaagctccta agctgctgat ctacgccgct tctaaactgg caagcggagt gccaagccgg     240
ttctctggaa gtgggtcagg aactgacttt accctgacaa ttagctccct gcagtgcgag     300
gatgcagcca cctactattg tctgggcgtc tactcaatct caaccgacga cggagctgct     360
tttggagggg gcactaaggt ggaaatcaaa cgaactgtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct caatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga             714
```

<210> SEQ ID NO 136
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Gln Ala Ser Gln Ser Ile
        35                  40                  45

Ser Asn Tyr Leu Ser Trp Tyr Gln Gln Lys Pro Gly Lys Ala Pro Lys
    50                  55                  60

Leu Leu Ile Tyr Ala Ala Ser Lys Leu Ala Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Cys Glu Asp Ala Ala Thr Tyr Tyr Cys Leu Gly Val Tyr Ser
            100                 105                 110

Ile Ser Thr Asp Asp Gly Ala Ala Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 137
<211> LENGTH: 993
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

| | | | | | |
|---|---|---|---|---|---|
| gcatccacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | cacctgaact | cctgggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |
| gagtacaagt | gcaaggtctc | caacaaagcc | ctcccagccc | ccatcgagaa | aaccatctcc | 660 |
| aaagccaaag | ggcagccccg | agaaccacag | gtgtacaccc | tgcccccatc | ccgggatgag | 720 |

```
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcttatat tcaaagctca ccgtggacaa gagcaggtgg    900
cagcagggga acgtcttctc atgctccgtg atgcatgagg ctctgcacaa ccactacacg    960
cagaagagcc tctccctgtc tcccgggaaa tga                                 993
```

<210> SEQ ID NO 138
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 139
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttga                                            324

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 141
<211> LENGTH: 972
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gggcaaccta aggctccatc agtcttccca ctggccccct gctgcgggga cacacccagc      60
tccacggtga ccctgggctg cctggtcaaa ggctacctcc ggagccagt gaccgtgacc     120 tggaactcgg gcaccctcac caatgggta cgcaccttcc cgtccgtccg gcagtcctca     180
ggcctctact cgctgagcag cgtggtgagc gtgacctcaa gcagccagcc cgtcacctgc     240
```

```
aacgtggccc acccagccac caacaccaaa gtggacaaga ccgttgcacc ctcgacatgc    300
agcaagccca cgtgcccacc ccctgaactc ctggggggac cgtctgtctt catcttcccc    360
ccaaaaccca aggacaccct catgatctca cgcaccccg aggtcacatg cgtggtggtg     420
gacgtgagcc aggatgaccc cgaggtgcag ttcacatggt acataaacaa cgagcaggtg    480
cgcaccgccc ggccgccgct acgggagcag cagttcaaca gcacgatccg cgtggtcagc    540
accctcccca tcacgcacca ggactggctg aggggcaagg agttcaagtg caaagtccac    600
aacaaggcac tcccggcccc catcgagaaa accatctcca agccagaggg cagcccctg     660 gagccgaagg tctacaccat gggccctccc cgggaggagc tgagcagcag gtcggtcagc    720
ctgacctgca tgatcaacgg cttctaccct tccgacatct cggtggagtg ggagaagaac    780
gggaaggcag aggacaacta caagaccacg ccggccgtgc tggacagcga cggctcctac    840
ttcctctaca caagctctc agtgcccacg agtgagtggc agcggggcga cgtcttcacc     900
tgctccgtga tgcacgaggc cttgcacaac cactacacgc agaagtccat ctcccgctct    960
ccgggtaaat ga                                                        972
```

<210> SEQ ID NO 142
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Thr His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220
```

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
            245                 250                 255

Trp Glu Lys Asn Gly Lys Ala Glu Asp Asn Tyr Lys Thr Thr Pro Ala
        260                 265                 270

Val Leu Asp Ser Asp Gly Ser Tyr Phe Leu Tyr Asn Lys Leu Ser Val
    275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 143
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
ggtgatccag ttgcacctac tgtcctcatc ttcccaccat ctgctgatct tgtggcaact    60
ggaacagtca ccatcgtgtg tgtggcgaat aaatactttc ccgatgtcac cgtcacctgg   120
gaggtggatg caccacccca aacaactggc atcgagaaca gtaaaacacc gcagaattct   180
gcagattgta cctacaacct cagcagcact ctgacactga ccagcacaca gtacaacagc   240
cacaaagagt acacctgcaa ggtgacccag ggcacgacct cagtcgtcca gagcttcaat   300
aggggtgact gttag                                                    315

<210> SEQ ID NO 144
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Asp Pro Val Ala Pro Thr Val Leu Ile Phe Pro Pro Ser Ala Asp
1               5                   10                  15

Leu Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 145
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggattctccc tcaatagcta tgcg                                            24

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Phe Ser Leu Asn Ser Tyr Ala
1               5

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
attactactg gtggtaccac a                                               21

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Thr Thr Gly Gly Thr Thr
1               5

<210> SEQ ID NO 149
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gatcgggtta aaagctacga tgactatggt gatttagatg ctttcgagcc c              51

<210> SEQ ID NO 150
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Arg Val Lys Ser Tyr Asp Asp Tyr Gly Asp Leu Asp Ala Phe Glu
1               5                   10                  15

Pro Trp Gly Pro
```

-continued

```
                    20

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggcttttccc tgaacagcta cgct                                              24

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Ser Leu Asn Ser Tyr Ala
1               5

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
attaccacag gagggactac c                                                 21

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Thr Thr Gly Gly Thr Thr
1               5

<210> SEQ ID NO 155
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gatcgggtga atcttacga cgattatgga gacctggatg ctttcgaacc a                 51

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156
```

Asp Arg Val Lys Ser Tyr Asp Asp Tyr Gly Asp Leu Asp Ala Phe Glu
1               5                   10                  15

Pro Trp Gly Pro
            20

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggattctcct tcagtagcag ctac                                            24

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Phe Ser Phe Ser Ser Ser Tyr
1               5

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
atttatggtg gtagtagtgg taccact                                         27

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Tyr Gly Gly Ser Ser Gly Thr Thr
1               5

<210> SEQ ID NO 161
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gtgactaatg gtggtgattg ggattttaaa ttg                                  33

<210> SEQ ID NO 162
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 162

Val Thr Asn Gly Gly Asp Trp Asp Phe Lys Leu
1               5                   10

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggaatcgacc tcagtaatta tgca                                            24

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Ile Asp Leu Ser Asn Tyr Ala
1               5

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
attagtagta atgataagac a                                               21

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ser Ser Asn Asp Lys Thr
1               5

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gctgctatgc ctggtggttt aaagaatgct ttcgatccc                            39

<210> SEQ ID NO 168
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Ala Met Pro Gly Gly Leu Lys Asn Ala Phe Asp Pro
1               5                   10

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggcattgatc tgtctaacta cgct                                          24

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ile Asp Leu Ser Asn Tyr Ala
1               5

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
attagctcca atgacaagac c                                             21

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ile Ser Ser Asn Asp Lys Thr
1               5

<210> SEQ ID NO 173
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gccgctatgc ctggcggact gaagaacgca tttgatcct                          39
```

```
<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Ala Met Pro Gly Gly Leu Lys Asn Ala Phe Asp Pro
1               5                   10

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggaatctccc tcagtagcga tgca                                            24

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Ile Ser Leu Ser Ser Asp Ala
1               5

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
attaatggtg gtggtaacac a                                               21

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ile Asn Gly Gly Gly Asn Thr
1               5

<210> SEQ ID NO 179
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggcattcaac atggtggtgg taatagtgat tattattatt acggcatgga cctc           54
```

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Ile Gln His Gly Gly Gly Asn Ser Asp Tyr Tyr Tyr Tyr Gly Met
1               5                   10                  15

Asp Leu

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggaatttccc tctcctccga cgcg                                          24

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ile Ser Leu Ser Ser Asp Ala
1               5

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atcaacggcg gcggaaacac c                                             21

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ile Asn Gly Gly Gly Asn Thr
1               5

<210> SEQ ID NO 185
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggcatccagc acggtggtgg aaacagcgac tactactact atgggatgga tctg    54

<210> SEQ ID NO 186
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Ile Gln His Gly Gly Gly Asn Ser Asp Tyr Tyr Tyr Tyr Gly Met
1               5                   10                  15
Asp Leu

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ggattctccc tcagtaacta tgca    24

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Phe Ser Leu Ser Asn Tyr Ala
1               5

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
attagtactg gcggtatcac a    21

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ile Ser Thr Gly Gly Ile Thr
1               5

<210> SEQ ID NO 191
<211> LENGTH: 39
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 191
aatgctggtg gtagttatat tttctattat tttgacttg                              39

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asn Ala Gly Gly Ser Tyr Ile Phe Tyr Tyr Phe Asp Leu
1               5                   10

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ggattctccc tcagtaacta tgca                                              24

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Phe Ser Leu Ser Asn Tyr Ala
1               5

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
attagtactg gcggtatcac a                                                 21

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ile Ser Thr Gly Gly Ile Thr
1               5

<210> SEQ ID NO 197

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aatgctggtg gtagttatat tttctattat ttcgacttg                              39

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asn Ala Gly Gly Ser Tyr Ile Phe Tyr Tyr Phe Asp Leu
1               5                   10

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ggattctccc tcagtagtta ccac                                             24

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Phe Ser Leu Ser Ser Tyr His
1               5

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
attactgcta tgagtcgcac a                                                21

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ile Thr Ala Met Ser Arg Thr
1               5
```

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gaacctggtt ttgttagtaa catc                                          24

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Pro Gly Phe Val Ser Asn Ile
1               5

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggattctccc tcagtagcta tgca                                          24

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Phe Ser Leu Ser Ser Tyr Ala
1               5

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
attagtactg gtggtattac a                                             21

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Ser Thr Gly Gly Ile Thr

<210> SEQ ID NO 209
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtgggtagta gtggttatct tttctacttc tttaacttg                              39

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Val Gly Ser Ser Gly Tyr Leu Phe Tyr Phe Phe Asn Leu
1               5                   10

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggattctccc tcagtaggta taca                                              24

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Phe Ser Leu Ser Arg Tyr Thr
1               5

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
atagatagta gtagtagtgc a                                                 21

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Ile Asp Ser Ser Ser Ser Ala
1               5
```

<210> SEQ ID NO 215
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gacagagtcc taagctacga tgactatggt gatttgcccg atggtttcga tccc         54

<210> SEQ ID NO 216
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Asp Arg Val Leu Ser Tyr Asp Asp Tyr Gly Asp Leu Pro Asp Gly Phe
1               5                   10                  15

Asp Pro
```

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gggtttagcc tgtcccgata cacc                                           24

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Gly Phe Ser Leu Ser Arg Tyr Thr
1               5
```

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
attgacagct cctctagtgc c                                              21

<210> SEQ ID NO 220
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 220

Ile Asp Ser Ser Ser Ala
1               5

<210> SEQ ID NO 221
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gatagagtcc tgagctacga cgattatggg gacctgcctg acggctttga tcct            54

<210> SEQ ID NO 222
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asp Arg Val Leu Ser Tyr Asp Asp Tyr Gly Asp Leu Pro Asp Gly Phe
1               5                   10                  15

Asp Pro

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
cagagcatta gtagctac                                                   18

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Ser Ile Ser Ser Tyr
1               5

<210> SEQ ID NO 225
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225 tatgcatcc                                                              9

<210> SEQ ID NO 226

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Ala Ser
1

<210> SEQ ID NO 227
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ctaggtgttt atggttatag ttttgatgat ggtattgct                              39

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Leu Gly Val Tyr Gly Tyr Ser Phe Asp Asp Gly Ile Ala
1               5                   10

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cagagtattt ccagctac                                                     18

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Ser Ile Ser Ser Tyr
1               5

<210> SEQ ID NO 231
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231 tatgctagt                                                                9
```

<210> SEQ ID NO 232
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Tyr Ala Ser
1

<210> SEQ ID NO 233
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ctgggggtgt acggttattc tttcgacgat ggcatcgca                    39

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Leu Gly Val Tyr Gly Tyr Ser Phe Asp Asp Gly Ile Ala
1               5                   10

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
cagagtattt ccagctac                                            18

<210> SEQ ID NO 236
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Ser Ile Ser Ser Tyr
1               5

<210> SEQ ID NO 237
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237 tatgctagt                                                                 9

<210> SEQ ID NO 238
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Ala Ser
1

<210> SEQ ID NO 239
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctgggggtgt acggttattc tttcgacgat ggcatcgca                               39

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Leu Gly Val Tyr Gly Tyr Ser Phe Asp Asp Gly Ile Ala
1               5                   10

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cagagtattt ccagctac                                                      18

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Ser Ile Ser Ser Tyr
1               5

<210> SEQ ID NO 243
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 243 tatgctagt                                                                  9

<210> SEQ ID NO 244
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Tyr Ala Ser
1

<210> SEQ ID NO 245
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ctgggggtgt acggttattc tttcgacgat ggcatcgca                                39

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Leu Gly Val Tyr Gly Tyr Ser Phe Asp Asp Gly Ile Ala
1               5                   10

<210> SEQ ID NO 247
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cagagtattt ccagctac                                                       18

<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Ser Ile Ser Ser Tyr
1               5

<210> SEQ ID NO 249
<211> LENGTH: 9
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 249 tatgctagt                                                                                              9

<210> SEQ ID NO 250
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Tyr Ala Ser
1

<210> SEQ ID NO 251
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ctgggggtgt acggttattc tttcgacgat ggcatcgca                                                            39

<210> SEQ ID NO 252
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Leu Gly Val Tyr Gly Tyr Ser Phe Asp Asp Gly Ile Ala
1               5                   10

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cagagtattt ccagctac                                                                                   18

<210> SEQ ID NO 254
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gln Ser Ile Ser Ser Tyr
1               5

<210> SEQ ID NO 255
<211> LENGTH: 9
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 255 tatgctagt                                                                  9

<210> SEQ ID NO 256
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Tyr Ala Ser
1

<210> SEQ ID NO 257
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ctgggggtgt acggttattc tttcgacgat ggcatcgca                                39

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Leu Gly Val Tyr Gly Tyr Ser Phe Asp Asp Gly Ile Ala
1               5                   10

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cagagtattt ccagctac                                                       18

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gln Ser Ile Ser Ser Tyr
1               5

<210> SEQ ID NO 261
<211> LENGTH: 9
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261 tatgctagt                                                            9

<210> SEQ ID NO 262
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Tyr Ala Ser
1

<210> SEQ ID NO 263
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ctgggggtgt acggttattc tttcgacgat ggcatcgca                          39

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Leu Gly Val Tyr Gly Tyr Ser Phe Asp Asp Gly Ile Ala
1               5                   10

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cagagtattt ccagctac                                                 18

<210> SEQ ID NO 266
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gln Ser Ile Ser Ser Tyr
1               5
```

```
<210> SEQ ID NO 267
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267 tatgctagt                                                                 9

<210> SEQ ID NO 268
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Tyr Ala Ser
1

<210> SEQ ID NO 269
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ctgggggtgt acggttattc tttcgacgat ggcatcgca                               39

<210> SEQ ID NO 270
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Leu Gly Val Tyr Gly Tyr Ser Phe Asp Asp Gly Ile Ala
1               5                   10

<210> SEQ ID NO 271
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cagtccatct cctcctac                                                      18

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Ser Ile Ser Ser Tyr
1               5
```

<210> SEQ ID NO 273
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273 tacgcctcc                                                                  9

<210> SEQ ID NO 274
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Ala Ser
1

<210> SEQ ID NO 275
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ctgggggtgt atggttactc gttcgacgat ggaatcgca                                 39

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Leu Gly Val Tyr Gly Tyr Ser Phe Asp Asp Gly Ile Ala
1               5                   10

<210> SEQ ID NO 277
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
cagagcatct cctcatac                                                        18

<210> SEQ ID NO 278
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

```
Gln Ser Ile Ser Ser Tyr
1               5
```

<210> SEQ ID NO 279
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279 tacgcctcc                                                              9

<210> SEQ ID NO 280
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Tyr Ala Ser
1
```

<210> SEQ ID NO 281
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ctgggagtct acgggtactc cttcgatgac ggcattgca                            39

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

```
Leu Gly Val Tyr Gly Tyr Ser Phe Asp Asp Gly Ile Ala
1               5                   10
```

<210> SEQ ID NO 283
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
cagtcgatct cctcttac                                                   18

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 284

Gln Ser Ile Ser Ser Tyr
1               5

<210> SEQ ID NO 285
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285 tacgcgtcg                                                                 9

<210> SEQ ID NO 286
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Tyr Ala Ser
1

<210> SEQ ID NO 287
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ctgggggtgt acggctactc cttcgatgac ggaatcgcc                               39

<210> SEQ ID NO 288
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Leu Gly Val Tyr Gly Tyr Ser Phe Asp Asp Gly Ile Ala
1               5                   10

<210> SEQ ID NO 289
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cagtccatct cctcatac                                                      18

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 290

Gln Ser Ile Ser Ser Tyr
1               5

<210> SEQ ID NO 291
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291 tacgcttcc                                                            9

<210> SEQ ID NO 292
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Tyr Ala Ser
1

<210> SEQ ID NO 293
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ttgggtgtct acggatactc cttcgacgac gggatcgca                          39

<210> SEQ ID NO 294
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Leu Gly Val Tyr Gly Tyr Ser Phe Asp Asp Gly Ile Ala
1               5                   10

<210> SEQ ID NO 295
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
cagtcaattt cctcgtac                                                 18

<210> SEQ ID NO 296
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 296

Gln Ser Ile Ser Ser Tyr
1               5

<210> SEQ ID NO 297
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297 tacgcatcc                                                                 9

<210> SEQ ID NO 298
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Tyr Ala Ser
1

<210> SEQ ID NO 299
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ctgggggtgt acgggtactc atttgacgat ggcatcgcc                               39

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Leu Gly Val Tyr Gly Tyr Ser Phe Asp Asp Gly Ile Ala
1               5                   10

<210> SEQ ID NO 301
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cagtccattt cgtcctac                                                      18

<210> SEQ ID NO 302
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln Ser Ile Ser Ser Tyr
1               5

<210> SEQ ID NO 303
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303 tacgcctcc                                                            9

<210> SEQ ID NO 304
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Tyr Ala Ser
1

<210> SEQ ID NO 305
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ctgggcgtgt acggttactc gtttgatgac ggcatcgcg                           39

<210> SEQ ID NO 306
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Leu Gly Val Tyr Gly Tyr Ser Phe Asp Asp Gly Ile Ala
1               5                   10

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cagtccattt cgagctac                                                  18
```

```
<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Ser Ile Ser Ser Tyr
1               5

<210> SEQ ID NO 309
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309 tacgcctcc                                                              9

<210> SEQ ID NO 310
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Tyr Ala Ser
1

<210> SEQ ID NO 311
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
ctgggggtgt acggatactc attcgacgac gggatcgcc                            39

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Leu Gly Val Tyr Gly Tyr Ser Phe Asp Asp Gly Ile Ala
1               5                   10

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cagagcatta atacctac                                                   18
```

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gln Ser Ile Asn Thr Tyr
1               5

<210> SEQ ID NO 315
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315 agggcatcc                                                                9

<210> SEQ ID NO 316
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Arg Ala Ser
1

<210> SEQ ID NO 317
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
caacagagtg ttcgtgttat tgatgttgat aatact                                 36

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gln Gln Ser Val Arg Val Ile Asp Val Asp Asn Thr
1               5                   10

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319

```
cagaccattg gtggtagcga c                                              21

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Thr Ile Gly Gly Ser Asp
1               5

<210> SEQ ID NO 321
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321 tatgcaacc                                                             9

<210> SEQ ID NO 322
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Tyr Ala Thr
1

<210> SEQ ID NO 323
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ctaggtggtt atgctgctgc ttcttacaga actgct                              36

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Leu Gly Gly Tyr Ala Ala Ala Ser Tyr Arg Thr Ala
1               5                   10

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 325
cagaccattg gcgggagcga c                                              21

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gln Thr Ile Gly Gly Ser Asp
1               5

<210> SEQ ID NO 327
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327 tatgctaca                                                             9

<210> SEQ ID NO 328
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Tyr Ala Thr
1

<210> SEQ ID NO 329
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329 ctgggggget atgccgccgc aagctaccgc accgcc                               36

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Leu Gly Gly Tyr Ala Ala Ala Ser Tyr Arg Thr Ala
1               5                   10

<210> SEQ ID NO 331
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 331
cagaccattg gcgggagcga c                                           21

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gln Thr Ile Gly Gly Ser Asp
1               5

<210> SEQ ID NO 333
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333 tatgctaca                                                          9

<210> SEQ ID NO 334
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Tyr Ala Thr
1

<210> SEQ ID NO 335
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335 ctgggggggct atgccgccgc aagctaccgc accgcc                          36

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Leu Gly Gly Tyr Ala Ala Ala Ser Tyr Arg Thr Ala
1               5                   10

<210> SEQ ID NO 337
<211> LENGTH: 18
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 337
cagagcatta gtagtgtc                                                        18

<210> SEQ ID NO 338
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Ser Ile Ser Ser Val
1               5

<210> SEQ ID NO 339
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339 ctggcatcc                                                                   9

<210> SEQ ID NO 340
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Leu Ala Ser
1

<210> SEQ ID NO 341
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
caaaccaatt atggtactag tagtagtaat tatggttttg ct                              42

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Gln Thr Asn Tyr Gly Thr Ser Ser Ser Asn Tyr Gly Phe Ala
1               5                   10

<210> SEQ ID NO 343
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
cagtcaatta gcagcgtg                                                 18

<210> SEQ ID NO 344
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gln Ser Ile Ser Ser Val
1               5

<210> SEQ ID NO 345
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345 ttggcctcc                                                            9

<210> SEQ ID NO 346
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Leu Ala Ser
1

<210> SEQ ID NO 347
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
caaaccaact acggaacctc cagctccaac tacggctttg cc                       42

<210> SEQ ID NO 348
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gln Thr Asn Tyr Gly Thr Ser Ser Ser Asn Tyr Gly Phe Ala
1               5                   10
```

<210> SEQ ID NO 349
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
cagtcaatta gcagcgtg                                                      18

<210> SEQ ID NO 350
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gln Ser Ile Ser Ser Val
1               5

<210> SEQ ID NO 351
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351 ttggcctcc                                                                 9

<210> SEQ ID NO 352
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Leu Ala Ser
1

<210> SEQ ID NO 353
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
caaaccaact acggaacctc cagctccaac tacggctttg cc                            42

<210> SEQ ID NO 354
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Thr Asn Tyr Gly Thr Ser Ser Ser Asn Tyr Gly Phe Ala

```
                1               5                    10
```

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
cagtcaatta gcagcgtg                                                 18

<210> SEQ ID NO 356
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gln Ser Ile Ser Ser Val
1               5

<210> SEQ ID NO 357
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357 ttggcctcc                                                            9

<210> SEQ ID NO 358
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Leu Ala Ser
1

<210> SEQ ID NO 359
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
caaaccaact acggaacctc cagctccaac tacggctttg cc                       42

<210> SEQ ID NO 360
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gln Thr Asn Tyr Gly Thr Ser Ser Asn Tyr Gly Phe Ala
1               5                   10

<210> SEQ ID NO 361
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
cagagcattt acagttat                                                    18

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gln Ser Ile Tyr Ser Tyr
1               5

<210> SEQ ID NO 363
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363 tctgcatcc                                                               9

<210> SEQ ID NO 364
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Ala Ser
1

<210> SEQ ID NO 365
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
caaacctatt atgatattgt tactagtact                                       30

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 366

Gln Thr Tyr Tyr Asp Ile Val Thr Ser Thr
1               5                   10

<210> SEQ ID NO 367
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
cagagcattt acagttat                                                 18

<210> SEQ ID NO 368
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gln Ser Ile Tyr Ser Tyr
1               5

<210> SEQ ID NO 369
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369 tctgcatcc                                                            9

<210> SEQ ID NO 370
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ser Ala Ser
1

<210> SEQ ID NO 371
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
caaacctatt atgatattgt tactagtact                                    30

<210> SEQ ID NO 372
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 372

Gln Thr Tyr Tyr Asp Ile Val Thr Ser Thr
1               5                   10

<210> SEQ ID NO 373
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
cagaacattt acagcaat                                                   18

<210> SEQ ID NO 374
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gln Asn Ile Tyr Ser Asn
1               5

<210> SEQ ID NO 375
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375 gatgcatcc                                                              9

<210> SEQ ID NO 376
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Asp Ala Ser
1

<210> SEQ ID NO 377
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
caaagtatta gtagtgttga caataatgtt                                      30

<210> SEQ ID NO 378
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 378

Gln Ser Ile Ser Ser Val Asp Asn Asn Val
1               5                   10

<210> SEQ ID NO 379
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
cagaacatta agagctac                                                   18

<210> SEQ ID NO 380
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gln Asn Ile Lys Ser Tyr
1               5

<210> SEQ ID NO 381
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381 gaagcatcc                                                              9

<210> SEQ ID NO 382
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Glu Ala Ser
1

<210> SEQ ID NO 383
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
caaagctatt atgctgctag tagtaatgct                                      30

<210> SEQ ID NO 384
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gln Ser Tyr Tyr Ala Ala Ser Ser Asn Ala
1               5                   10

<210> SEQ ID NO 385
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
cagagcatta gtaactac                                                 18

<210> SEQ ID NO 386
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gln Ser Ile Ser Asn Tyr
1               5

<210> SEQ ID NO 387
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387 gctgcatcc                                                            9

<210> SEQ ID NO 388
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ala Ala Ser
1

<210> SEQ ID NO 389
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
ctaggagttt atagtattag tactgatgat ggagctgct                          39
```

<210> SEQ ID NO 390
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Leu Gly Val Tyr Ser Ile Ser Thr Asp Asp Gly Ala Ala
1               5                   10

<210> SEQ ID NO 391
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
cagagcatca gcaactac                                                       18

<210> SEQ ID NO 392
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln Ser Ile Ser Asn Tyr
1               5

<210> SEQ ID NO 393
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393 gccgcttct                                                                  9

<210> SEQ ID NO 394
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Ala Ser
1

<210> SEQ ID NO 395
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395

```
ctgggcgtct attcaatctc aactgacgac ggagccgca                    39
```

<210> SEQ ID NO 396
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Leu Gly Val Tyr Ser Ile Ser Thr Asp Asp Gly Ala Ala
1               5                   10

<210> SEQ ID NO 397
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397

```
cagagcatca gcaactac                                           18
```

<210> SEQ ID NO 398
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gln Ser Ile Ser Asn Tyr
1               5

<210> SEQ ID NO 399
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399

```
gccgcttct                                                      9
```

<210> SEQ ID NO 400
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ala Ala Ser
1

<210> SEQ ID NO 401
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 401
ctgggcgtct attcaatctc aactgacgac ggagccgca                              39

<210> SEQ ID NO 402
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Leu Gly Val Tyr Ser Ile Ser Thr Asp Asp Gly Ala Ala
1               5                   10

<210> SEQ ID NO 403
<211> LENGTH: 100
<212> TYPE: PRT
<213> ORGANISM: Oryctolagus cuniculus

<400> SEQUENCE: 403

Ala Gln Val Leu Thr Gln Thr Glu Ser Pro Val Ser Ala Pro Val Gly
1               5                   10                  15

Gly Thr Val Thr Ile Asn Cys Gln Ala Ser Gln Ser Val Tyr Asp Asn
            20                  25                  30

Asn Trp Leu Ser Trp Tyr Gln Gln Lys Pro Gly Gln Pro Pro Lys Leu
        35                  40                  45

Leu Ile Tyr Asp Ala Ser Lys Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Ser Tyr Tyr Ser
                85                  90                  95

Ser Gly Trp Tyr
            100

<210> SEQ ID NO 404
<211> LENGTH: 95
<212> TYPE: PRT
<213> ORGANISM: Homo sapiens

<400> SEQUENCE: 404

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 405
<211> LENGTH: 103
<212> TYPE: PRT
<213> ORGANISM: Oryctolagus cuniculus
```

<400> SEQUENCE: 405

Asp Pro Val Ala Pro Thr Val Leu Ile Phe Pro Pro Ala Ala Asp Gln
1               5                   10                  15

Val Ala Thr Gly Thr Val Thr Ile Val Cys Val Ala Asn Lys Tyr Phe
            20                  25                  30

Pro Asp Val Thr Val Thr Trp Glu Val Asp Gly Thr Thr Gln Thr Thr
        35                  40                  45

Gly Ile Glu Asn Ser Lys Thr Pro Gln Asn Ser Ala Asp Cys Thr Tyr
    50                  55                  60

Asn Leu Ser Ser Thr Leu Thr Leu Thr Ser Thr Gln Tyr Asn Ser His
65                  70                  75                  80

Lys Glu Tyr Thr Cys Lys Val Thr Gln Gly Thr Thr Ser Val Val Gln
                85                  90                  95

Ser Phe Asn Arg Gly Asp Cys
            100

<210> SEQ ID NO 406
<211> LENGTH: 107
<212> TYPE: PRT
<213> ORGANISM: Homo sapiens

<400> SEQUENCE: 406

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 407
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Ala Leu Val Met Thr Gln Thr Pro Ser Pro Val Ser Ala Ala Val Gly
1               5                   10                  15

Gly Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Gly Val Glu Cys Asp Asp
    50                  55                  60

Ala Ala Thr Tyr Tyr Cys
65                  70

```
<210> SEQ ID NO 408
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Ala Gln Val Leu Thr Gln Thr Glu Ser Pro Val Ser Ala Pro Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 409
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Ala Gln Val Leu Thr Gln Thr Glu Ser Pro Val Ser Ala Pro Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 410
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Ala Gln Val Leu Thr Gln Thr Pro Ala Ser Val Ser Ala Ala Val Gly
1               5                   10                  15

Gly Thr Val Thr Ile Asn Cys Trp Tyr Gln Gln Lys Leu Gly Gln Pro
            20                  25                  30

Pro Lys Leu Leu Ile Tyr Gly Val Pro Ser Arg Phe Lys Gly Ser Gly
        35                  40                  45

Ser Gly Thr Glu Tyr Thr Leu Thr Ile Ser Gly Val Gln Cys Asp Asp
    50                  55                  60

Ala Ala Thr Tyr Tyr Cys
65                  70

<210> SEQ ID NO 411
```

<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Ala Gln Val Met Thr Gln Thr Pro Ala Ser Val Ser Ala Ala Val Gly
1               5                   10                  15

Gly Thr Val Thr Ile Ile Cys Trp Tyr Gln Gln Lys Leu Gly Gln Pro
            20                  25                  30

Pro Lys Leu Leu Ile Tyr Gly Val Pro Ser Arg Phe Lys Gly Ser Gly
        35                  40                  45

Ser Gly Thr Glu Tyr Thr Leu Thr Ile Ser Gly Val Gln Cys Asp Asp
    50                  55                  60

Ala Ala Thr Tyr Tyr Cys
65                  70

<210> SEQ ID NO 412
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Ala Ile Asp Met Thr Gln Thr Pro Ala Ser Val Glu Ala Ala Val Gly
1               5                   10                  15

Gly Thr Ile Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 413
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Asp Pro Val Met Thr Gln Thr Pro Ser Ser Thr Ser Ala Ala Val Gly
1               5                   10                  15

Gly Thr Val Thr Ile Asn Cys Trp Phe Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Lys Gln Phe Thr Leu Thr Ile Ser Gly Val Gln Cys Asp Asp
    50                  55                  60

Ala Ala Thr Tyr Tyr Cys
65                  70

<210> SEQ ID NO 414
<211> LENGTH: 70

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Asp Gly Val Met Thr Gln Thr Pro Ala Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Asn Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 415
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 416
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 417
<211> LENGTH: 70
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 417

Ala Ala Val Leu Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 418
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Asp Val Val Met Thr Gln Thr Pro Ser Ser Lys Ser Ala Ala Val Gly
1               5                   10                  15

Asp Thr Val Thr Ile Lys Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Asp Leu Glu Cys Ala Asp
    50                  55                  60

Ala Ala Thr Tyr Tyr Cys
65                  70

<210> SEQ ID NO 419
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 420
<211> LENGTH: 70
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 420

Asp Pro Val Leu Thr Gln Thr Ala Ser Pro Val Ser Ala Ala Val Gly
1               5                   10                  15

Gly Thr Val Thr Ile Ser Cys Trp Tyr Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 421
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Ala Leu Val Met Thr Gln Thr Pro Ser Pro Val Ser Ala Ala Val Gly
1               5                   10                  15

Ser Thr Val Thr Ile Ser Cys Trp Phe Gln
                20                  25

<210> SEQ ID NO 422
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Lys Pro Gly Gln Pro Pro Lys Leu Leu Ile Tyr Gly Val Pro Ser Arg
1               5                   10                  15

Phe Lys Gly Ser Gly Phe Gly Thr Gln Phe Thr Leu Thr Ile Ser Gly
                20                  25                  30

Ala Gln Cys Asp Asp Ala Ala Thr Tyr Tyr Cys
            35                  40

<210> SEQ ID NO 423
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Asp Pro Met Leu Thr Gln Thr Ala Ser Pro Val Ser Ala Ala Val Gly
1               5                   10                  15

Ser Thr Val Thr Ile Ser Cys Trp Tyr Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Ser Gly Val Gln Cys Asp Asp
```

Ala Ala Thr Tyr Tyr Cys
65                  70

<210> SEQ ID NO 424
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Ala Gln Gly Pro Thr Gln Thr Pro Ser Ser Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Asp Val Gln Cys Asp Asp
    50                  55                  60

Ala Ala Thr Tyr Tyr Cys
65                  70

<210> SEQ ID NO 425
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 426
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Ala Leu Val Met Thr Gln Thr Pro Ala Ser Val Glu Ala Ala Val Gly
1               5                   10                  15

Gly Thr Val Thr Ile Lys Cys Trp Tyr Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Glu Tyr Thr Leu Thr Ile Ser Gly Val Gln Cys Ala Asp
    50                  55                  60

Ala Ala Thr Tyr Tyr Cys
65                  70

<210> SEQ ID NO 427
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Ala Ala Val Met Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 428
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Ala Ala Val Leu Thr Gln Thr Pro Ser Pro Val Ser Ala Ala Val Gly
1               5                   10                  15

Gly Thr Val Thr Ile Lys Cys Trp Tyr Gln Gln Lys Pro Gly Gln Pro
            20                  25                  30

Pro Lys Leu Leu Ile Tyr Gly Val Pro Asp Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 429
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Asp Pro Met Leu Thr Gln Thr Ala Ser Pro Val Ser Ala Ala Val Gly
1               5                   10                  15

Ser Thr Val Thr Ile Ser Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 430
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Tyr Val Met Met Thr Gln Thr Pro Ser Ser Val Ser Glu Ala Val Gly
1               5                   10                  15

Gly Thr Val Thr Ile Tyr Cys Trp Tyr Gln Gln Lys Pro Gly Gln Pro
                20                  25                  30

Pro Lys Leu Leu Ile Tyr Gly Val Pro Ser Arg Phe Arg Gly Ser Gly
            35                  40                  45

Ser Gly Thr Gln Phe Thr Leu Thr Ile Ser Gly Met Lys Ala Glu Asp
        50                  55                  60

Val Ala Thr Tyr Tyr Cys
65                  70

<210> SEQ ID NO 431
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 432
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Asp Val Val Met Thr Gln Thr Pro Ser Pro Val Ser Ala Ala Val Gly
1               5                   10                  15

Gly Thr Val Thr Ile Asn Cys Trp Phe Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys

<210> SEQ ID NO 433
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 433

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 434
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 434

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 435
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 435

Asp Pro Met Leu Thr Gln Thr Ala Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 436
<211> LENGTH: 70
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 436

Tyr Val Met Met Thr Gln Thr Pro Ser Ser Val Ser Glu Ala Val Gly
1               5                   10                  15

Gly Thr Val Thr Ile Tyr Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Glu Tyr Thr Leu Thr Ile Ser Gly Val Gln Cys Asp Asp
    50                  55                  60

Ala Ala Thr Tyr Tyr Cys
65                  70

<210> SEQ ID NO 437
<211> LENGTH: 70
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 437

Asp Pro Met Leu Thr Gln Thr Ala Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 438
<211> LENGTH: 70
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 438

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 439
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 440
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Asp Ile Val Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 441
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Ala Val Val Leu Thr Gln Thr Ala Ser Pro Val Ser Ala Ala Val Gly
1               5                   10                  15

Gly Thr Val Thr Ile Asn Cys Trp Tyr Gln Gln Lys Pro Gly Gln Arg
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

```
<210> SEQ ID NO 442
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Asp Pro Met Leu Thr Gln Thr Ala Ser Pro Val Ser Ala Ala Val Gly
1               5                   10                  15

Ser Thr Val Thr Ile Ser Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 443
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Glu Phe Thr Leu Thr Ile Ser Asp Leu Glu Cys Ala Asp
    50                  55                  60

Ala Ala Thr Tyr Tyr Cys
65                  70

<210> SEQ ID NO 444
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Arg Gly Ser Gly
        35                  40                  45

Ser Gly Thr Gln Phe Thr Leu Thr Ile Ser Gly Met Lys Ala Glu Asp
    50                  55                  60

Val Ala Thr Tyr Tyr Cys
65                  70

<210> SEQ ID NO 445
```

<211> LENGTH: 70
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 445

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Lys Gly Ser Arg
        35                  40                  45

Ser Gly Thr Glu Phe Thr Leu Thr Ile Ser Asp Leu Glu Cys Ala Asp
    50                  55                  60

Ala Ala Thr Tyr Tyr Cys
65                  70

<210> SEQ ID NO 446
<211> LENGTH: 70
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 446

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Asp Leu Glu Cys Ala Asp
    50                  55                  60

Ala Ala Thr Tyr Tyr Cys
65                  70

<210> SEQ ID NO 447
<211> LENGTH: 70
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 447

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 448
<211> LENGTH: 70

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Asp Pro Val Leu Thr Gln Thr Ala Ser Pro Val Ser Ala Ala Val Gly
1               5                   10                  15

Gly Thr Val Thr Ile Ser Cys Trp Tyr Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 449
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Ala Ala Val Leu Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
                20                  25                  30

Pro Lys Leu Leu Ile Tyr Gly Val Ser Ser Arg Phe Lys Gly Ser Gly
            35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 450
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Asp Pro Met Leu Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
                20                  25                  30

Pro Lys Leu Leu Ile Tyr Gly Val Pro Pro Arg Phe Lys Gly Ser Gly
            35                  40                  45

Ser Gly Thr Glu Phe Thr Leu Thr Ile Ser Asp Leu Glu Cys Ala Asp
        50                  55                  60

Ala Ala Thr Tyr Tyr Cys
65                  70

<210> SEQ ID NO 451
<211> LENGTH: 70
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 451

Ala Ala Val Leu Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Pro Gly Asp
    50                  55                  60

Ala Ala Thr Tyr Tyr Cys
65                  70

<210> SEQ ID NO 452
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Asp Pro Met Leu Thr Gln Thr Ala Ser Pro Val Ser Ala Ala Val Gly
1               5                   10                  15

Ser Thr Val Thr Ile Ser Cys Trp Tyr Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Glu Tyr Thr Leu Thr Ile Ser Gly Val Gln Cys Asp Asp
    50                  55                  60

Ala Ala Thr Tyr Tyr Cys
65                  70

<210> SEQ ID NO 453
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Asp Pro Val Leu Thr Gln Thr Ala Ser Pro Val Ser Ala Ala Val Gly
1               5                   10                  15

Gly Thr Val Thr Ile Ser Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 454
<211> LENGTH: 70
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 454

Ala Ile Lys Met Thr Gln Thr Pro Ser Ser Val Ser Ala Ala Val Gly
1               5                   10                  15

Gly Thr Val Thr Ile Asn Cys Trp Tyr Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys
65                  70

<210> SEQ ID NO 455
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
                20                  25                  30

Pro Lys Leu Leu Ile Tyr Gly Val Ser Ser Arg Phe Lys Gly Ser Gly
            35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 456
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Asp Pro Val Leu Thr Gln Thr Pro Ser Ser Ala Cys Glu Pro Val Gly
1               5                   10                  15

Gly Thr Val Thr Ile Lys Cys Trp Tyr Gln Gln Lys Pro Gly Gln Ser
                20                  25                  30

Pro Lys Leu Leu Ile Tyr Gly Val Pro Ser Arg Phe Lys Gly Ser Gly
            35                  40                  45

Ser Gly Thr Glu Tyr Thr Leu Thr Ile Ser Asp Leu Glu Cys Ala Asp
        50                  55                  60

Ala Ala Thr Tyr Tyr Cys
65                  70

<210> SEQ ID NO 457
<211> LENGTH: 70
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 457

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Ser Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 458
<211> LENGTH: 70
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 458

Tyr Val Met Met Thr Gln Thr Pro Ser Ser Val Ser Glu Ala Val Gly
1               5                   10                  15

Gly Thr Val Thr Ile Tyr Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 459
<211> LENGTH: 70
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 459

Asp Pro Met Leu Thr Gln Thr Ala Ser Pro Val Ser Ala Ala Val Gly
1               5                   10                  15

Gly Thr Val Thr Ile Ser Cys Trp Tyr Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 460
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 460

Tyr Val Met Met Thr Gln Thr Pro Ser Ser Val Ser Glu Ala Val Gly
1               5                   10                  15

Gly Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 461
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Asp Val Val Met Thr Gln Thr Pro Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 462
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Ser Gly Ser Gly
        35                  40                  45

Ser Gly Thr Gln Phe Thr Leu Thr Ile Ser Gly Val Gln Cys Asp Asp
    50                  55                  60

Ala Ala Thr Tyr Tyr Cys
65                  70

<210> SEQ ID NO 463
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Asp Pro Val Leu Thr Gln Thr Ala Ser Pro Val Ser Ala Ala Val Gly
1               5                   10                  15

Gly Thr Val Thr Ile Ser Cys Trp Phe Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys
65                  70

<210> SEQ ID NO 464
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
                20                  25                  30

Pro Lys Leu Leu Ile Tyr Gly Val Pro Ser Trp Val Ser Ser Ser Gly
            35                  40                  45

Ser Gly Thr Glu Phe Thr Leu Thr Ile Ser Gly Val Gln Pro Gly Asp
        50                  55                  60

Ala Ala Thr Tyr Tyr Cys
65                  70

<210> SEQ ID NO 465
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Asp Val Val Met Thr Gln Thr Pro Ser Pro Val Ser Ala Ala Val Gly
1               5                   10                  15

Gly Thr Val Thr Ile Asn Cys Trp Tyr Gln Gln Lys Pro Gly Gln Pro
                20                  25                  30

Pro Lys Leu Leu Ile Tyr Gly Val Pro Ser Arg Phe Ser Gly Ser Gly
            35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 466
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 466

Ala Ala Val Leu Thr Gln Thr Pro Ser Pro Val Ser Val Ala Val Gly
1               5                   10                  15

Gly Thr Val Thr Ile Ser Cys Trp Tyr Gln Gln Lys Pro Gly Gln Pro
                20                  25                  30

Pro Lys Leu Leu Ile Tyr Gly Val Ser Ser Arg Phe Lys Gly Ser Gly
                35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 467
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Asp Pro Val Leu Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
                20                  25                  30

Pro Lys Leu Leu Ile Tyr Gly Val Ser Ser Arg Phe Lys Gly Ser Gly
                35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 468
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Ala Leu Val Met Thr Gln Thr Pro Ser Ser Thr Ser Glu Pro Val Gly
1               5                   10                  15

Gly Thr Val Thr Ile Asn Cys Trp Phe Gln Gln Lys Pro Gly Gln Pro
                20                  25                  30

Pro Lys Leu Leu Ile Tyr Gly Val Ser Ser Arg Phe Lys Gly Ser Gly
                35                  40                  45

Ser Gly Thr Gln Phe Thr Leu Thr Ile Ser Gly Val Gln Cys Asp Asp
        50                  55                  60

Ala Ala Thr Tyr Tyr Cys
65                  70

<210> SEQ ID NO 469
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469
```

Asp Val Val Met Thr Gln Thr Ala Ser Pro Val Ser Ala Val Gly
1               5                   10                  15

Ser Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65              70

<210> SEQ ID NO 470
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Ala Ala Val Leu Thr Gln Thr Pro Ser Pro Val Ser Val Ala Val Gly
1               5                   10                  15

Gly Thr Val Thr Ile Asn Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65              70

<210> SEQ ID NO 471
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Asp Pro Val Leu Thr Gln Thr Ala Ser Pro Val Ser Ala Ala Val Gly
1               5                   10                  15

Gly Thr Val Thr Ile Ser Cys Trp Phe Gln Gln Lys Pro Gly Gln Pro
            20                  25                  30

Pro Lys Leu Leu Ile Tyr Gly Val Pro Ser Arg Phe Lys Gly Ser Gly
        35                  40                  45

Ser Gly Thr Gln Phe Thr Leu Thr Ile Asn Gly Val Gln Cys Asp Asp
    50                  55                  60

Ala Ala Thr Tyr Tyr Cys
65              70

<210> SEQ ID NO 472
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

```
Tyr Val Met Met Thr Gln Thr Pro Ser Ser Val Ser Glu Ala Val Gly
1               5                   10                  15

Gly Thr Val Thr Ile Tyr Cys Trp Tyr Gln Gln Lys Pro Gly Gln Pro
                20                  25                  30

Pro Lys Leu Leu Ile Tyr Gly Val Pro Ser Arg Phe Arg Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys
65              70
```

<210> SEQ ID NO 473
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

```
Asp Pro Met Leu Thr Gln Thr Ala Ser Pro Val Ser Ala Ala Val Gly
1               5                   10                  15

Ser Thr Val Thr Ile Ser Cys Trp Phe Gln Gln Lys Pro Gly Gln Pro
                20                  25                  30

Arg Lys Leu Leu Ile Tyr Gly Val Pro Ser Arg Phe Lys Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys
65              70
```

<210> SEQ ID NO 474
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

```
Asp Val Val Met Thr Gln Thr Pro Ser Ser Lys Ser Ala Ala Val Gly
1               5                   10                  15

Asp Thr Val Thr Ile Lys Cys Trp Tyr Gln Gln Lys Pro Gly Gln Pro
                20                  25                  30

Pro Lys Leu Leu Ile Tyr Gly Val Pro Ser Arg Phe Lys Gly Ser Gly
            35                  40                  45

Ser Gly Thr Gln Phe Thr Leu Thr Ile Asn Gly Val Gln Cys Asp Asp
        50                  55                  60

Ala Ala Thr Tyr Tyr Cys
65              70
```

<210> SEQ ID NO 475
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

```
Ala Ala Val Leu Thr Gln Thr Pro Ser Pro Val Ser Val Ala Val Gly
```

```
1               5                   10                  15
Gly Thr Val Thr Ile Asn Cys Trp Phe Gln Gln Lys Pro Gly Gln Pro
                    20                  25                  30

Pro Lys Leu Leu Ile Tyr Gly Val Ser Ser Arg Phe Lys Gly Ser Gly
            35                  40                  45

Ser Gly Thr Gln Phe Thr Leu Thr Ile Asn Gly Val Gln Cys Asp Asp
    50                  55                  60

Ala Ala Thr Tyr Tyr Cys
65                  70

<210> SEQ ID NO 476
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gln Ser Val Lys Glu Ser Gly Gly Arg Leu Val Thr Pro Gly Thr Pro
1               5                   10                  15

Leu Thr Leu Thr Cys Thr Val Ser Gly Phe Ser Leu Asn Ser Tyr Ala
                    20                  25                  30

Met Ile Trp Val Arg Gln Ala Pro Gly Glu Gly Leu Glu Tyr Ile Gly
            35                  40                  45

Phe Ile Thr Thr Gly Gly Thr Thr Tyr Tyr Ala Ser Trp Ala Lys Gly
    50                  55                  60

Arg Phe Thr Ile Ser Arg Thr Ser Thr Thr Val Asp Leu Lys Leu Thr
65                  70                  75                  80

Arg Pro Thr Thr Glu Asp Thr Ala Thr Tyr Phe Cys Ala Arg
                85                  90

<210> SEQ ID NO 477
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
                    20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 478
<211> LENGTH: 95
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 478

Glu Ser Gly Gly Gly Leu Val Gln Pro Gly Arg Ser Leu Arg Leu Ser
1               5                   10                  15

Cys Thr Ala Ser Gly Phe Thr Phe Gly Asp Tyr Ala Met Ser Trp Val
            20                  25                  30

Arg Gln Ala Pro Gly Lys Gly Leu Glu Trp Val Gly Phe Ile Arg Ser
        35                  40                  45

Lys Ala Tyr Gly Gly Thr Thr Glu Tyr Ala Ala Ser Val Lys Gly Arg
    50                  55                  60

Phe Thr Ile Ser Arg Asp Asp Ser Lys Ser Ile Ala Tyr Leu Gln Met
65                  70                  75                  80

Asn Ser Leu Lys Thr Glu Asp Thr Ala Val Tyr Tyr Cys Thr Arg
                85                  90                  95

<210> SEQ ID NO 479
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Glu Ser Gly Gly Gly Leu Val Gln Pro Gly Gly Ser Leu Arg Leu Ser
1               5                   10                  15

Cys Ala Ala Ser Gly Phe Thr Phe Ser Ser Tyr Ala Met His Trp Val
            20                  25                  30

Arg Gln Ala Pro Gly Lys Gly Leu Glu Tyr Val Ser Ala Ile Ser Ser
        35                  40                  45

Asn Gly Gly Ser Thr Tyr Tyr Ala Asn Ser Val Lys Gly Arg Phe Thr
    50                  55                  60

Ile Ser Arg Asp Asn Ser Lys Asn Thr Leu Tyr Leu Gln Met Gly Ser
65                  70                  75                  80

Leu Arg Ala Glu Asp Met Ala Val Tyr Tyr Cys Ala Arg
                85                  90

<210> SEQ ID NO 480
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Glu Phe Thr Leu Thr Ile Thr Gly Val Gln Cys
65                  70                  75                  80

Asp Asp Ala Ala Thr Tyr Tyr Cys Leu Gly Val Tyr Gly Tyr Ser
                85                  90                  95

<210> SEQ ID NO 481
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 482
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 483
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Met Thr Gln Ser Pro Ser Ser Phe Ser Ala Ser Thr Gly Asp Arg Val
1               5                   10                  15

Thr Ile Thr Cys Arg Ala Ser Gln Gly Ile Ser Ser Tyr Leu Ala Trp
            20                  25                  30

Tyr Gln Gln Lys Pro Gly Lys Ala Pro Lys Leu Leu Ile Tyr Ala Ala

```
                    35                  40                  45

Ser Thr Leu Gln Ser Gly Val Pro Ser Arg Phe Ser Gly Ser
 50                  55                  60

Gly Thr Asp Phe Thr Leu Thr Ile Ser Cys Leu Gln Ser Glu Asp Phe
 65                  70                  75                  80

Ala Thr Tyr Tyr Cys Gln Gln Tyr Tyr Ser Tyr
                 85                  90

<210> SEQ ID NO 484
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Glu Leu Val Met Thr Gln Thr Pro Ser Ser Val Ser Ala Ala Val Gly
 1               5                  10                  15

Gly Thr Val Thr Ile Asn Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
             35                  40                  45

Tyr Tyr Ala Ser Thr Leu Ala Ser Gly Val Pro Ser Arg Phe Lys Gly
 50                  55                  60

Ser Gly Ser Gly Thr Glu Phe Thr Leu Thr Ile Thr Gly Val Gln Cys
 65                  70                  75                  80

Asp Asp Ala Ala Thr Tyr Tyr Cys Leu Gly Val Tyr Gly Tyr Ser Phe
                 85                  90                  95

Asp Asp Gly Ile Ala Phe Gly Gly Gly Thr Glu Leu Glu Ile Lys
                100                 105                 110

<210> SEQ ID NO 485
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Asp Ile Gln Met Thr Gln Ser Pro Ser Thr Leu Ser Ala Ser Val Gly
 1               5                  10                  15

Asp Arg Val Thr Ile Thr Cys Gln Ala Ser Gln Ser Ile Ser Ser Tyr
                20                  25                  30

Leu Ala Trp Tyr Gln Gln Lys Pro Gly Lys Ala Pro Lys Leu Leu Ile
             35                  40                  45

Tyr Tyr Ala Ser Thr Leu Ala Ser Gly Val Pro Ser Arg Phe Ser Gly
 50                  55                  60

Ser Gly Ser Gly Thr Glu Phe Thr Leu Thr Ile Ser Ser Leu Gln Cys
 65                  70                  75                  80

Asp Asp Phe Ala Thr Tyr Tyr Cys Leu Gly Val Tyr Gly Tyr Ser Phe
                 85                  90                  95

Asp Asp Gly Ile Ala Phe Gly Gly Gly Thr Lys Val Glu Ile Lys
                100                 105                 110

<210> SEQ ID NO 486
<211> LENGTH: 111
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 486

Glu Leu Val Met Thr Gln Thr Pro Ser Tyr Thr Ser Ala Ala Val Gly
1               5                   10                  15

Asp Thr Val Thr Ile Lys Cys Gln Ala Ser Gln Thr Ile Gly Gly Ser
            20                  25                  30

Asp Leu Ser Trp Tyr Gln Gln Lys Pro Gly Gln Pro Pro Lys Leu Leu
        35                  40                  45

Ile Trp Tyr Ala Thr Asn Leu Pro Ser Gly Val Pro Ser Arg Phe Ser
50                  55                  60

Gly Ser Arg Ser Gly Thr Glu Tyr Thr Leu Thr Ile Ser Gly Val Gln
65                  70                  75                  80

Cys Glu Asp Ala Ala Thr Tyr Tyr Cys Leu Gly Gly Tyr Ala Ala Ala
                85                  90                  95

Ser Tyr Arg Thr Ala Phe Gly Gly Gly Thr Glu Val Val Lys
            100                 105                 110

<210> SEQ ID NO 487
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Asp Ile Gln Met Thr Gln Ser Pro Ser Phe Leu Ser Ala Ser Val Gly
1               5                   10                  15

Asp Arg Val Thr Ile Thr Cys Gln Ala Ser Gln Thr Ile Gly Gly Ser
            20                  25                  30

Asp Leu Ser Trp Tyr Gln Gln Lys Pro Gly Lys Ala Pro Lys Leu Leu
        35                  40                  45

Ile Tyr Tyr Ala Thr Asn Leu Pro Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Cys Glu Asp Phe Ala Thr Tyr Tyr Cys Leu Gly Gly Tyr Ala Ala Ala
                85                  90                  95

Ser Tyr Arg Thr Ala Phe Gly Gly Gly Thr Lys Val Glu Ile Lys
            100                 105                 110

<210> SEQ ID NO 488
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Ile Ser Asn Tyr
            20                  25                  30

Leu Ser Trp Tyr Gln Gln Lys Pro Gly Gln Pro Pro Lys Leu Leu Ile
        35                  40                  45
```

```
Phe Ala Ala Ser Lys Leu Ala Ser Trp Val Pro Lys Arg Phe Ser Gly
            50                  55                  60

Ser Arg Ser Gly Ile Glu Tyr Thr Leu Thr Ile Ser Gly Val Gln Cys
 65                  70                  75                  80

Asp Asp Ala Ala Thr Tyr Phe Cys Leu Gly Val Tyr Ser Ile Ser Thr
                 85                  90                  95

Asp Asp Gly Ala Ala Phe Gly Gly Gly Thr Glu Val Val Val Lys
                100                 105                 110

<210> SEQ ID NO 489
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 489

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Asn Tyr
                20                  25                  30

Leu Ser Trp Tyr Gln Gln Lys Pro Gly Lys Ala Pro Lys Leu Leu Ile
             35                  40                  45

Tyr Ala Ala Ser Lys Leu Ala Ser Gly Val Pro Ser Arg Phe Ser Gly
         50                  55                  60

Ser Gly Ser Gly Thr Asp Phe Thr Leu Thr Ile Ser Ser Leu Gln Cys
 65                  70                  75                  80

Glu Asp Phe Ala Thr Tyr Tyr Cys Leu Gly Val Tyr Ser Ile Ser Thr
                 85                  90                  95

Asp Asp Gly Ala Ala Phe Gly Gly Gly Thr Lys Val Glu Ile Lys
                100                 105                 110

<210> SEQ ID NO 490
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Glu Val Leu Met Thr Gln Thr Pro Ser Ser Val Ser Ala Ala Val Gly
 1               5                  10                  15

Asp Thr Val Thr Ile Lys Cys Gln Ala Ser Gln Ser Ile Ser Ser Val
                20                  25                  30

Leu Ser Trp Tyr Gln Gln Lys Pro Gly Gln Pro Pro Lys Leu Leu Ile
             35                  40                  45

Tyr Leu Ala Ser Thr Leu Ala Ser Gly Val Pro Ser Arg Phe Ser Gly
         50                  55                  60

Ser Arg Ser Gly Thr Glu Phe Thr Leu Thr Ile Ser Asp Leu Glu Cys
 65                  70                  75                  80

Asp Asp Ala Ala Thr Tyr Tyr Cys Gln Thr Asn Tyr Gly Thr Ser Ser
                 85                  90                  95

Ser Asn Tyr Gly Phe Ala Phe Gly Gly Gly Thr Glu Val Val Val Lys
            100                 105                 110

<210> SEQ ID NO 491
```

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Val
            20                  25                  30

Leu Ser Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Thr Asn Tyr Gly Thr Ser Ser
                85                  90                  95

Ser Asn Tyr Gly Phe Ala Phe Gly Gly Gly Thr Lys Val Glu Ile Lys
            100                 105                 110
```